(12) United States Patent
Wang et al.

(10) Patent No.: US 8,163,805 B2
(45) Date of Patent: Apr. 24, 2012

(54) SMALL MOLECULE ANTAGONISTS OF BCL-2 FAMILY PROTEINS

(75) Inventors: Shaomeng Wang, Saline, MI (US);
Dajun Yang, Rockville, MD (US);
Liang Xu, Ann Arbor, MI (US)

(73) Assignees: The Regents of the University of Michigan, Ann Arbor, MI (US);
Georgetown University, Washington, DC (US)

( * ) Notice: Subject to any disclaimer, the term of this patent is extended or adjusted under 35 U.S.C. 154(b) by 129 days.

(21) Appl. No.: 12/242,380

(22) Filed: Sep. 30, 2008

(65) Prior Publication Data
US 2009/0092684 A1    Apr. 9, 2009

Related U.S. Application Data

(63) Continuation of application No. 10/729,156, filed on Dec. 5, 2003, now Pat. No. 7,432,304, which is a continuation-in-part of application No. 10/158,769, filed on May 30, 2002, now abandoned, and a continuation-in-part of application No. PCT/US02/17206, filed on May 30, 2002.

(60) Provisional application No. 60/293,983, filed on May 30, 2001.

(51) Int. Cl.
*A61K 31/12* (2006.01)

(52) U.S. Cl. ...................................... 514/682

(58) Field of Classification Search .................. 514/682
See application file for complete search history.

(56) References Cited

U.S. PATENT DOCUMENTS

| | | | |
|---|---|---|---|
| 3,347,885 A | 10/1967 | Jones et al. | 260/412.4 |
| 3,364,242 A | 1/1968 | Johnson et al. | 260/420 |
| 3,647,791 A | 3/1972 | Rossi et al. | 260/268 |
| 4,297,341 A | 10/1981 | Waller et al. | 424/80 |
| 4,747,979 A | 5/1988 | Gimber et al. | 260/412.4 |
| 4,806,568 A | 2/1989 | Vander Jagt et al. | 514/522 |
| 5,026,726 A | 6/1991 | Jagt et al. | 514/468 |
| 5,059,717 A | 10/1991 | Ibragimov et al. | 568/438 |

(Continued)

FOREIGN PATENT DOCUMENTS

CH    9710990    12/1987

(Continued)

OTHER PUBLICATIONS

Figgitt et al., Drugs, Mar. 2000 59(3):621-651.*

(Continued)

*Primary Examiner* — San-Ming Hui
(74) *Attorney, Agent, or Firm* — Casimir Jones SC

(57) ABSTRACT

The present invention relates to naturally occurring and chemically synthesized small molecule antagonists of Bcl-2 family proteins. In particular, the present invention provides gossypol compounds (e.g., isomers, enantiomers, racemic compounds, metabolites, derivatives, pharmaceutically acceptable salts, in combination with acids or bases, and the like) and methods of using these compounds as antagonists of the anti-apoptotic effects of Bcl-2 family member proteins (e.g., Bcl-2, Bcl-$X_L$, and the like). The present invention also provides compositions comprising gossypol compounds and optionally one or more additional therapeutic agents (e.g., anticancer/chemotherapeutic agents). The present invention also provides methods for treating diseases and pathologies (e.g., neoplastic diseases) comprising administering a composition comprising gossypol compounds and optionally one or more additional therapeutic agents (e.g., anticancer/chemotherapeutic agents) and/or techniques (e.g., radiation therapies, surgical interventions, and the like) to a subject or in vitro cells, tissues, and organs.

20 Claims, 55 Drawing Sheets

```
Bcl-2      5    NREIVMKYIHYKLSQRGYEWDAGDVGAAPPGAAPAPGIFSSQP

Bcl-X_L    5    NRELVVDFLSYKLSQKGYSWSQFSDVEENRTEAPEG---TESE

Bcl-2     88    VVHLTLRQAGDDFSRRYRRDFAEMSRQLHLTPFTARGRFATVV  130

Bcl-X_L   85    AVKQALREAGDEFELRYRRAFSDLTSQLHITPGTAYQSFEQVV  127

Bcl-2    131    EELFRDGVNWGRIVAFFEFGGVMCVESVNREMSPLVDNIALWM  173

Bcl- X_L 128    NELFRDGVNWGRIVAFFSFGGALCVESVDKEMQVLVSRIAAWM  170

Bcl-2    174    TEYLNRHLHTWIQDNGGWDAFVELYG  199

Bcl-X_L  171    ATYLNDHLEPWIQENGGWDTFVELYG  196
```

U.S. PATENT DOCUMENTS

| | | | |
|---|---|---|---|
| 5,077,441 A | 12/1991 | Kuk et al. | 568/761 |
| 5,112,637 A | 5/1992 | Hron, Sr. et al. | 426/629 |
| 5,260,327 A | 11/1993 | Kim et al. | 514/405 |
| 5,277,909 A | 1/1994 | Schmidt et al. | 424/195.1 |
| 5,385,936 A * | 1/1995 | Flack et al. | 514/548 |
| 5,759,837 A | 6/1998 | Kahajda et al. | 435/193 |
| 5,780,675 A | 7/1998 | Royer et al. | 562/467 |
| 6,113,397 A | 9/2000 | Flack et al. | 514/682 |
| 6,114,397 A | 9/2000 | Flack | |
| 6,576,660 B1 | 6/2003 | Liao et al. | 514/456 |
| 6,608,107 B2 | 8/2003 | Wong et al. | 514/548 |
| 2002/0137081 A1 | 9/2002 | Wong et al. | |
| 2003/0082101 A1 | 5/2003 | Taylor et al. | |
| 2003/0119894 A1 | 6/2003 | Murthy et al. | |
| 2005/0027000 A1 | 2/2005 | Reed et al. | |
| 2006/0084647 A1 | 4/2006 | Wang | |

FOREIGN PATENT DOCUMENTS

| | | |
|---|---|---|
| CH | 676360 A5 | 12/1988 |
| CN | 87105990 | 12/1987 |
| CN | 1033795 | 12/1989 |
| CN | 1094392 | 11/1994 |
| CN | 1406919 | 9/2001 |
| DE | 1 917 341 | 4/1969 |
| DE | 1917341 | 10/1970 |
| JP | 01132542 | 4/1969 |
| JP | 01132542 A | 11/1987 |
| JP | 0 651 636 B1 | 7/1993 |
| JP | WO 02/47673 A2 | 6/2002 |
| RU | 2067111 | 9/1996 |
| SU | 212245 | 1/1973 |
| SU | 322042 | 5/1976 |
| SU | 1351915 A1 | 6/1982 |
| WO | WO 94/20497 | 9/1994 |
| WO | WO 96/04250 | 2/1996 |
| WO | WO 97/40015 | 10/1997 |
| WO | WO 02/41828 A2 | 5/2002 |

OTHER PUBLICATIONS

Kreis et al., Ann Oncol, 1999;10(1):33-38.*

Japanese Search Report, Japanese Patent Application No. 2003-500222, dated Dec. 18, 2008.

Balci A et al.,Abstract, "Gossypol induced apoptosis in the human promyelocytic leukemia cell line HL 60", Tohuku J. Exp. Med. 1999, vol. 1989(1), pp. 51-57.

Blackstaff, L., et al., Abstract, "Cytotoxicity of gossypol enantiomers and its quinine metabolite gossypolone in melanoma cell lines", Melanoma Res., vol. 7(5), Oct. 1997, pp. 364-372.

Bushunow, P., et al., Abstract, "Gossypol treatment of recurrent adult malignant gliomas", US National Library of Medicine (NLM) & Journal of Neuro-Oncology, May 1999, vol. 43, No. 1, May 1999, pp. 79-86.

Dao, V-T., et al., "Synthesis and cytotoxicity of gossypol related compounds", European Journal of Medicinal Chemistry, Editions Scientifique Elsevier, Paris, FR, vol. 35, No. 9, Sep. 2000, pp. 805-813.

EP Search Report, EP Patent Application No. 02 734 614.7 dated Oct. 18, 2007.

Flack, M.R., et al., "Oral gossypol in the Treatment of metastatic Adrenal Cancer", Journal of Clinical Endocrinology and Metabolism, vol. 76, No. 4, pp. 1019-1024.

Gilbert, N.E., et al., "Antiproliferative Activity of Gossypol and Gossypolone on Human Breast Cancer Cells", Life Sciences, vol. 57, No. 1, pp. 61-67 (1995).

International Search Report, PCT/US02/17206, dated Jul. 23, 2004.

Jarvis, et al., Abstract, "Induction of apoptotic DNA fragmentation and cell death in HL-60 human promyelocytic leukemia cells by pharmacological inhibitors of protein kinase C.", Cancer Res., vol. 54(7), Apr. 1994, pp. 1707-1714.

Johnson, et al., "Relationships between drug activity in NCI preclinical in vitro and in vivo models and early clinical trials", British Journal of Cancer, 2001; 84(10), pp. 1424-1431.

Joseph, A., et al., Abstract, "Cytoxicity of enantiomers of gossypol", Database medline 'Online! US national Library of Medicine (NLM), Bethesda, MD, Sep. 1986 & British Journal of Cancer, Sep. 1986, vol. 54, No. 3, Sep. 1986, pp. 511-513.

Mace, Marshall, et al., Abstract, "Toxicity of cotton phytoalexins to zoopathogenic fungi", ISSN 1056-9014, Natural Toxins, 1993.

Manmade, A., et al., Abstract, "Gossypol. Synthesis and in vitro spermicidal activity of isomeric hemigossypol derivates", Experientia, Switzerland, Nov. 15, 1983.

U.S. Appl. No. 10/806,088 Office Communication mailed Feb. 23, 2009.

Crown, et al., "Docetaxel: use in non-small cell lung cancer and metastatic breast cancer and formulation update," J. Oncol. Pharm. Practice 6 (No. 3 Part 2):S10-S12 (2000).

Dunsford, et al., "Severe pulmonary toxicity in patients treated with a combination of docetaxel and gemcitabine for metastatic transitional cell carcinoma," Annals of Oncology 10:943-947 (1999).

Holmes, "Paclitaxel Combination Therapy in the Treatment of Metastatic Breast Cancer: A Review", Seminars in Oncology 23 (No. 5 Suppl 11): 46-56 (1996).

Mileshkin, et al., "Severe interstitial pneumonitis following high-dose cyclophosphamide, thiotepa and docetaxel: two case reports and a review of the literature," Bone Marrow Transplantation 27:559-563 (2001).

Smorenburg, et al., "Combination chemotherapy of the taxanes and antimetabolites: its use and limitations", European Journal of Cancer 37:2310-2323 (2001).

Sartor, et al., "Effect of Prednisone on Prostate-Specific Antigen in Patients with Hormone-Refractory Prostate Cancer," Urology, (1998) 52(2):252-256.

Petrylak, et al., "Phase I Trial o Docetaxel With Estramustine in Androgn-Independent Prostate Cancer", Journal of Clinical Oncology, vol. 17, No. 3 (Mar. 1999), pp. 958-967.

Office Action mailed May 26, 2010, U.S. Appl. No. 12/242,388, filed Sep. 30, 2010.

Office Action mailed Nov. 16, 2009, U.S. Appl. No. 12/242,388, filed Sep. 30, 2008.

Office Action mailed Apr. 29, 2010, U.S. Appl. No. 12/242,419, filed Sep. 30, 2008.

Office Action mailed Nov. 4, 2005, U.S. Appl. No. 10/729,156, filed Dec. 5, 2003.

Office Action mailed Jul. 6, 2006, U.S. Appl. No. 10/729,156, filed Dec. 5, 2003.

Office Action mailed Dec. 1, 2006, U.S. Appl. No. 10/729,156, filed Dec. 5, 2003.

Office Action mailed Jul. 3, 2007, U.S. Appl. No. 10/729,156, filed Dec. 5, 2003.

U.S. Appl. No. 12/609,761, filed Oct. 30, 2009.

Office Action mailed May 1, 2008, U.S. Appl. No. 11/209,998, filed Aug. 22, 2005.

Office Action mailed Aug. 15, 2008, U.S. Appl. No. 11/209,998, filed Aug. 22, 2005.

Office Action mailed Feb. 12, 2009, U.S. Appl. No. 11/209,998, filed Aug. 22, 2005.

Office Action mailed Nov. 4, 2009, U.S. Appl. No. 11/209,998, filed Aug. 22, 2005.

Notice of Allowance and Fees Due mailed Jan. 28, 2008, U.S. Appl. No. 10/729,156, filed Dec. 5, 2003.

Notice of Allowance and Fees Due mailed May 30, 2008, U.S. Appl. No. 10/729,156, filed Dec. 5, 2003.

Mace, et al "Toxicity of Cotton Phytoalexins to Zoopathogenic Fung," Natural Toxins 1:294-295 (1993).

Macvicar, G., et al., "Phase I/II, Open-Label Study of AT-101 in Combination With Docetaxel and Predisone in Men With Hormone-Refractory Prostate Cancer (HRPC)", Sixth International Congress on Targeted Therapies in Cancer, Aug. 24-26, 2007, Washington, D.C.

U.S. Appl. No. 10/806,088—Office Communication Mailed Dec. 21, 2004.

U.S. Appl. No. 10/806,088—Office Communication Mailed Oct. 3, 2005.

U.S. Appl. No. 10/806,088—Office Communication Mailed May 1, 2006.

U.S. Appl. No. 10/806,088—Office Communication Mailed Aug. 4, 2006.

U.S. Appl. No. 10/806,088—Office Communication Mailed Jan. 16, 2007.
U.S. Appl. No. 10/806,088—Office Communication Mailed Mar. 19, 2007.
U.S. Appl. No. 11/581,734—Office Communication Mailed Mar. 22, 2007.
Becattini et al., Rational Design and Real Time, In-Cell Detection of the Proapoptotic Activity of a Novel Compound Targeting Bcl-XL; Chem Biol 11:389 (2004).
Brzezinski et al., Selective Esterification of Gossypol by Copper Acetate in Acetonitrile-Spectroscopi Studies; Spectroscopy Lett 27:1143 (1994).
Dowd et al., Crystal and Molecular Structure of an Enantiomeric Gossypol-Acetic Acid Clathrate; J am Oil Chem Soc 76:1343 (1999).
Dowd et al., A Correction to the Molecular Structure of Enantiomeric Gossypol; J Am Oil Chem Soc 78:1171 (2001).
Dowd et al., The Gossypol-Cyclododecanone (½) inclusion Complex; Acta Crystallogr C 59:397 (2003).
Dowd et al., The (−)—Gossypol-2,4-pentanedione (1:2) inclusion Complex; J. Chem Crystallogr 34:559 (2004).
Freedman et al., Determination of the Absolute Configuration and Solution Conformation of Gossypol by Vibrational Circular Dichroism; Chirality 15:196 (2003).
Gdaniec et al., Gossypol; Compregensive Supramolecular Chemistry 6:117-200, 1996.
Gonzalez Correa et al., New Gossypol Derivatives; J Am Oil Chem Soc 43:678 (1966).
Han, X Y Jie He Za Zhi 2:159 (1982 (Chinese).
Hei et al., Electron Microscope Examination of Biopsy of Testis Tissue from the Patients with Tumors after Oral Treatment with Gossypol; Acta Acad Med Sinicae 61:527 (1981) (Chinese with Translation).
Jaroszewski et al., Effects of Gossypol on Drug-Sensitive and Drug-Resistant Cancer Cells; Proc Am Assoc Cancer Res 31:377 (1990).
Kable et al., Potency, Selectivity and Cell Cycle Dependence of Catechols in Human Tumour Cells In Vitro; Biochem Pharmacol 37:1711 (1988).
Kim et al., Gossypol, a Hyperthermic Sensitizer of HeLa Cells; Cancer Res 45:6338 (1985).
Liu et al., The (−)-Enantiomer of Gossypol Possesses Higher Anticancer Potency than Racemic Gossypol in Human Breast Cancer; Anticancer Res 22:33 (2002).
McClarty et al., Ribonucleotide Reductase: A Intracellular Target for the Male Antifertility Agent, Gossypol; Biochem Biophys Res Commun 133:300 (1985).
Miller et al., Structure of Gossypol. IV. Anhydrogossypol and its Derivatives; J Am Chem Cos 59:1736 (1937).
Molla et al., Influence of 5-Hydroxytryptamine on the Combination Effect of Lonidamine or Gossypol and Hyperthermia on Ehrlich Tumour In Vivo; Anticancer Res 7:361 (1987).
Senzer, Hyperthermia: Chemotherapeutic and biologic response Modifications; Strahlenther Onkol 165:729 (1989).
Tripathy et al., Gossypol Effects on Breast Cancer Oncogene Expression and Membrane Receptor Signal Transduction; Breast Cancer Res Treat 16:160 (1990).
Vermel, The Search for Antitumour Substances of Plant Origin; Acta Unio Internationalis Contra Cancrum 20:211 (1964).
Vermel et al., Voprosy Oncologii 10:88 (1964) (Russian).
Xu, A Laboratory Investigation on the Antitumor Effects of Gossypol; Med J Jinan Univ 2:39 (1987) (Chinese with translation).
Zakhidov et al., Ezvestiia Akademii Nauk SSSR Seriia Biologicheskaia 4:694 (1994) (Russian).
Zhang et al., Comparison of the Killing Effect of Levorotatory, Dextrorotatory and Recemic Gossypol on HeLa Cells; Acta Acad Med Sinicae 7:384 (1985) (Chinese with translation).
Zhang et al., Analysis of the Possible Mechanism of the Cytotoxic Effect of Gossypol in Mice, Rats and Human Tumor Cell Lines; Acta Acad Med Sinicae 8:486 (1986) ( Chinese with translation).
Zhang et al., In Vitro Antiproliferative Effect of Two New Platinum-Containing Bile Acid Derivatives:Bamet-U2 and Bamet-D3; Anticancer Res 18:4807 (1998).
Zhang et al., Differential Proliferative Responses to the (−)-enantiomer of Gossypol in Cultured Human Breast Epithelial and Stromal Cells; Proc Amer Assoc Cancer Res 40:4 (1999).
Vichanova et al., Antibiotics (moscow) 13:828-829 (1968) (Abstract in English).
Wu et al., J. Chromatography 433:141 (1988).
Shen et al., Ch. J. Magnetic Resonance 20:373 (2003).
Meyers et al., Tetrahedron 54:10493 (1998).
Brzezinski et al., J. Mol. Structure 230:261 (1990).
Matlin et al., J. Liquid Chromatography 12:1485 (1989).
Jaroazewski et al., Chirality 4:216 (1992).
Przybylski et al., J. Mol. Structure 691:227 (2004).
Przybylski et al., J. Mol. Structure 654:167 (2003).
Przybylski et al., J. Mol Structure 569:147 (2001).
Haas et al., J. Org. Chem. 30:4111 (1965).
Przyblski et al., J. Mol. Structure 699:65 (2004).
Dao, Disssertation, University of Paris XI (2002).
Boyfield et al., "n-(substituted-phenyl)piperazines:" Bioorganic and Medicinal Chemistry Letters, 6:1227-32 (1996).
Rao, "Agents acting on the central nervous system. XIII:", Journal of Medicinal Chemistry 13:516-22 (1970).
Singh et al., "Antihypertensive and cns depressant properties of 3-(gamma-p-fluorobenzoylpropyl)2,3,4,4a,5,6-hexahydro-1(h)-pyrazinol(1,-2-a)quinoline hydrochloride", Experientia 29:1529-30 (1973).
Singh et al., "Pharmacological studies on 3[gamma-(p-fluorobenzoly)propyl]-2,3,4,4a,5,6,hexahydro-1-(H)pyrazinol(1,2,-a)quinoline hydrochloride (Compound 69/83)" Arrzneimittel Forschung Drug Research 28:1641-4 (1978).
V. Amberger, et al., Cancer Res., 58:149-158 (1998).
Wick et al. (W. Wick, et al., FEBS Lett., 440:419-424 (1998).
S. Mohanam, et al., Cancer Res. 53:4143-4147 (1993).
P. Pedersen, et al., Cancer Res., 53:5158-5165 (1993).
Nuria Rubio, Lab Invest, 81:725-734 (2001).
Fernández et al., Cell Death Differ., 7:350-359 (2000).
J. Reed, Nature, 387:773-776 (1997).
S. Frisch and E. Ruoslahti, Curr. Opin. Cell Biol., 9:701-706 ((1997).
D. Del Bufalo, et al., FASEB J., 11:947-953 (1997).
Razakantoanina et al. Parasitol. Res., 86:665-668 (2000).
Dao et al. Bioorg. Med. Chem., 11:2001-2006 (2003).
Deck et al. J. Med. Chem., 34:3301-3305 (1991).
Przybylski et al. J. Mol. Structure, 611(1-3):193-201 (2002).
R.E. Royer et al., J. Med. Chem., 38:2427-2432 (1995).
R.E. Royer et al., Biologically active derivativse of gossypol: synthesis and antimalarial activities of peri-acylated gossylic nitriles:, J. Med. Chem., 29:1799-1801 (1986).
C.M. Venuti, J. Org. Chem., 46(15):3124-3127 (1981).
P.C. Meltzer et al., J. Org. Chem., 50(17):3121-3124 (1985).
R. Adams et al., J. Am. Chem. Soc., 60:2193-2204 (1938).
Le Blanc et al. "An in vitro study of inhibitory activity of gossypol, a cottonseed extract, in human carcinoma cell lines", Pharmacol. Res., 46:551-555 (2002).
Baumgrass et al., "Reversible inhibition of calcineurin by the polyphenolic aldehyde gossypol", J. Biol. Chem., 276:47914-47921 (2001).
Shelley et al., "Structure-activity studies on gossypol in tumor cell lines," Anticancer Drugs, 11:209-216 (2000).
Sonenberg et al., "Anti-fertility and othe ractions of gossypol analogues", Contraception, 37:247-255, (1988).
Whaley et al, ."Monkey lactate dehydrogenase-C4 as a model for the interaction of enzymes with gossypol", Contraception, 33:605-616 (1986).
Dorsett et al., "Letter: Antivrial activity of gossypol and apogossypol", J. Pharm. Sci., 64:1073-1075 (1975).
Wu et al., "Synthesis and antifertility actions of gossypol derivatives and phenol aldehydes", Yao Xue Xue Bao, 24:502-511 (1989).
Hoffer et al., "Antifertility, spermicidal and ultrastructural effects of gossypol and derivatives administered orally and by intratesticular injections", Contraception, 37:301-331 (1988).
Guo et al., "Synthesis of mono-aldehyde gossypol and its analogues", Yao Xue Xue Bao, 22:597-602 (1987).

Manmade et al., "Gossypol. Synthesis and in vitro spermicidal activity of isomeric hemigossypol derivatives", Experientia, 39:1276-1277 (1983).
Dowd, Chirality, 15:486 (2003).
Ciesielska et al., Chem. Phys. Lett. 353:69 (2002).
Vermel et al., Antitumour Activity of Gossypol in Experiments on Transplanted Tumours 39-43 (1963).
Freedman et al., Chirality, 15:196 (2003).
J.C. Reed, Pharmacology, 41:501-553 (1997).
J.C. Reed et al., J. Cell Biochem., 6:23-32 (1996).
Z. Han et al., Cancer Res., 56:621-628 (1996).
S.W. Muchmore el al., Nature, 381:335-341 (1996).
A.M. Petros et al., Protein Sci., 9:2528-2534 (2000).
A.M. Petros et al., Proc. Natl. Acad. Sci. U.S.A., 98:3012-3017 (2001).
X.M. Yin et al., Nature, 369:321-323 (1994).
S.C. Cosulich et al., Curr. Biol., 7:913-920 (1997).
A. Sali et al., Structure, Function, and Genetics, 23:318-326 (1995).
A. Sali, Curr. Opin. Biotech., 6:437-451 (1995).
J.L. Wang et al., Cancer Res., 60:1498-1502 (2000).
J.L. Wang et al., Proc. Natl. Acad. Sci. U.S.A., 97:7124-7129 (2000).
Sattler et al., Science, 275:983-986 (1997).
B.R. Brooks et al., J. Comp. Chem., 4,187-217 (1983).
P.V.R. Schleyer et al., CHARMM: The Energy Function and Its Parameterization with an Overview of the Program, in the Encyclopedia of Computational Chemistry, 1:271-277 eds., John Wiley & Sons, Chichester (1998).
S. Makino and I.D. Kuntz, J. Comput. Chem. 18:1812-1825 (1997).
I.J. Enyedy et al., J. Med. Chem., 44:313-4324 (2001).
Leschev, "Influence of the Extract of Eleutherococcus senticosus on development of experimental pituitary adenomas in rats", Institute of Oncology of the U.S.S.R. Academy of Medical Sciences, 60-67 (1966).
Willemsen, An Oxazoline-Based Approach to the Total Asymmetric Synthesis of (S)-Gossypol, UMI PROQuest Digial Disserations—Full Citation & Abstract.
La Blanc et al., An in vitro study of inhibitory activity of gossypol, a cottonseed extract, in human carcinoma cell lines, Pharmacol. Res. 46(6):551-5 (2002).
Griffith et al., Bioenvision Successfully Completes Formulation Research to Develop Gossypol as a Novel Anti-Cancer Agent, Bioenvision News (2003).
Saydachmov et al., Uebekskii Khimicheski Zhurnal (1):11-13 (1994).
Zakhidov et al., Modifying Cytogenetic Effects of Gossypol and Derivatives, Library National Institutes of Health (1994).
Yerukhimov, Treatment of Bladder Tumors With Gossipol and Ionol in Combination With Surgical Intervention, Issues in Oncology, XI (1966).
Kuznezova et al., Pharmacol. Toxicol., Boston Library Boston Spa (1979).
Zhong et al., National Library of Medicine, 2:159-161 (1982).
Zhang et al., Inhibitory effects (−)-gossypol on proliferation and keratinocyte growth factor expression in human breast epithelial cells, stromal cells, and adipocytes, American Association fro Cancer Research 38:218 (1997).
Zheng et al., Gossypol (GP) Stimulates Transforming Growth Factor Beta (TGF-β) Gene Expression in Human Breast Cancer Cell Line, The FASEB Journal 10:A757 (1996).
Zheng et al., Studies on the Resolution of Racemic Gossypol, ACTA Pharmaceutica Simica 25(6):430-434 (1990).
Adlakha et al., Inhibition of DNA Polymerase α and Ribonucleotide Reductase by By Gossypol, Proceedings of AACR 26:249:982 (1985).
Akhila et al., Biosynthesis of Gossypol in *Thespesia Populnea*, Phytochemistry 33:335-340 (1993).
Badria et al., Antimitotic Activity of Gossypol and Gossypolone, Pharmaceutical Biology, 39:120-126 (2001).
P. Bailie et al., Clin. Cancer Res., 3:1535-1538 (1997).
Balci et al., Gossypol induced apoptosis in the human promyelocytic cell line HL60, Cytogenet Cell Genet 85:5-181 (1999).
Balci et al., Gossypol Induced Apoptosis in the Human Promyelocytic Leukemia Cell Line HL 60, Tohoku J. Exp. Med. 189:51-57 (1999).
Band et al., Antiproliferative Effect of Gossypol and Its Optical Isomers on Human Reproductive Cancer Cell Lines, Gynecologenic Oncology 32:273-277 (1989).
Band et al., Cytocidal Effects of Gossypol and Its Optical Isomers on Reproductive Cancer Cell Lines,Gynecologic Oncology 23:261 (1986).
Benz et al., Lactic Dehydrogenase Isozymes, $^{31}P$ Magnetic Resonance Spectroscopy, and In Vitro Antimitochondrial Tumor Toxicity with Gossypol and Rhodamine-123, J. ClinInvest. 79:517-523 (1987).
Benz et al., Selective Toxicity of Gossypol Against Epithelial Tumors and its Detection by Magnetic Resonance Spectroscopy, Contraception 37:221-229 (1988).
Benz et al., Gossypol Enantiomers (+, −) Differentially Uncouple Tumor Mitochondria, Block Glutathione-S-Transferase Acitivity, and Inhibit Cellular Proliferation, Proceedings of AACR 29:322 (1988).
Benz et al., Biochemical Correlates of the Antitumor and Antimitochondrial Properties of Gossypol Enantiomers, Molecular Pharmacology 37:840-847 (11990).
Benz et al., Gossypol Effects on Endothelial Cells and Tumor Flow, Life Sciences 49:67-72 (1991).
Blackstaffe et al., Cytotoxicity of gossypol enantiomers and its quinone metabolite gossypolone in melanoma cell lines, Melanoma Research 7:364-372 (1997).
Bourinbaiar et al., Comparative in vitro study of contraceptive agents with anti-HIV activity: *Gramicidin, nonoxynol-9, and gossypol*, Contraception 49:131-137 (1994).
Brandes et al., New Drugs in Recurrent High Grade Gliomas, Anticancer Research 20:1913-1920 (2000).
Brandes et al., New therapeutic agents in the treatment of recurrent high-grade gliomas, FORUM Trends in Experimental and Clinical Medicine 10:121-131 (2000).
R. Bruno et al., J. Clin. Oncol., 16:187-196 (1998).
Bushunow et al., Gossypol Treatment of Recurrent Adult Malignant-Gliomas, Proceedings of ASCO, 14:282 (1995).
Bushunow et al., Gossypol Treatment of recurrent adult malignant gliomas, Journal of Neuro-Oncology 43:79-86 (1999).
Chang et al., Antiproliferative and Antimetastatic Effects of Gossypol (GP) on Mat-Lylu-Bearing Rats, FASEB Journal, 6:3794 (1992).
Chang et al., Prostate, begin hypertrophy and prostatic carcinoma: A study of cell biology of prostate and chemotherapy for prostatic hypertrophy and prostatic cancer, Dissertation Abstract International, 55:4330-B (1995).
Chang et al., Potential of Gossypol (GP) and Transforming Growth Factor-β, (TGF-β$_1$) as Inhibitors of Canine Prostate Growth, FASEB Journal, 9:4813-4814 (1995).
Chang et al., Antiproliferative and Antimetastatic Effects of Gossypol on Dunning Prostate Cell-Bearing Copenhagen Rats, Research Communications in Chemical Pathology and Pharmacology 79:293-312 (1993).
Chen et al., Application of 2D NMR Techniques in the Structure Determination of Ganosporelactone A and B, ACTA Pharmaceutica Simica 26:430-436 (1991).
Coyle et al., In-Vitrop and in vivo cytotoxicity of gossypol against central nervous system tumor cell lines, Journal of Neur-Oncology 19:25-35 (194), 1994.
Dallacker er al., Uber Gossypol- and Hemigossypol-Derivate—Darstellung von Hydroxy-methyl-naphto[1,3]dioxolen, Chemiker-Zeitung 113:5-11 (1989).
Dallacker et al, Darstellung von Methyl-isopropyl-naphthol-derivaten durch Pd-katalysierte Cyclocarbonylierung, Chemiker-Zeitung 114:144-147 (1990).
Dao et al., Synthesis and cytotoxicity of gossypol related compounds, Eur. J. Med. Chem. 35:805-813 (2000).
Darzynkiewicz et al., Cytometry in Cell Necrobiology: Analysis of Apoptosis and Accidental Cell Death (Necrosis), Cytometry 27:1-20 (1997).

Data et al. A Study of the Derivatives of (±)-Gossypol, Indian Journal of Chemistry 10:691-693 (1972).

Davila et al., Toxicological Studies of Gossypol in Primary Culture of Postnatal Rat Hepatocytes, Journal of Molecular and Cellular Toxicology, 4:161-170 (1991).

Deck er al, Gossypol and Derivatives: A New Class of Aldose Reductase Inhibitors, J. Med. Chem. 34:3301-3305 (1991).

DeMartino et al., Electron microscopic and biochemical studies of the effect of Gossypol on Ehrlich ascites tumor cells, Caryologia, International Journal of Cytology, Cytosystematics and Cytogenetics 35:114-115 (1982).

de Peyster et al., Genetic toxicity studies of gossypol, Mutation Research 197:293-312 (1993).

De-yu et al., Mutagenicity of gossypol analyzed by inductio of meiotic micronuclei in vitro, Mutation Research 208:69-72 (1988).

Dhaliwal et al., Cytogenetic Analysis of a Gossypol-Induced Murine Myxosarcoma, Journal of the National Cancer Institute, 78:1203-1209 (1987).

A. Degterev et al., Nat. Cell Biolog., 3:173-182 (2001).

Dogliotti et al., Cytotoxic chemotherapy for adrenocortical carcinoma, Minerva Endocrinologica, 20:105-109 91995).

Edwards et al., Sysnthesis of Gossypol and Gossypol Derivatives, Journal of the American Oil Chemists' Society 47:441-442 (1970).

Finaly et al. Mechanism of the Gossypol Inactivation of Pepsinogen, Journal of Biological Chemistry 248:4827-4833 (1973).

Fish et al., The Photo-epimerisation of Gossypol Schiff's Bases, Tetrahedron: Asymmetry 6:873-876 (1995).

Flack et al., Treatment of adrenocortical carcinoma with gossypol, Proceedings of American Association for Cancer Research 31:198 (1990).

Flack et al., Oral Gossypol in the Treatment of Metastatic Adrenal Cancer, Journal of Clinical Endocrinology and Metabolism, 76:1019-1024 (1993).

Floridi et al., The Effect of the Association of Gossypol and Lonidamine on the Energy Metabolism of Ehrlich Ascites Tumor Cells, Experimental and Molecular Pathology 38:322-335 (1983).

Floridi et al., The Effect of Gossypol and Lonidamine on Electron Transport in Ehrlich Ascites Tumor Mitochondria, Experimental and Molecular Pathology 40:246-261 (1984).

Ford et al., Modulatio nof resistance of alkylating agents in cancer cell by gossypol enantiomers, Cancer Letters 56:85-94 91991).

Gilbert et al., Antiproliferative Activity of Gossypola nd Gossypolone on Human Breast Cancer Cells, Life Sciences 57:61-67 (1995).

Gonzalez-Garza et al., Cytotoxic Effects of Gossypol and Vitamin E on Human and Rat Lymphocytes and Spermatozoa, Nutrition Reports International (1995).

Gorczyca et al., The Cell Cycle Related Differences in Susceptibility of HL-60 Cells to Apoptosis Induced by Various Antitumor Agents, Cancer Research 53:3186-3192 (1993).

Grankvist, Gossypol-Induced Free Radical Toxicity to Isolated Islet Cells, Int. J. Biochem. 21:853-856 (1989).

Hamasaki et al., Gossypol, a potent inhibitor of arachidonate 5- and 12-lipoxygenases, Biochimica et Biophysics Acta 834:37-41 (1985).

Han et al., Gossypol in the Treatment of Endometriosis and Uterine Myoma, Chontr. Gynec. Obstet. 16:268-270 (1987).

Haroz et al., Tumor Initiating and Promoting Activity of Gossypol, Toxicology letters, 72 (1980).

Haspel et al. Cytocidal Effect of Gossypol on Cultured Murine Erythroleukemia Cells is Prevented by Serum Protein, Journal of Pharmacology and Experimental Therapeutics 229:218-225 (1984).

J. Hirth et al., Clin. Cancer Res., 6:1255-1258 (2000).

Heinstein et al., The Biosynthesis of Gossypol, Biochemistry 28:1342-B (1967).

Hendricks et al., Hepatocarcinogenicity of Glandless Cottonseeds and Cottonseed Oil to Rainbow Trout (*Salmo gairdnerii*), Science 208:309-311 (1980).

Herve et al., Contraceptive gossypol blocks cell-to-cell communication in human and rat cells, European Journal of Pharmacology 313:243-255 (1966).

Hong et al., Study of the Effects of Acetate Gossypol, High Energy Shock Waves (HESW) and Their Combination on the Human Bladder Cancer Cell Line $BT_{5637}$, ACTA Anatomica Sinica 25:291-296-(1994).

Hu et al., Gossypol Effects on Cultured Normal and Malignant Melanocytes, In Vitro Cellular & Development Biology 22:583-588 (1986).

Hu et al., Gossypol Inhibits Basal and Estrogen ($E_2$)-Stimulated DNA Synthesis in Human Breast Carcinoma (HBC) Cells, FASEB Journal, 7:3982 (1993).

Hu et al., Gossypol Inhibits Basal and Estrogen-Stimulated DNA Synthesis in Human Breast Carcinoma Cells, Life Sciences 53:433-439 (1993).

Hu et al., Presence of antitumor activities in the milk collected from gossypol-treated dairy cows, Cancer Letters 87:17-23 (1994).

Huang et al., Resolution of Racemic Gossypol, Journal of Ethnopharmacology 20:13-20 (1987).

Huchinson et al., The mechanism of gossypol acetic acid cytotoxicity, Dissertation Abstracts Inernational, 59:1612-B (1998).

Hutchinson et al., Attenuation of Gossypol Cytotoxicity by Cyclic AMP in a Rat Liver Cell Line, Toxicology and Applied Pharmacology 151:311-318 (1998).

Jaroszewski et al., Action of Gossypol and Rhodamine 123 on Wild type and Multidrug-resistant MCF-7 Human Breast Cancer Cells: $^{31}$P Nuclear Magnetic Resonance and Toxicity Studies, Cancer Research 50:6936-6943 (1990).

Jarvis el al., INduction of Apoptotic DNA Fragmentation and Cell Death in HL-60 Human Promyelocytic Leukemia Cells by Pharmacological Inhibitors of Protein Kinase $C^1$, Cancer Research 54:1707-1714 (1994).

Jiang et al., Inhibitory Action of Gossypol on the Growth of MAT-LyLu Prostate Cancer Cells is Associated with Stimulation of Transforming Growth Factor-$\beta_1$, (TGF-$\beta$), Biology of Reproduction 60:252.

Jiang et al., Differing Effects of Gossypol on MAT-LYLU Cells and MAT-LYLU Cells Isolated From Metastasized Lung of MAT=Lylu Cell-Bearing Copenhagen Rats, Society for the Study of Reproduction 58:89.

Jiang et al., The Effects of Gossypol on the Invasiveness of MAT-LyLu Cells and MAT-LyLu Cells from the Metastasized Lungs of MAT-LyLu-Bearing Copenhagen Rats, Anticancer Research 20:4591-4598 (2000).

Jia-xin et al., Studies on the Synthesis of Gossypol Derivatives and Their Antifertility Action, Reproduction and Contraception 6:48:51 (1986).

Joingfang et al., Of Gossypol in Mice, Rats and Human Tumor Cell Lines and Its Possible Mechanism, ACTA Academiae Medicinae Sinicase 8:486-488 (1986).

Jolad et al., Tumor-Inhibitory Agent from *Montezuma speciosissima* (Malvaceae), Journal of Pharmaceutical Scicnes 64:1889-1890 (1975).

Joseph et al., Cytotoxicity of enantiomers of gossypol, Br. J. Cancer 54:511-513 (1986).

Jung et al., Recent Studies on Natural Products as Anti-HIV Agents, Current Medicinal Chemistry 7:649-651 (2000).

Kai et al., Resolution of Racemic Gossypol, J. Chem. Soc., Chem. Commun. 3:168:169 (1985).

Kaplan et al., Metabolism of breast cancer cells as revealed by non-invasive magnetic resonance spectroscopy studies, Breast Cancer Research and Treatment 31:285-299 (1994).

Keller et al., Novel pharmacophore-based methods reveal gossypol as a reverse transcriptase inhibitor, Journal of Molecular Graphics and Modelling 5346:1-9 92002).

Keniry et al., Magnetic Resonance Spectroscopy (MRS) and Imaging (MRI) in the Evaluation of Tumor Growth and Chemotherapy Response, Proceedings of AACR 27:384 (1986).

Keniry et al., The Effect of Gossypola nd 6-Aminonicotinamide on Tumor Cell Metabolism: A $^{31}$P-Magnetic Resonance Spectroscopic Study, Biochemical and Biophysical Research Communications 164:947-953 (1989).

Kim et al, Comparative In Vitro Spermicidal Effects of (±)-Gossypol, (=)-Gossypol, (−)-Gossypol and Gossypolone, Contraception 30:253-259 (1984).

Koll et al., A Phase I Study of Gossypol (GP) in HIV-Infected Patients (pts) in Mexico, Abstracts of the 33rd ICAC 245-687.

Koryakin et al., Ultrasound investigation of blood supply in scrotal organs, 10th World Congress on Human Reproduction 307 (1999).

Latronico et al., Extensive Personal Experience Adrenocortical Tumors, Journal of Clinical Endocrinology and Metabolism 82:1317-1324 (1997).

LaVoie et al., Investigation of Intracellular Signals Mediating the Anti-Apoptotic Action of Prolactin in Nb2 Lymphoma Cells, Society for Experimental Biology and Medicine 257-269 (1995).

Lee, Novel Antitumor Agents from Higher Plants, Medical Research Reviews, 19:569-596 (1999).

Lee et al., Plant PHenolic Compounds as Cytotoxic Antitumor Agents, American Chemical. Society 29:367-379 (1992).

Lefeng et al., Clincal Effects and Experimental Study on Gossypol in Endometriosis, Chin. J. Integr Med. 9(8):451-464 (1989).

Levine, Inhibition of the A-23187-Stimulated Leukotriene and Prostaglandin Biosynthesis of Rat Basophil Leukemia (RBL-1) Cells by Non-Steroidal Anti-Inflammatory Drugs, Anti-Oxidants, and Calcium Channel Blockers, Biochemical Pharmacology 32:3023-3025 (1983).

Li et al., DNA-Breaking Versus DNA-Protecting Activity of Four Phenolic Compounds in vitro, Free Rad. Res. 33:551-566 (2000).

Llian et al., Hepatoma Initiating and Promoting Effects of Gossypol, ACTA Academiae Medicinae Sinicase (1985).

Liang et al., Developing gossypol derivatives with enhanced antitumor activity, Investigational New Drugs 13:181-186 (1995).

Liqueros et al., The antiproliferative Effects of Gossypol and the Retinoblastoma Gene Protein, Clinical Pharmacology & therapeutics 57:206 (1995).

Liqueros et al., Gossypol inhibition of mitosis, cyclin D1 and Rb protein in human mammary cancer cells and cyclin-D1 transfected human fibrosarcoma cells, British Journal of Cancer 76:(1):21-28 (1997).

Lin et al., Selective Inhibition of Human Immunodeficiency Virus Type 1 Replication by the (−) but Not the (=) Enantiomer of Gossypol, Antimicrobial Agents and Chemotherapy, 2149-2151 (1989).

Lin et at, Anti-HIV-1 Activity and Cellular Pharmacology of Various Analogs of Gossypol, Biochemical Pharmacology 46:251-255 (1993).

Lin et al., Gossypol and tamoxifen prevent estrogen-induced renal carcinogenesis in hamsters, Proceedings of the American Association for Cancer Research 36:391-2329 (1995).

Majumdar et al., Genotoxic Effects of Gossypol Acetic Acid on Cultured Murine Erythroleukemia Cells, Environmental and Molecular Mutagenesis 18:212-219 (1991).

Matlin et al., Large-Scale Resolution of Gossypol Enantiomers for Biological Evaluation, Contraception 37:229-237 (1988).

McSheehy et al., Gossypol, a cytoxic agent, may uncouple respiration of Ehrlich ascites tumour cells, Biochemical Society Transactions 16:616-617 (1988).

Meiling, Gossypol Treatment for Menopausal Functional Bleeding, Myoma of Uterus and Endometriosis—Prelimnary Report, ACTA Academiae Medicinae Sinicae 2:167-169 (1980).

Meltzer et al., A Regioselective Route to Gossypol Analogues: The Synthesis of Gossypol and 5,5'-Didesisopropyl-5,5'-diethylgossypol, J. Org. Chem. 50:3121-3124 (1985).

Fujii et al., "Effect of cerulenin, an inhibitor of fatty acid synthesis, on the immune cytolysis of tumor cells" Jpn. J. Exp. Med Jun. 1986;56(3):99-106 (Abstract only).

Gossypol, Xian Oil 7 Fat Works, Drugs of the Future, vol. 21, No. 5, 1996.

Meyers et al., The synthesis of (S)-(=)-gossypol via an asymmetric Ullmann coupling, Chem. Commun., 1573-1584 (1997).

Moh et al.., Effect of Gossypol (GP) on a 5α-Reductase and a 3α-Hydroxysteroid Dehydrogenase (3αHSD) in Adult Rat Testes, FASEB Journal 6342 (1992.

Mohan, Problems and Perspectives in the Design of Anti-HIV-I Agents, Drug Development Research 29:1-17 (1993).

S.W. Muchmore et al., Nature, 381:335-341 (1996))., and.

Mushtaq et al., Gossypol (GP) Inhibits in Vitro Porcine Oocyte Maturation and Early Embryonic Development in Modified Simple Media, Society for the Study of Reproduction, 52:172 (1998).

Naik et al.. Preclinical studies of gossypol in prostate carcinoma, International Journal of Oncology 6:209-213 (1995).

Nayak et al., Induction of Sister Chromatid Exchanges and Chromosome Damage by Gossypol in Bone Marrow Cells of Mice, Teratogenesis, Carcinogenesis, and Mutagenesis 6:83-91 (1986).

Newman et al., Pharmacokinetics and toxicity of 120-hour continuous-infusion hydroxyurea in patients with advanced solid tumors, Cancer Chermother Pharmacol 39:254-258 (1997).

Ng et al., Anti-Human Immunodeficiency virus (Anti-HIV) Natural Products with Special Emphasis on HIV Reverse Transcriptase Inhibitors, Life Sciences 61:933-949 (1997).

Ognyanov et al., Synthesis of Gossypol Analogues, Helvetica Chimica ACTA 72:353-360 (1989).

Ohuchi et al., Inhibition of gossypol of tumor promoter-induced arachidonic acid metabolism in rat peritoneal macrophages, Biochimica et Biophysica Acta, 971:85-91 (1988).

Olgiati et al., Gossypol Inhibition of Adenylate Cyclase, Archives of Biochemistry and Biophysics 231:411-415 (1984).

Papageorgiou et al., A New Method for the Isolation of Gossypol From Cottonseed-Oil Fatty Acids, Chimika Chronika 7:101-109 (1978).

Perez et al., Studies on spermatogenesis and apoptosis in the bovine, Disseration Abstracts International 50:526-B (1999).

Phung et al., Isolation and Purification of Gossypol in Cotton Seeds of Vietnam, Tap chi Hoa hov, 35:91-93 (1997).

Pirogov et al., Postoperative Bronchopleural Complications in Combined Treatment of Pulmonary Cancer, Issues of Oncology, 20:24-28 (1974).

Polsky et al., Inactivation of Human Immunodeficiency Virus (RIV) by Gossypol (GP), Clinical Research 35(3)487A (1987).

Polsky et al, Inactivation of Human Immunodeficiency Virus in Vitro by Gossypol, Contraception, 39:579-587 (1989).

Przybylski et al., Spectroscopic studies and PM5 semiempirical calculations of new Schiff bases of gossypol with amino derivatives of crown ethers, Journal of Molecular Structure, 16:04-1-9 (2002).

Qian, Gossypol: A Potential Antifertility Agent for Males, Ann. Rev. Pharmacol. Toxicol. 24:329-60 (1984).

Qui et al., The Search for Gene(s) Conferring Sensitivity to Cell Killing by Gossypol, The FASEB Journal 13:A151A (1999).

J. O'Quigley et al., Biometrics 46:33-48 (1990).

Quintana et al., Gossypol-induced Dna breaks in rat lymphocytes are secondary to cytotoxicity, Toxicology Letters 117:85-94 (2000).

Rao et al.. Antitumor effects of gossypol on murine tumors, Cancer Chemother Pharmacol. 15:20-25 (1985).

Razakantoanina et al., Antimalarial activity of new gossypol derivatives, Parasitol Res. 86:665-668 (2000).

Reidenberg, Studies of gossypol in the treatment of cancer, Reproductive Medicine, 305-308.

Reidenberg et al. Gossypol Treatment of Metastatic Adrenal Cancer, Clinical Pharmacology and Therapeutics, 51:PI-96 (1992).

Rekha et al., Inhibition of Human Class 3 Aldehyde Dehydrogenase, and Sensitization of Tumor Cells that Express Significant Amounts of this Enzyme to Oxazaphosphorines, by the Naturally Occurring Compounds Gossypol, Enzymology and Molecular Biology of Carbonyl Metabolism 6, 133-146 (1996).

Resnick et al.. Comparative Evaluation of Spermicidal Agents with Virucidal Activity Against HIV, IXth International Conference on AIDS, 11:PO-C22-3154 (1993).

Rosenberg et al., Biochemical Basis for the Gossypol-indiced Inhibition of DNA Replication in Mammalian Cells, American Association for Cancer Research, 29:1291 (1988).

Royer et al., Inhibition of Human Immunodeficiency Virus Type I Replication by Derivatives of Gossypol, Pharmacological Research, 24:407-412 (1991).

G. Rassidakis et al., Amer. J. Path., 159:527-535 (2001).

J.C. Reed et al, Ann. Oncol., 5:61-65 (1994).

Sampath et al., A Rapid Procedure for the Resolution of Racemic Gossypol, J. Chem. Soc., Chem. Commun., 649-650 (1986).

Schinazi et al.. Insights Into HIV Chemotherapy, Aids Research and Human Retroviruses, 8:963-990 (1992).

A.F. Schott et al., Oncogene, 11:1389-1394 (1995).

Seidman et al., Gossypol in Advanced Breast Cancer, Journal of Investigative Medicine 46:213A (1998).

Seidman, Chemotherapy for Advanced Breast Cancer: A Current Perspective, Seminars in Oncology, 23:55-59 (1996).

Shelly et al., Stereo-specific cytotoxic effects of gossypol enantiomers and gossypolone in tumour cells lines, Cancer Letters, 135:171-180 (1999).

Shelly et al., Structure-activity studies on gossypol in tumor cell lines, Anti-Cancer Drugs, 11:209-216 (2000).

S. Shi et al., J. Histochem. Cytochem., 39:741-748 (1991).

Shidaifat et al., Differential regulation of gene expression by gossypo01: A potential inhibitor of prostate cell growth, Dissertation Abstracts International, 57:6097-B (1997).

Shidaifat et al., Inhibition of human prostate cancer cells growth by gossypol is associated with stimulation of transforming growth factor-$\beta$, Cancer Lettesr 107:37-44 (1996).

Shidaifat et al., Gossypol Arrests Human Benign Prostatic Hyperplastic Cell Growth at G0/G1 Phase of the Cell Cycle, Anticancer Research 17:1003-1010 (1997).

Sinnhuber et al., Dietary Factors and Hepatoma in Rainbow Trout (*Salmo gairdneri*). ri Cocarcinogenesis by Fatty Acids and the Effect of Gossypol and Altered Lipids on Aflatoxin-lnduced Liver Cancer, Journal of the National Cancer Institute, 41:1293-1299 (1968).

Stein et al., A preliminary clinical study of gossypol in advanced human cancer, Cancer Chemother Pharmacol 30:480-481 (1992).

Sugimoto et al., Differential proliferative rseponses to the (−)-enantiomer of gossypol in cultured human breat epithelial and stromal cells, American Association for Cancer Research 40:4 (1999).

Tai, Rat Basophilic Leukemia-I Cell Possesses 12-Lipoxygenase and 5-Lipoxygenase activities which are specifically inhiibited by gossypol acetic acid, Japanese Journal of Allergology 33:1040-1046 (1984).

Tan et al., Evaluation of Natural Products As Inhibitors of Human Immunodeficiency Virus Type 1 (HIV-1) Reverse Transcriptase[1], Jouranl of Natural Products, 54:143-154 (1991).

Tanphaichitr et al., Direct Effect of Gossypol on TR-ST Cells: Perturbation of Rhodamine 123 Accumulation in Mitochondria, Biology of Reproduction, 31:1049-1060 (1984).

Tao et al., The Effects of Gossypol on Human Bph Cells In Vitro, 21:31 (1994).

Teng et al., c-MYC Protein Expression in spermatocytes During Gossylpol-Induced Apoptosis, Molecular Biology of the Cell, 364a:2116 (1997).

Teng et al., Biphasic c-Myc Protein Expression During Gossypol-Induced Apoptosis in Rat Spermatocytes, Contraception 57:117-123 (1998).

Teng, C-Fos Protein Expression in Apoptotic Rat Spermatocytes Induced by Gossypol, Contraception 57:281-286 (1998).

Thoenes et al., Cytotoxic Effects of Adriamycin, Bleomycin, Gossupol and Hydroxyanisol to Cultured Human Malignant Melonoma Cells, Journal of Cancer Research and Clinical Onocology, 113:D-THER:12, S46 (1987).

Thomas et al., Effects of Gossylpol on the Cell Cycle Phases in T-47D Human Breat Cancer Cells, Anticancer Research 11:1469-1476 (1991).

D.K. Trask et al., Laryngoscope, 112:638-644 (2002).

Troll et al., Free Oxygen Radicals: Necessary Contributors to Tumor Promotion and Cocarcinogenesis, Proceedings of the 14th International Symposium of the Princess Takamatsu Cancer Research Fund, 207-218 (1984).

Tso, Gossypol Inhibits Ehrlich Ascites Tumor Cell Proliferation, Cancer Letters 24:257-261 (1984).

Tuszynski et al., Differential Cytotoxic Effect of Gossypol on Human Melanoma, Colon Carcinoma, and Other Tissue Culture Cell Lines, Cancer Research 44:768-771 (1984).

Vander Jagt et al., Gossypol: Prototype of Inhibitors Targeted to Dinucleotide Folds, Current Medicinal Chemistry 7:479-498 (2000).

Van Poznak et al., Oral Gossypol in the treatment of patients with refractory metastatic breast cancer: A phase I/II clinical trial, Breat Cancer Research and Treatment 66:239-248 (2001).

Vlietinck et al., Plant-Derived Leading Compounds for Chemotherapy of Human Immunodeficiency Virus (HIV) Injection, PlantaMedica 64:97-109 (1998).

Wang et al., Effect of Gossypol on DNA Synthesis and Cell Cycle Progression of Mammalian Cells in Vitro, Cancer Research 44:35-38 (1984).

Wang et al., Cytotoxic effect of gossypol on olonn carcinoma cells, Life Sciences 67:2663-2671 (2000).

P. Watkins, Pharmacogenetics, 4:171-184 (1994).

Wichmann et al., Inhibiting herpes simplex virus tyupe 2 infection in human epithelial cells by gossypol, a potent spermicidal and contraceptive agent, Am. J. Obstet. Gynecol. 142:593-594 (1982).

Wu ei al., Pharmacokinetics of ($\pi$)-, and (−)-gossypol in humans and dogs, Clinical Pharmacology & Therapeutics 39:613-618 (1996).

Wu et al., An in Vitro and in Vivo Study of Antitumor Effects of Gossypol on Human SW-13 Andrenocortical Carcinoma, Cancer Research 49:3743-3758 (1989).

Wu et al., In vitro antitumor activity of gossypol alone or in combination with amsacrine, European Journal of Pharmacology 183:230 (1990).

Xueqing et al., Clinical Observation and Experimental Study of Gossypol in Treatment of Dysfunctional Menorrhagia, Endometriosis and Fibromyoma of Uterus, Chinese Journal of Integrated Traditional and Western Medicine8:197 (1988).

Ye et al., The Modulation of Gap Junctional Communication by Gossypol in Various Mammalian Cell Lines in Vitro, Fundamental and Applied Toxicology 14:817-832 (1990).

Ye et al., Toxicity of a Male Contraceptive, Gossypol, in Mammalian Cell Cultures, in Vitro 19:53-57 (1983).

Yikang et al., Studies on Resolution of Racemic Gossypol, Scientia Sinica 30:297-303 (1987).

Ying et al., Studies on Frequencies of Sister Chromatid Exchange in Peripheral Blood Lymphocytes Before and After Gossypol Treatment, Proc. DAMS and PUMC 1:34-36 (1986).

Youfang et al., Ultrastructural Changes of Smooth Muscle Cells in Leiomyoma and Myometrium of Human Uterus after Gossypol Treatment, ACTA Academiae Medicinae Sinicae, 9:299-301 (1987).

Yu, Probing Into the Mechanism of Action, Metabolism and Toxicity of Gossypol by Studying its (=)- and (−)- Stereoisomers, Journal of Ethnopharmacology 20:65-78 (1987).

Zhang et al., The (−)-enantiomer of gossypol inhibits proliferation of stromal cells derived from human breast adipose tissues by enhancing transforming growth factor $\beta_1$ production, International Journal of Oncology 13:1291-1297 (1998).

\* cited by examiner

Figure 1

| | | |
|---|---|---|
| Bcl-2 | 5 | NREIVMKYIHYKLSQRGYEWDAGDVGAAPPGAAPAPGIFSSQP |
| Bcl-X$_L$ | 5 | NRELVVDFLSYKLSQKGYSWSQFSDVEENRTEAPEG---TESE |

| | | | |
|---|---|---|---|
| Bcl-2 | 88 | VVHLTLRQAGDDFSRRYRRDFAEMSRQLHLTPFTARGRFATVV | 130 |
| Bcl-X$_L$ | 85 | AVKQALREAGDEFELRYRRAFSDLTSQLHITPGTAYQSFEQVV | 127 |

| | | | |
|---|---|---|---|
| Bcl-2 | 131 | EELFRDGVNWGRIVAFFEFGGVMCVESVNREMSPLVDNIALWM | 173 |
| Bcl-X$_L$ | 128 | NELFRDGVNWGRIVAFFSFGGALCVESVDKEMQVLVSRIAAWM | 170 |

| | | | |
|---|---|---|---|
| Bcl-2 | 174 | TEYLNRHLHTWIQDNGGWDAFVELYG | 199 |
| Bcl-X$_L$ | 171 | ATYLNDHLEPWIQENGGWDTFVELYG | 196 |

Binding of gossypolone to Bcl-$X_L$

Binding of Ethyl Schiff's base of (-)-Gossypol $IC_{50}$ (after 18h30min)   7.346 uM
Ki   2.561 uM

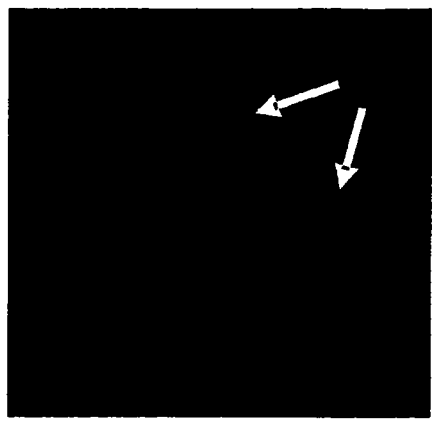 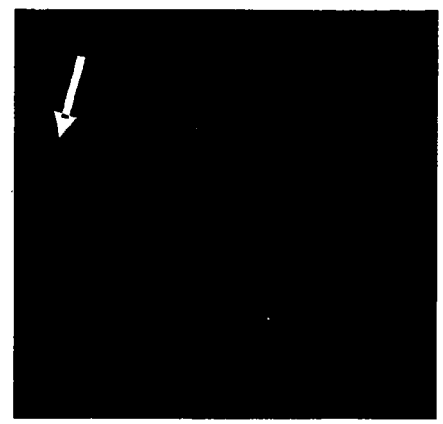
MDA-MB-231  WI-38
Figure 8A  Figure 8B

T-47D

This experiment used 100:1 ratio between (-)-gossypol and Taxol, and between (+)-gossypol and Taxol MDA-MB-231  DOX + G- 1:2.5uM Effect of (-)-gossypol on inhibition of tumor growth of human breast cancer xenograft MDA-231

Effect of (-)-gossypol on inhibition of tumor growth of human breast cancer xenograft MDA-231

Effect of (-)-gossypol on inhibition of tumor growth of human non-samll cell lung carcinoma cell xenograft A-549

Figure 25
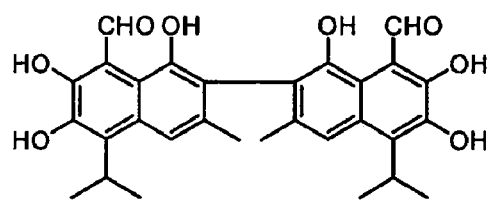
Gossypol
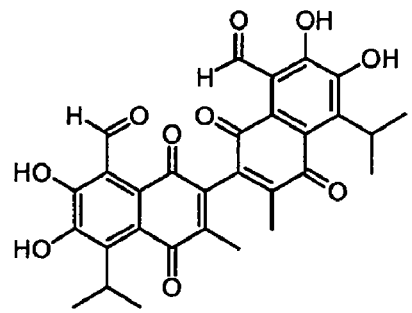
Gossypolone
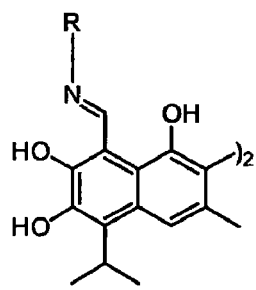
R = aliphatic or aromatic group
Schiff's base of Gossypol
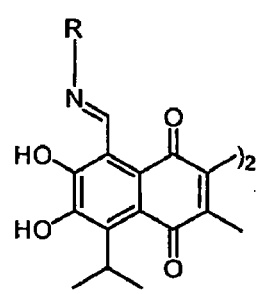
R = aliphatic or aromatic group
Schiff's base of Gossypolone
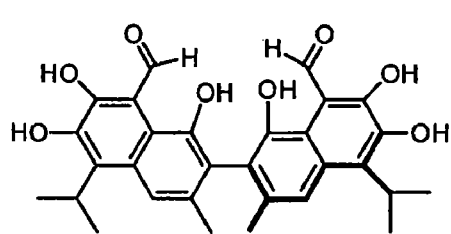
(−)-(R)-Gossypol
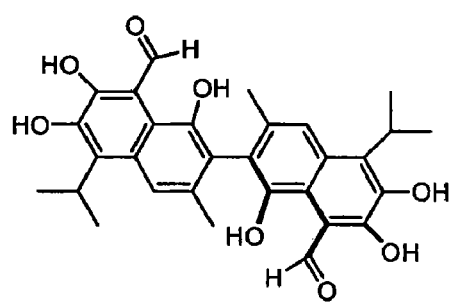
(+)-(S)-Gossypol

*In vitro* effects of gossypol-(-) in combination with various doses of radiation on PC-3 clonogenic assays

Figure 35B

| G- µM | 0 | 1 | 2 | 3 | 4 | 5 |
|---|---|---|---|---|---|---|
| D bar = Mean inactivation dose | 2.22 | 2.06 | 1.95 | 1.63 | 1.26 | 1.05 |
| Gy(1%)= Dose required for 1% cell survival | 7.84 | 7.11 | 7.03 | 6.25 | 5.59 | 4.84 |
| SF(2Gy)= Survival fraction at 2Gy | 0.45 | 0.43 | 0.4 | 0.31 | 0.21 | 0.15 |

(-)-gossypol in combination with radiation in an androgen-independent prostate PC-3 xenograft model (−)-gossypol in combination with radiation in an androgen-independent prostate PC-3 xenograft model (-)-gossypol in combination with radiation in an androgen-independent prostate PC-3 xenograft model Basal levels of Bcl-2 family proteins expression in three prostate cancer cell lines. HSP70: heat shock protein 70kDa for gel loading control.

Figure 43A
Figure 43B
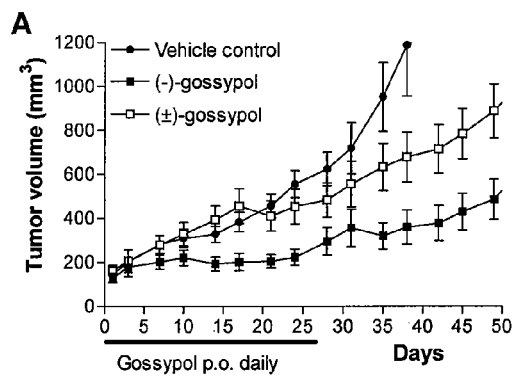
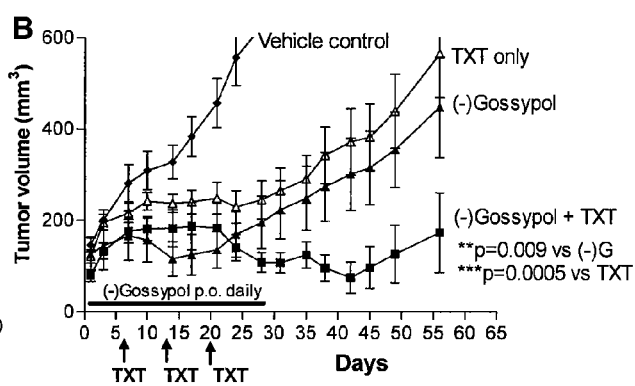

Competitive binding curve of apogossypol against Bcl-2

Competitive binding curve of apogossypol against Bcl-X$_L$.

SMALL MOLECULE ANTAGONISTS OF BCL-2 FAMILY PROTEINS

CROSS REFERENCE TO RELATED APPLICATIONS

This application is a continuation of allowed U.S. patent application Ser. No. 10/729,156 filed Dec. 5, 2003, which will issue on Oct. 7, 2008 as U.S. Pat. No. 7,432,304, which is a continuation in part of abandoned U.S. patent application Ser. No. 10/158,769 filed May 30, 2002, and is a continuation in part of converted International Patent Application No. PCT/US02/17206 filed May 30, 2002, both of which claim priority to expired U.S. Provisional Patent Application Ser. No. 60/293,983, filed May 30, 2001, the contents of each are fully incorporated herein by reference.

STATEMENT REGARDING FEDERALLY SPONSORED RESEARCH OR DEVELOPMENT

None.
Applicants attached hereto a Sequence Listing text file entitled "8477-US-4-CON _ST25.txt".
This application is a continuation in part of U.S. patent application Ser. No. 10/158,769 filed May 30, 2002, and PCT/US02/17206 filed May 30, 2002, both of which claim priority to U.S. Provisional Patent Application Ser. No. 60/293,983, filed May 30, 2001, the contents of each of which are fully incorporated herein by reference.

FIELD OF THE INVENTION

The present invention relates to naturally occurring and chemically synthesized small molecule antagonists of Bcl-2 family proteins. In particular, the present invention provides gossypol compounds (e.g., isomers, enantiomers, racemic compounds, metabolites, derivatives, pharmaceutically acceptable salts, in combination with acids or bases, and the like) and methods of using these compounds as antagonists of the anti-apoptotic effects of Bcl-2 family member proteins (e.g., Bcl-2, Bcl-$X_L$, and the like). The present invention also provides compositions comprising gossypol compounds and optionally one or more additional therapeutic agents (e.g., anticancer/chemotherapeutic agents). The present invention also provides methods for treating diseases and pathologies (e.g. neoplastic diseases) comprising administering a composition comprising gossypol compounds and optionally one or more additional therapeutic agents (e.g., anticancer/chemotherapeutic agents) and/or techniques (e.g., radiation therapies, surgical interventions, and the like) to a subject or in vitro cells, tissues, and organs.

BACKGROUND OF THE INVENTION

Multicellular organisms use a process called apoptosis to instruct damaged or unnecessary cells to destroy themselves for the good of the organism. Control of the apoptotic process is very important for the normal development of the organism. For example, fetal development of fingers and toes requires the controlled removal, by apoptosis, of excess interconnecting tissues, as does proper formation of neural synapses within the brain. Careful control of apoptosis is also important to adult organisms, for instance, controlled apoptosis is responsible for the sloughing of the inner lining of the uterus (the endometrium) at the start of menstruation.
Apoptosis not only plays an important role in tissue sculpting during fetal development and normal cellular maintenance, it is also the primary defense against rogue cells that threaten the well being of the entire organism. For instance, in the cell mediated immune response, effector cells (e.g., cytotoxic T lymphocytes "CTLs") destroy virus-infected host cells by inducing the infected host cells to undergo apoptosis. The organism subsequently relies in turn upon the apoptotic process to destroy the effector cells when they are no longer needed. Autoimmunity is prevented by the CTLs inducing apoptosis in each other and even in themselves. Defects in this process are associated with a variety of autoimmune diseases such as lupus erythematosus and rheumatoid arthritis.

Multicellular organisms use the apoptotic process to instruct cells with damaged nucleic acids (e.g., DNA) to destroy themselves prior to becoming cancerous. However, some cancer-causing viruses prevent apoptosis in transformed cells. For example, several human papilloma viruses (HPVs) are implicated in causing cervical cancer by suppressing apoptotic removal of transformed cells through the production of a protein, E6, which inactivates the p53 apoptosis promoter. Epstein-Barr virus (EBV), the causative agent of mononucleosis and Burkitt's lymphoma, a solid tumor of B lymphocytes, produces a first protein similar to Bcl-2, and a second that causes transformed cells to increase production of Bcl-2. The expression of various Bcl-2 family proteins helps virus-transformed cells resist apoptosis. Still other viruses manipulate the cell's apoptotic machinery without directly resulting in the development of a cancer. For example, destruction of the immune system in individuals infected with the human immunodeficiency virus (HIV) is thought to progress through infected CD4+ T cells (about 1 in 100,000) instructing their sister cells to undergo apoptosis. Faulty regulation of the apoptotic machinery has also been implicated in various degenerative conditions and vascular diseases.

Some cancers that arise by non-viral means have also developed mechanisms to escape destruction by apoptosis. Melanoma cells, for instance, avoid apoptosis by inhibiting the expression of the gene encoding the apoptosis effector protein Apaf-1. Other cancers, especially lung and colon, secrete elevated levels of soluble decoy molecules that bind FasL, inhibiting it from binding to Fas. CTLs are thus prohibited from destroying these cancer cells. Other cancer cells express high levels of FasL, again, avoiding destruction by the CTLs.

It is apparent that the controlled regulation of the apoptotic process and the apoptotic machinery is vital to the survival of multicellular organisms. Typically, the biochemical changes that occur in a cell instructed to undergo apoptosis occur in an orderly procession. However, as shown above, flawed regulation of these process can cause serious harm.

There have been various attempts to use small molecules to control and restore regulation of the apoptotic machinery in aberrant cells (e.g., cancer cells). Generally, these attempts have had limited success as treatments for the underlying diseases for a number of reasons, including high toxicity, low bioavailability, high costs, and the like. What is needed are improved methods and compositions for regulating apoptosis in subjects afflicted with diseases and conditions that are characterized by faulty regulation of the apoptotic process.

SUMMARY OF THE INVENTION

It is generally accepted in the field of molecular oncology that most, if not all, malignant cancer cells harbor (at a minimum) two derangements that lead to the malignant phenotype: a proliferative lesion, causing cells to multiply inappropriately, and an apoptotic lesion, that prevents the cell(s) from executing the apoptosis program in response to either the detection, within the cell, of these genetic abnormalities (e.g., up-regulation of a growth or mitosis oncogene like Ras or Myc), or the pharmacological effects of cell death-inducing cancer therapeutic drugs or radiation therapy. The apoptotic lesion confers on the cells a survival advantage in the face of either further accumulated oncogenic lesions, or exposure to pharmacologically effective levels of cancer therapeutic drugs or radiation therapy.

A number of apoptotic lesions have been described in tumor cells (e.g. loss of p53, decreased Apaf-1, increased IAPs, decreased caspases), both in vitro and in vivo, most notably enhanced expression and accumulation of proteins of the anti-apoptotic Bcl-2 gene family. Bcl-2 is the prototypical member of this family, which includes Bcl-$X_L$, Mcl-1, A1, and Boo/Diva proteins. Bcl-2 is a human oncogene that prevents the activation of the apoptosis program in many cells, and when expressed at inappropriately high levels in cancerous or pre-cancerous cells, confers on them a selective advantage. Bcl-2 and Bcl-$X_L$ are overexpressed in many types of human cancer (e.g., breast, prostate, colorectal, lung, etc.), including Non-Hodgkin's lymphoma, which is caused by a chromosomal translocation (t14, 18) that leads to overexpression of Bcl-2, suggesting that many cancer cell types depend on the elevated levels of Bcl-2 and/or Bcl-$X_L$ to survive the other cellular derangements that simultaneously both define them as cancerous or pre-cancerous cells and cause them to attempt to execute the apoptosis pathway. Also, increased expression of Bcl-2 family proteins has been recognized as a basis for the development of resistance to cancer therapeutic drugs and radiation that act in various ways to induce cell death in tumor cells.

The induction of apoptosis in cancer cells or their supporting cells (e.g., neovascular cells in the tumor vasculature) is thought to be a universal mechanism of action for virtually all of the effective cancer therapeutic drugs or radiation therapies on the market or in practice today. The present invention contemplates that exposure of humans suffering from cancer to therapeutically effective amounts of drug(s) (e.g., small molecules) that inhibit the function(s) of Bcl-2 and Bcl-$X_L$ kills cancer cells or supporting cells outright (those cells whose continued survival is dependent on the overactivity of Bcl-2 or Bcl-$X_L$) or to render such cells as a population more susceptible to the cell death-inducing activity of cancer therapeutic drugs or radiation therapies. The present invention contemplates that inhibitors of Bcl-2/Bcl-$X_L$ satisfy an unmet need for the treatment of multiple cancer types, either when administered as monotherapy to induce apoptosis in cancer cells dependent on Bcl-2/Bcl-$X_L$ function, or when administered in a temporal relationship with other cell death-inducing cancer therapeutic drugs or radiation therapies so as to render a greater proportion of the cancer or supportive cells vulnerable to executing the apoptosis program compared to the corresponding proportion of cells in a subject treated only with the cancer therapeutic drug or radiation therapy alone.

During the course of the development of the present invention, gossypol was found to bind to a key binding site (the BH3-binding site) in both Bcl-2 and Bcl-$X_L$, to which the natural protein antagonists of Bcl-2/Bcl-$X_L$, including Bax, Bak, Bad, Bim, NOXA, and PUMA bind. Thus, particularly preferred embodiments provide compositions and methods comprising gossypol compounds (e.g., (−)-gossypol, (−)-gossypol acetic acid, and the like) having Bcl-2/B Bcl-$X_L$ inhibitory activity, and that cause cells that depend for their survival, at least in part, on Bcl-2 and/or Bcl-$X_L$ to execute the apoptosis program and die. The present invention is not limited to a particular mechanism. Indeed, an understanding of the mechanism is not necessary to practice (make and use) the present invention. Nonetheless, it is contemplated that two classes of such Bcl-2/Bcl-X-dependent cells are 1) a first class of cells that are internally deranged to such an extent that the "flux" through the apoptosis pathway would be sufficient, were it not for the elevated levels of Bcl-2 and/or Bcl-$X_L$, to trigger execution of the apoptosis program; and 2) a second class of cells whose apoptosis program has been stimulated in response to a cancer therapeutic drug or radiation but below a threshold that has been set in that cell by the elevated levels of Bcl-2/Bcl-$X_L$. Either class of cells, by virtue of being dependent on Bcl-2, Bcl-X or both for their survival, can be killed by an effective amount of a Bcl-2/Bcl-$X_L$ inhibiting compound (e.g., (−)-gossypol, (−)-gossypol acetic acid, and the like).

Indeed, gossypol compounds (e.g., (−)-gossypol) can induce the death of tumor cells in vitro and can reduce tumor burden in mice bearing human tumor xenografts (See, Examples). In addition, gossypol compounds (e.g., (−)-gossypol), by virtue of reducing the activity of Bcl-2 and/or Bcl-$X_L$ in cancer cells or supporting cells, increases the proportion of cells in a subject that will respond to the cell-damaging effects of cancer therapeutic drugs or radiation therapy by executing the apoptosis program, leading to a greater tumor response in subjects treated in combination with gossypol and the cancer therapeutic drug or radiation therapy compared to those treated with chemo/radiation alone. This enhanced tumor response will be reflected in any of a number of clinically desirable endpoints, including tumor shrinkage and/or loss, time to tumor progression (TTP), or survival. In additional preferred embodiments, gossypol compounds (e.g., (−)-gossypol), in combination with any of a number of cancer therapeutic drugs or radiation, produces added tumor reductions over chemo/radiation alone (See, Examples). In some examples, gossypol compounds (e.g., (−)-gossypol) produce "synergistic" apoptosis (in vitro isobologram Examples) or tumor responses (in vivo Examples). The in vivo synergism even leads, in some cases, to regression of tumors that would not regress with either agent alone.

From these observations, combination treatment of human subjects with a therapeutically effective amount of a gossypol compound (e.g., (−)-gossypol) and an approved course of cancer therapeutic drugs or radiation, produces a greater tumor response and clinical benefit in such subjects compared to those treated with gossypol compound or cancer drugs/radiation alone. It is contemplated that gossypol (e.g., (−)-gossypol) acts either to kill cells outright or to increase the proportion of cancer or supporting cells that respond to the apoptosis-inducing effects of drugs/radiation by executing the apoptosis program. Put another way, because gossypol compounds lower the apoptotic threshold of all cells that express Bcl-2 and/or Bcl-$X_L$, the proportion of cells that successfully execute the apoptosis program in response to the apoptosis-inducing activity of cancer drugs/radiation is increased. Alternatively, gossypol compounds can be used to allow administration of a lower, and therefore less toxic and more tolerable, dose of a cancer therapeutic drug or radiation to produce the same tumor response/clinical benefit as the conventional dose of the drug/radiation alone. Since the doses for all approved cancer drugs and radiation treatments are known, the present invention contemplates the various combinations of them with gossypol compounds. Also, since gossypol compounds act at least in part by inhibiting Bcl-2 and/or Bcl-$X_L$, the exposure of cancer and supporting cells to a therapeutically effective amount of gossypol can be temporally linked to coincide with the attempts of cells to execute the apoptosis program in response to the cancer drug or radiation therapy. Thus, in some embodiments, administering the compositions and methods of the present invention in view of certain temporal relationships, which can be tested in clinical trials, provides especially efficacious therapeutic practices.

The present invention relates to naturally occurring and chemically synthesized small molecule antagonists of Bcl-2 family proteins. In particular, the present invention provides gossypol compounds (e.g., isomers, enantiomers, racemic compounds, metabolites, derivatives, pharmaceutically acceptable salts, in combination with acids or bases, and the like) and methods of using these compounds as antagonists of the anti-apoptotic effects of Bcl-2 family member proteins (e.g., Bcl-2, Bcl-$X_L$, and the like). The present invention also provides compositions comprising gossypol compounds and optionally one or more additional therapeutic agents (e.g., anticancer/chemotherapeutic agents). The present invention also provides methods for treating diseases and pathologies (e.g., neoplastic diseases) comprising administering a composition comprising gossypol compounds and optionally one or more additional therapeutic agents (e.g., anticancer/chemotherapeutic agents) and/or techniques (e.g., radiation therapies, surgical interventions, and the like) to a subject or in vitro cells, tissues, and organs.

The term cancer is generally used to described hundreds of neoplastic diseases and neoplasias. The neoplastic growths can be benign or malignant. There are three broad types of cancer: carcinomas, sarcomas, and hematologic malignancies (more commonly known as lymphomas and leukemias). Each type of cancer can affect almost any organ or part of the body. Carcinomas originate in the outer layer of cells of the skin and internal membranes (e.g., breasts, lungs, intestines, skin, prostate, etc.). Sarcomas arise from connective tissue such as bone, muscle, cartilage and blood vessels. Lymphomas and leukemias, hematologic cancers, arise in the blood or blood-forming organs such as the spleen, lymph nodes and bone marrow.

Cancer cells include tumor cells, neoplastic cells, malignant cells, metastatic cells, and hyperplastic cells. Neoplastic cells can be benign or malignant. Neoplastic cells are benign if they do not invade or metastasize. A malignant cell is one that is able to invade and/or metastasize. Hyperplasia is a pathologic accumulation of cells in a tissue or organ, without significant alteration in structure or function.

Malignant tumors are generally referred to as being either primary or secondary. Primary tumors arise directly in the tissue in which they are found. Secondary tumors, or metastases, are tumors that originated elsewhere in the body, but have now spread, to a distant tissues and organs. There are some malignancies that are predisposed to spreading to the skeleton. Prostrate cancer and breast carcinoma typically metastasize to bone. Another frequent site of tumor metastasis is the brain.

The common routes for tumor metastasis are direct growth into adjacent structures, spread through the vascular or lymphatic systems, and tracking along tissue planes and body spaces (e.g., peritoneal fluid, cerebrospinal fluid, etc.). Clinically, most patients die from metastatic disease.

The present invention is not limited to any particular mechanism. Indeed, an understanding of any particular mechanism is unnecessary to practice (make and use) the compositions and methods of the present invention. Nonetheless, it is believed that the molecular mechanisms involved in metastatic tumor maintenance are different from those involved in primary tumor maintenance. The present invention contemplates that elucidation of the cellular mechanisms associated with metastatic cancer maintenance and metastasis provides insight into the development of new effective anticancer treatments.

Malignant tumor progression, in many cases, is correlated with increased migratory capacity involving, at least in part, altered metalloproteolytic activity. Tumor invasion is thought to rely on the modification of cell adhesion and the proteolysis of extracellular matrix components. Bcl-2 is though to have specific effects on the molecules involved in cancer cell migration and invasion (See, V. Amberger, et al., Cancer Res., 58:149-158 (1998)). Cancer cells that express Bcl-2 proteins may be more invasive than other cancer cells. Bcl-2 proteins are also thought to enhance cancer cell migration and invasion by altering the expression of metalloproteinases and their inhibitors. Wick et al. (W. Wick, et al., FEBS Lett., 440:419-424 (1998)) reported that ectopic expression of Bcl-2 in two glioma cell lines significantly enhanced migration and invasion in a Matrigel-coated membrane invasion assay (See, S. Mohanam, et al., Cancer Res. 53:4143-4147 (1993)) and a fetal rat brain confrontation assay (See, P. Pedersen, et al., Cancer Res., 53:5158-5165 (1993)). Bcl-2 expression is also thought to lead to activation and/or increase of matrix metalloproteinases (e.g., MMP-2, MMP-9) or the cell surface urokinase-type plasminogen activator (u-PA), and reductions of metalloproteinases tissue inhibitors (TIMPs).

Successful migration and invasion of cancer cells requires the ability to survive, or to become resistant to, the endogenous apoptotic death program signals once the cancer cell has detached from the primary tumor tissue. The present invention is not limited to any particular mechanism. Indeed, an understanding of any particular mechanism is unnecessary to practice (make and use) the compositions and methods of the present invention. Nonetheless, the present invention contemplates that overexpression of anti-apoptotic Bcl-2 proteins provides tumor cells with a mechanism for surviving in new and non-permissive environments (e.g., metastatic sites), and contributes to the organospecific pattern of clinical metastatic cancer spread. It is further contemplated that overexpression of Bcl-$X_L$ counteracts the proapoptotic signals in the cancer cells' microenvironment, thus favoring successful development of metastases. The bcl-$X_L$ gene is further thought to play a role in breast cancer dormancy by promoting the survival of cells in metastatic foci in specific organs (See, Nuria Rubio, Lab Invest, 81:725-734 (2001)). For example, in human breast carcinomas, the overexpression of anti-apoptotic Bcl-$X_L$ protein is thought to increase metastatic potential by providing, at least in part, increased resistance to cytokines, overriding apoptotic signals, enhancing anchorage-independent growth (e.g., caused by a modified interaction with the extracellular matrix), and increasing cell survival in the circulation (Fernandez et al., Cell Death Differ., 7:350-359 (2000)). It has been shown that a number of cell adhesion molecules play a role in metastasis and that integrins are especially involved in tumorigenic spread. Integrins are implicated in cell-cell and cell-extracellular matrix (ECM) interactions, signaling, sensing cellular microenvironment, and in moderating cellular activities including, but not limited to, migration, differentiation, survival and tissue (re)modeling in both normal and pathological states. The present invention contemplates that anti-apoptotic proteins such as Bcl-2 and/or Bcl-$X_L$ regulate cell-cell interactions (See, J. Reed, Nature, 387:773-776 (1997)). Down-regulation of cell surface integrins by antibodies could lead to induction of apoptosis. For example, Bcl-2 expression is up-regulated by $\alpha_5\beta_1$ integrins preventing apoptosis when cells are detached from the matrix (See, S. Frisch and E. Ruoslahti, Curr. Opin. Cell Biol., 9:701-706 ((1997)). Expression of Bcl-2 is contemplated to promote the metastatic potential of the human breast cancer cell line MCF7 in vivo and migratory and invasive properties in vitro (See, D. Del Bufalo, et al., FASEB J., 11:947-953 (1997)).

In some embodiments, the present invention provides methods of inhibiting tumor metastasis in a subject, comprising administering to the subject a gossypol compound (e.g., (−)-gossypol) that decreases the survival of metastatic cells by inhibiting cellular activity of Bcl-2/Bcl-$X_L$ proteins. In certain other embodiments, the present invention provides methods of treating (e.g., ameliorating and/or preventing) cancer metastasis comprising administering to a subject having a cancer metastasis a therapeutically effective amount of a gossypol compound (e.g., (−)-gossypol), and optionally one or more anticancer and/or anti-neoplastic agents. The present invention is not intended to be limited to administering any particular gossypol compound, or compounds for the prevention (or retarding) of tumor metastasis. Indeed, a number of gossypol compounds are contemplated as being useful in the preventing, attenuating, or retarding of tumor metastasis including, but not limited to, (±)-gossypol; (−)-gossypol; (+)-gossypol; (±)-gossypolone; (−)-gossypolone; (+)-gossypolone; (±)-gossypol acetic acid; (−)-gossypol acetic acid; (+)-gossypol acetic acid; (±)-ethyl gossypol; (−)-ethyl gossypol; (+)-ethyl gossypol; (±)-hemigossypolone; (−)-hemigossypolone; (+)-hemigossypolone; Schiff's base of (±)-gossypol; Schiff's base of (−)-gossypol; Schiff's base of (+)-gossypol; Schiff's base of (±)-gossypolone; Schiff's base of (−)-gossypolone; Schiff's base of (+)-gossypolone; Schiff's base of (±)-gossypol acetic acid; Schiff's base of (−)-gossypol acetic acid; Schiff's base of (+)-gossypol acetic acid; Schiff's base of (±)-ethyl gossypol; Schiff's base of (−)-ethyl gossypol; Schiff's base of (+)-ethyl gossypol; Schiff's base of (±)-hemigossypolone; Schiff's base of (−)-hemigossypolone; Schiff's base of (+)-hemigossypolone, (±)-apogossypol, (−)-apogossypol, (+)-apogossypol, (t)-apogossypol acetic acid, (−)-apogossypol acetic acid, (+)-apogossypol acetic acid, (±)-ethyl apogossypol, (−)-ethyl apogossypol, (+)-ethyl apogossypol, and the like. The present invention further contemplates that a range of additional (second) chemotherapeutic, anticancer, or anti-neoplastic agents, radiation therapies, and/or surgical interventions can optionally be combined (in any temporal order) with gossypol compounds to prevent or retard tumor metastasis in a subject. In this regard, the present invention describes various exemplary additional (second) agents and therapies that are useful in certain embodiments of the present invention directed to tumor metastasis.

An important goal in oncology is to optimize the use of available treatment options (e.g., chemotherapy, radiation therapy, surgery, and the like) to achieve maximum obtainable therapeutic effect while preserving organs and the subject's general quality of life.

Bcl-2 is the founding member of a family of proteins and was first isolated as the product of an oncogene. The Bcl-2 family of proteins now includes both anti-apoptotic molecules such as Bcl-2 and Bcl-$X_L$ and pro-apoptotic molecules such as Bax, Bak, Bid, and Bad. Bcl-2 and Bcl-$X_L$ are thought to be important regulators of Bcl-2 family mediated apoptosis.

In preferred embodiments, the administration of gossypol compounds is contemplated to provide an effective treatment of neoplastic conditions and other disorders that involve either the aberrant hyperproliferation or defective apoptosis of cells (e.g., tumor cells).

In other preferred embodiments, the present invention provides methods of treatment or prophylaxis of cancers in a subject comprising administering to the subject a gossypol compound in an amount effective to inhibit Bcl-2 and/or Bcl-$X_L$, thus inducing apoptosis and suppressing tumor growth and/or proliferation. Preferably, a gossypol compound is administered in conjunction with another agent or treatment, such as a chemotherapeutic agent (e.g., a tumor cell apoptosis promoting agent) or radiation. The present invention is not limited to any particular mechanism. Indeed, an understanding of any particular mechanism is unnecessary to practice (make and use) the methods and compositions of the present invention. Nonetheless, it is contemplated that increasing apoptosis in target cells (e.g., pathogenic cells including, but not limited to, cancer cells) reestablishes normal apoptotic control associated with basal expression of Bcl-2 and/or Bcl-$X_L$ and/or another anti-apoptotic Bcl-2 family protein (e.g. Bcl-w).

The methods of the present invention are particularly well suited for the treatment of cancers characterized by overexpression of Bcl-2 family proteins including, but not limited to, Bcl-2 and/or Bcl-$X_L$.

In some preferred embodiments, the methods of the present invention provide effective amounts of gossypolone to a patient having a condition characterized by the overexpression of Bcl-2 family proteins, and optionally one or more anticancer or anti-neoplastic agent including, but not limited to radiation therapy.

In one preferred embodiment, the present invention provides a method of modulating apoptosis in a cell comprising: providing a cell, wherein the cell overexpresses a Bcl-2 family protein; a gossypol compound; and treating the cell with an effective amount of the gossypol compound under conditions such that apoptosis in the cell is modulated.

The methods of the present invention are not intended to be limited to administration of any particular gossypol compounds. Indeed, the present invention contemplates the administration of a number of gossypol enantiomers, metabolites, derivatives, and pharmaceutically acceptable salts, as well as Schiff's bases of these compounds. For example, gossypol compounds suitable for use in the present invention include, but are not limited to, (±)-gossypol; (−)-gossypol; (+)-gossypol; (±)-gossypolone; (−)-gossypolone; (+)-gossypolone; (±)-gossypol acetic acid; (−)-gossypol acetic acid; (+)-gossypol acetic acid; (±)-ethyl gossypol; (−)-ethyl gossypol; (+)-ethyl gossypol; (±)-hemigossypolone; (−)-hemigossypolone; (+)-hemigossypolone; Schiff's base of (±)-gossypol; Schiff's base of (−)-gossypol; Schiff's base of (+)-gossypol; Schiff's base of (±)-gossypolone; Schiff's base of (−)-gossypolone; Schiff's base of (+)-gossypolone; Schiff's base of (±)-gossypol acetic acid; Schiff's base of (−)-gossypol acetic acid; Schiff's base of (+)-gossypol acetic acid; Schiff's base of (±)-ethyl gossypol; Schiff's base of (−)-ethyl gossypol; Schiff's base of (+)-ethyl gossypol; Schiff's base of (±)-hemigossypolone; Schiff's base of (−)-hemigossypolone; Schiff's base of (+)-hemigossypolone, (±)-apogossypol, (−)-apogossypol, (+)-apogossypol, (±)-apogossypol acetic acid, (−)-apogossypol acetic acid, (+)-apogossypol acetic acid, (±)-ethyl apogossypol, (−)-ethyl apogossypol, (+)-ethyl apogossypol, and the like.

In preferred embodiments, the present invention provides administering the (−)-gossypol enantiomer to a patient having a condition characterized by overexpression of a Bcl-2 family protein. In some embodiments, the overexpressed Bcl-2 family proteins contemplated include, but are not limited to, Bcl-2, Bcl-$X_L$, Mcl-1, Bcl-w, A1/BFL-1, BOO-DIVA, Bcl-6, Bcl-8, and Bcl-y. In still some other embodiments, the overexpressed Bcl-2 family proteins have pro-apoptotic activity. In yet other embodiments, the overexpressed Bcl-2 family proteins have anti-apoptotic activity.

In some embodiments, the compositions and methods of the present invention are used to treat diseased cells, tissues, organs, or pathological conditions and/or disease states in a subject organism (e.g., a mammalian subject including, but not limited to, humans and veterinary animals), or in in vitro and/or ex vivo cells, tissues, and organs. In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic.

In some embodiments, infections suitable for treatment with the compositions and methods of the present invention include, but are not limited to, infections caused by viruses, bacteria, fungi, mycoplasma, prions, and the like. The present invention is not intended to be limited, however, to treating of any particular infections or infectious agents.

In one preferred embodiment, the present invention provides methods of modulating cell division in a tissue comprising: providing a tissue, wherein the tissue overexpresses a Bcl-2 protein; a gossypol compound; an anticancer agent; and treating the tissue with effective amounts of the gossypol compound and the anticancer agent under conditions such that cell division is modulated. In some of these embodiments, the present invention contemplates gossypol compounds bind to Bcl-2 family proteins thus modulating cell division. In still further embodiments, the methods optionally comprise one or more antineoplastic and/or anti-hyperproliferative chemotherapeutic agents (e.g., small or large molecule drugs, polypeptides, polynucleotides, synthetic or naturally occurring chemical compounds, and the like), or therapies (e.g., radiation therapy, surgical interventions, etc.).

In yet another embodiment, the present invention provides methods of treating a subject (e.g., a patient) comprising administering a gossypol compound to a subject overexpressing a Bcl-2 family protein. In a preferred example of these embodiments, the gossypol compound binds to a Bcl-2 family protein.

Some embodiments of the present invention are directed to providing methods of treating a subject comprising administering a gossypol compound and one or more anticancer agents to a subject overexpressing a Bcl-2 family protein.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins, etc.), toxins, radionuclides; biological response modifiers (e.g., interferons (e.g., IFN-α, etc.) and interleukins (e.g., IL-2, etc.), etc.); adoptive immunotherapy agents; hematopoietic growth factors; agents that induce tumor cell differentiation (e.g., all-trans-retinoic acid, etc.); gene therapy reagents (e.g., antisense therapy reagents and nucleotides); tumor vaccines; angiogenesis inhibitors; proteosome inhibitors: NF kappa β modulators; anti-CDK compounds; HDAC inhibitors; and the like. Numerous other examples of chemotherapeutic compounds and anticancer therapies suitable for co-administration with the disclosed gossypol compounds are known to those skilled in the art.

In preferred embodiments, anticancer agents comprise agents that induce or stimulate apoptosis. Agents that induce apoptosis include, but are not limited to, radiation (e.g. X-rays, gamma rays, UV); kinase inhibitors (e.g., Epidermal Growth Factor Receptor (EGFR) kinase inhibitor, Vascular Growth Factor Receptor (VGFR) kinase inhibitor, Fibroblast Growth Factor Receptor (FGFR) kinase inhibitor, Platelet-derived Growth Factor Receptor (PDGFR) kinase inhibitor, and Bcr-Abl kinase inhibitors such as GLEEVEC); antisense molecules; antibodies (e.g., HERCEPTIN, RITUXAN, ZEVALIN, and AVASTIN); anti-estrogens (e.g. raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSA/Ds)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; and staurosporine, and the like.

In still other embodiments, the compositions and methods of the present invention provide gossypol compounds and at least one anti-hyperproliferative or antineoplastic agent(s) selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4)

nitrosoureas (e.g., carmustine (BCNU); lomustine (CCNU); semustine (methyl-CCNU); and streptozocin (streptozotocin)); and 5) triazenes (e.g., dacarbazine (DTIC; dimethyl-triazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

In still other embodiments, the present invention provides methods of treating cancer in a subject comprising administering to a patient having a condition characterized by overexpression of a Bcl-2 family protein an effective amount of a gossypol compound.

Additional embodiments are directed to methods of treating cancer in a subject comprising administering to a subject having cancer, wherein the cancer is characterized by overexpression of a Bcl-2 family protein, an effective amount of a gossypol compound and one or more anticancer agents.

Still other methods are directed to treating cancer in a subject comprising administering to a patient having cancer, wherein the cancer is characterized by resistance to cancer therapies (e.g., chemoresistant, radiation resistant, hormone resistant, and the like), an effective amount of a gossypol compound.

In some embodiments, the present invention provides methods of treating cancer in a subject comprising administering to a patient having cancer, wherein the cancer is characterized by overexpression of a Bcl-2 family protein, a dose of a gossypol compound sufficient to reduce the overexpression of the Bcl-2 protein.

In some embodiments of the present invention, methods of treating cancer in a subject comprising administering to a patient having cancer, wherein the cancer is characterized by overexpression of a Bcl-2 family protein, a dose of a gossypol compound and one or more anticancer agents sufficient to reduce the overexpression of the Bcl-2 protein are described.

In still some other embodiments, the present invention provides methods of treating a hyperproliferative disease, wherein the hyperproliferative disease is characterized by the overexpression of an anti-apoptotic Bcl-2 family protein (e.g., Bcl-2 or Bcl-$X_L$), in a subject comprising administering to a subject a dose of a gossypol compound sufficient to inhibit the function of the anti-apoptotic Bcl-2 protein and/or to reduce the overexpression of the protein. In some of these embodiments, the methods further comprise administering one or more hyperproliferative and/or anti-neoplastic therapeutic agents to the subject.

Some other embodiments of the present invention provide pharmaceutical compositions comprising: a gossypol compound; and instructions for administering the gossypol compound to a subject, the subject characterized by overexpression of a Bcl-2 family protein (e.g., an anti-apoptotic Bcl-2 family member protein). Additional embodiments provide pharmaceutical compositions comprising: a gossypol compound; one or more anticancer agents; and instructions for administering the gossypol compound and the one or more anticancer agents to a subject.

Further embodiments of the present invention provide pharmaceutical compositions comprising: a gossypol compound; optionally one or more anticancer agents; and instructions for administering the gossypol compound to a subject, the subject characterized by resistance to a cancer therapy. In preferred embodiments, the instructions included with these kits meet U.S. Food and Drug Administration rules, regulations, and suggestions for the administration, preparation, and distribution of therapeutic kits, compounds, and methods. The instructions optionally also satisfy the domestic regulations placed on therapeutic kits, compounds, and methods, by countries and jurisdictions other than the U.S.

In yet another embodiment, the present invention provides methods of screening a gossypol compound and a test compound comprising: providing: a gossypol compound; a test compound; a first group of cells; and contacting the first group of cells with the gossypol compound and the test compound; and observing the effects of contacting the first group of cells with the gossypol compound and the test compound. In some of these embodiments, the present invention further provides the additional step of comparing the effects observed in the first cells against a second group of the cells contacted with the gossypol compound alone, or with the test compound alone. Effects that may be observed include, but are not limited to, changes in cell proliferation, changes in apoptotic status, and changes in the expression of Bcl-2 family proteins (e.g., Bcl-2 and/or Bcl-$X_L$), and the like. In still other embodiments, the present invention further contemplates additional methods for selling test compounds screened/identified by the above methods. In some of these embodiments, test compounds may be offered for sale by a third party in one or more forms (e.g. a kit, including instructions for administering the test compound to a patient). The present invention further provides kits comprising a gossypol compound, one or more chemotherapeutic agents, and instructions for administering the gossypol compound and the chemotherapeutic agents to a subject. In certain of these embodiments, the gossypol compound is (−)-gossypol and the chemotherapeutic agent is selected from docetaxel, TAXOL, cisplatin, and combinations thereof. The present invention is not limited however to kits comprising (−)-gossypol and docetaxel, TAXOL, cisplatin, and combinations thereof.

The present invention further provides a method of treating or ameliorating a hyperproliferative (or neoplastic) disease in a subject comprising administering to the subject a therapeutically effective dose of a gossypol compound and one or more second agent selected from a chemotherapeutic agent and radiation. In other embodiments, the present invention provides a method of treating or ameliorating a hyperproliferative (or neoplastic) disease in a subject comprising administering to the subject a therapeutically effective dose of a gossypol compound and one or more second agent selected from a chemotherapeutic agent and radiation, with the proviso that a combination of (±)-gossypol, heat, and radiation is not administered. In some embodiments, the one or more second agents comprise anti-neoplastic agents.

In some methods, a gossypol compound and a chemotherapeutic agent and/or radiation are administered simultaneously. In some other embodiments, a gossypol compound and a chemotherapeutic agent and/or radiation are administered sequentially. In still some other embodiments, a gossypol compound is administered prior to chemotherapeutic agent(s) and/or radiation. In yet other embodiments, a gossypol compound is administered after chemotherapeutic agent(s) and/or radiation.

The present invention further provides methods, wherein a gossypol compound and a chemotherapeutic agent or radiation are administered with different periodicities, different durations, different concentrations, and/or different administration routes.

Additional embodiments provide methods wherein a gossypol compound and a chemotherapeutic agent and/or radiation have a synergistic therapeutic effect in a subject or in vitro or ex vivo cells, tissues, or organs.

In some embodiments, the subject being treated is an animal such as a mammal, fish, or bird. In some embodiments, the mammal being treated is a human. In some other embodiments, the mammal being treated is laboratory animal (e.g. rodent (e.g., mouse, rat, gerbil, rabbit), monkey, dog, pig, cat, etc.). In still some other embodiments, the mammal is a veterinary animal (e.g., dog, cat, horse, cow, pig, goat, sheep, etc.).

In certain preferred methods, a gossypol compound is provided to a subject in a dose that sensitizes the subject to treatment by one or more second agents. The present invention provides compositions and methods directed at therapeutic treatment of resistant diseases (e.g., cancer). Diseases that are specifically contemplated by the present invention include, but are not limited to, chemotherapy resistant diseases (e.g., cancers) and radiation therapy resistant diseases (e.g., cancers). In particularly preferred embodiments, the administration of gossypol compound(s), and optionally one or more chemotherapeutic agents (e.g., anticancer drug) or therapeutic methods (e.g., radiation therapy) sensitizes the disease (e.g., disease cells) to treatment.

In some embodiments, the hyperproliferative (or neoplastic) disease is a cancer (e.g., breast cancer, prostate cancer, pancreatic cancer, colon cancer, lung cancer, lymphoma, melanoma, or head-neck cancer). The present invention contemplates treating metastatic cancers.

The present invention further provides compositions (e.g., pharmaceutical formulations) and methods for treating diseases (e.g., cancer) the use of which in a subject results in the regression of the disease. In other embodiments, the use of the compositions and methods of the present invention in a subject having a disease (e.g., cancer) results in the arrest or stasis of a disease.

The present invention further provides a pharmaceutical composition for the treatment of tumors characterized in that it comprises a gossypol compound and an additional therapeutic agent. Similarly, also provided are pharmaceutical compositions comprising a gossypol compound and an additional therapeutic agent, wherein the pharmaceutical composition is useful as an anti-tumor therapy.

In certain pharmaceutical compositions the gossypol compound is selected from the group comprising (−)-gossypol, (+)-gossypol, (−)-gossypolone, (+)-gossypolone, (−)-gossypol acetic acid, (+)-gossypol acetic acid, (−)-ethyl gossypol, (+)-ethyl gossypol, (−)-hemigossypolone, (+)-hemigossypolone, a Schiff's base of (−)-gossypol, a Schiff's base of (+)-gossypol, a Schiff's base of (−)-gossypolone, a Schiff's base of (+)-gossypolone, a Schiff's base of (−)-gossypol acetic acid, a Schiff's base of (+)-gossypol acetic acid, a Schiff's base of (−)-ethyl gossypol, a Schiff's base of (+)-ethyl gossypol, a Schiff's base of (−)-hemigossypolone, and a Schiff's base of (+)-hemigossypolone, (−)-apogossypol, (+)-apogossypol, (−)-apogossypol acetic acid, (+)-apogossypol acetic acid, (−)-ethyl apogossypol, (+)-ethyl apogossypol, or the racemate of any of the above enantiomeric pairs.

In still other pharmaceutical compositions and therapeutic methods the target tumor is selected from the group consisting of breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

The present invention further provides pharmaceutical compositions, wherein an additional therapeutic agent (one or more second agents) is selected from the group consisting of agents that induce apoptosis, pro-apoptotic Bcl-2 proteins, polynucleotides, polypeptides, photodynamic compounds, radiodynamic compounds, radionuclides, radioactive elements, gamma ray emitters, beta particle emitters, drugs, biological mimetics, alkaloids, alkylating agents, antibiotics, antimicrobials, antifungals, antimetabolites, hormones, platinum compounds, monoclonal antibodies, toxins, defensins, interferons, interleukins, adoptive immunotherapy agents, hematopoietic growth factors, agents that induce tumor cell differentiation, gene therapy reagents, antisense molecules, kinase inhibitors, vascular growth factor receptor kinase inhibitor, fibroblast growth factor receptor kinase inhibitor, platelet-derived growth factor receptor kinase inhibitor, GLEEVEC, anti-estrogens, anti-androgens, cyclooxygenase 2 (COX-2) inhibitors, non-steroidal anti-inflammatory drugs (NSAIDs), chemotherapeutic drugs, nucleotide analogue reverse transcriptase inhibitors, nucleoside analogue reverse transcriptase inhibitors, non-nucleoside reverse transcriptase inhibitors, protease inhibitors, and combinations thereof. In certain embodiments, the additional therapeutic agent (or one or more second agent) is selected from the group consisting of 3,7,11,15-tetramethyl-2,6,10,14-hexadecatraen-1-ol, a Bcl-2 family protein (e.g., Bax, Bak, Bid, Bad), DNA, RNA, ribozymes, RNAse, siRNAs, enzymes, $^{111}$In-oxine, $^{59}$Fe, $^{67}$Cu, $^{125}$L $^{99}$Te, $^{51}$Cr, $^{32}$P, $^{3}$H, $^{35}$S, $^{14}$C, IFN-α, IL-2, all-trans-retinoic acid, EGFR, VGFR, FGFR, PDGFR, STI-571, GLEEVEC, HERCEPTIN, RITUXAN, raloxifene, tamoxifen, flutamide, bicalutamide, finasteride, aminoglutethamide, ketoconazole, corticosteroids, celecoxib, meloxicam, NS-398, irinotecan CPT-11, fludarabine, dacarbazine, dexamethasone, mitoxantrone, MYLOTARG, VP-16, 5-FU, cisplatin, carboplatin, gemcitabine, doxorubicin, TAXOTERE, TAXOL, tenofovir disoproxil fumarate, zidovudine, lamivudine, abacavir, zalcitabine, didanosine, stavudine, nevirapine, delavirdine, efavirenz, saquinavir (SQV (HGC)), saquinavir (SQV (SGC)), ritonavir, indinavir, nelfinavir, amprenavir, mechlorethamine, cyclophosphamide, ifosfamide, melphalan, L-sarcolysin, chlorambucil, hexamethylmelamine, thiotepa, busulfan, carmustine, lomustine, semustine, streptozocin, dacarbazine, methotrexate, fluorouracil, floxuridine, cytarabine, mercaptopurine, thioguanine, pentostatin, vinblastine, vincristine, etoposide, teniposide, dactinomycin, daunorubicin, bleomycin, plicamycin, mitomycin, L-asparaginase, hydroxyurea, procarbazine, mitotane, aminoglutethimide, prednisone, hydroxyprogesterone caproate, medroxyprogesterone acetate, megestrol acetate, diethylstilbestrol, ethinyl estradiol, testosterone propionate, fluoxymesterone, flutamide, and leuprolide, and combinations thereof.

In still some other embodiments, the present invention provides compositions and methods for preventing (or attenuating) the onset or spread of a hyperproliferative disease. In some other embodiments, the present invention provides compositions and methods for preventing (or attenuating) the onset or spread of a neoplastic disease. In some preferred embodiments, the present invention provides methods of preventing (or attenuating) cancers in a subject comprising administering to the subject a gossypol compound (e.g., (−)-gossypol, (−)-gossypol acetic acid, etc.) in an amount effective to inhibit Bcl-2 family protein (e.g., Bcl-2 and/or Bcl-$X_L$). In some of these embodiments, the Bcl-2 family proteins contemplated include, but are not limited to, Bcl-2, Bcl-$X_L$, Mcl-1, Bcl-w, A1/BFL-1, BOO-DIVA, Bcl-6, Bcl-8, and Bcl-y.

Preferably, methods of preventing (or attenuating) hyperproliferative and/or neoplastic diseases comprise a gossypol compound administered in conjunction with another agent or treatment, such as an anticancer agent, an anti-neoplastic agent (e.g., a tumor cell apoptosis promoting agent), or radiation therapy. The present methods of preventing hyperproliferative and/or neoplastic diseases are not limited to the administration of any particular gossypol compound. Indeed, the present invention contemplates that a number of gossypol compounds can be administered to a subject to prevent (or attenuate) hyperproliferative and/or neoplastic diseases including, but not limited to, (±)-gossypol; (−)-gossypol; (+)-gossypol; (±)-gossypolone; (−)-gossypolone; (+)-gossypolone; (±)-gossypol acetic acid; (−)-gossypol acetic acid; (+)-gossypol acetic acid; (±)-ethyl gossypol; (−)-ethyl gossypol; (+)-ethyl gossypol; (O)-hemigossypolone; (−)-hemigossypolone; (+)-hemigossypolone; Schiff's base of (+)-gossypol; Schiff's base of (−)-gossypol; Schiff's base of (+)-gossypol; Schiff's base of (±)-gossypolone; Schiff's base of (−)-gossypolone; Schiff's base of (+)-gossypolone; Schiff's base of (O)-gossypol acetic acid; Schiff's base of (−)-gossypol acetic acid; Schiff's base of (+)-gossypol acetic acid; Schiff's base of (±)-ethyl gossypol; Schiff's base of (−)-ethyl gossypol; Schiff's base of (+)-ethyl gossypol; Schiff's base of (±)-hemigossypolone; Schiff's base of (−)-hemigossypolone; Schiff's base of (+)-hemigossypolone, (±)-apogossypol, (−)-apogossypol, (+)-apogossypol, (±)-apogossypol acetic acid, (−)-apogossypol acetic acid, (+)-apogossypol acetic acid, (±)-ethyl apogossypol, (−)-ethyl apogossypol, (+)-ethyl apogossypol, and the like.

Similarly, the present compositions and methods of preventing (or attenuating) a hyperproliferative and/or neoplastic disease are not limited to any particular additional (second) chemotherapeutic, anticancer, or anti-neoplastic agents or therapies. The present invention contemplates that any of the exemplary therapeutics described herein (or referenced herein) may find use in certain embodiments.

Those skilled in the art can determine the amount of attenuation or whether prevention of a hyperproliferative and/or neoplastic disease has occurred upon use of the compositions and methods of the present invention in a subject, or in in vitro or ex vivo cells, tissues, and organs using standard protocols in comparison to nonpathological subjects, cells, tissues, and organs.

Still further embodiments of the present invention provide the use of a gossypol compound and an additional therapeutic agent in the manufacture of a medicament for the treatment of a neoplastic and/or hyperproliferative disease.

Other embodiments of the present invention specifically contemplate chemical intermediates, and formulations of compounds (e.g. gossypol compounds and optionally one or more chemotherapeutic agents) used in medicaments, in the manufacture of medicaments, kits for the administration of medicaments, or diagnostic tests and other applications related thereto, and other beneficial formulations.

Also provided are uses of the compositions and methods of the present invention for the preparation of therapeutics, medicaments, and other therapeutic applications.

In yet other embodiments, the present invention provides methods and compositions according to any of the claims or substantially as described in any of the Examples or various embodiments disclosed herein.

Other advantages, benefits, and preferable embodiments of the present invention will be apparent to those skilled in the art.

DESCRIPTION OF THE FIGURES

The following figures form part of the specification and are included to further demonstrate certain aspects and embodiments of the present invention. The present invention is not intended to be limited however to the embodiments specifically recited in these figures.

The following figures form part of the specification and are included to further demonstrate certain aspects and embodiments of the present invention. The present invention is not intended to be limited however to the embodiments specifically recited in these figures.

FIG. 1 shows a sequence alignment of Bcl-2 (SEQ ID NO:1) and Bcl-$X_L$ (SEQ ID NO:2).

FIGS. 8A and 8B show the results of cell based assays in various embodiments of the present invention.

FIG. 25 shows the chemical structures of gossypol, gossyplone, Schiff's bases of gossypol and Schiff's bases of gossypolone, (−)-gossypol and (+)-gossypol in various embodiments of the present invention.

FIGS. 35A and 35B show the results of cell based assays in one embodiment of the present invention.

FIGS. 43A and 43B show the results of in vivo animal xenograft based assays in various embodiments of the present invention.

DEFINITIONS

Figure 2A:
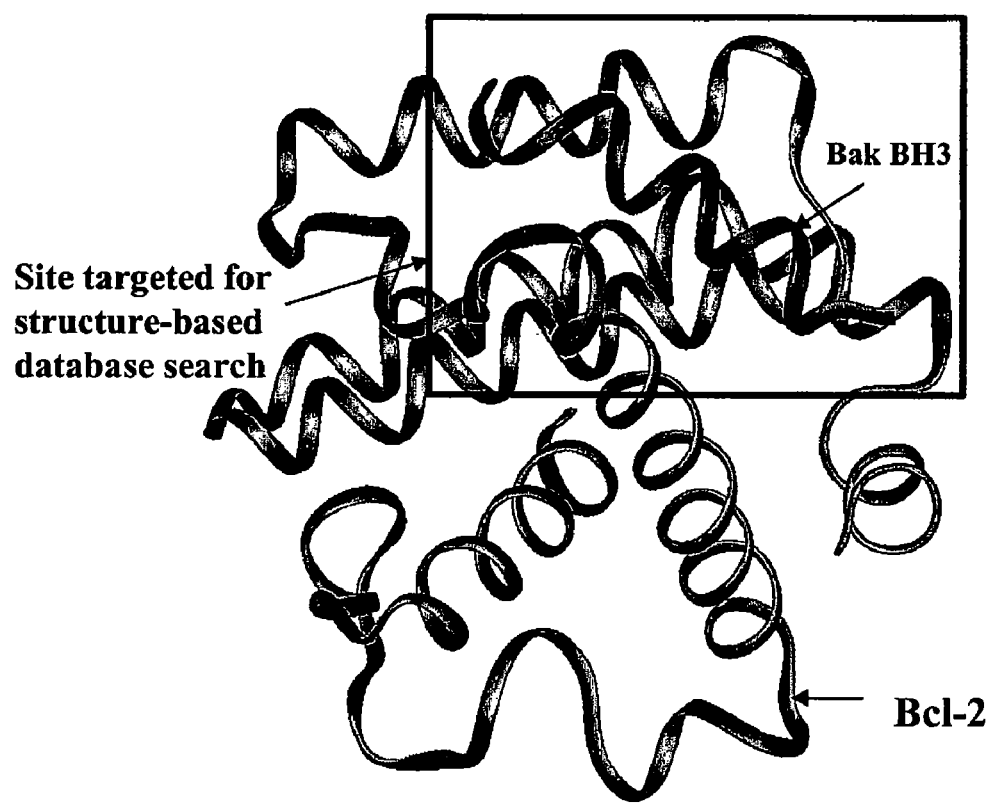
FIG. 2A shows a ribbon representation of the overall Bcl-2 structure in complex with the Bak BH3 peptide modeled from the structure of Bcl-$X_L$ in complex with Bak BH3 peptide.

To facilitate an understanding of the present invention, a number of terms and phrases are defined below.

As used herein, the term "gossypol compound" refers to enantiomers, isomers, derivatives, metabolites, Schiff's bases, combinations with acids or bases, and pharmaceutically acceptable salts of the gossypol molecule. Accordingly, gossypol compounds include, but are not limited to, (±)-gossypol; (−)-gossypol; (+)-gossypol; (±)-gossypolone; (−)-gossypolone; (+)-gossypolone; (±)-gossypol acetic acid; (−)-gossypol acetic acid; (+)-gossypol acetic acid; (±)-ethyl gossypol; (−)-ethyl gossypol; (+)-ethyl gossypol; (±)-hemigossypolone; (−)-hemigossypolone; (+)-hemigossypolone; Schiff's base of (±)-gossypol; Schiff's base of (−)-gossypol; Schiff's base of (+)-gossypol; Schiff's base of (±)-gossypolone; Schiff's base of (−)-gossypolone; Schiff's base of (+)-gossypolone; Schiff's base of (±)-gossypol acetic acid; Schiff's base of (−)-gossypol acetic acid; Schiff's base of (+)-gossypol acetic acid; Schiff's base of (±)-ethyl gossypol; Schiff's base of (−)-ethyl gossypol; Schiff's base of (+)-ethyl gossypol; Schiff's base of (±)-hemigossypolone; Schiff's base of (−)-hemigossypolone; Schiff's base of (+)-hemigossypolone, (t)-apogossypol, (−)-apogossypol, (+)-apogossypol, (±)-apogossypol acetic acid, (−)-apogossypol acetic acid, (+)-apogossypol acetic acid, (±)-ethyl apogossypol, (−)-ethyl apogossypol, (+)-ethyl apogossypol. Acids that may be used in combination with gossypol include, but are not limited to, formic acid, acetic acid, propionic acid, and butyric acid. Physiologically acceptable salts include, but are not limited to, salts comprising sodium hydroxide, potassium hydroxide, lithium hydroxide, barium hydroxide, sodium carbonate, potassium carbonate, sodium acetate, potassium acetate, pyridine, triethylamine, and quinoline.

Gossypol derivatives include any derivatives that are useful in the present invention. One of skill in the art is familiar with derivatization techniques. Many gossypol derivatives are known including, but not limited to, the following compounds:

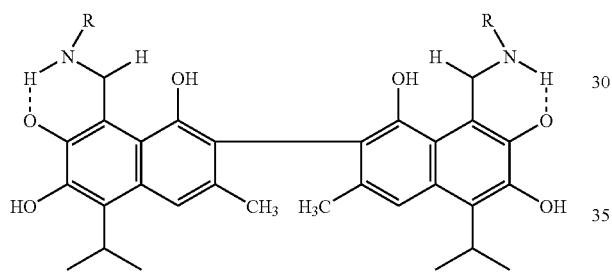

wherein R=methyl, ethyl, propyl, isopropyl, butyl, s-butyl, t-butyl, pentyl, hexyl, heptyl, dodecyl, β-methyl phenylalanine ethyl, phenylalanine methyl ester (Razakantoanina et al. Parasitol. Res., 86:665-668 (2000));

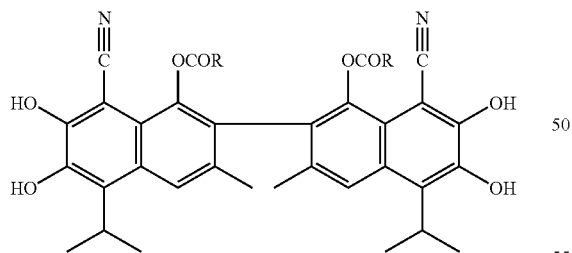

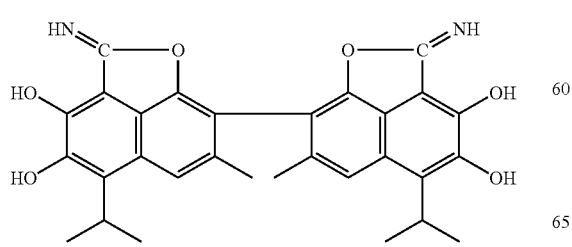

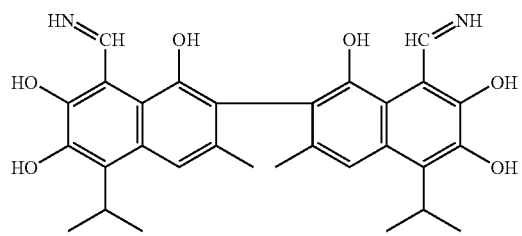

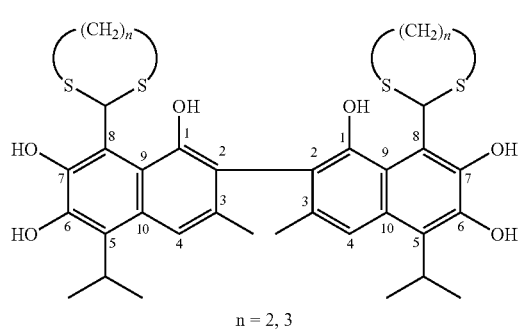

n = 2, 3

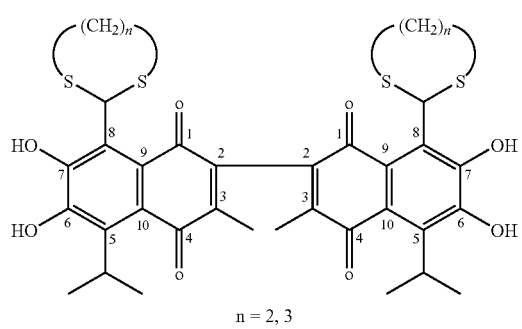

n = 2, 3

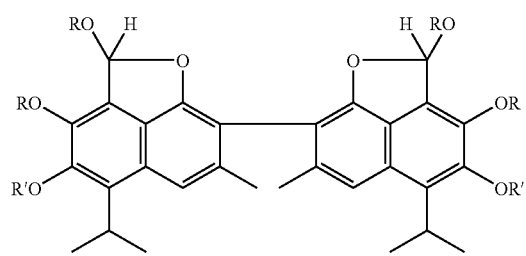

n = 2, 3

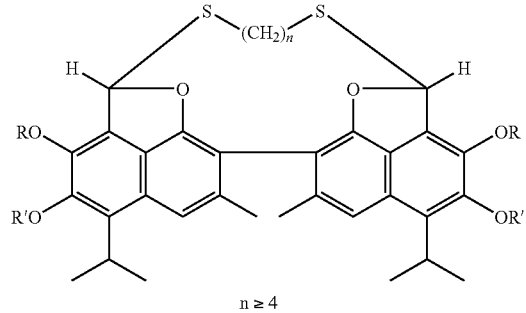

n ≥ 4

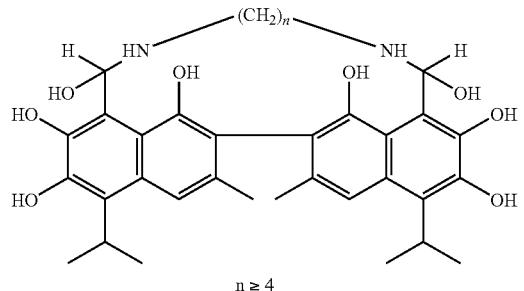
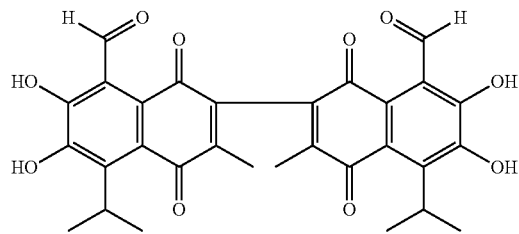
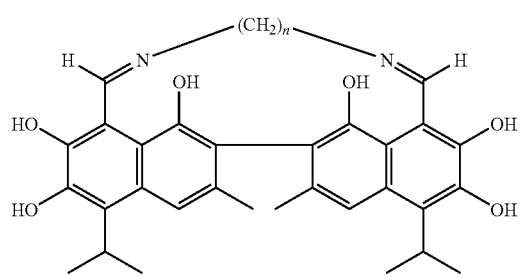
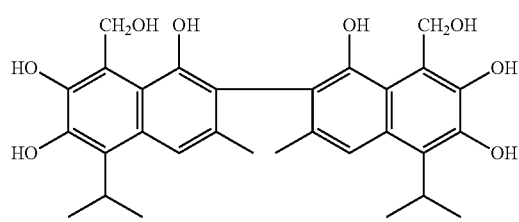
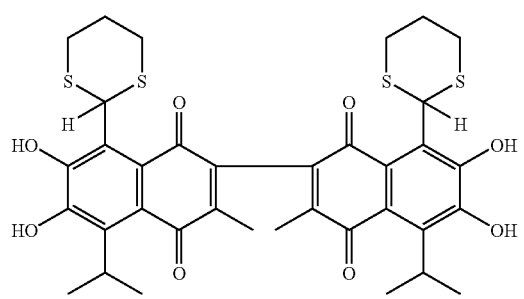
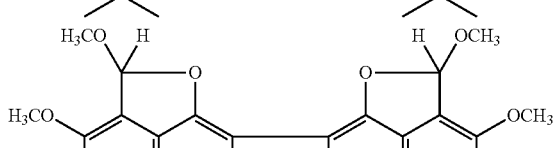
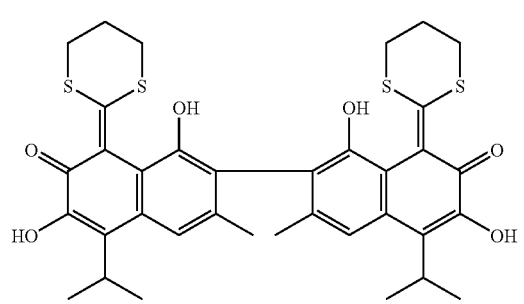
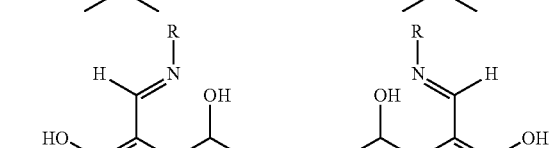
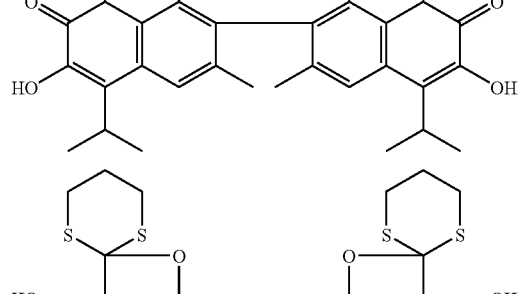
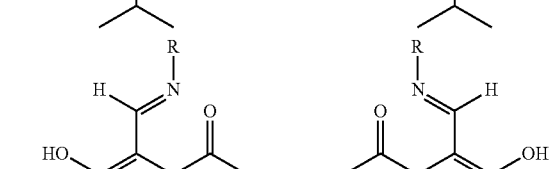
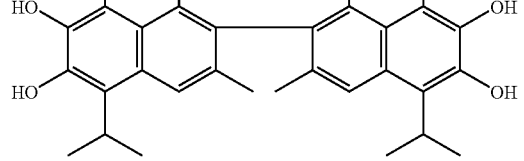
wherein R=methyl and R'=hydrogen, methyl (Dao et al. Bioorg. Med. Chem., 11:2001-2006 (2003));
wherein R=methyl, ethyl, propyl, isopropyl, butyl, s-butyl, t-butyl, pentyl, hexyl, heptyl, dodecyl, β-methyl phenylalanine ethyl, phenylalanine methyl ester (Dao et al. Eur. J. Med. Chem., 35:805-813 (2000));

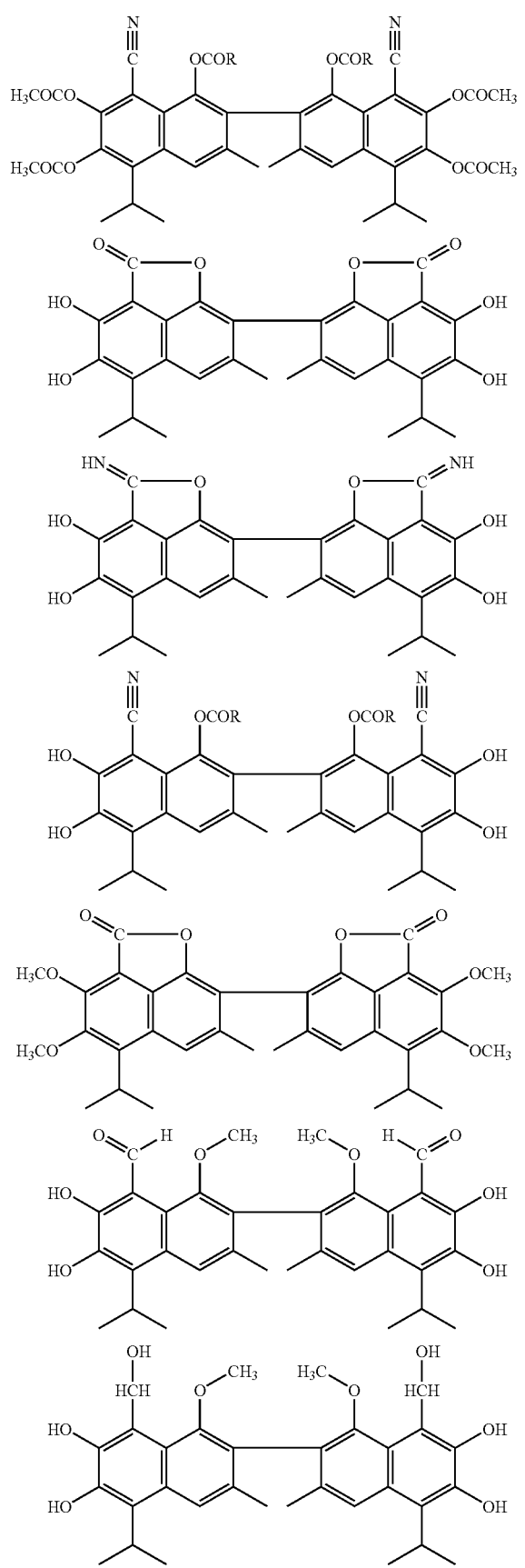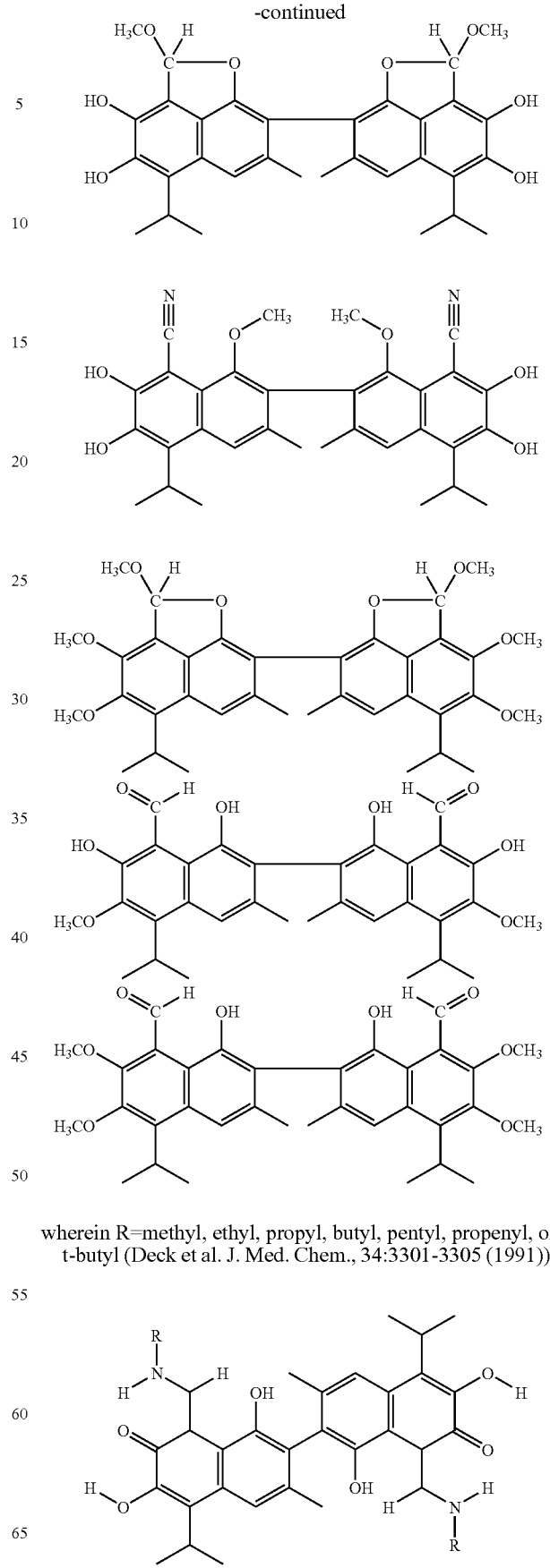
wherein R=methyl, ethyl, propyl, butyl, pentyl, propenyl, or t-butyl (Deck et al. J. Med. Chem., 34:3301-3305 (1991));

wherein
R=
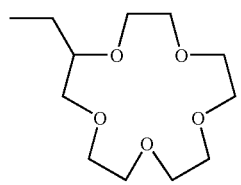
or
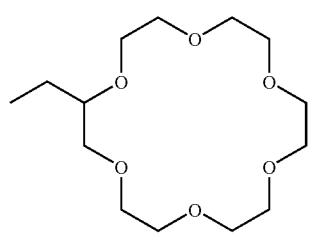
Przybylski et al. J. Mol. Structure, 611(1-3):193-201 (2002);
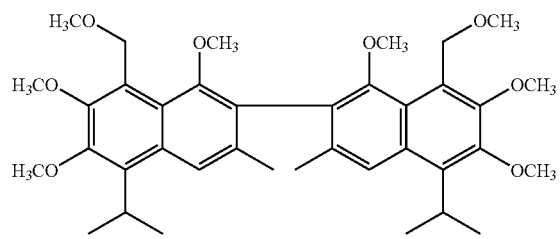
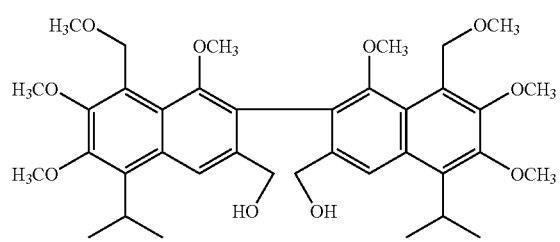
(A. I. Meyers and J. Jeffrey Willemsen, Chem. Commun., 16:1573-1574 (1997));
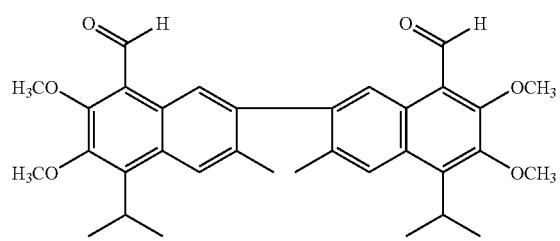
-continued
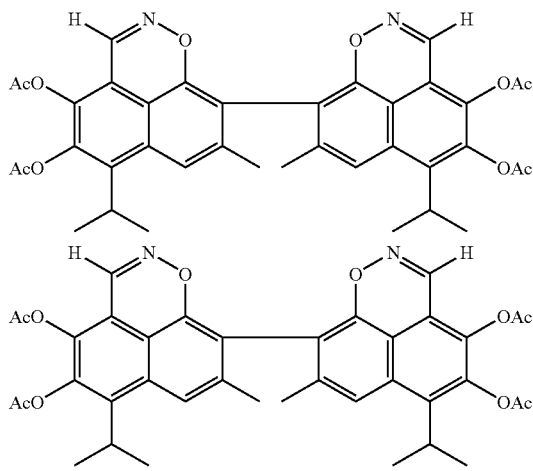
(R. E. Royer et al., J. Med. Chem., 38:2427-2432 (1995));
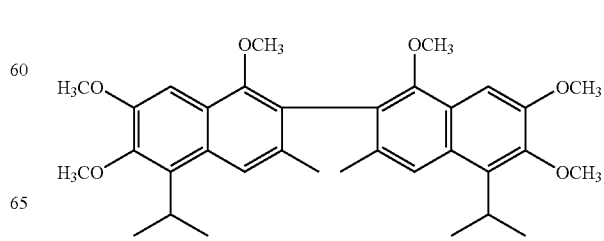
(R. E. Royer et al., J. Med. Chem., 29:1799-1801 (1986));

-continued
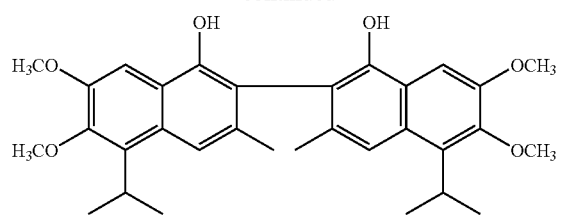
(C. M. Venuti, J. Org. Chem., 46(15):3124-3127 (1981));
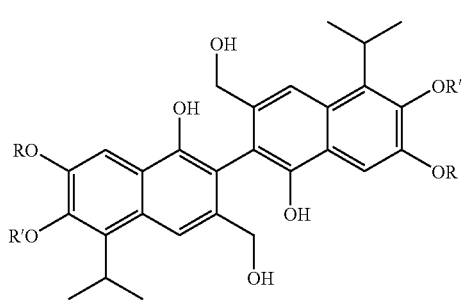
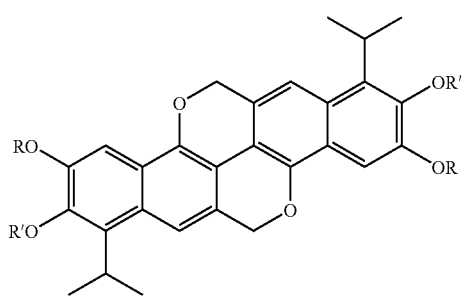
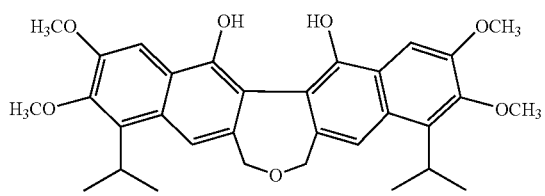
wherein R=Me, Bz and R'=Me, H, and Bz;
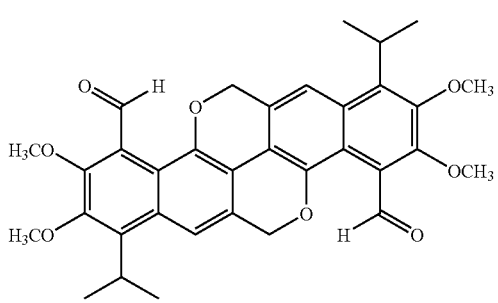
-continued
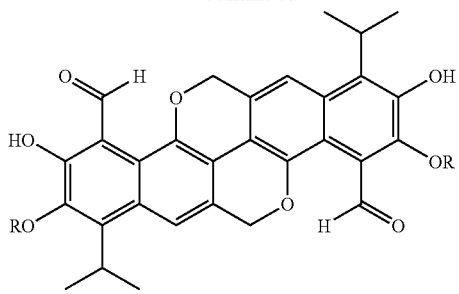
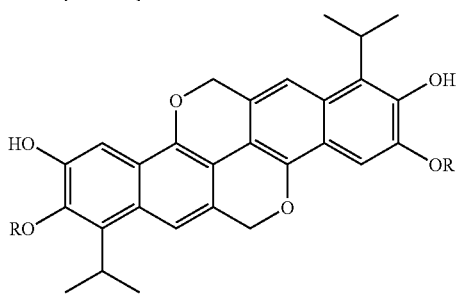
wherein R=Me, and H, (I. V. Ognyanoc et al., Helv. Chim. Acta, 72:353-360 (1989));
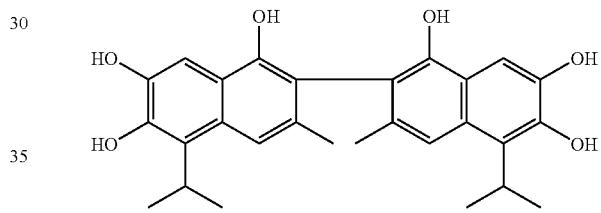
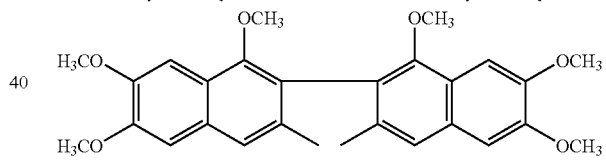
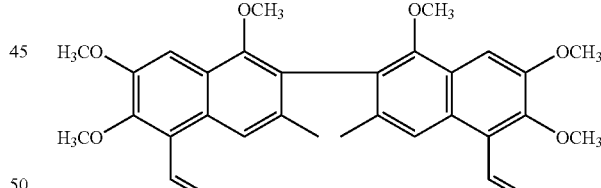
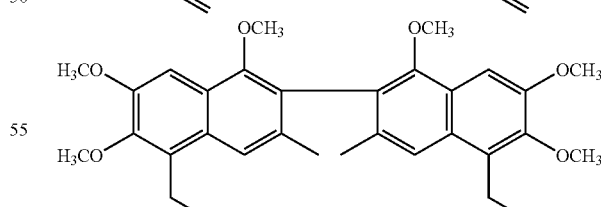
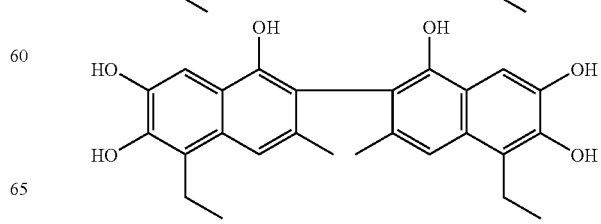

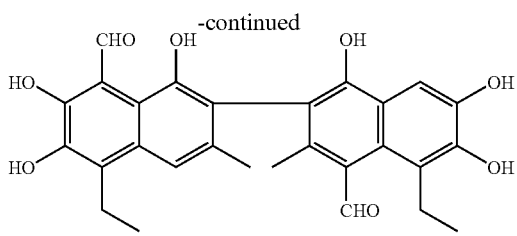

(P. C. Meltzer et al., J. Org. Chem., 50(17):3121-3124 (1985));

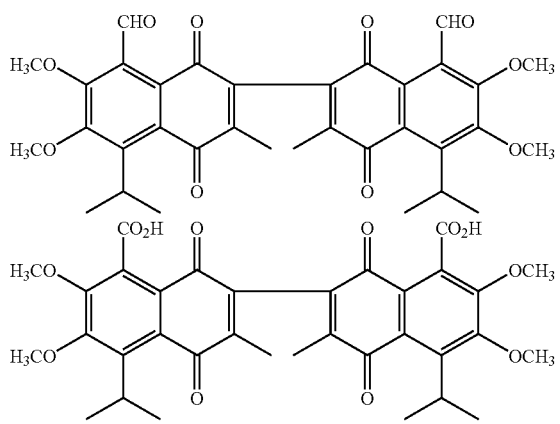

(R. Adams et al., J. Am. Chem. Soc., 60:2193-2204 (1938)).

Other derivatives of gossypol are disclosed in the following references: Le Blanc et al. Pharmacol. Res., 46:551-555 (2002); Baumgrass et al. J. Biol. Chem., 276:47914-47921 (2001); Shelley et al. Anticancer Drugs, 11:209-216 (2000); Sonenberg et al. Contraception, 37:247-255, (1988); Whaley et al. Contraception, 33:605-616 (1986); Dorsett et al. J. Pharm. Sci., 64:1073-1075 (1975); Wu et al. Yao Xue Xue Bao, 24:502-511 (1989); Hoffer et al. Contraception, 37:301-331 (1988); Guo et al. Yao Xue Xue Bao, 22:597-602 (1987); and Manmade et al. Experientia, 39:1276-1277 (1983).

As used herein, the term "gossypol acetic acid" refers to a composition of gossypol comprising an amount of acetic acid sufficient to detectably stabilize the gossypol composition as compared to gossypol compositions without acetic acid. The range of acetic acid in "gossypol acetic acid" compositions is preferably from about 0.01% to 99% (by weight), more preferably from about 0.1% to 50%, even more preferably from about 0.5% to 20%. In one embodiment, the gossypol acetic acid is a complex consisting of equimolar quantities of gossypol and acetic acid (Sigma-Aldrich Corp., St. Louis, Mo.).

As used herein, the terms "(−)-gossypol," or "(−)-gossypol compound/composition," refer to an optically active composition of gossypol wherein the active molecules comprising the composition rotate plane polarized light counterclockwise (e.g., levorotatory molecules) as measured by a polarimeter. Preferably, the (−)-gossypol compound has an enantiomeric excess of 1% to 100%. In one embodiment, the (−)-gossypol compound has an enantiomeric excess of at least 10%, 20%, 30%, 40%, 50%, 60%, 70%, 80%, 90%, 91%, 92%, 93%, 94%, 95%, 96%, 97%, 98%, 99%, or 100% (−)-gossypol. In one example of a "(−)-gossypol compound", the specific rotation ($[\alpha]_D$) of the compound is about −350° to about −390°, about −375° to about −390°, or about −385° to about −390°. (See e.g., Dowd, Chirality, 15:486 (2003); Ciesielska et al., Chem. Phys. Lett. 353:69 (2992); Freedman et al., Chirality, 15:196 (2003); and Zhou et al., Kexue Tongbao, 28:1574 (1983)). Methods for resolving racemic gossypol compounds into substantially purified (+)- or (−)-gossypol are known (See e.g., Zhou et al., Kexue Tongbao, 28:1574 (1983) (wherein: L-phenylalanine methyl ester was mixed with the aldehyde groups of gossypol to form a Schiff's base with two diastereoisomers which were then resolved on a normal silica flash chromatography column. The filtrate was concentrated, and the residue was purified by chromatography on silica gel eluting with hexanes:EtOAc=3:1 to give two fractions. Acid hydrolysis of the two fractions in 5N HCl: THF (1:5, room temperature, overnight) regenerated the individual gossypol enantiomers, respectively. The first fraction with a higher $R_f$ value contained (−)-gossypol, and the second fraction with a lower $R_f$ value contained (+)-gossypol. The crude gossypol fractions were extracted into ether from the residue after removing THF from the reaction mixture. The gossypol fractions were then purified by chromatography on silica gel and eluted with hexanes:EtOAc (3:1 ratio) to give optically pure gossypol, with a yield of 30-40% in two steps. The optical rotatory dispersion values for these products were $\alpha_D=-352°$ (c=0.65, $CHCl_3$) for (−)-gossypol, and $\alpha_D=+341°$ (c=0.53, $CHCl_3$)).

As used herein, the term "gossypol Schiff's base(s)" refers to the gossypol compound that results from the reaction of an aldehyde or ketone form of gossypol with a primary amine to yield an imine of gossypol. Examples of primary amines that can be used include, but are not limited to, branched and unbranched alkylamines (e.g., methylamine, ethylamine, propylamine, isopropylamine, butylamine, t-butylamine), substituted and unsubstituted arylamines (e.g., phenylamine, benzylamine), and amino acids, such as glycine, alanine, leucine, isoleucine, phenylalanine, tyrosine, tryptophan, lysine, arginine, histidine, aspartate, glutamate, asparagine, glutamine, cysteine, and methionine.

As used herein, the term "Bcl-2 family proteins," refers to both the anti-apoptotic members of the Bcl-2 family, including, but not limited to Bcl-2, Bcl-$X_L$, Mcl-1, A1/BFL-1, BOO-DIVA, Bcl-w, Bcl-6, Bcl-8 and Bcl-y, and the pro-apoptotic members of the Bcl-2 family, including, but not limited to Bak, Bax, Bad, tbid, Harakiri, Bim, Bmf, and optionally other proteins with BH3 (Bcl-2 homology 3) binding pockets that are regulated by gossypol compounds.

As used herein, the terms "overexpression of Bcl-2," or "overexpression of a Bcl-2 family protein" refer to an elevated level (e.g., aberrant) of mRNAs encoding for a Bcl-2 family protein(s), and/or to elevated levels of such Bcl-2 family protein(s) in cells or tissues as compared to similar normal corresponding nonpathological cells and tissues expressing basal levels of mRNAs encoding Bcl-2 family proteins or having basal levels of Bcl-2 family proteins. Methods for detecting the levels of mRNAs encoding Bcl-2 family proteins, or levels of Bcl-2 family proteins, in a cell or tissue include, but are not limited to, Western blotting using Bcl-2 family protein antibodies, immunohistochemical methods, and methods of nucleic acid amplification or direct RNA detection. As important as the absolute levels of Bcl-2 family proteins in cells, tissues, or organs are to determining that they overexpress Bcl-2 family proteins, so also are the relative levels of anti-apoptotic Bcl-2 family proteins to other pro-apoptotic signalling molecules (e.g., pro-apoptotic Bcl-2 family proteins) within such cells, tissues or organs. When the balance of these two are such that, were it not for the levels of the anti-apoptotic Bcl-2 family proteins, the pro-apototic signalling molecules would be sufficient to cause the cells to execute the apoptosis program and die, said cells in such tissues or organs would be dependent on the anti-apoptotic Bcl-2 family proteins for their survival. In such cells, exposure to an inhibiting effective amount of an anti-apoptotic Bcl-2 family protein inhibitor will be sufficient to cause the cells to execute the apoptosis program and die. Thus, the term "overexpression of Bcl-2 family protein" also refers to cells in tissues and organs that, due to the relative levels of pro-apoptotic signals and anti-apoptotic signals, undergo apoptosis in response to inhibiting effective amounts of compounds that inhibit the function of anti-apoptotic Bcl-2 proteins.

As used herein, the terms "anticancer agent," "conventional anticancer agent," or "cancer therapeutic drug" refer to any therapeutic agents (e.g., chemotherapeutic compounds and/or molecular therapeutic compounds), radiation therapies, or surgical interventions, used in the treatment of cancer (e.g., in mammals).

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

As used herein the term "prodrug" refers to a pharmacologically inactive derivative of a parent "drug" molecule that requires biotransformation (e.g., either spontaneous or enzymatic) within the target physiological system to release, or to convert (e.g., enzymatically, mechanically, electromagnetically, etc.) the "prodrug" into the active "drug." "Prodrugs" are designed to overcome problems associated with stability, toxicity, lack of specificity, or limited bioavailability. Exemplary "prodrugs" comprise an active "drug" molecule itself and a chemical masking group (e.g., a group that reversibly suppresses the activity of the "drug"). Some preferred "prodrugs" are variations or derivatives of compounds that have groups cleavable under metabolic conditions. Exemplary "prodrugs" become pharmaceutically active in vivo or in vitro when they undergo solvolysis under physiological conditions or undergo enzymatic degradation or other biochemical transformation (e.g., phosphorylation, hydrogenation, dehydrogenation, glycosylation, etc.). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common "prodrugs" include acid derivatives such as esters prepared by reaction of parent acids with a suitable alcohol (e.g., a lower alkanol), amides prepared by reaction of the parent acid compound with an amine (e.g., as described above), or basic groups reacted to form an acylated base derivative (e.g., a lower alkylamide).

The term "derivative" of a compound, as used herein, refers to a chemically modified compound wherein the chemical modification takes place either at a functional group of the compound, aromatic ring, or carbon backbone. Such derivatives include esters of alcohol-containing compounds, esters of carboxy-containing compounds, amides of amine-containing compounds, amides of carboxy-containing compounds, imines of amino-containing compounds, acetals of aldehyde-containing compounds, ketals of carbonyl-containing compounds, and the like.

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

An "effective amount" is an amount sufficient to effect beneficial or desired results. An effective amount can be administered in one or more administrations.

As used herein, the term "administration" refers to the act of giving a drug, prodrug, or other agent (e.g., a gossypol compound), or therapeutic treatment (e.g., radiation therapy) to a physiological system (e.g., a subject or in vivo, in vitro, or ex vivo cells, tissues, and organs). Exemplary routes of administration to the human body can be through the eyes (opthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

"Coadministration" refers to administration of more than one chemical agent (e.g., a gossypol compound and/or drugs, prodrugs, etc.) or therapeutic treatment (e.g. radiation therapy) to a physiological system (e.g., a subject or in vivo, in vitro, or ex vivo cells, tissues, and organs). "Coadministration" of the respective chemical agents (e.g., a gossypol compound and/or drugs, prodrugs, etc.) and therapeutic treatments (e.g., radiation therapy) may be concurrent, or in any temporal order or physical combination.

As used herein, the term "synergistic" refers to an effect obtained when gossypol and a second agent are administered together (e.g., at the same time or one after the other) that is greater than the additive effect of gossypol and the second agent when administered individually. The synergistic effect allows for lower doses of gossypol and/or the second agent to be administered or provides greater efficacy at the same doses. The synergistic effect obtained can be at least 10%, at least 20%, at least 30%, at least 40%, at least 50%, at least 60%, at least 70%, at least 80%, at least 90%, at least 100%, at least 125%, at least 150%, at least 175%, at least 200%, at least 250%, at least 300%, at least 350%, at least 400%, or at least 500% more than the additive effect of the gossypol compound and the second agent when administered individually. For example, with respect to the treatment of cancer, the synergistic effect can be a decrease in the rate of tumor growth, a decrease in tumor mass, a decrease in the number of metastases, an increase in time to tumor progression, or an increase in survival time. As described herein, gossypol compounds (e.g., (−)-gossypol) and chemotherapeutic agents, when administered individually, often only inhibit tumor cell proliferation rather than cause regression of the tumor mass. According to the present invention, it is possible to cause actual regression of tumor mass by the administration of gossypol compounds (e.g., (−)-gossypol) and chemotherapeutic agents. The co-administration of a gossypol compound and an anticancer agent may allow for the use of lower doses of the gossypol compound and/or the anticancer agent such that the cancer is effectively treated while avoiding any substantial toxicity to the subject.

The term "sensitize," and grammatical equivalents thereof, refers to making, through the administration of a first agent(s) (e.g., a gossypol compound and optionally a chemotherapeutic agent and/or radiation), a subject, cell, tissue, or organ more susceptible, or more responsive, to the biological effects (e.g., promotion or retardation of an aspect of cellular function including, but not limited to, cell growth, proliferation, invasion, angiogenesis, apoptosis) of a second or more agent. The "sensitizing effect" of a first agent (e.g., a gossypol compound and optionally a chemotherapeutic agent and/or radiation) on a target cell, tissue, or organ can be measured as the difference in the intended biological effect (e.g. promotion or retardation of an aspect of cellular function including, but not limited to, cell growth, proliferation, invasion, angiogenesis, apoptosis) observed upon the administration of a second or more agent with and without administration of the first agent. In this regard, the second or more agent can be exogenous to the subject, cell, tissue or organ. Further in this regard, the second or more agent can be endogenous to the subject, cell, tissue, or organ.

As used herein, the term "pharmacological properties" refers to any desirable or favorable biological activities or physicochemical characteristics of an agent (e.g., a gossypol compound) administered to a physiological system.

As used herein, the term "pharmacokinetic properties" refers to the action of an agent (e.g., a gossypol compound) in a subject, cell, tissue, or organ over a period of time including, but not limited to, the processes of absorption, distribution, localization in tissues, biotransformation, and excretion.

As used herein, the term "bioavailability" refers to any measure of the ability of a an agent (e.g., a gossypol compound) to be absorbed into a biological target fluid (e.g. blood, cytoplasm, CNS fluid, and the like), tissue, organelle or intercellular space after administration to a physiological system (e.g., a subject or in vivo, in vitro, or ex vivo cells, tissues, and organs).

As used herein, the term "biodistribution" refers to the location of an agent (e.g., a gossypol compound) in organelles, cells (e.g., in vivo or in vitro), tissues, organs, or organisms, after administration to a physiological system.

As used herein, the term "dysregulation of the process of cell death" refers to any aberration in the ability of (e.g., predisposition) a cell to undergo cell death via either necrosis or apoptosis. Dysregulation of cell death is associated with or induced by a variety of conditions, including for example, autoimmune disorders (e.g., systemic lupus erythematosus, rheumatoid arthritis, graft-versus-host disease, myasthenia gravis, Sjögren's syndrome, etc.), chronic inflammatory conditions (e.g., psoriasis, asthma and Crohn's disease), hyperproliferative disorders (e.g., tumors, B cell lymphomas, T cell lymphomas, etc.), viral infections (e.g., herpes, papilloma, HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

A "hyperproliferative disease," as used herein refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell or tissue means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, Celiac Sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

As used herein, the term "neoplastic disease" refers to any abnormal growth of cells or tissues being either benign (non-cancerous) or malignant (cancerous).

As used herein, the term "anti-neoplastic agent" refers to any compound that retards the proliferation, growth, or spread of a targeted (e.g., malignant) neoplasm.

As used herein, the term "regression" refers to the return of a diseased subject, cell, tissue, or organ to a non-pathological, or less pathological state as compared to basal nonpathogenic exemplary subject, cell, tissue, or organ. For example, regression of a tumor includes a reduction of tumor mass as well as complete disappearance of a tumor or tumors.

As used herein, the terms "prevent," "preventing," and "prevention" refer to a decrease in the occurrence of hyperproliferative or neoplastic cells in a subject. The prevention may be complete, e.g., the total absence of hyperproliferative or neoplastic cells in a subject. The prevention may also be partial, such that the occurrence of hyperproliferative or neoplastic cells in a subject is less than that which would have occurred without the present invention.

As used herein the term, "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reactions that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "subject" refers to organisms to be treated by the methods of the present invention. Such organisms include, but are not limited to, humans and veterinary animals (dogs, cats, horses, pigs, cattle, sheep, goats, and the like). In the context of the invention, the term "subject" generally refers to an individual who will receive or who has received treatment (e.g., administration of gossypol compound(s), and optionally one or more anticancer agents) for a disease characterized by overexpression of Bcl-2 family proteins (e.g., Bcl-2, Bcl-$X_L$, Bcl-w, Mcl-1, A-1(Bfl-1), and Boo).

The term "diagnosed," as used herein, refers to the recognition of a disease by its signs and symptoms (e.g., resistance to conventional cancer therapies), or genetic analysis, pathological analysis, histological analysis, and the like.

As used herein, the term "competes for binding" is used in reference to a first molecule (e.g., a gossypol compound) with an activity that binds to the same target (e.g., Bcl-2 and/or Bcl-$X_L$) as does a second molecule (e.g., a pro-apoptotic Bcl-2 family protein, such as Bax, Bak, Bid, and Bad, etc.). The efficiency (e.g., kinetics or thermodynamics) of binding by the first molecule may be the same as, or greater than, or less than, the efficiency of the target binding by the second molecule. For example, the equilibrium binding constant (Kd) for binding to the target may be different for the two molecules.

As used herein, the term "antisense" is used in reference to nucleic acid sequences (e.g., RNA, phosphorothioate DNA) that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. For example, once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand. Regions of nucleic acid sequences that are accessible to antisense molecules can be determined using available computer analysis methods.

The term "sample" as used herein is used in its broadest sense. A sample suspected of indicating a condition characterized by the overexpression of a Bcl-2 family protein may comprise a cell, tissue, or fluids, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g. the level of Bcl-2 family proteins in a cell). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In preferred embodiments, "test compounds" are anticancer agents. In particularly preferred embodiments, "test compounds" are anticancer agents that induce apoptosis in cells.

As used herein, the term "purified" or "to purify" refers to the removal of undesired components from a sample. As used herein, the term "substantially purified" refers to molecules (e.g., polynucleotides, polypeptides, chemical compounds (e.g., gossypol compounds)) that are removed from their natural environment, isolated or separated, and are at least 60% free, preferably at least 75% free, and most preferably at least 90% free from other components with which they are naturally associated. For example, an "isolated polynucleotide" is therefore a substantially purified polynucleotide.

As used herein, the term "genome" refers to the genetic material (e.g., chromosomes) of an organism or a host cell.

The term "nucleotide sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences, or portions thereof, of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand. As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain translated from the mRNA. The DNA or RNA sequence thus codes for the amino acid sequence.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "exogenous gene" refers to a gene that is not naturally present in a host organism or cell, or is artificially introduced into a host organism or cell.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decreases production. Molecules (e.g., transcription factors) that are involved in up-regulation or down-regulation are often called "activators" and "repressors," respectively.

The terms "homology" and "percent identity" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a single-stranded nucleic acid sequence, the term "substantially homologous" refers to any probe that can hybridize (i.e., it is the complement of) the single-stranded nucleic acid sequence under conditions of low stringency as described above. A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other. The present invention is not limited to the situation where hybridization takes place only between completely homologous sequences. In some embodiments, hybridization takes place with substantially homologous sequences.

As used herein, the term "protein of interest" refers to a protein encoded by a nucleic acid of interest.

As used herein, the term "native" (or wild type) when used in reference to a protein, refers to proteins encoded by partially homologous nucleic acids so that the amino acid sequence of the proteins varies. As used herein, the term "variant" encompasses proteins encoded by homologous genes having both conservative and nonconservative amino acid substitutions that do not result in a change in protein function, as well as proteins encoded by homologous genes having amino acid substitutions that cause decreased (e.g., null mutations) protein function or increased protein function.

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligo-ribonucleotide probe or RNA probe to detect DNA species complementary to the ribo probe used.

As used herein, the term "pathogen" refers to a biological agent that causes a disease state (e.g., infection, cancer, etc.) in a host. "Pathogens" include, but are not limited to, viruses, bacteria, archaea, fingi, protozoans, mycoplasma, and parasitic organisms.

As used herein, the term "microorganism" is used to refer to any species or type of microorganism, including but not limited to, bacteria, archaea, fungi, protozoans, mycoplasma, and parasitic organisms. As used herein, the term "fungi" is used in reference to eukaryotic organisms such as the molds and yeasts, including dimorphic fungi.

As used herein, the term "virus" refers to minute infectious agents, which with certain exceptions, are not observable by light microscopy, lack independent metabolism, and are able to replicate only within a living host cell. The individual particles (i.e., virions) consist of nucleic acid and a protein shell or coat; some virions also have a lipid containing membrane. The term "virus" encompasses all types of viruses, including animal, plant, phage, and other viruses.

The terms "bacteria" and "bacterium" refer to all prokaryotic organisms, including those within all of the phyla in the kingdom Procaryotae. It is intended that the term encompass all microorganisms considered to be bacteria including Mycoplasma, *Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms which are gram negative or gram positive. "Gram negative" and "gram positive" refer to staining patterns with the Gram-staining process which is well known in the art. (See e.g., Finegold and Martin, Diagnostic Microbiology, 6th Ed., C V Mosby St. Louis, pp 13-15 (1982)). "Gram positive bacteria" are bacteria which retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

As used herein, the term "antigen binding protein" refers to proteins which bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries. Various procedures known in the art are used for the production of polyclonal antibodies. For the production of antibodies, various host animals can be immunized by injection with the peptide corresponding to the desired epitope including, but not limited to, rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 (1975)), as well as the trioma technique, the human B-cell hybridoma technique (See e.g., Kozbor et al., Immunol. Today, 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)).

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science, 246:1275-1281 (1989)) to allow rapid and easy identification of monoclonal Fab fragments with the desired specificity.

Antibody fragments that contain the idiotype (antigen binding region) of the antibody molecule can be generated by known techniques. For example, such fragments include, but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

Genes encoding antigen binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.) etc.

As used herein, the term "instructions for administering said gossypol compound to a subject" includes instructions for using the compositions contained in the kit for the treatment of conditions characterized by the overexpression of a Bcl-2 family protein in a cell or tissue. The term also refers to instructions for using the compositions contained in the kit to treat cancers characterized as being resistant to at least one conventional anticancer therapy (e.g., chemotherapy). In some embodiments, the instructions further comprise a statement of the recommended or usual dosages of the compositions contained within the kit pursuant to 21 C.F.R. §201 et seq. Additional information concerning labeling and instruction requirements applicable to the methods and compositions of the present are available at the Internet web page of the U.S.F.D.A.

As used herein, the term "third party" refers to any entity engaged in selling, warehousing, distributing, or offering for sale a compound contemplated for co-administration with a gossypol compound for treating conditions characterized by the overexpression of the Bcl-2 family proteins.

As used herein, the term "modulate" refers to the activity of a compound (e.g., gossypol compound) to affect (e.g., to promote or retard) an aspect of the cellular function including, but not limited to, cell growth, proliferation, invasion, angiogenesis, apoptosis, and the like.

GENERAL DESCRIPTION OF THE INVENTION

Gossypol is a naturally occurring double biphenolic compound derived from crude cotton seed oil (*Gossypium* sp.). Naturally occurring gossypol exists in two enantiomeric forms, (+) or (−), that when present together comprise racemic gossypol. Human trials of racemic gossypol as a male contraceptive have demonstrated the safety of long term administration of gossypol. Racemic gossypol is well tolerated in humans.

Gossypol is a known inhibitor of spermatogenesis that may be administered orally with few side effects. Some researchers have shown, however, that hypokalemia may result from prolonged gossypol administration. Accordingly, in some embodiments, the present methods and compositions further comprise the co-administration of potassium supplements to patients being treated with gossypol compounds.

Although an understanding of the mechanism is not necessary to practice the present invention and the present invention is not so limited, the present invention contemplates that gossypol is a potent inhibitor of Bcl-2 and Bcl-$X_L$ and that the anti-tumor activity of gossypol is due, at least in part, to inhibition of the anti-apoptotic activity of Bcl-2 and Bcl-$X_L$ and the subsequent induction of apoptosis in cancer cells expressing Bcl-2 family proteins. Thus, the present invention provides compositions and methods for targeting subjects characterized as overexpressing a Bcl-2 family protein. In some of the embodiments, the cancer cells show elevated expression levels of Bcl-2 family proteins as compared to nonpathological samples (e.g., non-cancerous cells or tissues). In other embodiments, the cancer cells or supporting cells operationally manifest elevated expression levels of Bcl-2 family proteins by virtue of executing the apoptosis program and dying in response to an inhibiting effective amount of a gossypol compound (e.g., (−)-gossypol), said response occurring, at least in part, to the dependence in such cells on anti-apoptotic Bcl-2 family protein function for their survival.

In the clinical trials to date, gossypol has shown low toxicity in patients. In some embodiments, it is contemplated that gossypol compounds provide efficient single agent treatments for metastatic cancers. The present invention further contemplates that gossypol compounds represent new classes of anticancer agents that specifically antagonize the anti-apoptotic effects of Bcl-2 and Bcl-$X_L$.

The present invention provides in vivo data that show gossypol compounds significantly inhibit tumor growth, but that in some embodiments gossypol compounds achieve even greater inhibition of tumor growth inhibition when used in combination (co-administration) with one or more conventional anticancer agents (e.g., docetaxel). Accordingly, in preferred embodiments, gossypol compounds are administered to patients suffering from diseases characterized by the overexpression of Bcl-2 and/or Bcl-$X_L$ (e.g., cancer). Gossypol induces apoptosis in cancer cells expressing high levels of Bcl-2 and/or Bcl-$X_L$, but gossypol in general has less effect on cells with low levels Bcl-$X_L$ and/or Bcl-2 expression. In other preferred embodiments, gossypol compounds are administered with one or more anticancer agents and/or radiation.

Bcl-2 is the founding member of a family of proteins that includes both anti-apoptotic molecules (e.g., Bcl-2, Bcl-$X_L$, Mcl-1, A1/BFL-1, BOO-DIVA, Bcl-w, Bcl-6, Bcl-8, and Bcl-y, and the like) and pro-apoptotic molecules (e.g., Bax, Bak, Bid, and Bad, and the like). The bcl-2 gene is a human proto-oncogene located on chromosome 18. The bcl-2 gene was discovered as a translocated locus in a B-cell leukemia. This translocation is also found in some B-cell lymphomas. In cancerous B cells, the portion of chromosome 18 containing the bcl-2 locus undergoes a reciprocal translocation with the portion of chromosome 14 containing antibody heavy chains. This t(14;18) translocation places the bcl-2 gene close to the heavy chain gene enhancer. The product of the bcl-2 gene, Bcl-2 protein, is an integral membrane protein found in the membranes of the endoplasmic reticulum (ER), nuclear envelope, and the outer membrane of mitochondria. It is contemplated that Bcl-2, and Bcl-$X_L$, function as crucial antagonists of apoptosis.

Although an understanding of the mechanism is not necessary to practice the present invention and the present invention is not so limited, it is contemplated that anti-apoptotic proteins Bcl-2 and Bcl-$X_L$ suppress apoptosis by forming heterodimers with pro-apoptotic Bcl-2 family members such as Bak, Bad, Bax, Mtd (Bok), Bim, Hrk (DP5), Blk, Bnip3, Bnip3L, and Diva. Additional anti-apoptotic members (or related proteins) of the Bcl-2 family are thought to include, but are not limited to, Mcl-1, A1/BFL-1, BOO-DIVA, Bcl-w, Bcl-6, Bcl-8, and Bcl-y.

Research into the three-dimensional (3D) structures of Bcl-2 and Bcl-$X_L$ showed that both molecules have a hydrophobic binding pocket (named BH3) that is important to their anti-apoptotic affects. In particular, experimental 3D high resolution structures of Bcl-$X_L$ (S. W. Muchmore et al., Nature, 381:335-341 (1996); and M. Aritomi et al., J. Biol. Chem., 272:27886-27892 (1997)) alone and in complex with a Bak BH3 (Bcl-2 homology domain 3) peptide (S. Michael et al., Science, 275:983-986 (1997)) have been determined. Bcl-2 and Bcl-$X_L$ share a high degree of homology in their amino acid sequences (45% of identity and 56% of similarity). It has been demonstrated that when there exists a sequence identity of more than 30% between a target protein (Bcl-2) and a template protein (Bcl-$X_L$), current computational homology modeling methods, such as Modeller (A. Sali et al., Structure, Function, and Genetics, 23:318-326 (1995)) can provide accurate 3D structures of the target protein. (See, A. Sali, Curr. Opin. Biotech., 6:437-451 (1995)). Therefore, in preferred embodiments of the present invention, computational homology modeling is used to model the 3D structure of Bcl-2 (the target protein) based upon the experimental 3D structural coordinates of Bcl-$X_L$ (the template protein) before the three-dimensional experimental Bcl-2 structures were determined.

Fluorescence-polarization based assays showed that gossypol, (−)-gossypol and (+)-gossypol bind to Bcl-2 and Bcl-$X_L$ proteins and compete with pro-apoptotic Bid, Bad, and Bak BH3 peptides. Analysis using nuclear magnetic resonance (NMR) methods conclusively confirmed that gossypol, (−)-gossypol, and (+)-gossypol bind to the BH3 binding groove in Bcl-$X_L$. Thus, gossypol compounds bind to the surface groove in Bcl-2 and Bcl-$X_L$ and block the binding of pro-apoptotic proteins (e.g. Bid, Bad and Bak), therefore inhibiting the anti-apoptotic functions of Bcl-2 and Bcl-$X_L$.

In some embodiments, the present invention provides BH3 domain-containing proteins as targets for inhibition. It should be understood that where the specification refers to Bcl-2 families of proteins, the same disclosure pertains to BH3 domain-containing proteins. Thus, in some embodiments, the present invention provides compositions and methods for the regulation of biological conditions related to the aberrant expression of BH3 domain-containing proteins. Likewise, in some other embodiments, the present invention provides methods and compositions for screening agents and compounds that modulate (e.g., inhibit or promote) the aberrant expression of BH3 domain-containing proteins.

Bcl-2 and Bcl-$X_L$ are highly homologous proteins. Many forms of human cancers (e.g., myeloid leukemia and breast cancer) overexpress Bcl-2, and/or Bcl-$X_L$. Both Bcl-2 and Bcl-$X_L$ have been found to be overexpressed in human breast cancers. In particular, Bcl-2 is found to be overexpressed in 60-80% of human breast cancers. The expression of Bcl-2 is highly correlated with estrogen receptor (ER) positive breast cancer. Bcl-$X_L$ is overexpressed in 40-70% of human breast cancers, 30-60% of prostate cancers, 80% of B-cell lymphomas, 90% of colorectal adenocarcinomas, and many other forms of cancer. The expression of Bcl-$X_L$ is typically correlated with a poor prognosis and shortened survival.

Several lines of evidence indicate that Bcl-2 and Bcl-$X_L$ not only contribute to cancer progression, but also may confer on cancer cells a resistance to apoptosis induced by conventional anti-cancer therapies. High levels of intracellular Bcl-2 protect cells (e.g., cancer cells) from being destroyed by apoptosis. The majority of solid tumors are protected by at least one of the anti-apoptotic Bcl-2 proteins. Most of the currently available chemotherapeutic cancer agents disrupt cellular DNA integrity or replication, and indirectly trigger apoptosis in tumor cells. Cancers that express high levels of Bcl-2 and/or Bcl-$X_L$ are often resistant to chemotherapeutic agents or radiation therapy.

However, the expression patterns of Bcl-2 and Bcl-$X_L$ are different in some cancers that overexpress Bcl-2 family proteins. Several reports suggest that expression of either Bcl-2 or Bcl-$X_L$ proteins is sufficient for cancer cells to show Bcl-2 family mediated resistance to chemotherapy or radiation therapy. (See, J. C. Reed, Pharmacology, 41:501-553 (1997); J. C. Reed et al., J. Cell Biochem., 6:23-32 (1996)). Additional research suggests that some cancer cells are able to switch from overexpression of Bcl-2 to Bcl-$X_L$. (See, Z. Han et al., Cancer Res., 56:621-628 (1996)). Accordingly, some embodiments of the present invention provide administering a therapeutic amount of one or more Bcl-2 antagonists (e.g., small molecules, such as gossypol compounds) to patients having a cancer characterized by overexpression of a Bcl-2 family member protein. Similarly, other embodiments of the present invention provide administering a therapeutic amount of one or more Bcl-$X_L$ antagonists (e.g., small molecules, such as gossypol compounds) to patients having a cancer characterized by overexpression of Bcl-$X_L$. In still further embodiments, the present invention provides methods for administering a combination of two or more anti-apoptotic Bcl-2 family protein antagonists (e.g. small molecules, such as gossypol compounds) to a patient having a cancer characterized by the overexpression of anti-apoptotic Bcl-2 family proteins. In some embodiments, a Bcl-2 antagonist and/or a Bcl-$X_L$ antagonist are administered to a subject; optionally, one or more additional anticancer agents may also be administered. The present invention further contemplates providing compositions and methods comprising one or more antagonists to Bcl-2 family protein(s) (e.g., an anti-apoptotic Bcl-2 family protein) and one or more additional anticancer agents (e.g., TAXOL, TAXOTERE, etc.). In preferred embodiments, the present invention comprises anticancer methods and compositions comprising providing a subject with a therapeutically effective amount of a gossypol compound, e.g., gossypol, gossypolone, Schiff's bases of gossypol and gossypolone, enantiomers (e.g., (−)-gossypol and (+)-gossypol), and pharmaceutically acceptable salts of these compounds.

DETAILED DESCRIPTION OF THE INVENTION

The present invention relates to naturally occurring and chemically synthesized small molecule antagonists of Bcl-2 family proteins. In particular, the present invention provides gossypol compounds (e.g., isomers, enantiomers, racemic compounds, metabolites, derivatives, pharmaceutically acceptable salts, in combination with acids or bases, and the like) and methods of using these compounds as antagonists of the anti-apoptotic effects of Bcl-2 family member proteins (e.g., Bcl-2, Bcl-$X_L$, and the like). The present invention also provides compositions comprising gossypol compounds and optionally one or more additional therapeutic agents (e.g., chemotherapeutic or anti-neoplastic agents). The present invention also provides methods for treating diseases and pathologies (e.g., neoplastic diseases) comprising administering a composition comprising gossypol compounds and optionally one or more additional therapeutic agents (e.g., chemotherapeutic or anti-neoplastic agents) and/or techniques (e.g., radiation therapies, surgical interventions, and the like) to a subject or in vitro cells, tissues, and organs.

Exemplary compositions and methods of the present invention are described in more detail in the following sections: I. Binding activity of Bcl-2 and Bcl-$X_L$; II. Structure-based approach for discovery of small molecule inhibitors of Bcl-2 and Bcl-$X_L$; III. Characterization of Bcl-2 family of proteins in cancer cell lines; IV. Gossypol compounds inhibit cancer cell growth and proliferation; V. Proposed mechanism of gossypol activity; VI. Activity of gossypol in MDA-231 xenograft mice alone and in combination with conventional anticancer agents; VII. Therapeutic agents combined or co-administered with gossypol compounds; VIII. Targeting agents and techniques; IX. Pharmaceutical formulations, administration routes, and dosing considerations, and X. Exemplary combination therapies.

I. Binding Activity of Bcl-2 and Bcl-$X_L$

Although an understanding of the mechanism is not necessary to practice the present invention and the present invention is not so limited, it is contemplated that the anti-apoptotic effects of Bcl-2 and Bcl-$X_L$ proteins can be attributed, at least in part, to their ability to heterodimerize with pro-apoptotic Bcl-2 family member proteins such as Bak, Bax and Bad. The experimental structures of Bcl-2 and Bcl-$X_L$ show that BH1 (Bcl-2 Homology Domain 1), BH2, and BH3 domains of Bcl-2 and Bcl-$X_L$ form a hydrophobic binding pocket (the BH3 binding pocket) into which the Bak or Bad BH3 domain can bind. (See e.g., S. W. Muchmore et al., Nature, 381:335-341 (1996); M. Aritomi et al., J. Biol. Chem., 272:27886-27892 (1997); S. Michael et al., Science, 275:983-986 (1997); A. M. Petros et al., Protein Sci., 9:2528-2534 (2000); and A. M. Petros et al., Proc. Natl. Acad. Sci. U.S.A., 98:3012-3017 (2001)). The binding site in Bcl-2/Bcl-$X_L$ is essential for its anti-apoptotic function. (See e.g., X. M. Yin et al., Nature, 369:321-323 (1994); S. C. Cosulich et al., Curr. Biol., 7:913-920 (1997); S. Michael et al., supra; and A. M. Petros et al., supra).

In preferred embodiments, the present invention provides small molecules that bind to Bcl-2 and/or Bcl-$X_L$ BH3 binding sites thus blocking their hetero-dimerization with pro-apoptotic Bcl-2 family member proteins (e.g., Bad, Bak, and Bax etc.) such that their anti-apoptotic function is antagonized and apoptosis is induced in cells with Bcl-2 and/or Bcl-$X_L$ overexpression. In some of these embodiments, the present invention further provides methods comprising the administration of one or more additional therapeutic agents (e.g. anticancer agents such as TAXOL or TAXOTERE) in combination with the disclosed small molecule Bcl-2/Bcl-$X_L$ inhibitors (e.g., gossypol compounds). Particularly preferred compositions and methods comprise gossypol compounds administered in combination with at least one anticancer agent (e.g., TAXOL, TAXOTERE, or cisplatin).

The present invention provides small molecule Bcl-2/Bcl-$X_L$ inhibitors that have various advantages over other available protein antagonists (e.g., antisense oligonucleotides, antibodies, and peptides). For example, various compositions of the present invention have improved oral availability and lower cost among other advantages.

II. Structure-Based Approach for Discovery of Small Molecule Inhibitors of Bcl-2 and Bcl-$X_L$ Preferred embodiments of the present invention used a powerful structure-based virtual screening methodology to identify small molecule antagonists of anti-apoptotic Bcl-2 family proteins (e.g., Bcl-2 and Bcl-$X_L$) from large 3D chemical databases. The methods took advantage of powerful computational docking programs to identify small organic molecules that interact with binding sites in the targeted proteins (e.g., the BH3 site in Bcl-2 and/or Bcl-$X_L$).

In one embodiment, the targeted protein, Bcl-$X_L$, was screened in docking studies (e.g., using the united-atom approximation) to identify small-molecule inhibitors that bind to targeted protein from a library of chemicals (e.g., synthetic organic compounds and natural products). For example, in one embodiment, polar hydrogens were added to the targeted protein, and Kollman united-atom partial charges were assigned. All water molecules were removed. Atomic solvation parameters and fragmental volumes were assigned to the protein atoms using the AutoDock utility, AddSol. (See, AutoDock Web page; G. Morris et al., J. Comp. Chem., 19:1639-1662 (1998)).

Figure 2B:
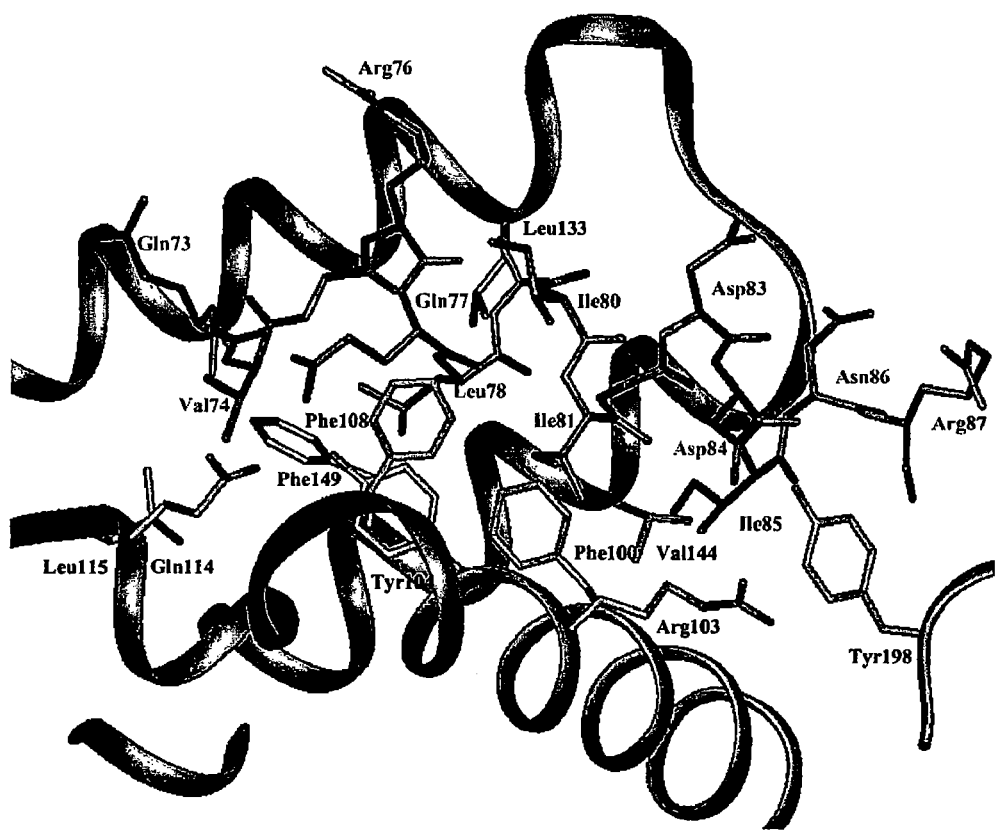
FIG. 2B shows a detailed representation of the BH3 binding site in Bcl-2.

In another embodiment, the 3D structure of Bcl-2 was modeled using the MODELLER homology modeling program and methods based upon the 3D structure of Bcl-$X_L$. (A. Sali et al., Structure, Function, and Genetics, 23:318-326 (1995); and A. Sali, Curr. Opin. Biotech., 6:437-451 (1995)). A BLAST sequence alignment of Bcl-2 (SEQ ID NO:1) and Bcl-$X_L$ (SEQ ID NO:2) proteins is shown in FIG. 1. In preferred embodiments, this sequence alignment was used in the various homology modeling experiments of the present invention. Since the Bak BH3 peptide binds to both Bcl-2 and Bcl-$X_L$ with good affinity (See, J. L. Wang et al., Cancer Res., 60:1498-1502 (2000); and J. L. Wang et al., Proc. Natl. Acad. Sci. U.S.A., 97:7124-7129 (2000)), the 3D structure of Bcl-2 in complex with the Bak BH3 peptide was modeled based upon the experimental NMR structure of Bcl-$X_L$ complexed with Bak BH3 peptide. (S. Michael et al., Science, 275:983-986 (1997)). The modeled 3D complex structure was further refined using molecular dynamic (MD) simulations in explicit water using the CHARMM program (B. R. Brooks et al., J. Comp. Chem., 4, 187-217 (1983); and P. V. R. Schleyer et al., CHARMM: The Energy Function and Its Parameterization with an Overview of the Program, in The Encyclopedia of Computational Chemistry, 1:271-277 eds., John Wiley & Sons, Chichester (1998)) with the MSI CHARMM force field. The refined structure of Bcl-2 in complex with Bak BH3 peptide is shown in FIGS. 2A and 2B, respectively. FIG. 2A shows a ribbon representation of the overall Bcl-2 structure complexed with Bak BH3 peptide. FIG. 2B shows a detailed representation of the BH3 binding site. The carbon atoms in the Bak BH3 peptide are in magenta, while the carbon atoms in the Bcl-2 protein are in green, the oxygen atoms are in red and the nitrogen atoms are in blue. The potential Bcl-2/Bcl-$X_L$ inhibitors were confirmed using biochemical and biological assays.

In some embodiments, as compared to random screening methods, the structure-based 3D-database screening methods of the present invention are more effective and less costly. In one embodiment, a three-dimensional structural database containing approximately 6,000 natural products isolated from traditional herbal medicine libraries was screened using the DOCK program to identify inhibitors of Bcl-2 and/or Bcl-$X_L$. In another embodiment, the latest version of the National Cancer Institute's (NCI) 3D-database of approximately 250,000 organic synthetic compounds and natural products (G. W. A. Milne et al., J. Chem. Inf. Comput. Sci., 34:1219-1224 (1994)) was screened using the DOCK program (S. Makino and I. D. Kuntz, J. Comput. Chem. 18:1812-1825 (1997)) to identify about 250-500 potential small molecule Bcl-2/Bcl-$X_L$ inhibitors. Of the 259 compounds initially selected, 141 were available from the NCI chemical repository and were thus obtained for use in in vitro binding assays.

In one embodiment, further testing of the potential non-peptide small molecule inhibitors was done using an established sensitive and quantitative in vitro fluorescence polarization (FP) based binding assay. (See, I. J. Enyedy et al., J. Med. Chem., 44:313-4324 (2001)). The 141 candidate compounds were screened using the FP bind assay for their ability to compete with Bak BH3 peptide in binding to Bcl-2. From the 141 compounds tested, a subset of 20 compounds was found to display $IC_{50}$ values ranging from 0.7 µM to 25 µM. Fifteen distinct classes of chemicals were represented within the 20 compound subset. The $IC_{50}$ value of the natural Bak BH3 peptide was 0.3 µM in the FP binding assays. Each of the 20 small molecules inhibitors identified blocked the binding (complexing) of Bcl-2 and Bak BH3 peptides. Several of the small molecule inhibitors also potently induced apoptosis and thus inhibited the viability and growth of cancer cells with Bcl-2 overexpression.

Since Bcl-$X_L$ and Bcl-2 have similar 3D structures, it was reasoned that some of the potential Bcl-2 inhibitors would also bind to Bcl-$X_L$. Accordingly, additional screening efforts were directed at discovering potential non-peptide small molecule antagonists of Bcl-$X_L$ using the FP based binding assay described above.

Figure 3:
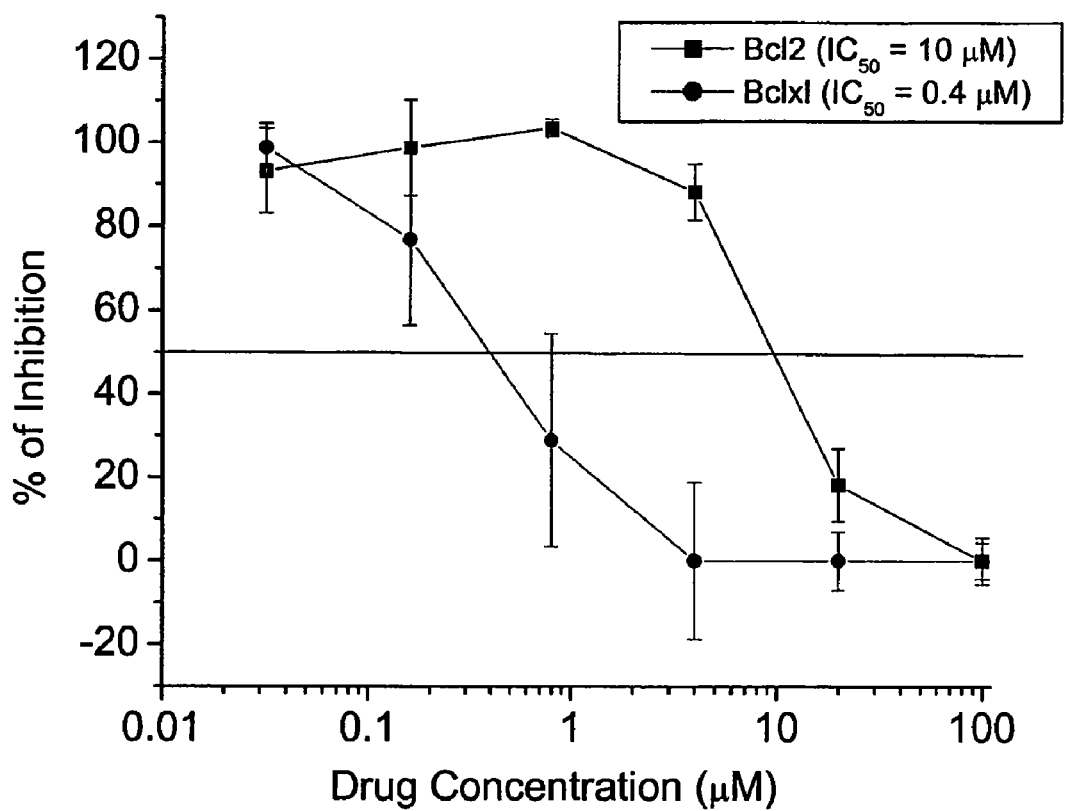
FIG. 3 shows gossypol directly inhibits binding between Bak BH3 peptide and Bcl-2, and between Bak BH3 peptide and Bcl-$X_L$ proteins in certain fluorescence polarization (FP) based binding assays.

Although Bcl-2 and Bcl-$X_L$ have similar functions, the two proteins have different expression patterns in human cancers. Furthermore, although Bcl-2 and Bcl-$X_L$ share structurally similar BH3 binding sites, there are differences between the two. It was discovered that while some small molecule inhibitors of Bcl-2 also have good binding affinity for Bcl-$X_L$, some other small molecule inhibitors only weakly bound Bcl-$X_L$ (although these molecules are still effective antagonists in some compositions and methods). Some relatively weak Bcl-2 small molecule inhibitors had much higher potency when binding to Bcl-$X_L$. In particular, it was found that gossypol binds to both Bcl-2 and Bcl-$X_L$ proteins. FIG. 3 shows direct inhibition of the binding between Bak BH3 peptide and Bcl-2 (Bcl-$X_L$) by gossypol measured using a FP based binding assay. The non-FP labeled Bak peptide has an $IC_{50}$ value of 0.3 µM to Bcl-$X_L$.

In one embodiment, it was found that racemic gossypol binds to Bcl-2 and Bcl-$X_L$. FIG. 3 shows racemic gossypol directly inhibits binding between Bak BH3 peptide and Bcl-2. FIG. 3 further shows that racemic gossypol directly inhibits binding between Bak BH3 peptide and Bcl-$X_L$.

Figure 4:
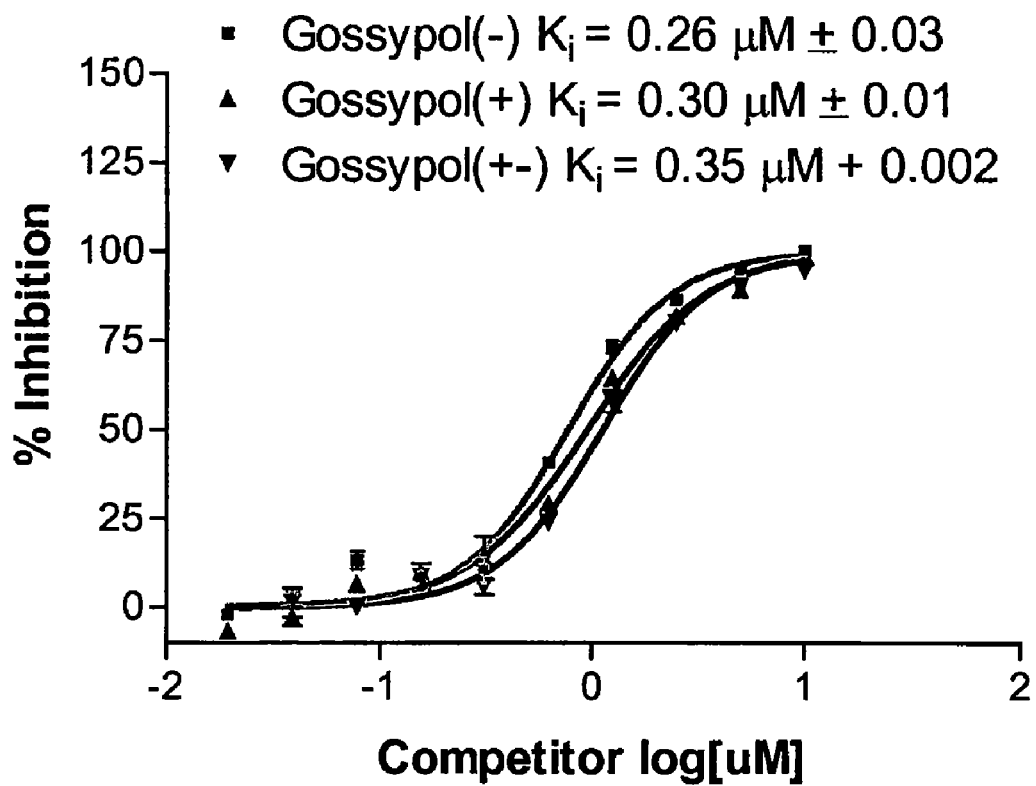
FIG. 4 shows the results of competitive inhibition assays using racemic gossypol, (−)-gossypol, and (+)-gossypol to directly block binding between Bid 21-residue BH3 peptide and Bcl-2.
Figure 5:
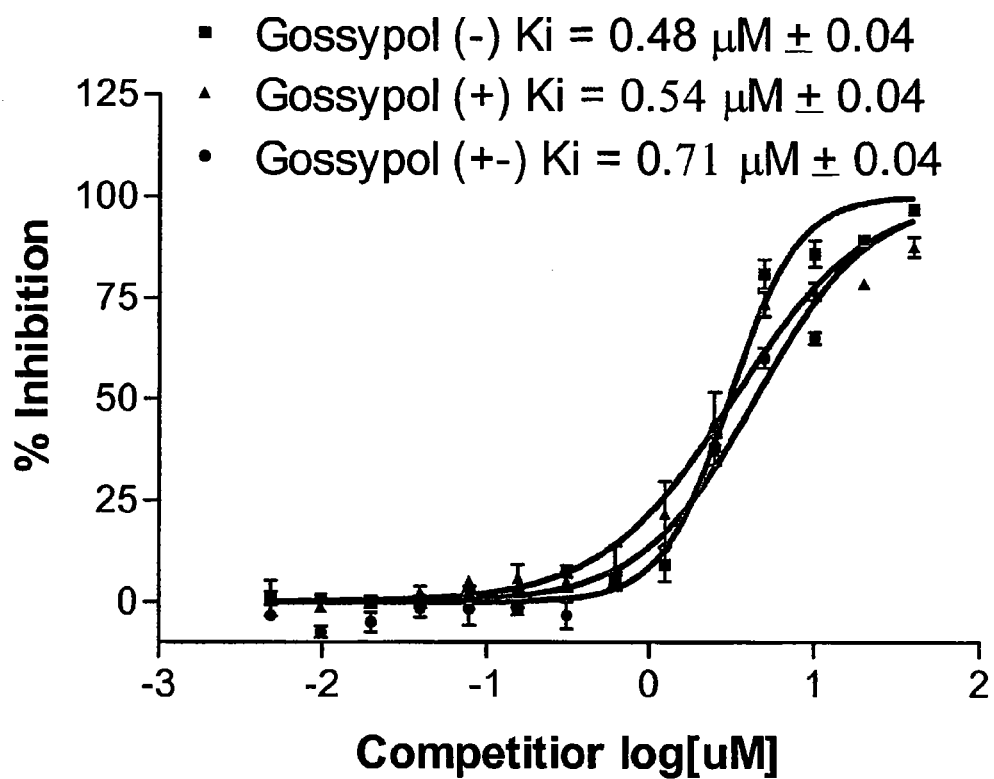
FIG. 5 shows the results of a competitive inhibition assay using racemic gossypol, (−)-gossypol, and (+)-gossypol to directly block binding between Bad 25-residue BH3 peptide and Bcl-$X_L$.

In another embodiment, it was found that enantiomers of gossypol (e.g., (−)-gossypol and (+)-gossypol) bind to Bcl-2 and Bcl-$X_L$ proteins. FIG. 4 shows racemic gossypol, (−)-gossypol, and (+)-gossypol directly inhibit binding between Bid BH3 peptide and Bcl-2. FIG. 5 shows racemic gossypol, (−)-gossypol, and (+)-gossypol directly inhibit binding between Bad BH3 peptide and Bcl-$X_L$.

Figure 6A:
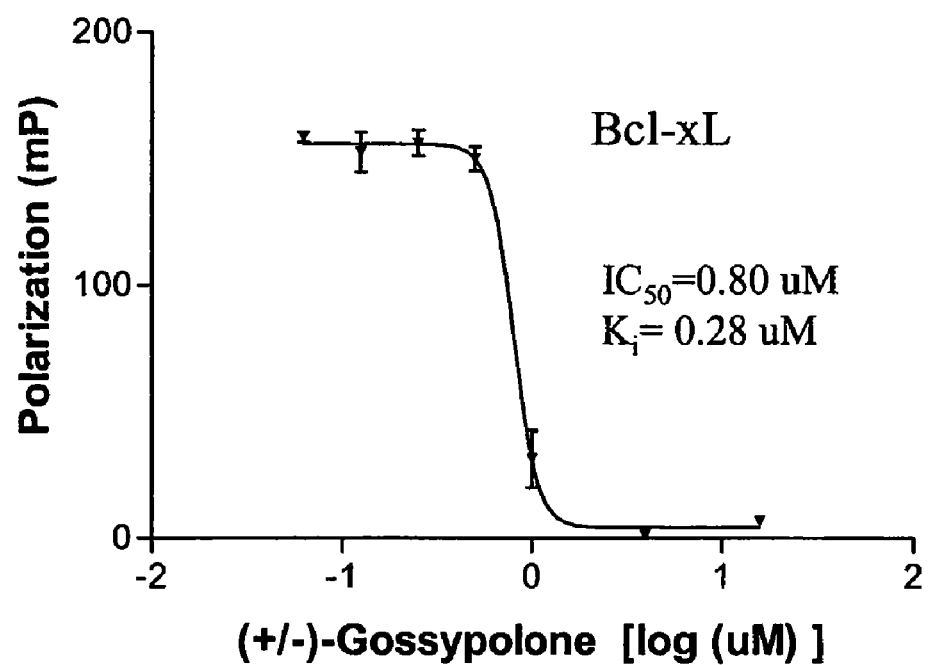
FIG. 6A shows the results of a FP-based binding assay of racemic gossypolone to Bcl-$X_L$ in one embodiment of the present invention.
Figure 6B:
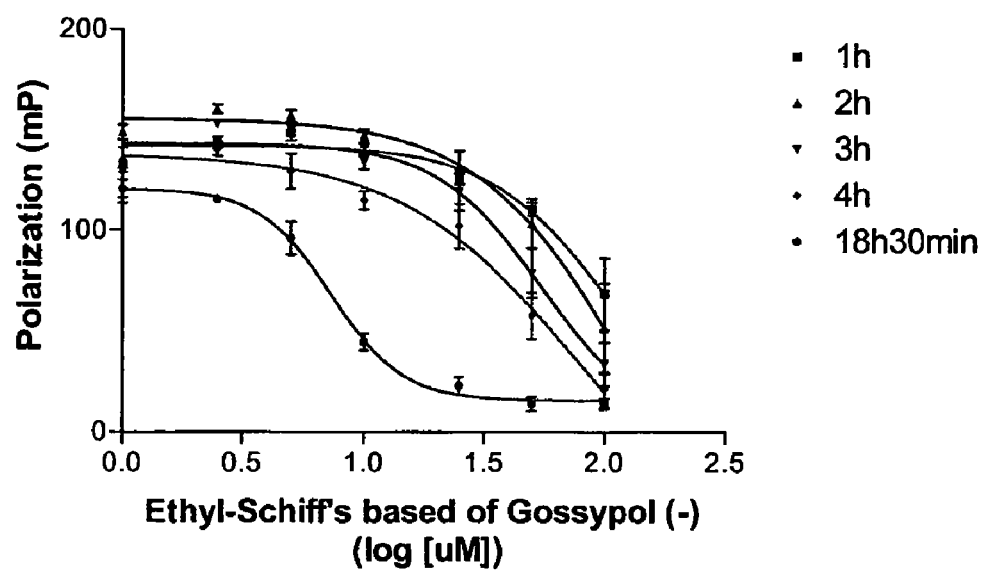
FIG. 6B shows the results of a FP-based binding assay of a ethyl Schiff's base of (−)-gossypol to Bcl-$X_L$ (time-course) in one embodiment of the present invention.

In yet another embodiment, it was found that gossypolone binds to Bcl-2 and Bcl-$X_L$ proteins. FIG. 6A shows racemic gossypolone directly inhibits binding between Bak BH3 peptide and Bcl-$X_L$. FIG. 6B shows competitive inhibition by (−)-gossypol ethyl Schiff's base of the binding of Bak BH3 peptide to Bcl-$X_L$ protein.

III. Characterization of Bcl-2 Family of Proteins in Cancer Cell Lines

Figure 7:
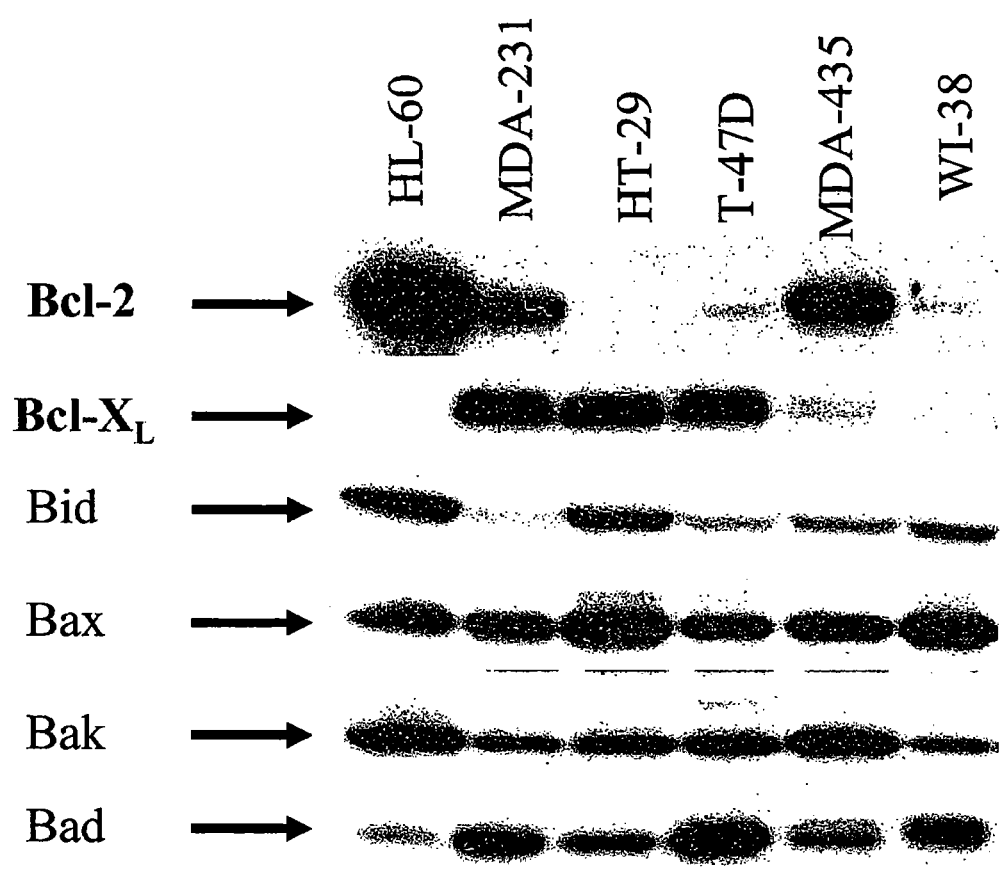
FIG. 7 shows the results of several cancer cell lines and one normal cell line that express various levels of Bcl-2 and/or Bcl-$X_L$ proteins in one embodiment of the present invention.

To better understand the molecular mechanism of small molecule inhibitors of Bcl-2 and Bcl-$X_L$, the expression of Bcl-2 family proteins was characterized in various breast and other cancer cell lines from the National Cancer Institute's anti-cancer drug screening program. The results from 5 representative cancer cell lines (i.e., the MDA-MB-231, T-47D, and MDA-435 breast cancer cell lines, the HL-60 leukemia cell line, and the HT-29 colon cancer cell line) and 1 normal fibroblast (WI-38) cell line are shown in FIG. 7. The HL-60 leukemia cell line had the highest level of Bcl-2 expression, MDA-MB-231 and MDA-MB-435 breast cancer cell lines also showed very high levels of Bcl-2. Breast cancer cell lines MDA-MB-231 and T-47D, as well as colon cancer cell line HT-29 showed very high levels of Bcl-$X_L$ expression. The normal fibroblast cell line showed low levels of Bcl-2 and Bcl-$X_L$ expression.

The Bcl-2 family proteins act as arbiters of programmed cell death. The balance between anti-apoptotic molecules (e.g., Bcl-2 and Bcl-$X_L$) and pro-apoptotic molecules (e.g., Bid, Bax, Bak and Bad) plays an important role in apoptosis. For this reason, the expression status of pro-apoptotic proteins Bid, Bax, Bak and Bad in cancer cell lines MDA-MB-231, T-47D, MDA-435, HL-60, and HT-29, and normal fibroblast cell line WI-38 were also determined (FIG. 7). All of the cell lines tested, including the normal fibroblast cell line WI-38, expressed high levels of Bax and most of the cancer cell lines also expressed high levels of Bak. There is significant variations in the expression levels of Bid and Bad between different cell lines. Taken together, all 5 of the cancer cell lines showed high levels of both anti-apoptotic and pro-apoptotic Bcl-2 family proteins, while the normal fibroblast cell line (WI-38) showed only low levels of Bcl-2 and Bcl-$X_L$, but high levels of pro-apoptotic Bcl-2 family members proteins Bax and Bad.

Several other breast cancer cell lines used by the National Cancer Institute (NCI) in their anticancer drug screening efforts were also tested. These cell lines include BT-549, HS 578T, MCF-7 and NCI/ADR-Resistant. Of these, MCF-7 and BT-549 showed high levels of Bcl-2 protein expression. BT-549 also showed a high level of Bcl-$X_L$ protein expression. The cell lines HS 578T and NCI/ADR-RES had medium levels of Bcl-$X_L$ protein. Thus, among the 7 human breast cancer cell lines examined (i.e., MDA-MB-231, T-47D, MDA-435, BT-549, HS 578T, MCF-7, and NCI/ADR-Resistant) 5 of the cell lines had high levels of either, or both, Bcl-2 and Bcl-$X_L$ expression. Two breast cancer cell lines had medium levels of Bcl-2 or Bcl-$X_L$ expression. None of the 7 breast cancer cell lines tested had low expression of Bcl-2 and Bcl-$X_L$.

IV. Gossypol Compounds Inhibit Cancer Cell Growth and Proliferation

The fluorescence polarization assays showed that gossypol antagonizes the binding of Bak, Bid, or Bad BH3 peptide to Bcl-2 and Bcl-$X_L$. Thus, the present invention contemplates that small molecule inhibitors (e.g., gossypol compounds) that bind to the BH3 binding domain in Bcl-2 and/or Bcl-$X_L$ will block the anti-apoptotic functions of these proteins, and in turn induce apoptosis in cells (e.g., cancer cells) with elevated Bcl-2 and/or Bcl-$X_L$ expression. It is further contemplated that small molecule inhibitors (e.g., gossypol compounds) also decrease cellular viability and proliferation in cells (e.g., cancer cells) with high Bcl-2 and/or Bcl-$X_L$ expression. Gossypol inhibits cell proliferation (and growth) in cancer, and more particularly, in human breast cancers (e.g., MDA-MB-231 cells). As described herein, the MDA-MB-231 breast cancer cell line has high levels of expression of both Bcl-2 and Bcl-$X_L$.

Various cancer cell inhibition studies were performed with gossypol compounds. For example, the ability of gossypol compounds to inhibit MDA-MB-231 cell growth was tested in a 5 day MTT assay. Gossypol was shown to inhibit MDA-MB-231 cell growth with an $IC_{50}$ value of 2.0 μM. The results in MB-231 and WI-38 cells treated with 20 μM of gossypol for 24 hours as detected by the Hoechst Dye assay are shown in FIGS. 8A and 8B, respectively. Treatment of MDA-MB-231 cancer cells with gossypol induces apoptosis. FIG. 8A shows the induction of apoptosis in the MDA-231 cells. Gossypol did not induce normal WI-38 fibroblast cells to undergo apoptosis. FIG. 8B shows that gossypol treatment did not induce apoptosis in normal WI-38 fibroblast cells having low levels (e.g., basal levels) of Bcl-2 and Bcl-$X_L$ expression.

In other tests, gossypol was shown to induce apoptosis in T-47D breast cancer cells having high levels of Bcl-$X_L$ expression, but low levels of Bcl-2 expression. It was also found that gossypol induces apoptosis in other cancer cell lines with high Bcl-$X_L$ expression such as HT-29, a human colon cancer cell line, but not in cancer cell lines with low levels of Bcl-2 and Bcl-$X_L$ expression such as DU-145, a prostate cancer cell line.

Figure 9:
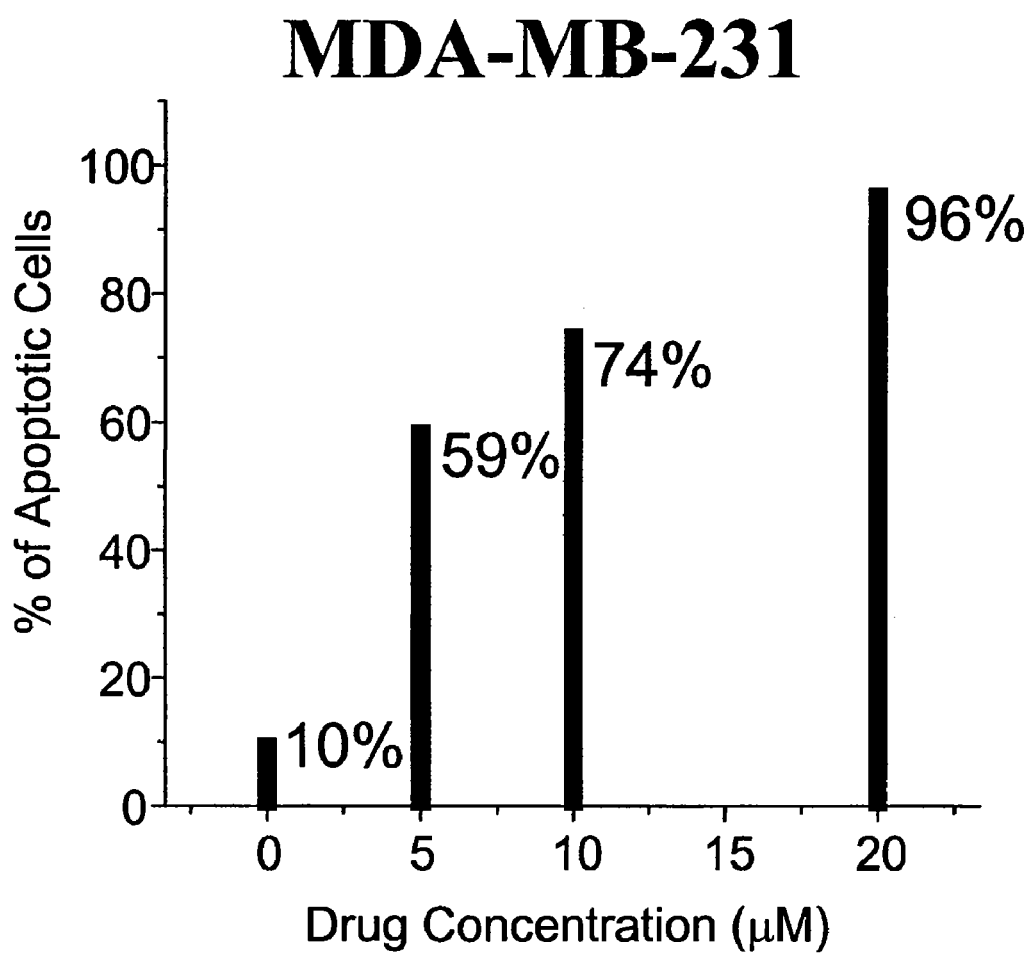
FIG. 9 shows the results of cell based assays in various embodiments of the present invention.

Further tests using Annexin-V flow cytometry (FACS) assays were conducted to more quantitatively assess the ability of gossypol to induce apoptosis in MDA-MB-231 breast cancer cells. For example, FIG. 9 shows gossypol induced apoptosis in human MDA-MB-231 breast cancer cells treated with gossypol for 24 hours detected using Annexin-V flow cytometry. It was observed that 5.0 μM of gossypol induced 59% of the MDA-MB-231 cells to undergo apoptosis. While the present invention is not limited to a particular mechanism(s), it is contemplated that induction of apoptosis by gossypol is dose-dependent. At administrations of 10.0 and 20.0 μM, respectively, gossypol induced 74% and 96% of cancer cells, again respectively, to undergo apoptosis. MDA-MB-231 cells overexpress Bcl-2 and Bcl-$X_L$.

Figure 10:
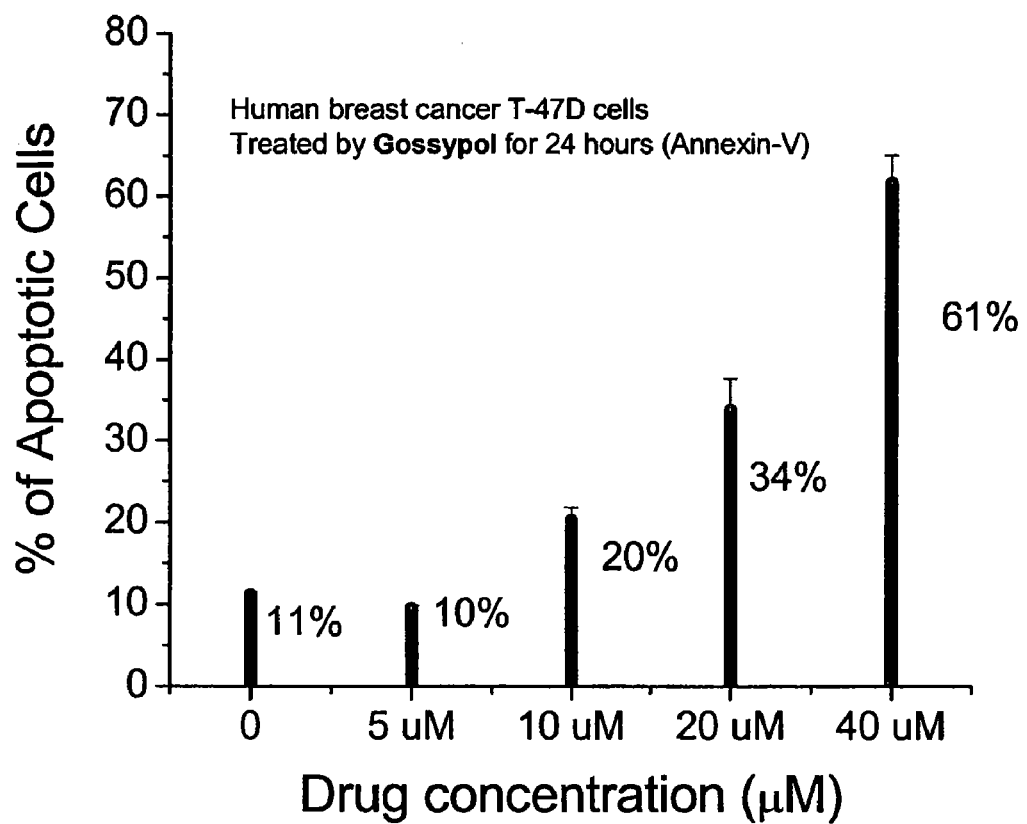
FIG. 10 shows the results of cell based assays in various embodiments of the present invention.

Since gossypol (e.g., racemic gossypol, (−)-gossypol and (+)-gossypol) is a potent inhibitor of Bcl-$X_L$, the present invention contemplates that in certain embodiments, gossypol induces apoptosis in cancer cells with high levels of Bcl-$X_L$ expression but low levels of Bcl-2. Indeed, gossypol induces dose-dependent apoptosis in human T-47D breast cancer cells, which as shown above, have high levels of Bcl-$X_L$ but low levels of Bcl-2. FIG. 10 shows the dose dependent induction of apoptosis in human TD-47 cancer cells treated with gossypol for 24 hours as detected using Annexin-V flow cytometry.

Since gossypol (e.g. racemic gossypol, (−)-gossypol and (+)-gossypol) is also a potent inhibitor of Bcl-2, the present invention contemplates that in certain embodiments, gossypol induces apoptosis in cancer cells with high expression levels of Bcl-2 expression but low levels of Bcl-$X_L$. Since gossypol binds to both Bcl-2 and Bcl-$X_L$ proteins, the present invention contemplates that, in certain embodiments, gossypol induces apoptosis in cancer cells with high levels of Bcl-2 and Bcl-$X_L$ expression.

These tests show that gossypol is a potent inhibitor of Bcl-$X_L$ and induces cancer cells expressing high levels (e.g., overexpression as compared to a basal expression rate for a normal example of the cell type) of Bcl-$X_L$ to undergo apoptosis, but does not induce apoptosis in cells with normal levels of Bcl-2 and Bcl-$X_L$ expression (e.g., WI-38 cells).

Preferred embodiments of the present invention provide methods of administering one or more gossypol compounds to a subject having a condition characterized by the overexpression of Bcl-2 family proteins. The gossypol compounds contemplated for use in the present inventive methods include, but are not limited to, (±)-gossypol; (−)-gossypol (Super G); (+)-gossypol; (±)-gossypolone; (−)-gossypolone; (+)-gossypolone; (±)-gossypol acetic acid; (−)-gossypol acetic acid; (+)-gossypol acetic acid; (±)-ethyl gossypol; (−)-ethyl gossypol; (+)-ethyl gossypol; (±)-hemigossypolone; (−)-hemigossypolone; (+)-hemigossypolone; Schiff's base of (±)-gossypol; Schiff's base of (−)-gossypol; Schiff's base of (+)-gossypol; Schiff's base of (O)-gossypolone; Schiff's base of (−)-gossypolone; Schiff's base of (+)-gossypolone; Schiff's base of (±)-gossypol acetic acid; Schiff's base of (−)-gossypol acetic acid; Schiff's base of (+)-gossypol acetic acid; Schiff's base of (±)-ethyl gossypol; Schiff's base of (−)-ethyl gossypol; Schiff's base of (+)-ethyl gossypol; Schiff's base of (±)-hemigossypolone; Schiff's base of (−)-hemigossypolone; Schiff's base of (+)-hemigossypolone, (±)-apogossypol, (−)-apogossypol, (+)-apogossypol, (±)-apogossypol acetic acid, (−)-apogossypol acetic acid, (+)-apogossypol acetic acid, (±)-ethyl apogossypol, (−)-ethyl apogossypol, (+)-ethyl apogossypol as well as derivatives, metabolites, isomers, acids, and pharmaceutically acceptable salts thereof.

In particularly, preferred embodiments, the (−)-gossypol enantiomer (including derivatives, metabolites, acids, Schiff's bases and pharmaceutically acceptable salts thereof) are administered to a subject or to in vitro cells, tissues, or organs.

Figure 11A:
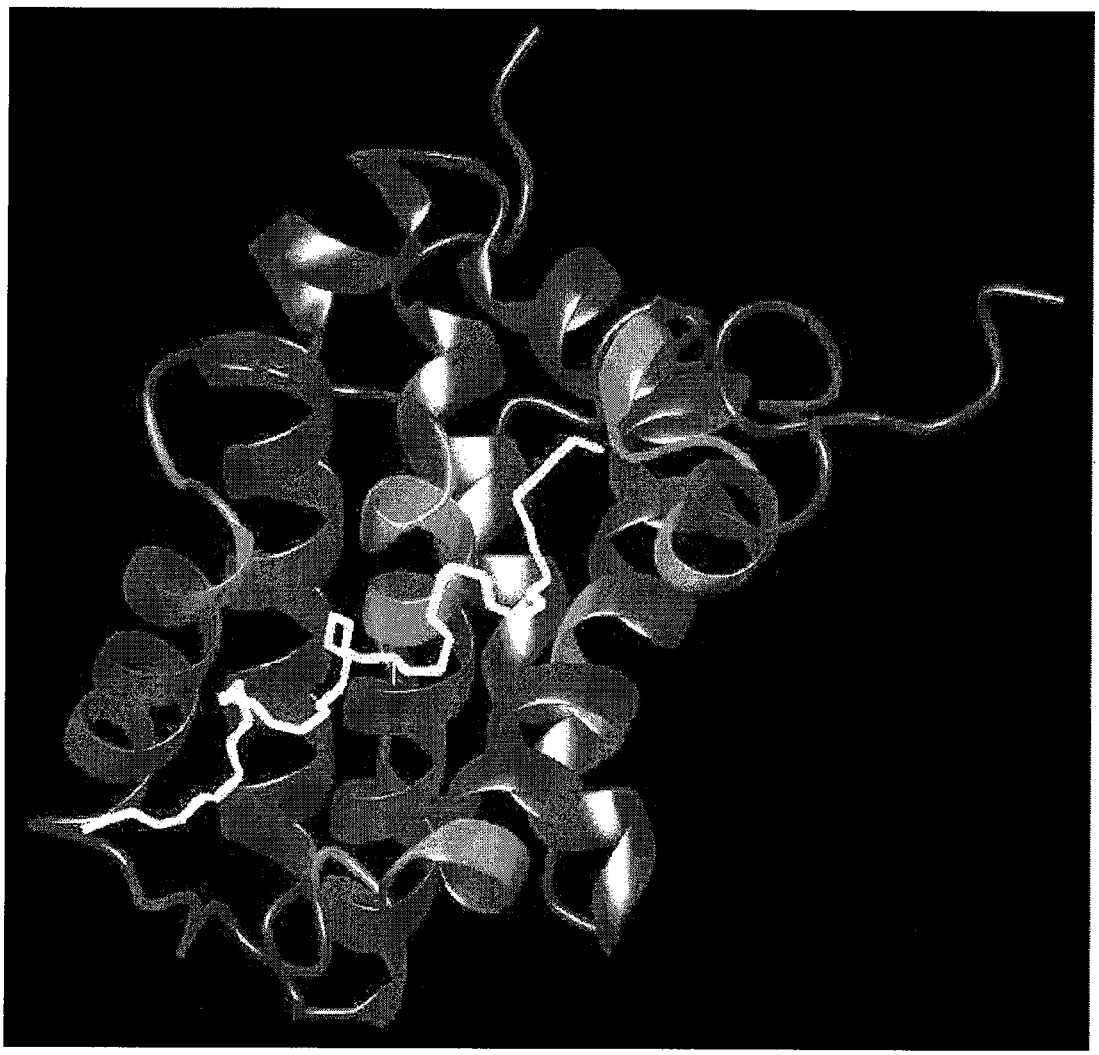
FIGS. 11A and 11B show the results of the interactions between (−)-gossypol and Bcl-$X_L$ protein using $^{15}N$ Heteronuclear Single Quantum Coherence Spectroscopy (HSQC) NMR methods in various embodiments of the present invention.
Figure 11B:
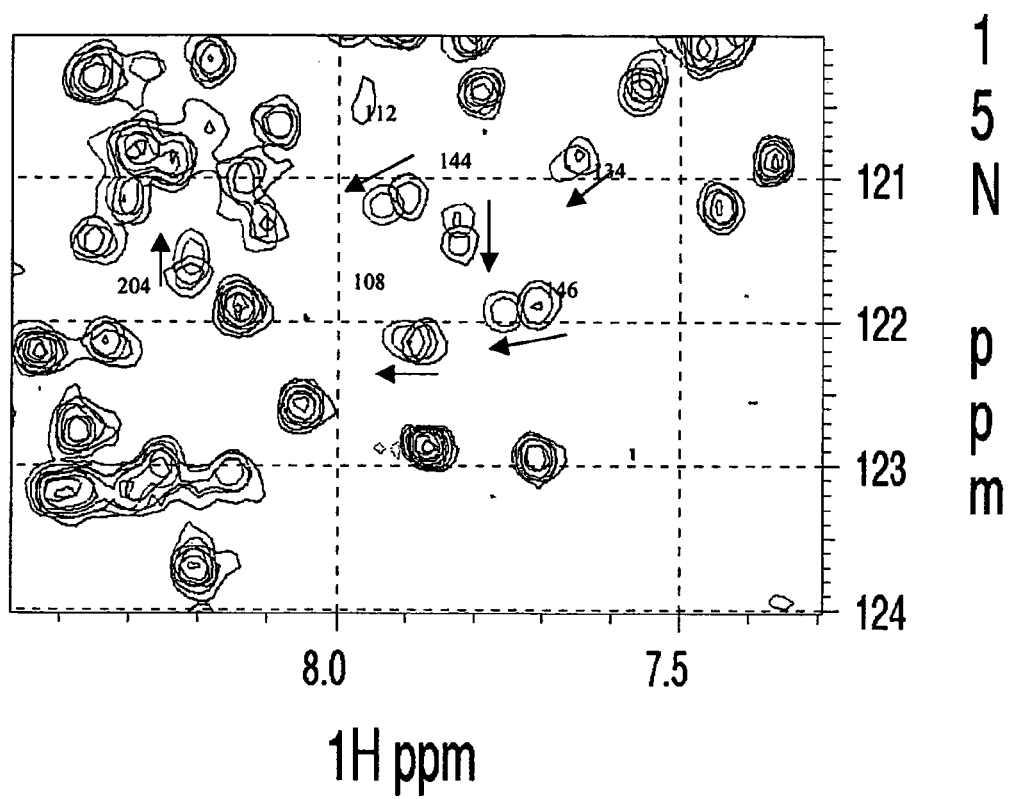
Figure 12:
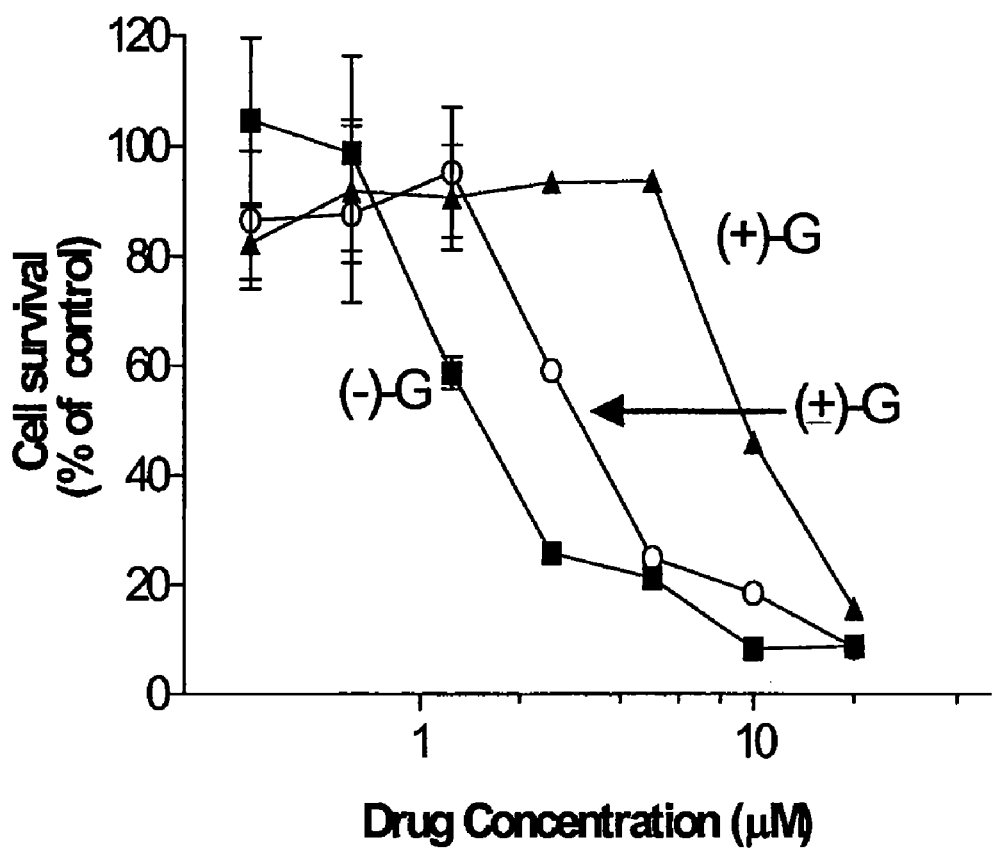
FIG. 12 shows the results of cell based assays in one embodiment of the present invention.

NMR analysis of the binding of the (−)-gossypol enantiomer shows that the (−)-gossypol specifically binds to the BH3 binding groove in Bcl-$X_L$ (See, FIGS. 11A and 11B). FIG. 12 shows data from growth inhibition experiments comparing (−)-gossypol and (+)-gossypol enantiomers and racemic gossypol in the MDA-MB-231 (2-LMP) breast cancer cell line using a 5-day MTT assay.

Additional experiments showed that the $T_{1/2}$ of elimination of (+)-gossypol enantiomer in humans is 29 times that of (−)-gossypol. In some embodiments, the present invention contemplates that the longer residency of the (+)-gossypol enantiomer is potentially beneficial in certain prolonged gossypol treatments methods. Therefore, in some embodiments, the (+)-gossypol enantiomer is potentially more toxic to cells. In still some embodiments, the present invention contemplates that the longer residency of the (+)-gossypol enantiomer is potentially beneficial in certain prolonged gossypol treatments methods.

In other embodiments, (−)-gossypol is administered to patients having a condition characterized by the overexpression of a Bcl-2 family protein. Table 1 compares the inhibition of cell growth in a number of head-neck cancer cell lines treated with (−)-gossypol and cisplatin (CTTP) (a standard agent for the treatment head-neck cancers). Briefly, Table 1 compares the inhibition of cell growth demonstrated by (−)-gossypol and cisplatin in a panel of human head-neck cancer cells and the expression status of Bcl-2 family proteins (Bcl-2, Bcl-$X_L$ and Bcl-$X_S$). The $IC_{50}$ value is the concentration of the drug (e.g., (−)-gossypol and cisplatin) required to inhibit the cell growth by 50% as compared to control cells.

TABLE 1

|  | (−)-gossypol ($IC_{50}$, μM) | Bcl-$X_L$ | Bcl-$X_S$ | Bcl-2 | Cisplatin ($IC_{50}$, μM) |
| --- | --- | --- | --- | --- | --- |
| UM-SCC-23 | 1.5 | +++ | + | − | 25 |
| UM-SCC-1 | 1.5 | +++ | + | − | 30 |
| UM-SCC-6 | 11 | +++ | +++ | − | >50 |
| UM-SCC-22A | 3 | ++ | + | − | 5 |
| UM-SCC-12 | 4 | ++ | + | − | 22 |
| UM-SCC-81B | 4 | ++ | − | − | 22 |
| UM-SCC-17B | 5 | ++ | + | ++ | 13 |
| UM-SCC-14A | 11 | + | +++ | − | 29 |
| UM-SCC-74B | 4 | − | + | ++ | 12 |
| UM-SCC-25 | 8 | + | − | − | 43 |
| Fib-1 | 20 | − | − | − | >50 |
| Fib-2 | 20 | − | − | − | >50 |
| Fib-3 | 18 | − | − | − | >50 |

V. Proposed Mechanism of Gossypol Activity

Figure 13:
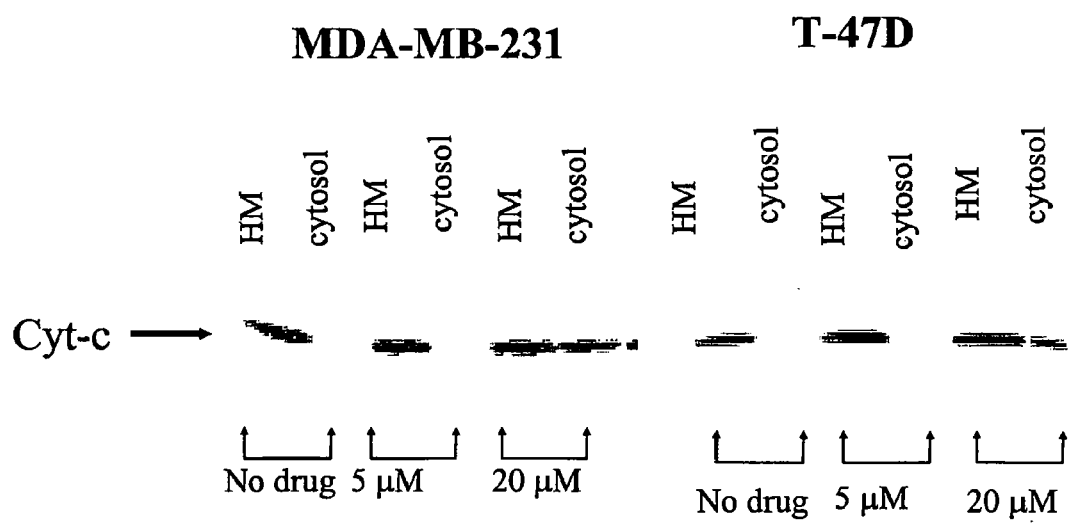
FIG. 13 shows the results of cell based assays in one embodiment of the present invention.

Although an understanding of any particular proposed mechanism is not necessary to make and use the compositions and methods of the present invention and the present invention is not limited to any particular mechanism(s), it is contemplated that one of the key molecules in the Bcl-2/Bcl-$X_L$ mediated apoptosis pathway is cytochrome-c (Cyt-c). It is further contemplated that one of the key functions of Bcl-2/Bcl-$X_L$ is to heterodimerize with Bax, Bak, or Bad and to block release of Cyt-c from mitochondria. Thus, the ability of gossypol to induce Cyt-c release from mitochondria to the cytosol in cancer cells was tested. Breast cancer cell lines MDA-231 and T47D were treated with either 5 or 20 μM of gossypol for 24 hours. FIG. 13 shows that Cyt-c was released from mitochondria into the cytosol after treatment with 20 μM of gossypol in both the MDA-231 and T47D breast cancer cell lines (HM, Cyt-c found in the heavy membrane; Cytosol, Cyt-c found in the cytosol).

Figure 14:
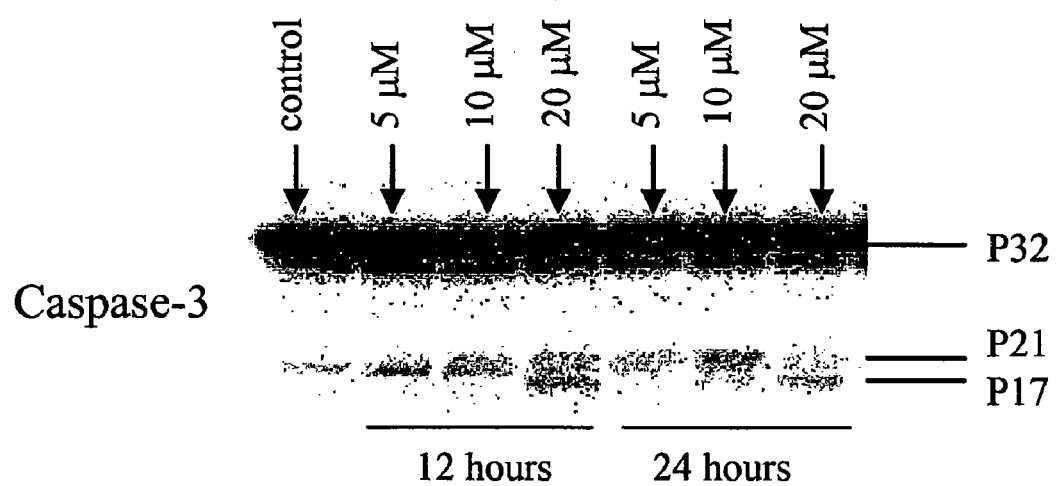
FIG. 14 shows the results of cell based assays in one embodiment of the present invention.

It is also contemplated that Bcl-2 mediated apoptosis involves caspase (e.g. caspase-3 and -9) activation once Cyt-c is released from the mitochondria. Therefore, tests were conducted to determine whether gossypol activates caspase-3. In one embodiment, the amount of caspase-3 cleavage in lysates of MDA-231 breast cancer cells was measured after 12 or 24 hours following treatment with gossypol. FIG. 14 shows that caspase-3 was cleaved after treatment with gossypol into 17 and 21 kD fragments in a dose dependent manner. Similar results were obtained in T-47D human breast cancer cells and HT-29 colon cancer cells treated with gossypol, both of which have high levels of Bcl-$X_L$ expression and relatively low levels of Bcl-2 expression following treatment with gossypol.

In contrast, treatment of human DU-145 prostate cancer cells, having low Bcl-2 and Bcl-$X_L$ expression, with 5, 10, or 20 μM of gossypol for 24 hours had no effect on caspase-3 activation. Therefore, activation of caspase-3 by gossypol is specific and correlative to expression levels of Bcl-2 and Bcl-$X_L$ in cancer cells.

VI. Activity of Gossypol in MDA-231 Xenograft Mice Alone and in Combination with Conventional Anticancer Agents The potential of gossypol compounds as anticancer therapeutics was further evaluated in MDA-231 xenograft mice. A gossypol treatment regime was started at day 7 after tumors had grown to 8-10 mm in diameter. Each treatment group had five mice bearing two tumors each (one tumor on each side). A control group of five mice received no gossypol. In the treated mice, gossypol was administered daily in two different oral doses, a 30 and a 90 mg/kg dose, for three weeks. It was found that at both 30 and 90 mg/kg daily doses, there is more than 70% inhibition of tumor growth by gossypol with more than a 95% confidence level at day 29. No weight loss or deaths were seen in the mice treated with gossypol. There did not appear to be any significant difference in the anticancer activity of gossypol in the 30 mg/kg and 90 mg/kg doses. These results suggest that a 30 mg/kg daily dose of gossypol successfully inhibits tumor growth without supplementing the gossypol therapy with adjuvants or additional anticancer compounds or therapies.

Overexpression of Bcl-2 and/or Bcl-$X_L$ proteins appears to protect cancer cells from apoptosis induced by some conventional anticancer therapies (e.g., docetaxel). Some embodiments of the present invention, therefore, provide methods for administering an effective dose(s) of gossypol (and enantiomers, derivatives, acids (e.g., acetic acid) and pharmaceutically acceptable salts thereof) in combination with at least one conventional anticancer therapy (e.g., chemotherapeutic agents, such as docetaxel and/or radiation therapy). In preferred embodiments, gossypol is administered in combination with one or more conventional anticancer therapies to treat diseases (e.g., cancer) characterized by overexpression of Bcl-2 family proteins (e.g., Bcl-2 and/or Bcl-$X_L$). In one embodiment of the present invention, when gossypol is administered, it is not co-administered with radiation and heat.

Although an understanding of any mechanism is not necessary to practice the present invention and the present invention is not so limited, it is contemplated that administration of at least one gossypol compound sensitizes cancer cells having high levels of expression of Bcl-2 family proteins (e.g., Bcl-2 and/or Bcl-$X_L$) which are resistant to conventional anticancer therapies, to treatment with additional anticancer agents (e.g., docetaxel). The present invention is, however, not limited to the administration of any particular combination of gossypol compounds and anticancer therapeutic agents, nor is the invention limited to any particular sequence or level of agents being administered.

In one embodiment of the present invention, the co-administration of a gossypol compound and one or more anticancer agents produces a synergistic effect, i.e., an effect that is more than the additive effect of each compound administered individually. In a further embodiment of the present invention, the co-administration of a gossypol compound and one or more anticancer agents allows lower doses of the gossypol compound and/or the one or more anticancer agents to be used. The ability to achieve efficacy using lower doses allows the administration of doses that do not induce any substantial toxicity in the subject. In another embodiment of the present invention, the co-administration of a gossypol compound and one or more anticancer agents may lead to complete regression of a tumor whereas either compound alone would provide only a partial regression. In a further embodiment of the present invention, the administration of a gossypol compound sensitizes neoplastic cells to the therapeutic effect of anticancer agents. Thus, a lower dose of the anticancer agent is sufficient to kill the neoplastic cells when co-administered with a gossypol compound.

Examples of lower dose ranges of gossypol compounds and some anticancer agents that can be used in combination with gossypol compounds for the treatment of particular cancers are presented in Tables 2-4 below. These examples are not intended to limit the present invention in any way.

TABLE 2

| | Racemic Gossypol | Cisplatin | Docetaxel | Radiation |
|---|---|---|---|---|
| Breast Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-30 mg/m$^2$ every wk; 5, 10, 15, 20, 25, 30 mg/m$^2$ every wk; 5-120 mg/m$^2$ every 3 wk; 5, 10, 15, 20, 25, 30, 35, 40, 45, 50, 55, 60, 65, 70, 75, 80, 85, 90, 95, 100, 105, 110, 115, 120 mg/m$^2$ every 3 wk | 10-40 mg/m$^2$ every wk; 10, 15, 20, 25, 30, 35, 40 mg/m$^2$ every wk; 10-60 mg/m$^2$ every 2 wk; 10, 15, 20, 25, 30, 35, 40, 45, 50, 55, 60 mg/m$^2$ every 2 wk; 20-100 mg/m$^2$ every 3 wk; 20, 25, 30, 35, 40, 45, 50, 55, 60, 65, 70, 75, 80, 85, 90, 95, 100 mg/m$^2$ every 3 wk | 2-65 Gy total dose; 2, 5, 10, 15, 20, 25, 30, 35, 40, 45, 50, 55, 60, 65 Gy total dose |
| Prostate Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-20 mg/m$^2$/d for 3 d; 5, 10, 15, 20 mg/m$^2$/d for 3 d; 5-20 mg/m$^2$ every other d; 5, 10, 15, 20 mg/m$^2$ every other d; 10-70 mg/m$^2$ every 4 wk; 10, 15, 20, 25, 30, 35, 40, 45, 50, 55, 60, 65, 70 mg/m$^2$ every 4 wk | 5-35 mg/m$^2$/d for 2 d; 5, 10, 15, 20, 25, 30, 35 mg/m$^2$/d for 2 d; 5, 10, 15, 20, 25 mg/m$^2$/d for 4 d | 2-78 Gy total dose; 2, 5, 10, 15, 20, 25, 30, 35, 40, 45, 50, 55, 60, 65, 70, 75, 78 Gy total dose |

TABLE 2-continued

|  | Racemic Gossypol | Cisplatin | Docetaxel | Radiation |
|---|---|---|---|---|
| Colon Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-30 mg/m$^2$/d for 3 d; 5, 10, 15, 20, 25, 30 mg/m$^2$/d for 3 d | 10-185 mg/m$^2$ every 3 wk; 10, 15, 25, 35, 45, 55, 65, 75, 85, 95, 105, 115, 125, 135, 145,, 155, 165, 175, 185 mg/m$^2$ every 3 wk | 2-60 Gy total dose; 2, 5, 10, 15, 20, 25, 30, 35, 40, 45, 50, 55, 60 Gy total dose |
| Pancreatic Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 25-50 mg/m$^2$ every wk; 25, 30, 35, 40, 45, 50 mg/m$^2$ every wk; 5-15 mg/m$^2$ every 3 wk; 5, 10, 15 mg/m$^2$ every 3 wk; 10-100 mg/m$^2$ every 4 wk; 10, 15, 20, 25, 30, 35, 40, 45, 50, 55, 60, 65, 70, 75, 80, 85, 90, 95, 100 mg/m$^2$ every 4 wk | 5-35 mg/m$^2$ every wk; 5, 10, 15, 20, 25, 30, 35 mg/m$^2$ every wk; 6-100 mg/m$^2$ every 3 wk; 6, 10, 15, 20, 25, 30, 35, 40, 45, 50, 55, 60, 65, 70, 75, 80, 85, 90, 95, 100 mg/m$^2$ every 3 wk; 6-60 mg/m$^2$ every 4 wk; 6, 10, 15, 20, 25, 30, 35, 40, 45, 50, 55, 60 mg/m$^2$ every 4 wk | 2-65 Gy total dose; 2, 5, 10, 15, 20, 25, 30, 35, 40, 45, 50, 55, 60, 65 Gy total dose |
| Head/Neck Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40-400 mg every wk; 40, 50, 60, 70, 80, 90, 100, 120, 140, 160, 180, 200, 220, 240, | 5-20 mg/m$^2$/d for 3 d; 5, 10, 15, 20 mg/m$^2$/d for 3 d; 5-10 mg/m$^2$ every wk; 5, 7.5, 10 mg/m$^2$ every wk; 10-65 mg/m$^2$ every 2 wk; 10, 15, 20, 25, 30, 35, 40, 45, 50, 55, 60, 65 mg/m$^2$ every 2 wk; 10-100 mg/m$^2$ every 3 wk; 10, 15, 20, 25, 30, 35, 40, 45, 50, 55, 60, 65, 70, 75, 80, 85, 90, 95, 100 mg/m$^2$ every 3 wk; 5-20 mg/m$^2$ for | 2-40 mg/m$^2$ every wk; 2, 5, 10, 15, 20, 25, 30, 35, 40 mg/m$^2$ every wk; 6-60 mg/m$^2$ every 3 wk; 6, 10, 15, 20, 25, 30, 35, 40, 45, 50, 55, 60 mg/m$^2$ every 3 wk; 6-80 mg/m$^2$ every 4 wk; 6, 10, 15, 20, 25, 30, 35, 40, 45, 50, 55, 60, 65, 70, 75, 80 mg/m$^2$ every 4 wk | 2-66 Gy total dose; 2, 5, 10, 15, 20, 25, 30, 35, 40, 45, 50, 55, 60, 66 Gy total dose |

TABLE 2-continued

| | Racemic Gossypol | Cisplatin | Docetaxel | Radiation |
|---|---|---|---|---|
| | 260, 280, 300, 320, 340, 360, 380, 400 mg every week | 5 d every 4 wk; 5, 10, 15, 20 mg/m$^2$/d for 5 d every 4 wk | | |
| Non-Small Cell Lung Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-30 mg/m$^2$/d for 2 d every 3 wk; 5, 10, 15, 20, 25, 30 mg/m$^2$/d for 2 d every 3 wk; 10-100 mg/m$^2$ every 3 wk; 10, 15, 20, 25, 30, 35, 40, 45, 50, 55, 60, 65, 70, 75, 80, 85, 90, 95, 100 mg/m$^2$ every 3 wk; 10-100 mg/m$^2$/d every 4 wk; 10, 15, 20, 25, 30, 35, 40, 45, 50, 55, 60, 65, 70, 75, 80, 85, 90, 95, 100 mg/m$^2$/d every 4 wk | 5-40 mg/m$^2$ every wk; 5, 10, 15, 20, 25, 30, 35, 40 mg/m$^2$ every wk; 6-175 mg/m$^2$ every 3 wk; 6, 10, 15, 25, 35, 45, 55, 65, 75, 85, 95, 105, 115, 125, 135, 145, 155, 165, 175 mg/m$^2$ 8-80 mg/m$^2$ every 4 wk; 8, 15, 20, 25, 30, 35, 40, 45, 50, 55, 60, 65, 70, 75, 80 mg/m$^2$ every 4 wk | 2-86 Gy total dose; 2, 5, 10, 15, 20, 25, 30, 35, 40, 45, 50, 55, 60, 65, 70, 75, 80, 86 Gy total dose |
| Melanoma | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 10-80 mg/m$^2$ every wk; 10, 15, 20, 25, 30, 35, 40, 45, 50, 55, 60, 65, 70, 75, 80 mg/m$^2$ every wk; 5-20 mg/m$^2$ for 4 d every 2 wk; 5, 10, 15, 20 mg/m$^2$/d for 4 d every 2 wk; 5-25 mg/m$^2$/d for 2 d every 3 wk; 5, 10, 15, 20, 25 mg/m$^2$/d for 2 d every 3 wk; 5-30 mg/m$^2$/d for 3 d every 3 wk; 5, 10, 15, 20, 25, 30 mg/m$^2$/d for 3 d every 3 wk; 10-100 mg/m$^2$ every 3 wk; 10, 15, 20, 25, 30, 35, 40, 45, 50, 55, 60, 65, 70, 75, 80, 85, 90, 95, 100 mg/m$^2$ every 3 wk | 5-100 mg/m$^2$ every 3 wk; 5, 10, 15, 20, 25, 30, 35, 40, 45, 50, 55, 60, 65, 70, 75, 80, 85, 90, 95, 100 mg/m$^2$ every 3 wk; 8-80 mg/m$^2$ every 4 wk; 8, 10, 15, 20, 25, 30, 35, 40, 45, 50, 55, 60, 65, 70, 75, 80 mg/m$^2$ every 4 wk | 2-60 Gy total dose; 2, 5, 10, 15, 20, 25, 30, 35, 40, 45, 50, 55, 60 Gy total dose |
| Ovarian Cancer | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; | 10-100 mg/m$^2$ every 3 wk; 10, 15, 20, 25, 30, 35, 40, 45, 50, 55, 60, 65, 70, 75, 80, 85, 90, 95, 100 mg/m$^2$ every 3 wk; 10-100 mg/m$^2$ every 4 wk; 10, 15, 20, 25, 30, 35, 40, 45, 50, 55, 60, 65, 70, 75, 80, 85, 90, 95, 100 mg/m$^2$ | 5-30 mg/m$^2$ every wk; 5, 10, 15, 20, 25, 30 mg/m$^2$ every wk; 5-60 mg/m$^2$ every 2 wk; 5, 10, 15, 20, 25, 30, 35, 40, 45, 50, 55, 60 mg/m$^2$ every 2 wk; 10-100 mg/m$^2$ every 3 wk; 10, 15, 20, 25, 30, 35, 40, 45, | 2-52 Gy total dose; 2, 5, 10, 15, 20, 25, 30, 35, 40, 45, 50, 52 Gy total dose |

TABLE 2-continued

|  | Racemic Gossypol | Cisplatin | Docetaxel | Radiation |
|---|---|---|---|---|
|  | 40-400 mg every wk; 40, 50, 60, 70, 80, 90, 100, 120, 140, 160, 180, 200, 220, 240, 260, 280, 300, 320, 340, 360, 380, 400 mg every week | every 4 wk | 50, 55, 60, 65, 70, 75, 80, 85, 90, 95, 100 mg/m² every 3 wk; 6-60 mg/m² every 4 wk; 6, 10, 15, 20, 25, 30, 35, 40, 45, 50, 55, 60 mg/m² every 4 wk |  |
| Lymphoma | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-25 mg/m²/d for 4 d; 5, 10, 15, 20, 25 mg/m²/d for 4 d; 10-75 mg/m² every 3 wk; 10, 15, 20, 25, 30, 35, 40, 45, 50, 55, 60, 65, 70, 75 mg/m² every 3 wk | 10-100 mg/m² every 3 wk; 10, 15, 20, 25, 30, 35, 40, 45, 50, 55, 60, 65, 70, 75, 80, 85, 90, 95, 100 mg/m² every 3 wk | 2-55 Gy total dose; 2, 5, 10, 15, 20, 25, 30, 35, 40, 45, 50, 55 Gy total dose |
| Hepatoma | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-30 mg/m² every wk; 5, 10, 15, 20, 25, 30 mg/m² every wk; 10-80 mg/m²; 10, 15, 20, 25, 30, 35, 40, 45, 50, 55, 60, 65, 70, 75, 80 mg² | 5-36 mg/m² every wk; 5, 10, 15, 20, 25, 30, 36 mg/m² every wk; 5-40 mg/m² every 3 wk; 5, 10, 15, 20, 25, 30, 35, 40 mg/m² every 3 wk; 10-60 mg/m² every 4 wk; 10, 15, 20, 25, 30, 35, 40, 45, 50, 55, 60 mg/m² every 4 wk | 2-70 Gy total dose; 2, 5, 10, 15, 20, 25, 30, 35, 40, 45, 50, 55, 60, 65, 70 Gy total dose |
| Sarcoma | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; | 5-20 mg/m²/d for 5 d every 3 wk; 5, 10, 15, 20 mg/m²/d for 5 d every 3 wk; 5-20 mg/m²/d for 5 d every 4 wk; 5, 10, 15, 20 mg/m²/d for 5 d every 4 wk; 5-30 mg/m²; 5, 10, 15, 20, 25, 30 mg/m² | 4-100 mg/m² every 3 wk; 4, 10, 15, 20, 25, 30, 35, 40, 45, 50, 55, 60, 65, 70, 75, 80, 85, 90, 95, 100 mg/m² every 3 wk | 2-66 Gy total dose; 2, 5, 10, 15, 20, 25, 30, 35, 40, 45, 50, 55, 60, 66 Gy total dose |

TABLE 2-continued

| | Racemic Gossypol | Cisplatin | Docetaxel | Radiation |
|---|---|---|---|---|
| | 40-400 mg every wk; 40, 50, 60, 70, 80, 90, 100, 120, 140, 160, 180, 200, 220, 240, 260, 280, 300, 320, 340, 360, 380, 400 mg every week | | | |
| Chronic Lymphocytic Leukemia | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | 5-35 mg/m$^2$/d for 2 d; 5, 10, 15, 20, 25, 30, 35 mg/m$^2$/d for 2 d; 5-25 mg/m$^2$/d for 4 d; 5, 10, 15, 20, 25 mg/m$^2$/d for 4 d | | 2-8 Gy total dose; 2, 4, 6, 8 Gy total dose |
| Acute Myelogenous Leukemia | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; 40-400 mg every wk; 40, 50, 60, 70, 80, 90, 100, 120, 140, 160, 180, 200, 220, 240, 260, 280, 300, 320, 340, 360, 380, 400 mg every week | | | 2-45 Gy total dose; 2, 5, 10, 15, 20, 25, 30, 35, 40, 45 Gy total dose |
| Multiple Myeloma | 1-200 mg/d; 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 mg/d; 40-400 mg every wk; | | 10-75 mg/m$^2$ every 3 wk; 10, 15, 20, 25, 30, 35, 40, 45, 50, 55, 60, 65, 70, 75 mg/m$^2$ every 3 wk | 2-40 Gy total dose; 2, 5, 10, 15, 20, 25, 30, 35, 40 Gy total dose |

TABLE 2-continued

| Racemic Gossypol | Cisplatin | Docetaxel | Radiation |
|---|---|---|---|
| 40-400 mg every wk; 40, 50, 60, 70, 80, 90, 100, 120, 140, 160, 180, 200, 220, 240, 260, 280, 300, 320, 340, 360, 380, 400 mg every week | | | |

TABLE 3

| | Gemcitabine | CHOP | Carboplatin | Doxorubicin |
|---|---|---|---|---|
| Breast Cancer | 100-1200 mg/m$^2$ every wk; 100, 200, 300, 400, 500, 600, 700, 800, 900, 100, 1100, 1200 mg/m$^2$ every wk; 100-2,000 mg/m$^2$ every 2 wk; 100, 200, 400, 600, 800, 1000, 1200, 1400, 1600, 1800, 2000 mg/m$^2$ every 2 wk; 150-1500 mg/m$^2$ every 3 wk; 150, 300, 600, 900, 1200, 1500 mg/m$^2$ every 3 wk | C-100-1000 mg/m$^2$; H-10-50 mg/m$^2$; O-1-2 mg/m$^2$; P-10-40 mg; C-100, 200, 300, 400, 500, 600, 700, 800, 900, 1000 mg/m$^2$; H-10, 20, 30, 40, 50 mg/m$^2$; O-1, 1.2, 1.4, 1.6, 1.8, 2 mg/m$^2$; P-10, 20, 30, 40 mg | 40-265 mg/m$^2$/d for 4 d; 40, 80, 120, 160, 200, 265 mg/m$^2$/d for 4 d; 5-20 mg/m$^2$/d for 20 d; 5, 10, 15, 20 mg/m$^2$/d for 20 d; 50-300 mg/m$^2$ every 4 wk; 50, 100, 150, 200, 250, 300 mg/m$^2$ every 4 wk; 500-1600 mg/m$^2$; 500, 750, 1000, 1250, 1600 mg/m$^2$ | 2-20 mg/m$^2$ every wk; 2, 4, 6, 8, 10, 12, 14, 16, 18, 20 mg/m$^2$ every wk; 10-75 mg/m$^2$ every 2 wk; 10, 20, 30, 40, 50, 60, 75 mg/m$^2$ every 2 wk; 10-75 mg/m$^2$ every 3 wk; 10, 20, 30, 40, 50, 60, 75 mg/m$^2$ every 3 wk; 10-50 mg/m$^2$ every 4 wk; 10, 15, 20, 25, 30, 35, 40, 45, 50 mg/m$^2$ every 4 wk; 5-30 mg/m$^2$/d for 3 d every 4 wk; 5, 10, 15, 20, 25, 30 mg/m$^2$/d for 3 d every 4 wk |
| Prostate Cancer | 60-1200 mg/m$^2$ every 2 wk; 60, 120, 200, 400, 600, 800, 100, 1200 mg/m$^2$ every 2 wk | | 40-800 mg/m$^2$ every 4 wk; 40, 100, 200, 300, 400, 500, 600, 700, 800 mg/m$^2$ every 4 wk; 2-20 mg/m$^2$/d for 21 d every 6 wk; 2, 4, 8, 12, 16, 20 mg/m$^2$/d for 21 d every 6 wk | 2-20 mg/m$^2$ every wk; 2, 4, 6, 8, 10, 12, 14, 16, 18, 20 mg/m$^2$ every wk; 4-50 mg/m$^2$ every 3 wk; 4, 10, 15, 20, 25, 30, 35, 40, 45, 50 mg/m$^2$ every 3 wk; 3-50 mg/m$^2$ every 4 wk; 3, 6, 10, 15, 20, 25, 30, 35, 40, 45, 50 mg/m$^2$ every 4 wk |
| Colon Cancer | 60-2200 mg/m$^2$ every wk; 60, 120, 200, 400, 600, 800, 1000, 1200, 1400, 1600, 1800, 2000, 2200 mg/m$^2$ every wk | | 2-20 mg/m$^2$/d for 20 d; 2, 4, 8, 12, 16, 20 mg/m$^2$/d for 20 d | 3-30 mg/m$^2$ every wk; 3, 6, 10, 15, 20, 25, 30 mg/m$^2$ every wk; 1-15 mg/m$^2$/d for 4 d; 1, 3, 5, 7, 9, 11, 13, 15 mg/m$^2$/d for 4 d |
| Pancreatic Cancer | 100-1500 mg/m$^2$ every wk; 100, 300, 500, 700, 900, 1100, 1300, 1500 mg/m$^2$ every wk | | 10-100 mg/m$^2$ every wk; 10, 20, 30, 40, 50, 60, 70, 80, 90, 100 mg/m$^2$ every wk; 30-300 mg/m$^2$ every 3 wk; | 4-40 mg/m$^2$ every 3 wk; 4, 8, 12, 16, 20, 24, 28, 32, 36, 40 mg/m$^2$ every 3 wk; 2-40 mg/m$^2$ every 4 wk; 2, 4, 8, 12, 16, |

TABLE 3-continued

| | Gemcitabine | CHOP | Carboplatin | Doxorubicin |
|---|---|---|---|---|
| | | | 30, 60, 90, 120, 150, 180, 210, 240, 270, 300 mg/m$^2$ every 3 wk; 20-200 mg/m$^2$ every 8 wk; 20, 40, 60, 80, 100, 120, 140, 160, 180, 200 mg/m$^2$ every 8 wk | 20, 24, 28, 32, 36, 40 mg/m$^2$ every 4 wk |
| Head/Neck Cancer | 50-1800 mg/m$^2$ every wk; 50, 150, 300, 600, 900, 1200, 1500, 1800 mg/m$^2$ every wk | | 10-90 mg/m$^2$ every wk; 10, 20, 30, 40, 50, 60, 70, 80, 90 mg/m$^2$ every wk; 10-70 mg/m$^2$/d for 5 d every 4 wk; 10, 20, 30, 40, 50, 60, 70 mg/m$^2$/d for 5 d every 4 wk | 2-20 mg/m$^2$ every wk; 2, 4, 6, 8, 10, 12, 14, 16, 18, 20 mg/m$^2$ every wk; 5-75 mg/m$^2$ every 3 wk; 5, 15, 25, 35, 45, 55, 65, 75 mg/m$^2$ every 3 wk; 5-30 mg/m$^2$ every 4 wk; 5, 10, 15, 20, 25, 30 mg/m$^2$ every 4 wk; 5-30 mg/m$^2$/d for 3 d every 4 wk 5, 10, 15, 20, 25, 30 mg/m$^2$/d for 3 d every 4 wk |
| Non-Small Cell Lung Cancer | 75-1500 mg/m$^2$ every wk; 75, 150, 300, 600, 900, 1200, 1500 mg/m$^2$ every wk | | 4-40 mg/m$^2$/d for 33 d; 4, 10, 15, 20, 25, 30, 35, 40 mg/m$^2$/d for 33 d | 5-55 mg/m$^2$ every 2 wk; 5, 10, 15, 20, 25, 30, 35, 40, 45, 50, 55 mg/m$^2$ every 2 wk; 5-50 mg/m$^2$ every 3 wk; 5, 10, 15, 20, 25, 30, 35, 40, 45, 50 mg/m$^2$ every 3 wk; 5-30 mg/m$^2$ every 4 wk; 5, 10, 15, 20, 25, 30 mg/m$^2$ every 4 wk |
| Melanoma | 80-1000 mg/m$^2$ every wk; 80, 150, 300, 500, 750, 1000 mg/m$^2$ every wk | | 40-400 mg/m$^2$ every 3 wk; 40, 80, 120, 160, 200, 240, 280, 320, 360, 400 mg/m$^2$ every 3 wk; 30-400 mg/m$^2$ every 4 wk; 30, 50, 100, 150, 200, 250, 300, 350, 400 mg/m$^2$ every 4 wk | 5-50 mg/m$^2$ every 3 wk; 5, 10, 15, 20, 25, 30, 35, 40, 45, 50 mg/m$^2$ every 3 wk |
| Ovarian Cancer | 60-1250 mg/m$^2$ every wk; 60, 120, 250, 500, 750, 1000, 1250 mg/m$^2$ every wk; 80-2000 mg/m$^2$ every 2 wk; 80, 2090, 400, 600, 800, 1000, 1200, 1400, 1600, 1800, 2000 mg/m$^2$ every 2 wk | | 30-360 mg/m$^2$ every 4 wk; 30, 60, 90, 120, 150, 180, 210, 240, 270, 300, 330, 360 mg/m$^2$ every 4 wk | 4-50 mg/m$^2$ every wk; 4, 10, 15, 20, 25, 30, 35, 40, 45, 50 mg/m$^2$ every wk; 5-75 mg/m$^2$ every 3 wk; 5, 15, 25, 35, 45, 55, 65, 75 mg/m$^2$ every 3 wk; 5-30 mg/m$^2$/d for 3 d every 4 wk; 5, 10, 15, 20, 25, 30 mg/m$^2$/d for 3 d every 4 wk; 5-40 mg/m$^2$/d for 4 d; 5, 10, 15, 20, 25, 30, 35, 40 mg/m$^2$/d for 4 d |

TABLE 3-continued

|  | Gemcitabine | CHOP | Carboplatin | Doxorubicin |
|---|---|---|---|---|
| Lymphoma | 80-1250 mg/m² every wk; 80, 150, 250, 500, 750, 1000, 1250 mg/m² every wk; 1500-2000 mg/m² every 2 wk; 1500, 1600, 1700, 1800, 1900, 2000 mg/m² every 2 wk; 2-10 mg/m²/min for 12 hr; 2, 4, 6, 8, 10 mg/m²/min for 12 hr | C-100-1500 mg/m²; H-10-70 mg/m²; O-1-2 mg/m²; P-10-100 mg; C-100, 300, 500, 700, 900, 1100, 1300, 1500 mg/m²; H-10, 30, 50, 70 mg/m²; O-1, 1.2, 1.4, 1.6, 1.8, 2 mg/m²; P-10, 20, 30, 40, 50, 60, 70, 80, 90, 100 mg | 30-300 mg/m² every 3 wk; 30, 60, 90, 120, 150, 180, 210, 240, 270, 300 mg/m² every 3 wk; 30-400 mg/m² every 4 wk; 30, 50, 100, 150, 200, 250, 300, 350, 400 mg/m² every 4 wk | 2-20 mg/m² every wk; 2, 4, 6, 8, 10, 12, 14, 16, 18, 20 mg/m² every wk; 5-75 mg/m² every 3 wk; 5, 15, 25, 35, 45, 55, 65, 75 mg/m² every 3 wk; 5-80 mg/m² every 4 wk; 5, 10, 15, 20, 25, 30, 35, 40, 45, 50, 55, 60, 65, 70, 75, 80 mg/m² every 4 wk; 3-30 mg/m²/d for 3 d every 4 wk; 3, 6, 10, 15, 20, 25, 30 mg/m²/d for 3 d every 4 wk |
| Hepatoma |  |  | 70-700 mg/m² every 3 wk; 70, 150, 300, 450, 600, 700 mg/m² every 3 wk; 25-560 mg/m² every 4 wk; 25, 50, 100, 150, 200, 250, 300, 350, 400, 450, 500, 560 mg/m² every 4 wk | 2-20 mg/m² every wk; 2, 4, 6, 8, 10, 12, 14, 16, 18, 20 mg/m² every wk; 4-60 mg/m² every 3 wk; 4, 10, 15, 20, 25, 30, 35, 40, 45, 50, 55, 60 mg/m² every 3 wk; 3-50 mg/m² every 4 wk; 3, 5, 10, 15, 20, 25, 30, 35, 40, 45, 50 mg/m² every 4 wk |
| Sarcoma |  |  | 50-500 mg/m² every 3 wk; 50, 100, 150, 200, 250, 300, 350, 400, 450, 500 mg/m² every 3 wk; 30-300 mg/m² every 4 wk; 30, 60, 90, 120, 150, 180, 210, 240, 270, 300 mg/m² every 4 wk; 30-300 mg/m²/d for 4 d; 30, 60, 90, 120, 150, 180, 210, 240, 270, 300 mg/m² for 4 d | 3-60 mg/m² every 3 wk; 3, 5, 10, 15, 20, 25, 30, 35, 40, 45, 50, 55, 60 mg/m² every 3 wk; 5-75 mg/m² every 4 wk; 5, 15, 25, 35, 45, 55, 65, 75 mg/m² every 4 wk; 2-20 mg/m²/d for 3 d; 2, 4, 6, 8, 10, 12, 14, 16, 18, 20 mg/m²/d for 3 d; 1-4 mg/m²/d for 4 d; 1, 1.5, 2, 2.5, 3, 3.5, 4 mg/m²/d for 4 d |
| Chronic Lymphocytic Leukemia |  | C-100-1500 mg/m²; H-10-70 mg/m²; O-1-2 mg/m²; P-10-100 mg; C-100, 300, 500, 700, 900, 1100, 1300, 1500 mg/m²; H-10, 30, 50, 70 mg/m²; O-1, 1.2, 1.4, 1.6, 1.8, 2 mg/m²; P-10, 20, 30, 40, 50, 60, 70, 80, 90, 100 mg |  | 5-50 mg/m²; 5, 10, 15, 20, 25, 30, 35, 40, 45, 50 mg/m²; 3-36 mg/m²/d for 4 d every 3 wk 3, 6, 9, 12, 15, 18, 21, 24, 27, 30, 33, 36 mg/m²/d for 4 d every 3 wk |
| Acute Myelogenous |  |  | 15-150 mg/m²/d for 3 d every wk; | 2-25 mg/m² every wk; |

TABLE 3-continued

|  | Gemcitabine | CHOP | Carboplatin | Doxorubicin |
|---|---|---|---|---|
| Leukemia |  |  | 15, 30, 45, 60, 75, 90, 105, 120, 135, 150 mg/m²/d for 3 d every wk; 30-315 mg/m²/d for 5 d every 2 wk; 30, 60, 90, 120, 150, 180, 210, 240, 270, 315 mg/m²/d for 5 d every 2 wk; 20-216 mg/m²/d for 5 d; 20, 50, 80, 110, 140, 170, 216 mg/m²/d for 5 d | 2, 5, 10, 15, 20, 25 mg/m² every wk; 2-25 mg/m²/d for 3 d; 2, 5, 10, 15, 20, 25 mg/m²/d for 3 d; 5-50 mg/m²; 5, 10, 15, 20, 25, 30, 35, 40, 45, 50 mg/m² |
| Multiple Myeloma |  |  | 10-200 mg/m²/d for 4 d; 10, 25, 50, 75, 100, 125, 150, 175, 200 mg/m²/d for 4 d; 40-400 mg/m² every 4 wk; 40, 80, 120, 160, 200, 240, 280, 320, 360, 400 mg/m² every 4 wk | 3-30 mg/m² every 3 wk; 3, 6, 10, 15, 20, 25, 30 mg/m² every 3 wk; 3-50 mg/m²; 3, 6, 10, 15, 20, 25, 30, 35, 40, 45, 50 mg/m² |

TABLE 4

|  | Oxaliplatin | Bortezomib | Gefitinib | Bevacizumab |
|---|---|---|---|---|
| Colon Cancer | 10-85 mg/m² every 2 wk; 10, 15, 20, 25, 30, 35, 40, 45, 50, 55, 60, 65, 70, 75, 80, 85 mg/m² every 2 wk; 10-130 mg/m² every 3 wk; 10, 20, 30, 40, 50, 60, 70, 80, 90, 100, 110, 120, 130 mg/m² every 3 wk |  |  | 5-10 mg/kg every 2 wk; 5, 6, 7, 8, 9, 10 mg/kg every 2 wk |
| Pancreatic Cancer | 10-100 mg/m² every wk; 10, 20, 30, 40, 50, 60, 70, 80, 90, 100 mg/m² every wk; 8, 15, 20, 25, 30, 35, 40, 45, 50, 55, 60, 65, 70, 75, 80, 85 mg/m² every 2 wk; 8-85 mg/m² every 2 wk |  |  |  |
| Head/Neck Cancer | 5-60 mg/m² every wk; 5, 10, 15, 20, 25, 30, 35, 40, 45, 50, 55, 60 mg/m² every wk |  | 25-500 mg/d; 25, 50, 75, 100, 150, 200, 250, 300, 350, 400, 450, 500 mg/d |  |
| Non-Small Cell Lung Cancer | 5-65 mg/m² every wk; 5, 10, 15, 20, 25, 30, 35, 40, 45, 50, 55, 60, 65 mg/m² every wk; 10-130 mg/m² every 3 wk; |  | 25-500 mg/d; 25, 50, 75, 100, 150, 200, 250, 300, 350, 400, 450, 500 mg/d |  |

TABLE 4-continued

| | Oxaliplatin | Bortezomib | Gefitinib | Bevacizumab |
|---|---|---|---|---|
| Ovarian Cancer | 10, 20, 30, 40, 50, 60, 70, 80, 90, 100, 110, 120, 130 mg/m² every 3 wk 10-130 mg/m² every wk; 10, 20, 30, 40, 50, 60, 70, 80, 90, 100, 110, 120, 130 mg/m² every wk | | | |
| Lymphoma | | 0.2-1.04 mg/m² 2x wk; 0.2, 0.3, 0.4, 0.5, 0.6, 0.7, 0.8, 0.9, 1.04 mg/m² 2x wk | | |
| Multiple Myeloma | | 0.1-1.3 mg/m² 2x wk; 0.1, 0.2, 0.3, 0.4, 0.5, 0.6, 0.7, 0.8, 0.9, 1.0, 1.1, 1.2, 1.3 mg/m² 2x wk | | |

Figure 15:
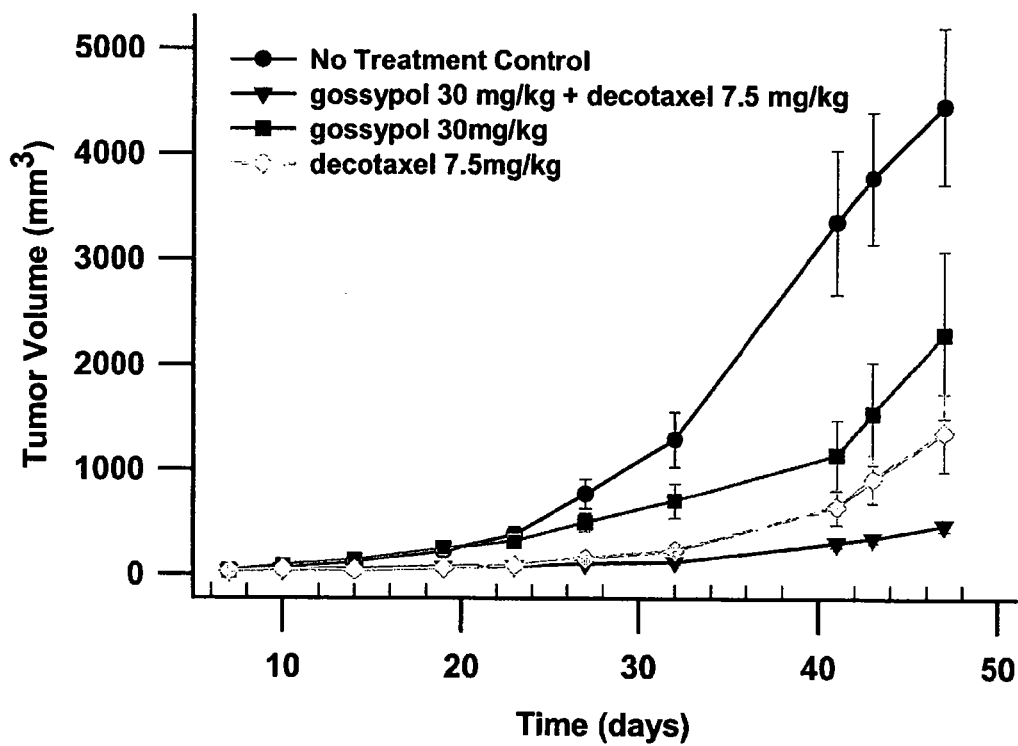
FIG. 15 shows the results of in vivo animal xenograft based assays in one embodiment of the present invention.

Since racemic gossypol achieves significant inhibition of tumor growth at a daily dose of about 30 mg/kg, this dose level was initially selected for testing gossypol in combination with conventional anticancer therapeutics. A group of 10 mice received an orally administered daily dose of 30 mg/kg gossypol starting at day 7 and lasting for 4 weeks. Also starting at day 7, the same 10 mice were administered a weekly i.p. dose (7.5 mg/kg) of docetaxel for 3 weeks. The results of this experiment are shown in FIG. 15. In particular, FIG. 15 shows the inhibition of tumor growth by gossypol, or by gossypol and docetaxel in human breast cancer xenograft MDA-MB-231 nude mice. Each experimental group had 10 animals. FIG. 15 shows that administration of gossypol alone (30 mg/kg daily), or docetaxel alone in a sub-optimal dose (7.5 mg/kg weekly), significantly inhibited tumor growth in the test animals, however, test animals that received a combination therapy of gossypol and docetaxel showed even greater tumor growth inhibition. Importantly, 3 out of 10 mice (6 tumors) treated with a combination gossypol and docetaxel showed complete tumor regression. Overall, there was more than 90% inhibition in tumor growth in the combination therapy group as compared to the control group. Statistical analyses were performed using the SAS (See, G. Verbeke and G. Molenberghs, Linear mixed models in practice: An SAS-orientated approach, Springer-Verlag, vol. 126 (1997)) program. Results of these experiments are provided in Table 5.

TABLE 5

| | Control | Gossypol | Docetaxel |
|---|---|---|---|
| Racemic Gossypol | 0.008* (0.06‡) | | |
| Docetaxel | 0.003 (0.01) | | |
| Racemic Gossypol + Docetaxel | 0.00001 (0.0000004) | 0.005 (0.009) | 0.01 (0.002) |

*day 41
‡day 47

The results show that the anticancer activity of gossypol and docetaxel is statistically significant as compared to controls at both day 41 and day 47 of the study. Furthermore, the anticancer activity of the combination of gossypol and docetaxel is significant as compared to the control (untreated) groups, and to the groups treated with gossypol or docetaxel alone. Taken together, these data indicate that gossypol has a significant anticancer activity alone, but in some embodiments achieves even greater activity when administered in combination with a conventional anticancer agent (e.g., chemotherapeutic such as docetaxel).

Figure 16:
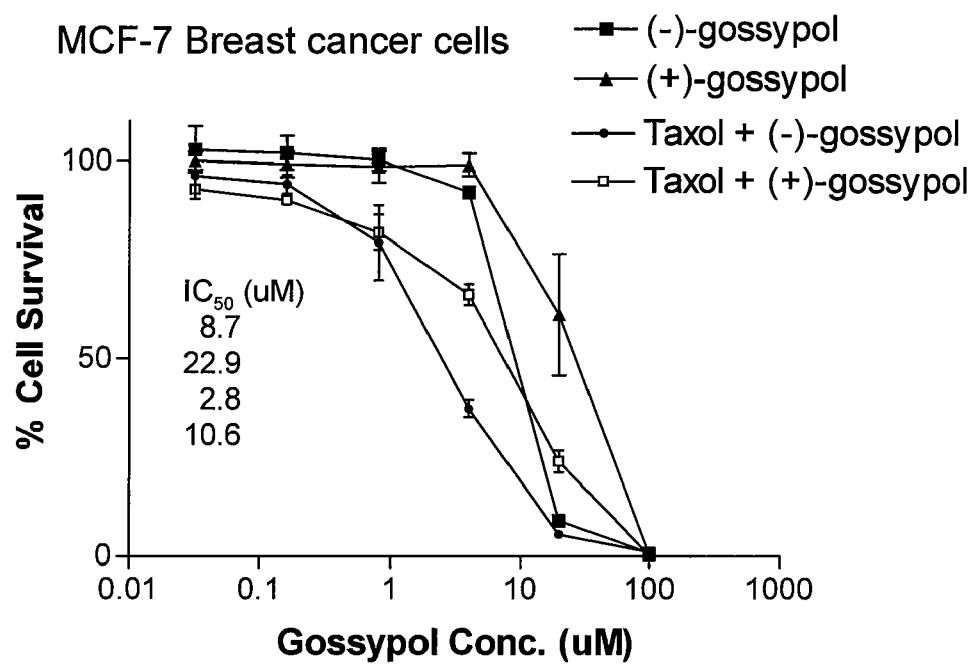
FIG. 16 shows the results of cell based assays in various embodiments of the present invention.
Figure 17A:
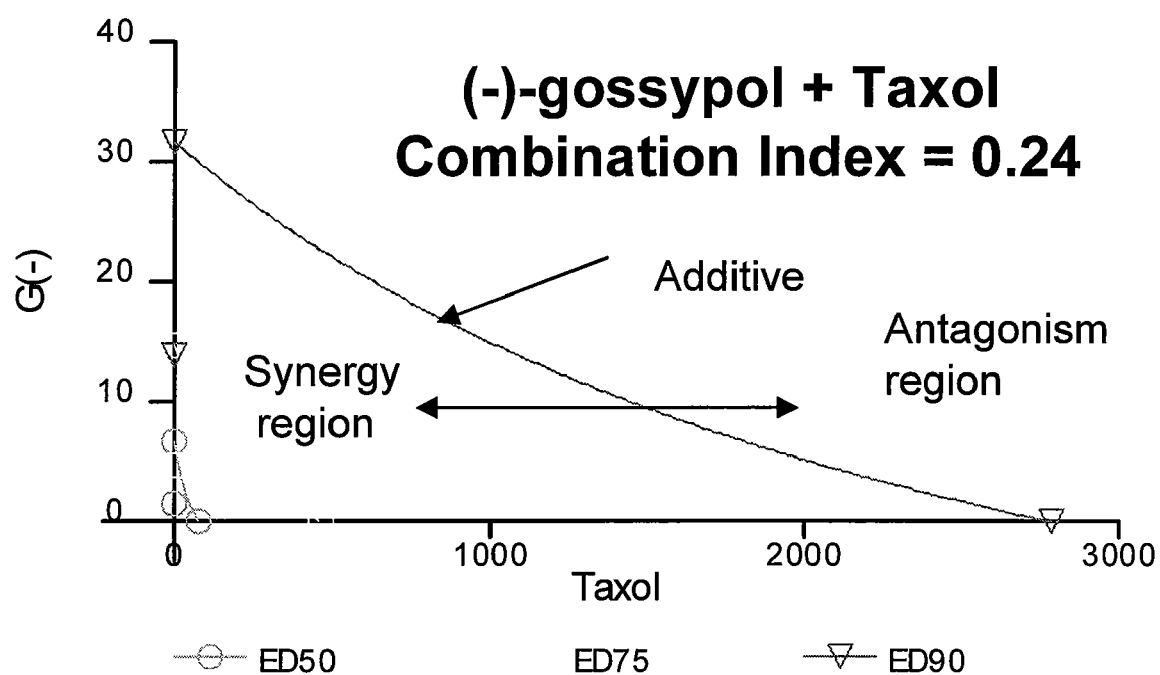
FIGS. 17A and 17B show the results of cell based assays in various embodiments of the present invention.
Figure 17B:
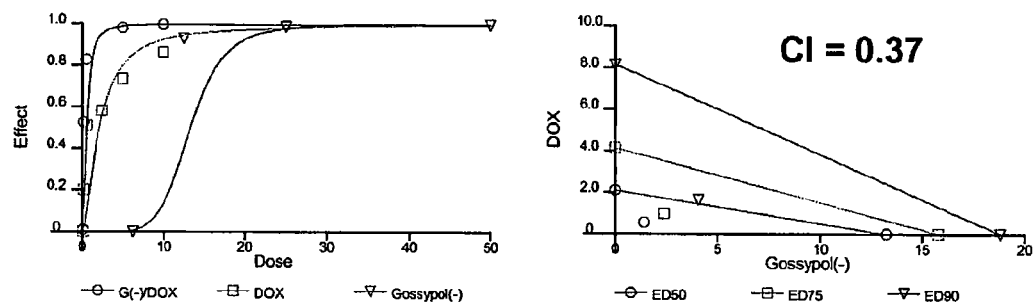

Although an understanding of any mechanism is not necessary to practice the present invention and the present invention is not so limited, it is contemplated that the synergistic effects observed in some combinations of conventional anticancer agents and gossypol compounds are due to a similarity of the compounds' mechanisms of action (e.g. induction of apoptosis). For example, in one embodiment (−)-gossypol enantiomer co-administered with the conventional anticancer therapeutic agent TAXOL provides a synergistic benefit. FIG. 16 shows the synergistic effects of co-administration of (−)-gossypol enantiomer and TAXOL. Briefly, this experiment used (−)-gossypol or (+)-gossypol in a fixed ratio to TAXOL in a MCF-7 breast cancer cell line ((−)-gossypol $IC_{50}$ 8.71 µM; (+)-gossypol $IC_{50}$ 22.88 µM; TAXOL+(−)-gossypol $IC_{50}$ 2.755 µM; and TAXOL+(+)-gossypol $IC_{50}$ 10.57 µM). FIGS. 17A and 17B show that there is a strong synergy between (−)-gossypol and TAXOL as well as between (+)-gossypol and TAXOL.

VII. Therapeutic Agents Combined or Co-Administered with Gossypol Compounds

A wide range of therapeutic agents find use with the present invention. Any therapeutic agent that can be co-administered with gossypol compounds, or associated with gossypol compounds is suitable for use in the methods of the present invention.

Some embodiments of the present invention provide methods for administering an effective amount of gossypol (acids, enantiomers, isomers, metabolites, derivatives, and pharmaceutically acceptable salts thereof) and at least one additional non-gossypol therapeutic agent (e.g., including, but not limited to, chemotherapeutic antineoplastics, antimicrobials, antivirals, antifungals, and anti-inflammatory agents) and/or therapeutic technique (e.g., surgical intervention, radiotherapies). In some of these embodiments, the subject has a disease characterized by the intracellular overexpression of Bcl-2 family proteins (e.g. Bcl-2 and/or Bcl-$X_L$).

Various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g. tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 6 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 6

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* | TICE BCG | Organon Teknika, Corp., Durham, NC |

TABLE 6-continued

| | | |
|---|---|---|
| [BCG], substrain Montreal) | | |
| bexarotene capsules<br>(4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin<br>(cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine<br>(5'-deoxy-5-fluoro-N-[(pentyloxy)carbonyl]-cytidine) | Xeloda | Roche |
| Carboplatin<br>(platinum, diammine [1,1-cyclobutanedicarboxylato(2-)-0,0']-,(SP-4-2)) | Paraplatin | Bristol-Myers Squibb |
| Carmustine<br>(1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib<br>(as 4-[5-(4-methylphenyl)-3-(trifluoromethyl)-1H-pyrazol-1-yl] benzenesulfonamide) | Celebrex | Searle Pharmaceuticals, England |
| Chlorambucil<br>(4-[bis(2chlorethyl)amino]benzenebutanoic acid) | Leukeran | GlaxoSmithKline |
| Cisplatin<br>($PtCl_2H_6N_2$) | Platinol | Bristol-Myers Squibb |
| Cladribine<br>(2-chloro-2'-deoxy-b-D-adenosine) | Leustatin, 2-CdA | R.W. Johnson Pharmaceutical Research Institute, Raritan, NJ |
| Cyclophosphamide<br>(2-[bis(2-chloroethyl)amino] tetrahydro-2H-13,2-oxazaphosphorine 2-oxide monohydrate) | Cytoxan, Neosar | Bristol-Myers Squibb |
| Cytarabine<br>(1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine<br>(5-(3,3-dimethyl-1-triazeno)-imidazole-4-carboxamide (DTIC)) | DTIC-Dome | Bayer AG, Leverkusen, Germany |
| Dactinomycin, actinomycin D<br>(actinomycin produced by *Streptomyces parvullus*, $C_{62}H_{86}N_{12}O_{16}$) | Cosmegen | Merck |
| Darbepoetin alfa<br>(recombinant peptide) | Aranesp | Amgen, Inc., Thousand Oaks, CA |
| daunorubicin liposomal<br>((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin<br>((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox<br>(recombinant peptide) | Ontak | Seragen, Inc., Hopkinton, MA |
| Dexrazoxane<br>((S)-4,4'-(1-methyl-1,2-ethanediyl)bis-2,6-piperazinedione) | Zinecard | Pharmacia & Upjohn Company |
| Docetaxel<br>((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl<br>(8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |

TABLE 6-continued

| | | |
|---|---|---|
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-,3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl-N-[4-methyl-3-[[4-(3-pyridinyl)-2-pyrimidinyl]amino]-phenyl]benzamide methanesulfonate) | Gleevec | Novartis AG, Basel, Switzerland |

TABLE 6-continued

| | | |
|---|---|---|
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino) carbonyloxy]-1H-pyrano[3',4':6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |

TABLE 6-continued

| Drug | Brand | Company |
|---|---|---|
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |

TABLE 6-continued

| | | |
|---|---|---|
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Preferred conventional anticancer agents for use in administration with the disclosed gossypol compounds include, but are not limited to, adriamycin, 5-fluorouracil, etoposide, camptothecin, actinomycin-D, mitomycin C, cisplatin, docetaxel, gemcitabine, carboplatin, oxaliplatin, bortezomib, gefitinib, and bevacizumab. These agents can be prepared and used singularly, in combined therapeutic compositions, in kits, or in combination with immunotherapeutic agents, and the like.

In preferred embodiments, the present invention provides methods for the administration of effective amounts of gossypol compounds and at least one conventional anticancer agent (e.g., an agent that induces apoptosis). In some preferred embodiments, the subject has a disease characterized by the overexpression of Bcl-2 family protein(s) (e.g., Bcl-2 and/or Bcl-$X_L$). In yet other preferred embodiments, the present invention provides methods for the administration of effective amounts of gossypol compounds and a taxane (e.g., docetaxel) compound to subjects having diseases characterized by the overexpression of Bcl-2 family protein(s) (e.g., Bcl-2 and/or Bcl-$X_L$).

Generally, taxanes (e.g., docetaxel) are an effective class of anticancer chemotherapeutic agents. (See e.g., K. D. Miller and G. W. Sledge, Jr. Cancer Investigation, 17:121-136 (1999)). While the present invention is not limited to any particular mechanism(s), it is contemplated that taxane-mediated cell death occurs through intracellular microtubule stabilization and subsequent induction of the apoptotic pathway. (See e.g., S. Haldar et al., Cancer Research, 57:229-233 (1997)). In many systems, Bcl-$X_L$ functions as a negative control on this pathway.

In some other embodiments, cisplatin and TAXOL are specifically contemplated for administration with gossypol compounds. Cisplatin and TAXOL induce apoptosis in tumor cells. (See e.g., Lanni et al., Proc. Natl. Acad. Sci., 94:9679 (1997); Tortora et al., Cancer Research 57:5107 (1997); and Zaffaroni et al., Brit. J. Cancer 77:1378 (1998)). However, treatment with these and other chemotherapeutic agents is difficult to accomplish without subjecting the patient to significant toxicity. Many anticancer chemotherapeutic agents currently in use are generally poorly water soluble, toxic, and when given at efficacious levels affect normal cells as well as diseased cells.

For example, paclitaxel (TAXOL), is a very promising anticancer compound, and has shown excellent antitumor activity in a wide variety of tumor models such as the B16 melanoma, L1210 leukemias, MX-1 mammary tumors, and CS-1 colon tumor xenografts. However, is has poor aqueous solubility which presents a problem in human administration. Accordingly, paclitaxel formulations typically require the use of a cremaphor to solubilize the drug. The human clinical dose range of paclitaxel is about 110-500 mg/m$^2$. For administration, paclitaxel is usually dissolved in a solution of ethanol:cremaphor (1:1) then diluted into one liter of water or other aqueous mixture. Polyethoxylated castor oil is the most often used cremaphor. The cremaphor mixture is administered by infusion. Direct administration (e.g., subcutaneous) of the cremaphor mixture results in local toxicity and low levels of activity.

In still further embodiments, the present invention provides methods for monitoring the therapeutic success of cisplatin and/or TAXOL administration in a subject. Measuring the ability of these drugs to induce apoptosis in vitro is reported to be a marker for in vivo efficacy. (Gibb, Gynecologic Oncology, 65:13 (1997)). The effectiveness of cisplatin and/or TAXOL as anticancer chemotherapeutics can be measured using techniques of the present invention for monitoring induction of apoptosis. Cisplatin and/or TAXOL are active against a wide-range of tumor types including, but not limited to, breast cancer and colon cancer. (Akutsu et al., Eur. J. Cancer 31A:2341 (1995)).

In some embodiments of the present invention, therapeutic gossypol compound treatments further comprise one or more agents that directly cross-link nucleic acids (e.g., DNA) to facilitate DNA damage leading to a synergistic effect. Agents such as cisplatin and other DNA alkylating agents are preferred. Cisplatin has been widely used in cancer treatments. Efficacious doses used in clinical applications include, but are not limited to, about 20 mg/m$^2$ for 5 days every three weeks for a total of three courses, and 50-120 mg/m$^2$ every 3 weeks.

Agents that damage DNA also include compounds that interfere with DNA replication, mitosis, and chromosomal segregation. Such chemotherapeutic compounds include, but are not limited to, adriamycin, also known as doxorubicin, etoposide, verapamil, podophyllotoxin, and the like. These compounds are widely used in clinical settings for the treatment of neoplasms, and are typically administered as a bolus intravenous injection at doses ranging from about 25-75 mg/m$^2$ at 21 day intervals, 20-30 mg/m$^2$ every week, and similar doses for adriamycin, and 100-200 mg/m$^2$ for etoposide for three days every 3-4 weeks intravenously or double the intravenous dose when administered orally.

Agents that disrupt the synthesis and fidelity of nucleic acid precursors and subunits also lead to DNA damage and find use as chemotherapeutic agents in the present invention. A number of nucleic acid precursors have been developed. Particularly useful are agents that have undergone extensive testing and are readily available. 5-Fluorouracil (5-FU) is preferentially used by neoplastic tissues, making this agent particularly useful for targeting to neoplastic cells. The dose of 5-fluorouracil may range from about 3 to 15 mg/kg/day, although other doses may vary considerably according to various factors including stage of disease, amenability of the cells to the therapy, amount of resistance to the agent and the like.

In preferred embodiments, the anticancer agents used in the present invention are those that are amenable to co-administration with the disclosed gossypol compounds or are otherwise associated with the disclosed gossypol compounds such that they can be delivered into a subject, tissue, or cell without loss of fidelity of anticancer effect. For a more detailed description of cancer therapeutic agents such as a platinum complex, verapamil, podophyllotoxin, carboplatin, procarbazine, mechlorethamine, cyclophosphamide, camptothecin, ifosfamide, melphalan, chlorambucil, busulfan, nitrosourea, dactinomycin, daunorubicin, doxorubicin (adriamycin), bleomycin, plicomycin, mitomycin, etoposide (VP16), tamoxifen, TAXOL, transplatinum, 5-fluorouracil, vincristin, vinblastin and methotrexate and other similar anticancer agents, those skilled in the art are referred to any number of instructive manuals including, but not limited to, the Physician's Desk Reference and to Goodman and Gilman's "Pharmaceutical Basis of Therapeutics" ninth edition, Eds. Hardman et al., 1996.

In some embodiments, the drugs are attached to the gossypol compounds with photocleavable linkers. For example, several heterobifunctional, photocleavable linkers that find use with the present invention are described by Ottl et al. (Ottl et al., Bioconjugate Chem., 9:143 (1998)). These linkers can be either water or organic soluble. They contain an activated ester that can react with amines or alcohols and an epoxide that can react with a thiol group. In between the two groups is 3,4-dimethoxy-6-nitrophenyl photoisomerization group, which, when exposed to near-ultraviolet light (365 nm), releases the amine or alcohol in intact form. Thus, the therapeutic agent, when linked to the compositions of the present invention using such linkers, may be released in biologically active or activatable form through exposure of the target area to near-ultraviolet light.

In an exemplary embodiment, the alcohol group of TAXOL is reacted with the activated ester of the organic-soluble linker. This product in turn is reacted with the partially-thiolated surface of appropriate dendrimers (the primary amines of the dendrimers can be partially converted to thiol-containing groups by reaction with a sub-stoichiometric amount of 2-iminothiolano). In the case of cisplatin, the amino groups of the drug are reacted with the water-soluble form of the linker. If the amino groups are not reactive enough, a primary amino-containing active analog of cisplatin, such as Pt(II) sulfadiazine dichloride (Pasani et al., Inorg. Chim. Acta 80:99 (1983) and Abel et al., Eur. J. Cancer 9:4 (1973)) can be used. Thus conjugated, the drug is inactive and will not harm normal cells. When the conjugate is localized within tumor cells, it is exposed to laser light of the appropriate near-UV wavelength, causing the active drug to be released into the cell.

Similarly, in other embodiments of the present invention, the amino groups of cisplatin (or an analog thereof) are linked with a very hydrophobic photocleavable protecting group, such as the 2-nitrobenzyloxycarbonyl group (See e.g., Pillai, V. N. R. Synthesis: 1-26 (1980)). When exposed to near-UV light (about 365 nm), the hydrophobic group is cleaved, leaving the intact drug. A number of photocleavable linkers have been demonstrated as effective anti-tumor conjugates and can be prepared by attaching cancer therapeutics, such as doxorubicin, to water-soluble polymers with appropriate short peptide linkers (See e.g., Vasey et al., Clin. Cancer Res., 5:83 (1999)). The linkers are stable outside of the cell, but are cleaved by thiolproteases once within the cell. In a preferred embodiment, the conjugate PK1 is used. As an alternative to the photocleavable linker strategy, enzyme-degradable linkers, such as Gly-Phe-Leu-Gly (SEQ ID NO: 3) may be used. An alternative to photocleavable linkers are enzyme cleavable linkers.

The present invention is not limited by the nature of the therapeutic technique. For example, other conjugates that find use with the present invention include, but are not limited to, using conjugated boron dusters for BNCT (Capala et al., Bioconjugate Chem., 7:7 (1996)), the use of radioisotopes, and conjugation of toxins such as ricin.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

VIII. Targeting Agents and Techniques

In still further embodiments, the present invention provides gossypol compounds (and any other chemotherapeutic agents) associated with targeting agents (gossypol compound-targeting agent complexes) that are able to specifically target particular cell types (e.g., tumor cells). Generally, the gossypol compound that is associated with a targeting agent, targets neoplastic cells through interaction of the targeting agent with a cell surface moiety that is taken into the cell through receptor mediated endocytosis.

Any moiety known to be located on the surface of target cells (e.g., tumor cells) finds use with the present invention. For example, an antibody directed against such a moiety targets the compositions of the present invention to cell surfaces containing the moiety. Alternatively, the targeting moiety may be a ligand directed to a receptor present on the cell surface or vice versa. Similarly, vitamins also may be used to target the therapeutics of the present invention to a particular cell.

As used herein, the term "targeting molecules" refers to chemical moieties, and portions thereof useful for targeting chemical compounds (e.g., gossypol compounds, drugs, prodrugs, small molecules, therapeutic agents) to cells, tissues, and organs of interest. Various types of targeting molecules are contemplated for use with the present invention including, but not limited to, signal peptides, antibodies, nucleic acids, toxins and the like. Targeting moieties may additionally promote the binding of the associated chemical compounds (e.g., small molecules) or the entry of the compounds into the targeted cells, tissues, and organs. Preferably, targeting moieties are selected according to their specificity, affinity, and efficacy in selectively delivering attached compounds to targeted sites within a subject, tissue, or a cell, including specific subcellular locations and organelles.

In some preferred embodiments, the targeting molecules of the present invention are associated with a therapeutic or other small molecule (e.g., gossypol compound, drugs, prodrugs, small molecules, therapeutic agents, etc.). Targeting molecules can be associated to the therapeutic small molecules of the present invention using a variety of linking (e.g., cleavable linkers), spacer, and protecting groups. For example, in certain embodiments, targeting moieties are associated (e.g., covalently or noncovalently bound) to the small molecule therapeutic agents by short (e.g., direct coupling), medium (e.g., using small-molecule bifunctional linkers such as SPDP (Pierce Biotechnology, Inc., Rockford, Ill.)), or long (e.g., PEG bifunctional linkers (Nektar Therapeutics, Inc., San Carlos, Calif.)) chemical linkages.

Preferably, the various targeting molecules and therapeutic agents of the present invention are attached, associated, fixed, or conjugated such that each entity therein is sufficiently free of steric hindrance (e.g., via connection through a suitable linker) such that its chemical or biological activity is, at least partially, retained.

The small molecules of the present invention can be targeted to a wide range biological targets including, but not limited to, diseased cells (e.g., tumor cells) and tissues, healthy cells and tissues, nucleic acids (e.g., DNA, cDNA, RNA, mRNA, and siRNA), polypeptides (e.g., enzymes, cell surface proteins, etc.), cell surface proteins, cell surface receptors, cell surface polysaccharides, extracellular matrix proteins, intracellular proteins, and to microorganisms and other pathogens (e.g., bacteria, fungi, mycoplasma, prions, viruses, and the like).

A variety of targeting molecules are contemplated for use in association with the present compositions, including nucleic acids (e.g., RNA and DNA), polypeptides (e.g., receptor ligands, signal peptides, avidin, Protein A, antigen binding proteins, etc.), polysaccharides, biotin, hydrophobic groups, hydrophilic groups, drugs, and any organic molecules that bind to receptors. In some embodiments, the small molecules of the present invention are associated with multiple targeting molecules. In some of these embodiments, the various targeting molecules are similar (e.g., monoclonal antibodies). In other embodiments, the targeting molecules are dissimilar (e.g., antibodies with distinct idiotypes or isotypes, or antibodies and nucleic acids, etc.).

In some embodiments of the present invention, any number of cancer cell targeting groups are associated with the gossypol compounds. Thus, the gossypol compounds associated with targeting groups are specific for targeting cancer cells (i.e., much more likely to attach to cancer cells and not to healthy cells).

Utilization of more than one targeting molecule in a composition allows multiple biological targets to be targeted and/or provides the ability to increase affinity for specific targets. Multiple targeting molecules allow the compositions to be "stacked," wherein a first composition is targeted to a first biological target, and a second composition is targeted to the first composition or to the first biological target. A number of exemplary targeting molecules and targeting methods are describe in more detail below.

A. General Targeting Molecules and Targeting Considerations

Various efficiency issues affect the administration of all drugs—and of highly cytotoxic drugs (e.g., anticancer drugs) in particular. One issue of particular importance is ensuring that the administered agents affect only targeted cells (e.g., cancer cells), tissues, or organs. The nonspecific or unintended delivery of highly cytotoxic agents to nontargeted cells can cause serious toxicity issues.

Numerous attempts have been made to devise drug targeting schemes to address the problems associated with nonspecific drug delivery. (See e.g., K. N. Syrigos and A. A. Epenetos Anticancer Res., 19:606-614 (1999); Y. J. Park et al., J. Controlled Release, 78:67-79 (2002); R. V. J. Chari, Adv. Drug Deliv. Rev., 31:89-104 (1998); and D. Putnam and J. Kopecek, Adv. Polymer Sci., 122:55-123 (1995)). Conjugating targeting moieties such as antibodies and ligand peptides (e.g., RDG for endothelium cells) to drug molecules has been used to alleviate some collateral toxicity issues associated with particular drugs. However, conjugating drugs to targeting moieties alone does not completely negate potential side effects to nontargeted cells, since the drugs are usually bioactive on their way to target cells. Advances in targeting moiety-prodrug conjugates, which are inactive while traveling to specific targeted tissues, have diminished some of these concerns. A biotransformation, such as enzymatic cleavage, typically converts the prodrug into a biologically active molecule at the target site.

Accordingly, in some preferred embodiments, the present invention provides prodrug conjugates that are inactive until they reach their target site, where they are subsequently converted into an active therapeutic drug molecule. ADEPT and ATTEMPTS are two exemplary prodrug delivery systems compatible with certain embodiments of the present invention. (See K. N. Syrigos and A. A. Epenetos, Anticancer Res., 19:606-614 (1999); K. D. Bagshawe, Brit. J. Cancer, 56:531-532 (1987); Y. J. Park et al., J. Controlled Release, 72:145-156 (2001); and Y. J. Park et al., J. Controlled Release, 78:67-79 (2002)).

The rapid clearance of some types of therapeutic agents, especially water-soluble low-molecular weight agents, from the subject's bloodstream provides yet another obstacle to effective small molecule administration. Still other obstacles come from the rapid clearance (e.g., proteolytic degradation) or potential immunogenicity of the administered agents.

In natural systems, clearance and other pharmacokinetic behaviors of small molecules (e.g., drugs) in a subject are regulated by a series of transport proteins. (See e.g., H. T. Nguyen, Clin. Chem. Lab. Anim., (2nd Ed.) pp. 309-335 (1999); and G. J. Russell-Jones and D. H. Alpers, Pharm. Biotechnol., 12:493-520 (1999)). Thus, in preferred embodiments, the pharmacokinetics of agents are considered when testing and developing potential therapeutics.

The rate of agent clearance in a subject is typically manageable. For instance, attaching (e.g., binding) the agent to a macromolecular carrier normally prolongs circulation and retention times. Accordingly, some embodiments of the present invention provide small molecules (e.g., gossypol compounds, drugs, or prodrugs) conjugated to polyethylene glycol (PEG), or similar biopolymers, to decrease (prevent) the molecules' degradation and to improve its retention in the subject's bloodstream. (See e.g., R. B. Greenwald et al., Critical Rev. Therapeutic Drug Carrier Syst., 17:101-161 (2000)). The ability of PEG to discourage protein-protein interactions can reduce the immunogenicity of many drugs.

Another issue affecting the administration of some therapeutic agents, and especially hydrophilic and macromolecular drugs such as peptides and nucleic acids, is that these agents have difficulty crossing into targeted cellular membranes. Small (typically less than 1,000 Daltons) hydrophobic molecules are less susceptible to having difficulties entering target cell membranes. Moreover, low molecular weight cytotoxic drugs often localize more efficiently in normal tissues rather than in target tissues such as tumors (K. Bosslet et al., Cancer Res., 58:1195-1201 (1998)) due to the high interstitial pressure and unfavorable blood flow properties within rapidly growing tumors (R. K. Jain, Int. J. Radiat. Biol., 60:85-100 (1991); and R. K. Jain and L. T. Baxter, Cancer Res., 48:7022-7032 (1998)).

Certain embodiments, especially those directed to delivering cytotoxic agents, utilize one or more of the following methods or compositions to aid delivery of the therapeutic compositions of the present invention: microinjection (See e.g., M. Foldvari and M. Mezei, J. Pharm. Sci., 80:1020-1028, (1991)); scrape loading (See e.g., P. L. McNeil et al., J. Cell Biol., 98:1556-1564 (1984)); electroporation (See e.g., R. Chakrabarti et al., J. Biol. Chem., 26:15494-15500 (1989)); liposomes (See e.g., M. Foldvari et al., J. Pharm. Sci., 80:1020-1028 (1991); and J. N. Moreira et al., Biochim Biophys Acta., 515:167-176 (2001)); nanocarriers such as water-soluble polymers (e.g., enhanced permeation and retention "EPR", See e.g., H. Maeda et al., J. Controlled Release, 65:271-284 (2000); H. Maeda et al., supra; and L. W. Seymour, Crit. Rev. Therapeu. Drug Carrier Systems, 9:135-187 (1992)); bacterial toxins (See e.g., T. I. Prior et al., Biochemistry, 31:3555-3559 (1992); and H. Stenmark et al., J. Cell Biol., 113:1025-1032 (1991)); receptor-mediated endocytosis and phagocytosis, including the tumor-activated prodrug (TAP) system (See e.g., R. V. J. Chari, Adv. Drug Deliv. Rev., 31:89-104 (1998); I. Mellman, Annu. Rev. Cell Dev. Biol., 12:575-625 (1996); C. P. Leamon and P. S. Low, J. Biol. Chem., 267 (35):24966-24971 (1992); H. Ishihara et al., Pharm. Res., 7:542-546 (1990); S. K. Basu, Biochem. Pharmacol., 40:1941-1946 (1990); and G. Y. Wu and C. H. Wu, Biochemistry, 27:887-892 (1988)); other suitable compositions and methods are known in the art.

B. Antibodies as Targeting Molecules

In some embodiments of the present invention, targeting molecules comprise antigen binding proteins or immunoglobulins (antibodies). Immunoglobulins can be generated to allow for the targeting of antigens or immunogens (e.g., tumor, tissue, or pathogen specific antigens) on various biological targets (e.g., pathogens, tumor cells, normal tissue). Such immunoglobulins include, but are not limited to, polyclonal, monoclonal, chimeric, single chain, Fab fragments, and Fab expression libraries.

Immunoglobulins (antibodies) are proteins generated by the immune system to provide a specific molecule capable of complexing with an invading molecule commonly referred to as an antigen. Natural antibodies have two identical antigen-binding sites, both of which are specific to a particular antigen. The antibody molecule recognizes the antigen by complexing its antigen-binding sites with areas of the antigen termed epitopes. The epitopes fit into the conformational architecture of the antigen-binding sites of the antibody, enabling the antibody to bind to the antigen.

The immunoglobulin molecule is composed of two identical heavy and two identical light polypeptide chains, held together by interchain disulfide bonds. Each individual light and heavy chain folds into regions of about 110 amino acids, assuming a conserved three-dimensional conformation. The light chain comprises one variable region (termed $V_L$) and one constant region (CL), while the heavy chain comprises one variable region ($V_H$) and three constant regions (CH1, CH2 and CH3). Pairs of regions associate to form discrete structures. In particular, the light and heavy chain variable regions, $V_L$ and $V_H$, associate to form an "FV" area which contains the antigen-binding site.

The variable regions of both heavy and light chains show considerable variability in structure and amino acid composition from one antibody molecule to another, whereas the constant regions show little variability. Each antibody recognizes and binds an antigen through the binding site defined by the association of the heavy and light chain variable regions into an FV area. The light-chain variable region $V_L$ and the heavy-chain variable region $V_H$ of a particular antibody molecule have specific amino acid sequences that allow the antigen-binding site to assume a conformation that binds to the antigen epitope recognized by that particular antibody.

Within the variable regions are "sub-regions" in which the amino acid sequence is extremely variable from one antibody to another. Three of these so-called "hypervariable" regions or "complementarity-determining regions" (CDRs) are found in each of the light and heavy chains. The three CDRs from a light chain and the three CDRs from a corresponding heavy chain form the antigen-binding site.

Cleavage of naturally occurring antibody molecules with the proteolytic enzyme papain generates fragments that retain their antigen-binding site. These fragments, commonly known as Fabs (for Fragment, antigen binding site) are composed of the $C_L$, $V_L$, $C_H1$ and $V_H$ regions of the antibody. In the Fab the light chain and the fragment of the heavy chain are covalently linked by a disulfide linkage.

Antibody fragments that contain the idiotype (antigen binding region) of the antibody molecule can be generated by known techniques. For example, such fragments include but are not limited to: the F(ab')2 fragment that can be produced by pepsin digestion of the antibody molecule; the Fab' fragments that can be generated by reducing the disulfide bridges of the F(ab')2 fragment, and the Fab fragments that can be generated by treating the antibody molecule with papain and a reducing agent.

Various procedures known in the art are used for the production of polyclonal antibodies. For the production of antibody, various host animals can be immunized by injection with the peptide corresponding to the desired epitope including, but not limited to, rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

Monoclonal antibodies against target antigens (e.g., a cell surface protein such as a receptor) are produced by a variety of techniques including conventional monoclonal antibody methodologies such as the somatic cell hybridization techniques of Kohler and Milstein, Nature, 256:495 (1975). Although in some embodiments, somatic cell hybridization procedures are preferred, other techniques for producing monoclonal antibodies are contemplated as well (e.g., viral or oncogenic transformation of B lymphocytes).

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature 256:495-497 (1975)), as well as the trioma technique, the human B-cell hybridoma technique (See e.g., Kozbor et al., Immunol. Today 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)).

In an additional embodiment of the invention, monoclonal antibodies can be produced in germ-free animals utilizing recent technology (See e.g., PCT/US90/02545). According to the invention, human antibodies may be used and can be obtained by using human hybridomas (Cote et al., Proc. Natl. Acad. Sci. U.S.A., 80:2026-2030 (1983)) or by transforming human B cells with EBV virus in vitro (Cole et al., in Monoclonal Antibodies and Cancer Therapy, Alan R. Liss, pp. 77-96 (1985)).

In one embodiment, the preferred animal for preparing hybridomas is the mouse. Hybridoma production in the mouse is a well-established procedure. Immunization protocols and techniques for isolation of immunized splenocytes for fusion are known in the art. Fusion partners (e.g., murine myeloma cells) and fusion procedures are also known. In other preferred embodiments, avian (e.g., chickens) species are preferred for antibody production.

Human monoclonal antibodies (mAbs) directed against human proteins can be generated using transgenic mice carrying the complete human immune system rather than the mouse system. Splenocytes from the transgenic mice are immunized with the antigen of interest which are used to produce hybridomas that secrete human mAbs with specific affinities for epitopes from a human protein. (See e.g., Wood et al., WO 91/00906, Kucherlapati et al., WO 91/10741; Lonberg et al., WO 91/03918; Kay et al., WO 92/03917 (each of which is herein incorporated by reference in its entirety); N. Lonberg et al., Nature, 368:856-859 (1994); L. L. Green et al., Nature Genet., 7:13-21 (1994); S. L. Morrison et al., Proc. Nat. Acad. Sci. U.S.A., 81:6851-6855 (1994); Bruggeman et al., Immunol., 7:33-40 (1993); Tuaillon et al., Proc. Nat. Acad. Sci. U.S.A., 90:3720-3724 (1993); and Bruggernan et al. Eur. J. Immunol., 21:1323-1326 (1991)).

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies. (See e.g., Sastry et al., Proc. Nat. Acad. Sci. U.S.A., 86:5728 (1989); Huse et al., Science, 246:1275 (1989); and Orlandi et al., Proc. Nat. Acad. Sci. U.S.A., 86:3833 (1989)). After immunizing an animal with an immunogen as described above, the antibody repertoire of the resulting B-cell pool is cloned. Methods are available for obtaining DNA sequences from the variable regions of a diverse population of immunoglobulin molecules using a mixture of oligomer primers and PCR. For instance, mixed oligonucleotide primers corresponding to the 5' leader (signal peptide) sequences or framework 1 (FR1) sequences, as well as primer to a conserved 3' constant region primer can be used for PCR amplification of the heavy and light chain variable regions from a number of murine antibodies. (See e.g. Larrick et al., Biotechniques, 11:152-156 (1991)). A similar strategy can also been used to amplify human heavy and light chain variable regions from human antibodies (See e.g., Larrick et al., Methods: Companion to Methods in Enzymology, 2:106-110 (1991)).

In one embodiment, RNA is isolated from B lymphocytes, for example, peripheral blood cells, bone marrow, or spleen preparations, using standard protocols (e.g., U.S. Pat. No. 4,683,292 (incorporated herein by reference in its entirety); Orlandi, et al., Proc. Nat. Acad. Sci. U.S.A., 86:3833-3837 (1989); Sastry et al., Proc. Nat. Acad. Sci. U.S.A., 86:5728-5732 (1989); and Huse et al., Science, 246:1275 (1989). First strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries, examples of methods and reagents particularly amenable for use in generating a variegated antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809 (each of which is herein incorporated by reference in its entirety); Fuchs et al., Biol. Technology, 9:1370-1372 (1991); Hay et al., Hum. Antibod. Hybridomas, 3:81-85 (1992); Huse et al., Science, 46:1275-1281 (1989); Hawkins et al., J. Mol. Biol., 226:889-896 (1992); Clackson et al., Nature, 352:624-628 (1991); Gram et al., Proc. Nat. Acad. Sci. U.S.A., 89:3576-3580 (1992); Garrad et al., Bio/Technolog, 2:1373-1377 (1991); Hoogenboom et al., Nuc. Acid Res., 19:4133-4137 (1991); and Barbas et al., Proc. Nat. Acad. Sci. U.S.A., 88:7978 (1991). In certain embodiments, the V region domains of heavy and light chains can be expressed on the same polypeptide, joined by a flexible linker to form a single-chain Fv fragment, and the scFV gene subsequently cloned into the desired expression vector or phage genome.

As generally described in McCafferty et al., Nature, 348:552-554 (1990), complete $V_H$ and $V_L$ domains of an antibody, joined by a flexible linker (e.g., $(Gly_4\text{-}Ser)_3$) can be used to produce a single chain antibody which can render the display package separable based on antigen affinity. Isolated scFV antibodies immunoreactive with the antigen can subsequently be formulated into a pharmaceutical preparation for use in the subject method.

According to the invention, techniques described for the production of single chain antibodies (U.S. Pat. No. 4,946,778; herein incorporated by reference) can be adapted to produce specific single chain antibodies. An additional embodiment of the invention utilizes the techniques described for the construction of Fab expression libraries (Huse et al., Science, 246:1275-1281 (1989)) to allow rapid and easy identification of monoclonal Fab fragments with the desired specificity.

Once displayed on the surface of a display package (e.g., filamentous phage), the antibody library is screened with the target antigen, or peptide fragment thereof, to identify and isolate packages that express an antibody having specificity for the target antigen. Nucleic acid encoding the selected antibody can be recovered from the display package (e.g. from the phage genome) and subcloned into other expression vectors by standard recombinant DNA techniques.

Specific antibody molecules with high affinities for a surface protein can be made according to methods known to those in the art, e.g., methods involving screening of libraries. (See, e.g., U.S. Pat. No. 5,233,409 and U.S. Pat. No. 5,403,484 (both incorporated herein by reference in their entireties)). Further, the methods of these libraries can be used in screens to obtain binding determinants that are mimetics of the structural determinants of antibodies.

Generally, in the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.).

In particular, the Fv binding surface of a particular antibody molecule interacts with its target ligand according to principles of protein-protein interactions, hence sequence data for $V_H$ and $V_L$ (the latter of which may be of the κ or λ chain type) is the basis for protein engineering techniques known to those with skill in the art. Details of the protein surface that comprises the binding determinants can be obtained from antibody sequence in formation, by a modeling procedure using previously determined three-dimensional structures from other antibodies obtained from NMR studies or crystallographic data.

In one embodiment, a variegated peptide library is expressed by a population of display packages to form a peptide display library. Ideally, the display package comprises a system that allows the sampling of very large variegated peptide display libraries, rapid sorting after each affinity separation round, and easy isolation of the peptide-encoding gene from purified display packages. Peptide display libraries can be in, e.g., prokaryotic organisms and viruses, which can be amplified quickly, are relatively easy to manipulate, and which allows the creation of a large number of clones. Preferred display packages include, for example, vegetative bacterial cells, bacterial spores, and most preferably, bacterial viruses (especially DNA viruses). However, the present invention also contemplates the use of eukaryotic cells, including yeast and their spores, as potential display packages. Phage display libraries are known in the art.

Other techniques include affinity chromatography with an appropriate "receptor," e.g., a target antigen, followed by identification of the isolated binding agents or ligands by conventional techniques (e.g., mass spectrometry and NMR). Preferably, the soluble receptor is conjugated to a label (e.g., fluorophores, colorimetric enzymes, radioisotopes, or luminescent compounds) that can be detected to indicate ligand binding. Alternatively, immobilized compounds can be selectively released and allowed to diffuse through a membrane to interact with a receptor.

Combinatorial libraries of compounds can also be synthesized with "tags" to encode the identity of each member of the library. (See e.g., W. C. Still et al., WO 94/08051, incorporated herein by reference in its entirety). In general, this method features the use of inert but readily detectable tags that are attached to the solid support or to the compounds. When an active compound is detected, the identity of the compound is determined by identification of the unique accompanying tag. This tagging method permits the synthesis of large libraries of compounds that can be identified at very low levels among the total set of all compounds in the library.

The term modified antibody is also intended to include antibodies, such as monoclonal antibodies, chimeric antibodies, and humanized antibodies, which have been modified by, for example, deleting, adding, or substituting portions of the antibody. For example, an antibody can be modified by deleting the hinge region, thus generating a monovalent antibody. Any modification is within the scope of the invention so long as the antibody has at least one antigen binding region specific.

Chimeric mouse-human monoclonal antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See e.g., Robinson et al., PCT/US86/02269; European Patent Application 184,187; European Patent Application 171,496; European Patent Application 173,494; WO 86/01533; U.S. Pat. No. 4,816,567; European Patent Application 125,023 (each of which is herein incorporated by reference in its entirety) Better et al., Science, 240:1041-1043 (1988); Liu et al., Proc. Nat. Acad. Sci. U.S.A., 84:3439-3443 (1987); Liu et al., J. Immunol., 139:3521-3526 (1987); Sun et al., Proc. Nat. Acad. Sci. U.S.A., 84:214-218 (1987); Nishimura et al., Canc. Res., 47:999-1005 (1987); Wood et al., Nature, 314:446-449 (1985); and Shaw et al., J. Natl. Cancer Inst., 80:1553-1559 (1988)).

The chimeric antibody can be further humanized by replacing sequences of the Fv variable region which are not directly involved in antigen binding with equivalent sequences from human Fv variable regions. General reviews of humanized chimeric antibodies are provided by S. L. Morrison, Science, 229:1202-1207 (1985) and by Oi et al., Bio. Techniques, 4:214 (1986). Those methods include isolating, manipulating, and expressing the nucleic acid sequences that encode all or part of immunoglobulin Fv variable regions from at least one of a heavy or light chain. Sources of such nucleic acids are known and, for example, may be obtained from 7E3, an anti-GPIIbIIIa antibody producing hybridoma. The recombinant DNA encoding the chimeric antibody, or fragment thereof, is then cloned into an appropriate expression vector.

Suitable humanized antibodies can alternatively be produced by CDR substitution (e.g., U.S. Pat. No. 5,225,539 (incorporated herein by reference in its entirety); Jones et al., Nature, 321:552-525 (1986); Verhoeyan et al., Science, 239: 1534 (1988); and Beidler et al., J. Immunol., 141:4053 (1988)). All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody is humanized by any method that is capable of replacing at least a portion of a CDR of a human antibody with a CDR derived from a non-human antibody. The human CDRs may be replaced with non-human CDRs using oligonucleotide site-directed mutagenesis.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances.

In preferred embodiments, the fusion proteins include a monoclonal antibody subunit (e.g., a human, murine, or bovine), or a fragment thereof, (e.g., an antigen binding fragment thereof). The monoclonal antibody subunit or antigen binding fragment thereof can be a single chain polypeptide, a dimer of a heavy chain and a light chain, a tetramer of two heavy and two light chains, or a pentamer (e.g., IgM). IgM is a pentamer of five monomer units held together by disulfide bonds linking their carboxyl-terminal ($C\mu4/C\mu4$) domains and $C\mu3/C\mu3$ domains. The pentameric structure of IgM provides 10 antigen-binding sites, thus serum IgM has a higher valency than other types of antibody isotypes. With its high valency, pentameric IgM is more efficient than other antibody isotypes at binding multidimensional antigens (e.g., viral particles and red blood cells. However, due to its large pentameric structure, IgM does not diffuse well and is usually found in low concentrations in intercellular tissue fluids. The J chain of IgM allows the molecule to bind to receptors on secretory cells, which transport the molecule across epithelial linings to the external secretions that bathe the mucosal surfaces. In some embodiments, the present invention takes advantage of the low diffusion rate of pentameric IgM to help concentrate the fusion proteins of the present invention at a site of interest.

In some preferred embodiments, the monoclonal antibody is a murine antibody or a fragment thereof. In other preferred embodiments, the monoclonal antibody is a bovine antibody or a fragment thereof. For example, the murine antibody can be produced by a hybridoma that includes a 13 cell obtained from a transgenic mouse having a genome comprising a heavy chain transgene and a light chain transgene fused to an immortalized cell. The antibodies can be of the various isotypes, including, IgG (e.g., IgG1, IgG2, IgG3, IgG4), IgM, IgA1, IgA2, IgAsec, IgD, or IgE. In some preferred embodiments, the antibody is an IgG isotype. In other preferred embodiments, the antibody is an IgM isotype. The antibodies can be full-length (e.g., an IgG1, IgG2, IgG3, or IgG4 antibody) or can include only an antigen-binding portion (e.g., a Fab, F(ab')2, Fv or a single chain Fv fragment).

In preferred embodiments, the immunoglobulin subunit of the fusion proteins is a recombinant antibody (e.g., a chimeric or a humanized antibody), a subunit or an antigen binding fragment thereof (e.g., has a variable region, or at least a complementarity determining region (CDR)).

In preferred embodiments, the immunoglobulin subunit of the fusion protein is monovalent (e.g., includes one pair of heavy and light chains, or antigen binding portions thereof). In other embodiments, the immunoglobulin subunit of the fusion protein is divalent (e.g., includes two pairs of heavy and light chains, or antigen binding portions thereof). In preferred embodiments, the transgenic fusion proteins include an immunoglobulin heavy chain or a fragment thereof (e.g., an antigen binding fragment thereof).

In preferred embodiments of the present invention, the targeting agent is an antibody or antigen binding fragment of an antibody (e.g., Fab units). For example, a well-studied antigen found on the surface of many cancers (including breast HER2 tumors) is glycoprotein p185, which is exclusively expressed in malignant cells (Press et al., Oncogene 5:953 (1990)). Recombinant humanized anti-HER2 monoclonal antibodies (rhuMabHER2) have even been shown to inhibit the growth of HER2 overexpressing breast cancer cells, and are being evaluated (in conjunction with conventional chemotherapeutics) in phase III clinical trials for the treatment of advanced breast cancer (Pegrarn et al., Proc. Am. Soc. Clin. Oncol., 14:106 (1995)). Park et al. have attached Fab fragments of rhuMabHER2 to small unilamellar liposomes, which then can be loaded with the chemotherapeutic doxorubicin (dox) and targeted to HER2 overexpressing tumor xenografts (Park et al., Cancer Lett., 118:153 (1997) and Kirpotin et al., Biochem., 36:66 (1997)). These dox-loaded "immunoliposomes" showed increased cytotoxicity against tumors compared to corresponding non-targeted dox-loaded liposomes or free dox, and decreased systemic toxicity compared to free dox.

In some preferred embodiments, the antibodies recognize tumor specific epitopes (e.g., TAG-72 (Kjeldsen et al., Cancer Res., 48:2214-2220 (1988); U.S. Pat. Nos. 5,892,020; 5,892,019; and 5,512,443); human carcinoma antigen (U.S. Pat. Nos. 5,693,763; 5,545,530; and 5,808,005); TP1 and TP3 antigens from osteocarcinoma cells (U.S. Pat. No. 5,855,866); Thomsen-Friedenreich (TF) antigen from adenocarcinoma cells (U.S. Pat. No. 5,110,911); "KC-4 antigen" from human prostrate adenocarcinoma (U.S. Pat. Nos. 4,708,930 and 4,743,543); a human colorectal cancer antigen (U.S. Pat. No. 4,921,789); CA125 antigen from cystadenocarcinoma (U.S. Pat. No. 4,921,790); DF3 antigen from human breast carcinoma (U.S. Pat. Nos. 4,963,484 and 5,053,489); a human breast tumor antigen (U.S. Pat. No. 4,939,240); p97 antigen of human melanoma (U.S. Pat. No. 4,918,164); carcinoma or orosomucoid-related antigen (CORA) (U.S. Pat. No. 4,914,021); a human pulmonary carcinoma antigen that reacts with human squamous cell lung carcinoma but not with human small cell lung carcinoma (U.S. Pat. No. 4,892,935); T and Tn haptens in glycoproteins of human breast carcinoma (Springer et al., Carbohydr. Res., 178:271-292 (1988)), MSA breast carcinoma glycoprotein (Tjandra et al., Br. J. Surg., 75:811-817 (1988)); MFGM breast carcinoma antigen (Ishida et al., Tumor Biol., 10:12-22 (1989)); DU-PAN-2 pancreatic carcinoma antigen (Lan et al., Cancer Res., 45:305-310 (1985)); CA125 ovarian carcinoma antigen (Hanisch et al., Carbohydr. Res., 178:29-47 (1988)); YH206 lung carcinoma antigen (Hinoda et al., Cancer J., 42:653-658 (1988)). Each of the foregoing references is specifically incorporated herein by reference.

For breast cancer, the cell surface may be targeted with mammastatin, folic acid, EGF, FGF, and antibodies (or antibody fragments) to the tumor-associated antigens MUC1, cMet receptor and CD56 (NCAM).

A very flexible method to identify and select appropriate peptide targeting groups is the phage display technique (See e.g., Cortese et al., Curr. Opin. Biotechol., 6:73 (1995)), which can be conveniently carried out using commercially available kits. The phage display procedure produces a large and diverse combinatorial library of peptides attached to the surface of phage, which are screened against immobilized surface receptors for tight binding. After the tight-binding, viral constructs are isolated and sequenced to identify the peptide sequences. The cycle is repeated using the best peptides as starting points for the next peptide library. Eventually, suitably high-affinity peptides are identified and then screened for biocompatibility and target specificity. In this way, it is possible to produce peptides conjugated to dendrimers, producing multivalent conjugates with high specificity and affinity for the target cell receptors (e.g., tumor cell receptors) or other desired targets. In some embodiments, the gossypol compounds or other therapeutic agents are associated with dendrimers (e.g., PAMAM), or liposomes, or other carriers. Those skilled in the art will be able to readily design dendrimer gossypol compound molecules that take advantage of the multivalent structure of dendrimers.

Related to the targeting approaches described above is the "pretargeting" approach (See e.g., Goodwin and Meares, Cancer (suppl.), 80:2675 (1997)). An example of this strategy involves initial treatment of the patient with conjugates of tumor-specific monoclonal antibodies and streptavidin. Remaining soluble conjugate is removed from the bloodstream with an appropriate biotinylated clearing agent. When the tumor-localized conjugate is all that remains, a gossypol-linked, biotinylated agent is introduced, which in turn localizes at the tumor sites by the strong and specific biotin-streptavidin interaction.

In other preferred embodiments, the antibodies recognize specific pathogens (e.g., *Legionella peomophilia, Mycobacterium tuberculosis, Clostridium tetani, Hemophilus influenzae, Neisseria gonorrhoeae, Treponema pallidum, Bacillus anthracis, Vibrio cholerae, Borrelia burgdorferi, Comebacterium diphtheria, Staphylococcus aureus,* human papilloma virus, human immunodeficiency virus, rubella virus, polio virus, and the like).

C. Peptides as Targeting Molecules

In some preferred embodiments, targeting molecules comprise peptides that bind specifically to tumor blood vessels. (See e.g., Arap et al., Science, 279:377-80 (1998)). These peptides include, but are not limited to, peptides containing the RGD (Arg-Gly-Asp) motif (e.g., CDCRGDCFC; SEQ ID NO:4), the NGR (Asn-Gly-Arg) motif (e.g., CNGRCVSG-CAGRC; SEQ ID NO:5), and the GSL (Gly-Ser-Leu; SEQ ID NO:6) motif. These peptides and conjugates containing these peptides selectively bind to various tumors, including, but not limited to, breast carcinomas, Kaposi's sarcoma, and melanoma. It is not intended that the present invention be limited to any particular mechanism of action. Indeed, an understanding of the mechanism is not necessary to make and use the present invention. However, it is believed that these peptides are ligands for integrins and growth factor receptors that are absent or barely detectable in established blood vessels. In some preferred embodiments, the peptide is preferably produced using chemical synthesis methods. For example, peptides can be synthesized by solid phase techniques, cleaved from the resin, and purified by preparative high performance liquid chromatography. (See e.g., Creighton (1983) Proteins Structures and Molecular Principles, W.H. Freeman and Co, New York, N.Y.). In other embodiments, the composition of the synthetic peptides is confirmed by amino acid analysis or sequencing.

In some preferred embodiments, targeting molecules comprise peptides that specifically bind to glioma cells. (See e.g., Debinski et al., Nature Biotech., 16:449-53 (1998); Debinski et al., J. Biol. Chem., 270(28):16775-80 (1995); and Debinski et al., J. Biol. Chem., 271(37):22428-33 (1996)). In some embodiments, the present invention contemplates using drug delivery compositions comprising IL13, or one of its variants, so that the drug delivery compositions bind to IL13 binding sites in glioma cells.

Human high-grade gliomas are uniquely enriched in IL13 binding sites. Many of the established brain tumor cell lines, primarily malignant gliomas, over-express hIL13 binding sites. Human malignant glioma cell lines express a high number, up to 30,000, of binding sites for hIL13 per cell. Of interest, glioblastoma multiforme (GBM) explant cells showed an extraordinarily high number of hIL13 binding sites, up to 500,000 per cell. The binding of hL13 is not neutralized by hIL4 on an array of established human glioma cell lines that includes U-251 MG, U-373 MG, DBTRG MG, Hs-683, U-87 MG, SNB-19, and A-172 cells. hIL13 can be engineered to increase its specific targeting of high-grade gliomas. The pattern for IL13 and IL4R sharing on normal cells requires IL13 to bind hIL4R. This is confirmed by the fact that hIL13 binding is always fully competed by hIL4. The recently proposed model for this hIL13R suggests that the shared hIL13/4R is heterodimeric. This scenario would imply that hIL13 may contain at least two receptor-binding sites, each recognizing a respective subunit of the receptor. The engineered hIL13 variants (e.g., hIL13.E13K or hIL13.E13Y) are deprived of cell signaling abilities. This is desirable because interaction with physiological systems contributes prominently to the dose-limiting toxicity of some biological therapeutics (e.g., cytokines). Significantly, the molecule of hIL13 appears not to be sensitive to a variety of genetically engineered modifications and these variants can be produced in large quantities. It is thus possible to divert the molecule of hIL13 from its physiological receptor and make it a non-signaling compound, while the discovery of the expression of IL13 receptors on the surface of all of the malignancies of glial origin provides a novel strategy for the accumulation and retention of drug delivery compositions within CNS cancers. The high-grade glioma (HGG)-associated receptor for IL13 used in the present affinity toward the HGG-associated receptor remains intact or is increased. Such forms of IL13 can serve as rationally designed vectors for variety of imaging and therapeutic approaches of HGG.

Given the typically grim prognosis following the identification of an intracranial malignancy, any strategy for the pre-, intra- or post-operative identification and removal of cancer cells is a significant improvement. In some embodiments, nucleic acids encoding IL13 fragments, fusion proteins or functional equivalents or variants (e.g., hIL13.E13K or hIL13.E13Y) thereof are cloned into an appropriate expression vector, expressed and purified (e.g., preferably as described in Debinski et al., Nature Biotech., 16:449-53 (1998); Debinski et al., J. Biol. Chem., 270(28):16775-80 (1995); and Debinski et al., J. Biol. Chem., 271(37):22428-33 (1996)). In other embodiments of the present invention, vectors include, but are not limited to, chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. Large numbers of suitable vectors are known to those of skill in the art, and are commercially available. Such vectors include, but are not limited to, the following vectors: 1) Bacterial—pQE70: pQE60; pQE-9 (Qiagen, Inc., Valencia, Calif.); pBS; pD10; phagescript; psiX174; pbluescript SK; pBSKS; pNH8A; pNH16a; pNH18A; pNH46A (Stratagene, Inc., La Jolla, Calif.); ptrc99a; pKK223-3; pKK233-3; pDR540; pRIT5 (Pharmacia, Peapack, N.J.); and 2) Eukaryotic—pWLNEO; pSV2CAT; pOG44; PXT1; pSG (Stratagene); pSVK3; pBPV; pMSG; and pSVL (Pharmacia). Any other plasmid or vector can be used as long as they are replicable and viable in the host. In some preferred embodiments of the present invention, mammalian expression vectors comprise an origin of replication, a suitable promoter and enhancer, and any necessary ribosome binding sites, polyadenylation site, splice donor and acceptor sites, transcriptional termination sequences, and 5' flanking nontranscribed sequences. In other embodiments, DNA sequences derived from the SV40 splice, and polyadenylation sites are used to provide the required nontranscribed genetic elements.

In other embodiments, the IL13 peptide or variant thereof is expressed in a host cell. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomyces cerevisiae, Schizosaccharomyces pombe, Drosophila* S2 cells, *Spodoptera* Sf9 cells, Chinese Hamster Ovary (CHO) cells, COS-7 lines of monkey kidney fibroblasts, (Gluzman, Cell, 23:175 (1981)), C127, 3T3, HeLa and BHK cell lines.

In some embodiments of the present invention, IL13 or variants thereof are recovered or purified from recombinant cell cultures by methods including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein refolding steps are used, as necessary, in completing configuration of the mature protein. In still other embodiments of the present invention, high performance liquid chromatography (HPLC) is employed for final purification steps.

Some embodiments of the present invention provide polynucleotides having the coding sequence fused in frame to a marker sequence that allows for purification of the polypeptide of the present invention. A non-limiting example of a marker sequence is a hexahistidine tag that is supplied by a vector, preferably a pQE-9 vector, that provides for purification of the polypeptide fused to the marker in the case of a bacterial host, or, for example, the marker sequence may be a hemagglutinin (HA) tag when a mammalian host (e.g. COS-7 cells) is used. The HA tag corresponds to an epitope derived from the influenza hemagglutinin protein (Wilson, et al., Cell, 37:767 (1984)).

D. Signal Peptide as Targeting Molecules

In some embodiments of the present invention, the targeting molecules comprise signal peptides. These peptides are chemically synthesized or cloned, expressed and purified as described above. Signal peptides can assist the chemical address tags of the present invention target the drug delivery composition (or a portion thereof) to discrete regions within a cell. In some of these embodiments, the signal peptide is preferably: NH-Met-Leu-Ser-Leu-Arg-Gln-Ser-Ile-Arg-Phe-Phe-Lys-Pro-Ala-Thr-Arg-Thr-Leu-COOH (SEQ ID NO:7). The present invention is not limited to any particular mechanism, and an understanding of mechanisms is not necessary to make and use the present invention, however, it is contemplated that the peptide of SEQ ID NO:7 forms an amphipathic helix that associates with mitochondrial membrane protein import sites. This association allows peptide complexes to attach to mitochondrial membranes. It is unlikely that the complex is internalized, since there are few pores of nanometer size on intact mitochondria. In still other embodiments, the following nuclear localization signal is utilized: NH-Pro-Pro-Lys-Lys-Lys-Arg-Lys-Val-COOH (SEQ ID NO:8).

E. Nucleic Acids as Targeting Molecules

In some embodiments of the present invention, the targeting molecules comprise nucleic acids (e.g., RNA or DNA). In some embodiments, these nucleic acid moieties are designed to hybridize (by base pairing) to a particular nucleic acid (e.g., chromosomal DNA, mRNA, or ribosomal RNA) sequence in target cells and tissues. Exemplary nucleic acids include, but are not limited to, those coding for reverse transcriptase, REV and TAT proteins of HIV (Tuerk et al., Gene, 137(1):33-9 (1993)); human nerve growth factor (Binkley et al., Nuc. Acids Res., 23(16):3198-205 (1995)); and vascular endothelial growth factor (Jellinek et al., Biochem., 83(34):10450-6 (1994)). In other embodiments, the targeting molecules bind ligands or biological targets directly. In some embodiments, suitable nucleic acids that bind ligands are identified using the SELEX procedure (U.S. Pat. Nos. 5,475,096; 5,270,163; WO 97/38134; WO 98/33941; and WO 99/07724; all of which are herein incorporated by reference), although many additional methods are known in the art and are suitable in certain embodiments of the present invention.

F. Other Cellular Targeting Molecules

The targeting molecules of the present compositions may recognize a variety of epitopes on biological targets (e.g., pathogens, tumor cells, normal tissues). In some embodiments, cellular level targeting moieties are incorporated to recognize, target, or detect a variety of pathogenic organisms including, but not limited to, tumor specific antigens (e.g., carcinoembryonic antigen, prostate specific antigen, tyrosinase, ras, a sialyl lewis antigen, erb, MAGE-1, MAGE-3, BAGE, MN, gp100, gp75, p97, proteinase 3, a mucin, CD81, CID9, CD63, CD53, CD38, CO-029, CA125, GD2, GM2 and O-acetyl GD3, M-TAA, M-fetal or M-urinary). Alternatively, the targeting molecules may be a tumor suppressor, a cytokine, a chemokine, a tumor specific receptor ligand, a receptor, an inducer of apoptosis, or a differentiating agent.

Tumor suppressor proteins contemplated for targeting include, but are not limited to, p16, p21, p27, p53, p73, Rb, Wilms tumor (WT-1), DCC, neurofibromatosis type 1 (NF-1), von Hippel-Lindau (VHL) disease tumor suppressor, Maspin, Brush-1, BRCA-1, BRCA-2, the multiple tumor suppressor (MTS), gp95/p97 antigen of human melanoma, renal cell carcinoma-associated G250 antigen, KS 1/4 pan-carcinoma antigen, ovarian carcinoma antigen (CA125), prostate specific antigen, melanoma antigen gp75, CD9, CD63, CD53, CD37, R2, CD81, CO029, TI-1, L6 and SAS. Of course, these are merely exemplary tumor suppressors. It is envisioned that the present invention may be used in conjunction with any other agents that are or become known to those of skill in the art as a tumor suppressor or tumor marker.

In preferred embodiments of the present invention, the compositions are targeted to factors expressed by oncogenes. These include, but are not limited to, tyrosine kinases, both membrane-associated and cytoplasmic forms, such as members of the Src family, serine/threonine kinases, such as Mos, growth factor receptors, such as platelet derived growth factor (PDGF), SMALL GTPases (G proteins) including the ras family, cyclin-dependent protein kinases (cdk), members of the myc family, including c-myc, N-myc, and L-myc and bcl-2 and family members.

Receptors and their related ligands that find use in the context of certain embodiments of the present invention include, but are not limited to, the folate receptor, adrenergic receptor, growth hormone receptor, luteinizing hormone receptor, estrogen receptor, epidermal growth factor receptor, fibroblast growth factor receptor, and the like.

Hormones and their receptors that find use in the cellular level targeting aspects of the present invention include, but are not limited to, growth hormone, prolactin, placental lactogen, luteinizing hormone, follicle-stimulating hormone, chorionic gonadotropin, thyroid-stimulating hormone, leptin, adrenocorticotropin (ACTH), angiotensin I, angiotensin II, α-endorphin, α-melanocyte stimulating hormone (α-MSH), cholecystokinin, endothelin I, galanin, gastric inhibitory peptide (GIP), glucagon, insulin, amylin, lipotropins, GLP-1 (7-37) neurophysins, mammastatin, and somatostatin.

In addition, the present invention contemplates that vitamins (both fat soluble and non-fat soluble vitamins) can be used as targeting molecules to target biological targets (e.g., cells) that have receptors for, or otherwise take up, these vitamins. Particularly preferred for this aspect of the invention are the fat soluble vitamins D, E, and A, and analogues thereof, and the water soluble vitamin C.

IX. Pharmaceutical Formulations, Administration Routes, and Dosing Considerations The present invention provides pharmaceutical compositions which may comprise at least one gossypol compound, and in preferred embodiments, at least one conventional anticancer agent. The gossypol compounds and anticancer agents may be administered in any sterile, biocompatible pharmaceutical carrier, including, but not limited to, saline, buffered saline, dextrose, and water. In some embodiments, the pharmaceutical compositions of the present invention may contain one agent (e.g., a gossypol compound). In other embodiments, the pharmaceutical compositions contain a mixture of at least two agents (e.g., a gossypol compound and one or more conventional anticancer agents). In still further embodiments, the pharmaceutical compositions of the present invention contain at least two agents (e.g., gossypol compounds and one or more conventional anticancer agents) that are administered to a patient under one or more of the following conditions: at different periodicities, at different durations, at different concentrations, by different administration routes, etc. In some embodiments, the gossypol compound is administered prior to the anticancer agent, e.g., 0.5, 1, 2 3, 4, 5, 10, 12, or 18 hours, 1, 2, 3, 4, 5, or 6 days, 1, 2, 3, or 4 weeks prior to the administration of the anticancer agent. In some embodiments, the gossypol compound is administered after the anticancer agent, e.g., 0.5, 1, 2 3, 4, 5, 10, 12, or 18 hours, 1, 2, 3, 4, 5, or 6 days, 1, 2, 3, or 4 weeks after the administration of the anticancer agent. In some embodiments, the gossypol compound and the anticancer agent are administered concurrently but on different schedules, e.g., the gossypol compound is administered daily while the anticancer agent is administered once a week, once every two weeks, once every three weeks, or once every four weeks. In other embodiments, the gossypol compound is administered once a week while the anticancer agent is administered daily, once a week, once every two weeks, once every three weeks, or once every four weeks.

The compositions and methods of the present invention find use in treating diseases or in altering physiological states that are characterized by the overexpression of one or more Bcl-2 family proteins (e.g., Bcl-2, Bcl-$X_L$, Mcl-1, A1/BFL-1, and BOO-DIVA, etc.). The invention further provides methods for inducing apoptosis in cells by antagonizing the anti-apoptotic affects of some Bcl-2 family proteins including, but not limited to, Bcl-2, Bcl-$X_L$, Mcl-1, A1/BFL-1, and BOO-DIVA.

Depending on the condition being treated, preferred embodiments of the present pharmaceutical compositions are formulated and administered systemically or locally. Techniques for formulation and administration can be found in the latest edition of "Remington's Pharmaceutical Sciences" (Mack Publishing Co, Easton Pa.). Exemplary pharmaceutical formulations and methods of producing pharmaceuticals are described in U.S. 20030211046A1; U.S. 20030004182A1; U.S. 2002060356384; U.S. 20020015728A1; U.S. Pat. No. 6,511,660; U.S. Pat. No. 6,406,745; U.S. Pat. No. 6,346,269; U.S. Pat. No. 6,039,977; U.S. Pat. No. 5,858,408; U.S. Pat. No. 5,631,023; U.S. Pat. No. 5,476,667; U.S. Pat. No. 5,044,091; U.S. Pat. No. 4,867,970; and WO 0028969A2 each of which is incorporated herein by reference in its entirety). Suitable routes may, for example, include oral or transmucosal administration as well as parenteral delivery (e.g., intramuscular, subcutaneous, intramedullary, intrathecal, intraventricular, intravenous, intraperitoneal, or intranasal administration).

The present invention contemplates administering gossypol compounds and, in some embodiments, one or more conventional anticancer agents, in accordance with acceptable pharmaceutical delivery methods and preparation techniques. For example, gossypol compounds and suitable anticancer agents can be administered to a subject intravenously in a pharmaceutically acceptable carrier such as physiological saline. Standard methods for intracellular delivery of pharmaceutical agents are contemplated (e.g. delivery via liposome). Such methods are well known to those of ordinary skill in the art.

In some embodiments, the formulations of the present invention are useful for parenteral administration (e.g., intravenous, subcutaneous, intramuscular, intramedullary, and intraperitoneal). Therapeutic co-administration of some contemplated anticancer agents (e.g., therapeutic polypeptides) can also be accomplished using gene therapy reagents and techniques.

In some embodiments of the present invention, gossypol compounds are administered to a subject alone, or in combination with one or more conventional anticancer agents (e.g., nucleotide sequences, drugs, hormones, etc.) or in pharmaceutical compositions where the components are optionally mixed with excipient(s) or other pharmaceutically acceptable carriers. In preferred embodiments of the present invention, pharmaceutically acceptable carriers are biologically inert. In preferred embodiments, the pharmaceutical compositions of the present invention are formulated using pharmaceutically acceptable carriers well known in the art in dosages suitable for oral administration. Such carriers enable the pharmaceutical compositions to be formulated as tablets, pills, capsules, dragees, liquids, gels, syrups, slurries, solutions, suspensions and the like, for respective oral or nasal ingestion by a subject. In preferred embodiments, the gossypol compounds are administered orally to a subject.

Pharmaceutical preparations for oral use can be obtained by combining the active compounds (e.g., gossypol compounds) with solid excipients, optionally grinding the resulting mixture, and processing the mixture into granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc.; cellulose such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used. Such penetrants are known to those skilled in the art.

Pharmaceutical compositions suitable for use in the present invention include compositions wherein the active ingredients are contained in an effective amount to achieve the intended purpose. For example, an effective amount of a gossypol compound may be that amount that induces apoptosis in a cell or tissue having elevated levels of a Bcl-2 family protein as compared to normal nonpathological cells or tissues. The determination of an effective amount of an agent is well within the skills of those in the pharmacological arts, especially in view of the disclosure provided herein.

In addition to the active ingredients, preferred pharmaceutical compositions may contain suitable pharmaceutically acceptable carriers comprising excipients and auxiliaries that facilitate processing of the active compounds into pharmaceutically useful forms.

The pharmaceutical compositions of the present invention may be manufactured using any acceptable techniques for preparing pharmaceutical compositions including, but not limited to, by means of conventional mixing, dissolving, granulating, dragee-making, levigating, emulsifying, encapsulating, entrapping or lyophilizing processes, and the like.

Ingestible formulations of the present compositions may further include any material approved by the United States Department of Agriculture for inclusion in foodstuffs and substances that are generally recognized as safe (GRAS), such as food additives, flavorings, colorings, vitamins, minerals, and phytonutrients. The term phytonutrients, as used herein, refers to organic compounds isolated from plants that have a biological effect, and includes, but is not limited to, compounds of the following classes: isoflavonoids, oligomeric proanthcyanidins, indol-3-carbinol, sulforaphone, fibrous ligands, plant phytosterols, ferulic acid, anthocyanocides, triterpenes, omega 3/6 fatty acids, polyacetylene, quinones, terpenes, cathechins, gallates, and quercitin.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations contemplated for oral administration include push-fit capsules made of gelatin, as well as soft sealed capsules of gelatin and a coating such as glycerol or sorbitol. In some embodiments, push-fit capsules can contain the active ingredients mixed with fillers or binders such as lactose or starches, lubricants such as talc or magnesium stearate, and, optionally, stabilizers. In some soft capsule embodiments, the active compounds are dissolved or suspended in a suitable liquid or solvent, such as fatty oils, liquid paraffin, or liquid polyethylene glycol, with or without stabilizers.

Pharmaceutical formulations for parenteral administration include aqueous solutions of the active compounds. Aqueous injection suspensions optionally contain substances that increase the viscosity of the suspension such as sodium carboxymethyl cellulose, sorbitol, or dextran. Additionally, suspensions of the active compounds may be prepared as appropriate oily injection suspensions. In this aspect, suitable lipophilic solvents or vehicles include fatty oils such as sesame oil, or synthetic fatty acid esters, such as ethyl oleate or triglycerides, or liposomes. Optionally, suspensions contain suitable stabilizers or agents that increase the solubility of the compounds thus allowing for the preparation of highly concentrated solutions.

Compositions comprising a compound of the invention formulated in a pharmaceutical acceptable carrier may be prepared, placed in an appropriate container, and labeled for treatment of an indicated condition. For gossypol compounds, conditions indicated on the label may include treatment of conditions related to faulty regulation of apoptosis, hyperproliferative diseases, cancers, acquired immune deficiency syndrome (AIDS), degenerative conditions, and vascular diseases. The pharmaceutical compositions may be provided as salts and can be formed with many acids, including but not limited to hydrochloric, sulfuric, acetic, lactic, tartaric, malic, succinic, and the like. Salts tend to be more soluble in aqueous or other protonic solvents than are corresponding free base forms. In other cases, a preferred preparation comprises a lyophilized powder in 1 mM-50 mM histidine, 0.1%-2% sucrose, or 2%-7% mannitol at a pH range of from about 4.5 to 5.5, optionally combined with buffer prior to use.

In preferred embodiments, dosing and administration regimes are tailored by the clinician, or others skilled in the pharmacological arts, based upon well known pharmacological and therapeutic considerations including, but not limited to, the desired level of therapeutic effect, and the practical level of therapeutic effect obtainable. Generally, it is advisable to follow well-known pharmacological principles for administrating chemotherapeutic agents (e.g., it is generally advisable to not change dosages by more than 50% at time and no more than every 3-4 agent half-lives). For compositions that have relatively little or no dose-related toxicity considerations, and where maximum efficacy (e.g. destruction of cancer cells) is desired, doses in excess of the average required dose are not uncommon. This approach to dosing is commonly referred to as the "maximal dose" strategy.

Additional dosing considerations relate to calculating proper target levels for the agent being administered, the agent's accumulation and potential toxicity, stimulation of resistance, lack of efficacy, and describing the range of the agent's therapeutic index.

In certain embodiments, the present invention contemplates using routine methods of titrating the agent's administration. One common strategy for the administration is to set a reasonable target level for the agent in the subject. In some preferred embodiments, agent levels are measured in the subject's plasma. Proper dose levels and frequencies are then designed to achieve the desired steady-state target level for the agent. Actual, or average, levels of the agent in the subject are monitored (e.g., hourly, daily, weekly, etc.) such that the dosing levels or frequencies can be adjusted to maintain target levels. Of course, the pharmacokinetics and pharmacodynamics (e.g., bioavailability, clearance or bioaccumulation, biodistribution, drug interactions, etc.) of the particular agent or agents being administered can potentially impact what are considered reasonable target levels and thus impact dosing levels or frequencies.

Target-level dosing methods typically rely upon establishing a reasonable therapeutic objective defined in terms of a desirable range (or therapeutic range) for the agent in the subject. In general, the lower limit of the therapeutic range is roughly equal to the concentration of the agent that provides about 50% of the maximum possible therapeutic effect. The upper limit of the therapeutic range is usually established by the agent's toxicity and not by its efficacy. The present invention contemplates that the upper limit of the therapeutic range for a particular agent will be the concentration at which less than 5 or 10% of subjects exhibit toxic side effects. In some embodiments, the upper limit of the therapeutic range is about two times, or less, than the lower limit. Those skilled in the art will understand that these dosing consideration are highly variable and to some extent individualistic (e.g. based on genetic predispositions, immunological considerations, tolerances, resistances, and the like). Thus, in some embodiments, effective target dosing levels for an agent in a particular subject may be 1, . . . 5, . . . 10, . . . 15, . . . 20, . . . , . . . 75, . . . 100, . . . 200, . . . X %, greater than optimal in another subject. Conversely, some subjects may suffer significant side effects and toxicity related health issues at dosing levels or frequencies far less (1, . . . 5, . . . 10, . . . 15, . . . 20, . . . 50, . . . 75, . . . 100, . . . 200, . . . X %) than those typically producing optimal therapeutic levels in some or a majority of subjects. In the absence of more specific information, target administration levels are often set in the middle of the therapeutic range.

In certain embodiments, genetic screening methods (e.g., SNP testing) are used to test a subject's predisposition to adverse reactions in response to particular chemotherapeutic agents or classes of chemotherapeutic agents.

In still further embodiments, the present invention provides methods for repetitive dosing and/or the continuous (semi-continuous) infusion of therapeutic agents (e.g. small molecule Bcl-2 antagonists or agonists) sufficient to maintain, within a given therapeutic range, a steady-state concentration of agent(s) in a subject (e.g., in the subject's plasma). Those skilled in the art will appreciate that the compositions of the present invention can be administered such that a maintenance dose is provided. Thus, in some embodiments, the chosen agent target concentration or rate of drug delivery is adjusted to balance the rate of drug loss. Those skilled in the art of administering chemotherapeutic agents will appreciate the calculations and measurements used to ensure the balance of drug input versus drug loss to provide the desired target level of drug (or other therapeutic agent) in the subject. Particularly useful in performing these calculations are defined levels of agent clearance and availability in a particular subject.

In additional embodiments, the present invention provides intermittent dosing methods, since marked fluctuations in agent concentration between doses are generally undesirable. In situations where the absorption and distribution of the agent are balanced and spontaneous, concentration fluctuations are dictated by the agent's elimination half-life.

In embodiments where the administered compositions are relatively nontoxic, maximal dosing methods can be used, because even concentrations of the agent several times that necessary for ensuring therapeutic efficacy are well tolerated. In these embodiments, the dosing intervals are lengthened such that the concentration of the agent in the subject's system remains within the range of therapeutic effectiveness for relatively long periods of time before being cleared from the subject and additional administrations are required to bring the agent's level back into the therapeutically effective range. Thus, in certain of these embodiments, dosing intervals are longer than the agent's elimination half-life.

In other embodiments, where the compositions have relatively narrow therapeutic ranges, it may be important calculate the maximum and minimum concentrations that will occur at particular dosing interval(s). In preferred embodiments, the minimal steady-state concentration of administered agents are determined using equations, optionally corrected for the bioavailability of the agents, which are well known to those skilled in the pharmacological arts.

In still other embodiments, where the agents follow multiexponential kinetics and the agents are administered orally, the estimation of the maximal steady-state concentration involves manipulation of several exponential constants concerning agent distribution and absorption.

The present invention also provides methods for administering loading doses of an agent, or agents, to a subject. As used herein, a "loading dose" is one or a series of doses that when given at the onset of a treatment quickly provide the target concentration of the therapeutic agent. In some embodiments, loading doses are administered to a subject having an immediate need for the target level of an agent in relation to the time required to attain a steady-state target level of the agent provided using a constant rate of administration. Various negative considerations should be weighed against the exigency of the subject's condition and her need for a loading dose prior to its administration. These considerations include, but are not limited to: 1) loading doses are often administered in one large bolus which may abruptly subject the patient to a toxic concentration of the agent; 2) agents with long half-lives will remain at levels above the target-level as compared to agents administered under lower constant rate schemes. Loading doses are often large, rapid, and given parenterally, thus dangerous side effects can potentially occur at the site of administration before the agent can obtain equilibrium in the subject's plasma.

In preferred embodiments, the clinician rationally designs an individualized dosing regimen based on known pharmacological principles and equations. In general, the clinician designs an individualized dosing regimen based on knowledge of various pharmacological and pharmacokinetic properties of the agent, including, but not limited to, F (fractional bioavailability of the dose), Cp (concentration in the plasma), CL (clearance/clearance rate), Vss (volume of drug distribution at steady state) Css (concentration at steady state), and t1/2 (drug half-life), as well as information about the agent's rate of absorption and distribution. Those skilled in the art are referred to any number of well known pharmacological texts (e.g., Goodman and Gilman's, Pharmaceutical Basis of Therapeutics, 10th ed., Hardman et al., eds., 2001) for further explanation of these variables and for complete equations illustrating the calculation of individualized dosing regimes. Those skilled in the art also will be able to anticipate potential fluctuations in these variables in individual subjects. For example, the standard deviation in the values observed for F, CL, and Vss is typically about 20%, 50%, and 30%, respectively. The practical effect of potentially widely varying parameters in individual subjects is that 95% of the time the Css achieved in a subject is between 35 and 270% of the target level. For drugs with low therapeutic indices, this is an undesirably wide range. Those skilled in the art will appreciate, however, that once the agent's Cp (concentration in the plasma) is measured, it is possible to estimate the values of F, CL, and Vss directly. This allows the clinician to effectively fine tune a particular subject's dosing regimen.

In still other embodiments, the present invention contemplates that continuing therapeutic drug monitoring techniques be used to further adjust an individual's dosing methods and regimens. For example, in one embodiment, Css data is used is to further refine the estimates of CL/F and to subsequently adjust the individual's maintenance dosing to achieve desired agent target levels using known pharmacological principles and equations. Therapeutic drug monitoring can be conducted at practically any time during the dosing schedule. In preferred embodiments, monitoring is carried out at multiple time points during dosing and especially when administering intermittent doses. For example, drug monitoring can be conducted concomitantly, within fractions of a second, seconds, minutes, hours, days, weeks, months, etc., of administration of the agent regardless of the dosing methodology employed (e.g., intermittent dosing, loading doses, maintenance dosing, random dosing, or any other dosing method). However, those skilled in the art will appreciate that when sampling rapidly follows agent administration the changes in agent effects and dynamics may not be readily observable because changes in plasma concentration of the agent may be delayed (e.g., due to a slow rate of distribution or other pharmacodynamic factors). Accordingly, subject samples obtained shortly after agent administration may have limited or decreased value.

The primary goal of collecting biological samples from the subject during the predicted steady-state target level of administration is to modify the individual's dosing regimen based upon subsequently calculating revised estimates of the agent's CL/F ratio. However, those skilled in the art will appreciate that early postabsorptive drug concentrations do not typically reflect agent clearance. Early postabsorptive drug concentrations are dictated principally by the agent's rate of absorption, the central, rather than the steady state, volume of agent distribution, and the rate of distribution. Each of these pharmacokinetic characteristics have limited value when calculating therapeutic long-term maintenance dosing regimens.

Accordingly, in preferred embodiments, when the objective is therapeutic long-term maintenance dosing, biological samples are obtained from the subject, cells, or tissues of interest well after the previous dose has been administered, and even more preferably shortly before the next planned dose is administered.

In still other embodiments, where the therapeutic agent is nearly completely cleared by the subject in the interval between doses, then the present invention contemplates collecting biological samples from the subject at various time points following the previous administration, and most preferably shortly after the dose was administered.

In yet other embodiments, when low clearance of the agent is problematic, and toxicity issues are likely to result from its accumulation, the present invention contemplates measuring agent concentrations immediately before the administration of the subsequent dose. In these embodiments, the determination of maximal and minimal agent concentrations are preferred.

The methods of the present invention further contemplate that when a constant maintenance dosage is administered, steady state is reached only after expiration of four agent half-lives. Samples collected too soon after dosing begins do not accurately reflect agent clearance. However, for potentially highly toxic agents, significant toxicity and damage may already have ensued before expiration of the agent's fourth half-life. Thus, in some instances when it is important to maintain control over agent concentrations, a first sample is taken after two half-lives, assuming a loading dose has not been administered. If agent concentration already exceeds 90% of the eventual expected mean steady-state concentration, the dosage rate is halved, and another sample obtained following an additional two half-lives. The dosage is halved again if this sample once more exceeds the target level. If the first concentration does not exceed tolerable limits, subsequent administrations are given at the initial dose rate. If the concentration is lower than expected, the steady state can likely be achieved in about two half-lives, and at this point the dosage rate can be adjusted as described herein.

In embodiments comprising intermittent dosages, an additional concern related to timing of collection of concentration information, is if the sample was obtained immediately before the next scheduled dose, concentration will be at a minimal value, not the mean; however, as discussed herein, the estimated mean concentration can be calculated using equations known in the pharmacological arts.

When administering therapeutic agents having first-order kinetics, the average, minimum, and maximum concentrations at steady state are linearly related to the dose and dosing rate. Thus, in these embodiments, the ratio between the measured and the desired agent concentrations is used to adjust dosing.

In another aspect of the present invention, computer programs are helpful in designing dosing regimens. Typically, these programs take into account the measured drug concentrations and various factors (e.g., measured or predicted) related to the individual subjects.

The present invention is not limited to any particular temporal constraints on collecting subject, tissue, cell culture, or animal drug administration data or samples. Moreover, the present invention is not limited to collecting any particular type of samples (e.g., biological samples) from a subject, tissue, cell culture, or test animal laboratory animal or otherwise. Indeed, in some embodiments, the present invention contemplates acquiring biological samples including, but not limited to, polynucleotides, polypeptides, lipids, carbohydrates, glycolipids, ionic species, metabolites, inorganic molecules, macromolecules and macromolecular precursors as well as cell fractions, blood (e.g., cellular and soluble or insoluble blood components including, but not limited to, plasma, serum, metabolites, factors, enzymes, hormones, and organic or inorganic molecules), exudates, secretions, sputum, excreta, cell and tissue biopsies, CNS fluids (cerebrospinal fluid), secretions of lachrymal, salivary, and other glands, seminal fluids, etc., and combinations of these or any other subcellular, cellular, tissular, organismal, systemic, or organismic biological materials. Biological samples taken from a subject can be analyzed for chemical or biochemical changes (e.g., changes in gene expression) or other effects resultant from administration of the therapeutic agent. Further biological sample and sampling consideration are described below.

In some of these embodiments, the biological and pharmacological effects of the therapeutic compositions are determined using routine laboratory procedures on the collected samples including, but not limited to, microscopy (e.g., light, fluorescence (confocal fluorescence, immunofluorescence), phase-contrast, differential interference-contrast, dark field, or electron (transmission, scanning, cryo-), NMR, autoradiography), cell sorting techniques (e.g., fluorescence-activated), chromatography techniques (e.g., gel-filtration, ion exchange, hydrophobic, affinity, HPLC), electrophoretic techniques (e.g., SDS-PAGE, 2D-, 3D-, isoelectric focusing), ultracentrifugation, immunocytochemical and immunohistochemical technologies (e.g., ELISA, Western blotting, Immuno blotting), nucleic acid, including recombinant, technologies (e.g., PCR (inverse, reverse, nested), Northern blotting, Southern blotting, Southwestern blotting, in situ hybridization, FISH, nick-translation, DNAse footprinting, DNAse hypersensitivity site mapping, Maxam-Gilbert sequencing, Sanger sequencing, gel-shift (mobility shift) analysis, S1 nuclease analysis, RNAse protection assay, CAT assays, transgenic techniques, knock-out techniques, and reporter gene systems), amino acid analysis (e.g., Edman degradation), morphological, pathological, or phenotypical observations, and other observations with or without aid of instrumentation.

In some embodiments, subjects are questioned directly or indirectly regarding their state of health and any changes attributable to the administration of the therapeutic compositions (e.g., drugs, small molecules, and other therapeutic agents and techniques) and methods of the present invention.

Various interpatient and intrapatient pharmacokinetic considerations affect the design of dosing and administration regimens for individual patients. For any given drug, there may be wide variations in its pharmacokinetic properties in a particular subject, and up to one-half or more of the total variation in eventual response. The importance of these variable factors depends in part upon the agent and its usual route of elimination. For example, agents that are primarily removed by the kidneys and excreted unchanged into the urinary system, tend to show less interpatient variability in subjects with similar renal function than agents that are metabolically inactivated. Agents that are extensively metabolized, and agents that have high metabolic clearance and large first-pass elimination rates show large differences in interpatient bioavailability. Agents with slower rates of biotransformation typically have the largest variation in elimination rates among individual subjects. Differences in subject genotypes also plays an important part in determining different metabolic rates. Pathological and physiological variations in individual subjects' organ functions (e.g., renal or hepatic diseases) are major factors that can affect an agent's rate of disposition. Kidney or liver diseases often impair drug disposition and thus increase interpatient drug variability. Other factors (e.g. age) can also affect the responsiveness of targeted cells and tissues (e.g., the brain) to a particular composition or method of the present invention, and can alter the expected range of the therapeutic target level for the agent.

When invasive patient samples (e.g., blood, serum, plasma, tissues, etc.) are necessary to determine the concentration of the therapeutic agent(s) in a subject, design of the collection procedures should be undertaken after considering various criteria including, but not limited to: 1) whether a relationship exists between the concentration of the agent and any desired therapeutic effects or avoidable toxic effects; 2) whether these is substantial interpatient variability, but small intrapatient variation in agent disposition; 3) whether it is otherwise difficult or impractical to monitor the effects of the agent; and 4) whether the therapeutic concentration of the agent is close to the toxic concentration. In still other embodiments, concentration measurements are supplemented with additional measurements of pharmacokinetic, pharmacodynamic, or pharmacological effects.

In some instances, considerable interpatient response variations exist after the concentration of agent has been adjusted to the target level. For some agents, this pharmacodynamic variability accounts for much of the total variation in subject response. In some embodiments, the relationship among the concentration of an agent and the magnitude of the observed response may be complex, even when responses are measured in simplified systems in vitro, although typically a sigmoidal concentration-effect curve is seen. Often there is no single characteristic relationship between agent concentration (e.g. in the subject's plasma) and measured effect. In some embodiments, the concentration-effect curve may be concave upward. In other embodiments, the curve is concave downward. In still other embodiments, the data plots are linear, sigmoid, or in an inverted U-shape. Moreover, the resulting concentration-effect relationship curves can be distorted if the response being measured is a composite of several effects. In some preferred embodiments, the composite concentration-effect curves are resolved into simpler component curves using calculations and techniques available to those skilled in the art.

The simplified concentration-effect relationships, regardless of their exact shape, can be viewed as having four characteristic variables: potency, slope, maximal efficacy, and individual variation. Those skilled in the art will appreciate that the potency of an agent is measured by the intersection of the concentration-effect curve with the concentration axis. Although potency is often expressed as the dose of an agent required to produce the desired effect, it is more appropriately expressed as relating to the concentration of the agent in the subject (e.g. in plasma) that most closely approximates the desired situation in an in vitro system to avoid complicating pharmacokinetic variables. Although potency affects agent dosing, knowledge of an agent's potency alone is relatively unimportant in clinical use so long as a dose sufficient to obtain the target level can be conveniently administered to the subject. It is generally accepted that more potent agents are not necessarily therapeutically superior to less potent agents. One exception to this principle, however, is in the field of transdermal agents.

The maximum effect that an agent can induce in a subject is called its maximal or clinical efficacy. An agent's maximal efficacy is typically determined by the properties of the agent and its receptor-effector system and is reflected in the plateau of the concentration-effect curve. In clinical use, however, an agent's dosage may be limited by undesirable effects (e.g., toxicity), and the true maximal efficacy of the agent may not be practically achievable without harming the subject.

The slope and shape of the concentration-effect curve reflects the agent's mechanism of action, including the shape of the curve that, at least in part, describes binding to the agent's receptor. The rise of the concentration-effect curve indicates the clinically useful dosage range of the agent. Those skilled in the art will appreciate that the dosage ranges recited herein are approximations based on sound pharmacological principles and that actual responses will vary among different individuals given the same concentration of an agent, and will even vary in particular individuals over time.

It is well known that concentration-effect curves are either based on an average response, or are tailored to reflect an actual response in a particular individual at a particular time.

The concentration of an agent that produces a specified effect in a particular subject is called the individual effective concentration. Individual effective concentrations usually show a lognormal distribution, resulting in a normal variation curve from plotting the logarithms of the concentration against the frequency of achieving the desired effect. A cumulative frequency distribution of individuals achieving the desired effect as a function of agent concentration is called the concentration-percent curve or quantal concentration-effect curve. The shape of this curve is typically sigmoidal. The slope of the concentration-percent curve is an expression of the pharmacodynamic variability in the population rather than an expression of the concentration range from a threshold to a maximal effect in the individual patient.

Those skilled in the art will appreciate that the median effective dose ($ED_{50}$) is the dose of an agent sufficient to produce the desired effect in 50% of the population.

In preclinical drug studies, the dose (MTD) is determined in experimental animals. The ratio of the MTD to the $ED_{50}$ is an indication of the agent's therapeutic index and is a measurement of the selectivity of the agent in producing its desired effects. In clinical studies, the dose, or preferably the concentration, of an agent sufficient to produce toxic effects is compared to the concentration required for the therapeutic effects in the population to provide a clinical therapeutic index. However, due to individual pharmacodynamic variations in the population, the concentration or dose of an agent required to produce the therapeutic effect in most subjects occasionally overlaps the concentration that produces toxicity in some subjects despite the agent having a large therapeutic index. Those skilled in the art will appreciate that few therapeutic agents produce a single effect, thus, depending on the effect being measured, the therapeutic index for the agent may vary.

Preferred embodiments of the present invention provide approaches to individualize dosing levels and regimens. In preferred embodiments, optimal treatment regimens for particular subjects are designed after considering a variety of biological and pharmacological factors including, but not limited to, potential sources of variation in subject response to the administered agent(s), diagnosis specifics (e.g., severity and stage of disease, presence of concurrent diseases, etc.), other prescription and non prescription medications being taken, predefined efficacy goals, acceptable toxicity limits, cost-benefit analyses of treatment versus non treatment or treatment with other various available agents, likelihood of subject compliance, possible medication errors, rate and extent of agent absorption, the subject's body size and compositions, the agent's distribution, the agent's pharmacokinetic profile (e.g., physiological variables, pathological variables, genetic factors and predispositions, drug interactions, potential drug resistances, predicted rate of clearance), potential drug-receptor interactions, functional state, and placebo effects.

In preferred embodiments, the clinician selects an appropriate marker for measuring the ultimate effectiveness of the administered agent(s) in the subject. The present invention contemplates that in some embodiments, appropriate markers of an agent's effectiveness include a decrease (or increase) in some measurable biological state, condition, or chemical level (e.g., toxin load, viral titer, antigen load, temperature, inflammation, blood cell counts, antibodies, tumor morphology, and the like). A large number of diagnostic procedures and tests are available for gathering information on various markers including, but not limited to, cell culture assays (e.g., invasion assays in soft-agar and the like), radiographic examination (e.g., chest X-ray), computed tomography, computerized tomography, or computerized axial tomography (CAT) scans, positron emission tomography (PET) scans, magnetic resonance imaging (MRI or NMRI), mammography, ultrasonography (transvaginal, transcolorectal), scintimammography (e.g., technetium 99m sestamibi, technetium-99m tetrofosmin), aspiration (e.g., endometrial), palpation, PAP tests (e.g., smears), sigmoidoscopy (e.g., flexible fiberoptic), fecal occult blood testing (e.g., Guaiac-based FOBT), digital rectal examination, colonoscopy, virtual colonoscopy (also known as colonography), barium enema, stool analysis (See e.g., K. W. Kinzler and B. Vogelstein, Cell, 87(2):159-70 (1996); S. M. Dong et al., J. Natl. Cancer Inst., 93(11):858-865 (2001); G. Traverso et al., N. Engl. J. Med., 346(5):311-20 (2002), G. Traverso et al., Lancet, 359(9304):403 (2002); and D. A. Ahlquist et al., Gastroenterology, 119(5):1219-1227, (2000)), serum prostate-specific antigen (PSA) screening, endoscopy, gallium scans, marrow and tissue biopsies (e.g., core-needle, percutaneous needle biopsy, thoracotomy, endometrial, etc.) and histological examinations, direct and/or indirect clinical observations (e.g., patient surveys, inquiries, or questionnaires), cytological sampling and collection of biological tissues, fluids, and markers therein, (e.g., blood, urine (e.g., hematuria screening, urinary cytologic examinations), sputum (e.g., sputum cytology), feces, CNS fluids (e.g., LPs, spinal taps), blood products, including proteins and peptides (e.g. Bcl-2 family proteins), cancer markers (e.g., CA 125 (ovarian cancer), CA 15-3 (breast cancer), CEA (ovarian, lung, breast, pancreas, and gastrointestinal tract cancers), PSA (prostate cancer), p53 gene product, MIC2 gene product), metabolites (e.g., vanillylmandelic acid (VMA), and homovanillic acid (HVA)), antigens (e.g., serum alpha-fetoprotein (AFP)), salts, minerals, vitamins, soluble factors, insoluble factors, nucleic acids, and the like).

For any compound used in the methods of the invention, the therapeutically effective dose can be estimated initially from the concentration of compounds that causes fifty percent cell growth inhibition and/or cell killing in the cell culture assays. Subsequently, dosages can be formulated in animal models (e.g., murine models) to achieve a desirable circulating concentration (target-level) range that induces the desired effect (e.g., apoptosis) in target cells characterized by elevated expression levels of Bcl-2 family proteins. A therapeutically effective dose is the amount of gossypol compound (and in some embodiments, and additional therapeutic agents (e.g., chemotherapeutic and/or anit-neoplastic agents) sufficient to ameliorate (or prevent) the symptoms of a disease or pathology (e.g., unregulated cell proliferation, growth, invasion, autoimmunity).

In preferred embodiments, the toxicity and therapeutic efficacy of agents is determined using standard pharmaceutical procedures in cell cultures or experimental animals, e.g., for determining the MTD and the $ED_{50}$. Agents that exhibit large therapeutic indices are preferred. The data obtained from cell culture assays or animal models can be used to formulate dosing ranges in, for example, mammals (e.g., humans, *Equus caballus, Felis catus*, and *Canis familiaris*, etc.). Preferable dosing concentrations are near the calculated or observed $ED_{50}$ value for an agent. More preferable dosing concentrations are near an agent's $ED_{50}$ value and cause little or no toxicity. Any given dosage may vary within, exceed, or be less than, the therapeutic index for any particular agent, depending upon the formulation, sensitivity of the patient, and the route of administration.

In some embodiments, from 1, 2, 3, 4, 5, . . . 10, . . . 20, . . . 35, . . . 55, . . . 100, . . . 1,000, . . . 10,000, or more, units of time (e.g. minutes, hours, days, weeks, etc.) pass between the first administration of a therapeutic agent and subsequent administration. In some of these embodiments, the interval(s) between any two or more administration points are constant (e.g., of equal duration). In still other embodiments, the interval(s) between any two or more administration points are varied (e.g.; not of equal duration). Varied intervals can be either random or repeating and formulaic. Those skilled in the art will appreciate the steps necessary for designing and adjusting the dosing schedules and/or the dosing order of any one or more agents.

Accordingly, preferred methods of the present invention are not limited to providing any particular order or sequence for administering the gossypol compounds and non-gossypol additional therapeutic agents to a subject or to in vitro/ex vivo cells, tissues, or organs. For example, in some embodiments, a gossypol compound is administered to a subject or to in vitro cells, tissues, or organs, followed by one or more additional agents.

The present invention provides the following exemplary formulas to illustrate the flexibility available to the skilled clinician when designing dosing regimens comprising one or more gossypol compound and optionally one or more non-gossypol compound (e.g., conventional anticancer drug), therapy (e.g., radiotherapy), or technique (e.g., surgical intervention). Thus, each variable represents the subjection of the patient or in vitro cells, tissues, or organs of interest to a therapeutic event (e.g., the administration of a gossypol compound). It is understood that the exemplary formulas represent a portion of the total possible formulaic combinations and permutations of the particular variables used in this exemplary. It is further understood, one skilled in the art could complete the exemplary listing of formulas to recite every possible permutation of the recited variables. It is also understood that any implied time intervals between adjacent variables can represent simultaneous therapeutic events, or the elapse of milliseconds, seconds, minutes, hours, days, weeks, months, or years. G1=a first administration of a gossypol compound; G2=a second administration of a gossypol compound, G3=a third administration of a gossypol compound; Gn=a fourth administration of a gossypol compound; NGC1=a first administration of a non-gossypol compound, therapy, or technique; NGC2=a second administration of a non-gossypol compound, therapy, or technique; NGC3=a third administration of a non-gossypol compound, therapy, or technique; and NGCn=a fourth administration of a non-gossypol compound, therapy, or technique, such that the following exemplary administration regimens are possible: (G1); (G1, G2); (G1, G2, G3); (G1, G2, G3, Gn); (G1, NGC1, G1, NGC1, NGC2); (G1, NGC1, NGC2, NGC3); (G1, NGC1, NGC2, NGC3, NGCn); (G1, G2, NGC1); (G1, G2, NGC1, NGC2); (G1, G2, NGC1, NGC2, NGC3); (G1, G2, NGC1, NGC2, NGC3, NGCn); (G1, G2, G3, NGC1); (G1, G2, G3, NGC1, NGC2); (G1, G2, G3, NGC1, NGC2, NGC3); (G1, G2, G3, NGC1, NGC2, NGC3, NGCn); (G1, G2, G3, Gn, NGC1); (G1, G2, G3, Gn, NGC1, NGC2); (G1, G2, G3, Gn, NGC1, NGC2, NGC3); (G1, G2, G3, Gn, NGC1, NGC2, NGC3, NGCn); (NGC1, G1); (NGC1, G1, G2); (NGC1, G1, G2, G3); (NGC1, G1, G2, G3, Gn); (NGC1, NGC2, G1); (NGC1, NGC2, G1, G2); (NGC1, NGC2, G1, G2, G3); (NGC1, NGC2, G1, G2, G3, Gn); (NGC1, NGC2, NGC3, G1); (NGC1, NGC2, NGC3, G1, G2); (NGC1, NGC2, NGC3, G1, G2, G3); (NGC1, NGC2, NGC3, G1, G2, G3, Gn); (NGC1, NGC2, NGC3, NGCn, G1); (NGC1, NGC2, NGC3, NGCn, G1, G2); (NGC1, NGC2, NGC3, NGCn, G1, G2, G3); (NGC1, NGC2, NGC3, NGCn, G1, G2, G3, Gn); (G1, NGC1, G2); (G1, NGC1, G2, G3); (G1, NGC1, G2, G3, Gn); (G1, G2, NGC1, G3); (G1, G2, NGC1, G3, Gn); (G1, G2, G3, NGC1, Gn); (NGC1, G1, NGC2); (NGC1, G1, NGC2, NGC3); (NGC1, G1, NGC2, NGC3, NGCn); (NGC1, NGC2, G1, NGC3); (NGC1, NGC2, NGC3, G1, NGCn); (G1, NGC1, NGC2, G2); (G1, NGC1, NGC2, G2, G3); (G1, NGC1, NGC2, G2, G3, Gn); (G1, NGC1, NGC2, NGC3, G2); (G1, NGC1, NGC2, NGC3, G2, G3); (G1, NGC1, NGC2, NGC3, G2, G3, Gn); (G1, NGC1, NGC2, NGC3, NGCn, G2); (G1, NGC1, NGC2, NGC3, NGCn, G2, G3); (G1, NGC1, NGC2, NGC3, NGCn, G2, G3, Gn); (G1, NGC1, G2, NGC2); and (G1, NGC1, G2, NGC2, G3); (G1, NGC1, G2, NGC2, G3, Gn).

In some embodiments, from 1, 2, 3, 4, 5, . . . 10, . . . 20, . . . 35, . . . 55, . . . 100, . . . 1,000, . . . 10,000, or more, administrations of an agent (or agents) are required to produce the desired effect (e.g., amelioration of a disease such as a neoplastic disease) in a subject or in in vitro cells, tissues, or organs of interest. The methods of the present invention are not limited to the administration of any particular gossypol compound, and optionally any one or more additional therapeutic agents, surgical interventions, or radiotherapies. In some embodiments, at least one gossypol compound is administered to a subject substantially simultaneously with at least one additional therapeutic agent, surgical intervention, or radiotherapy.

The present invention is not limited to any particular pharmaceutical formulations. Indeed, in some contemplated pharmaceutical compositions and methods, a gossypol compound is formulated (e.g., in suspension) with a non-gossypol therapeutic agent. In other pharmaceutical compositions and methods, a multitude of gossypol compounds (e.g., 2 or more) and optionally a multitude of non-gossypol therapeutic agents (e.g., 2 or more) are formulated in any combination thereof. Accordingly, the present invention is not limited to any particular formulations for combining two or more gossypol compounds and/or two or more non-gossypol therapeutic agents. However, as described herein, and as routinely known in the chemical, biological, and pharmacological arts, certain gossypol compounds and non-gossypol therapeutic agents are preferentially combined or segregated. Certain pharmaceutical compositions optionally comprise stabilizers, preservatives, adjuvants, pH modifiers, bioavailability modifiers, additives, excipients, diluents, lubricants, anti-oxidants, disintegrating agents, binders, thickening agents, emulsifiers, surfactants, sweeteners, pigments, flavorings, perfuming agents and the like, to improve various biological, chemical, or pharmaceutical characteristics.

Normal dosage amounts may vary from about 0.001 to 1,000 mg, up to a total dose of about 1 g, depending upon the route of administration. Guidance as to particular dosages and methods of delivery are provided in the literature (See e.g., U.S. Pat. Nos. 4,657,760; 5,206,344; and 5,225,212, U.S. Pat. No. 6,041,788, U.S. Pat. No. 6,273,727, U.S. Pat. No. 6,558,957, U.S. 20030017459A1, U.S. Pat. No. 5,782,799, U.S. Pat. No. 6,056,734, U.S. Pat. No. 6,528,086, U.S.20020065483A1, WO 0168169A1, and WO02072178A1 all of which are herein incorporated by reference). Administration of some agents to a patient's bone marrow may necessitate delivery in a manner different from intravenous injections.

In some embodiments, the gossypol compounds are administered at a dosage range of about 1 to 1,000 mg/day, preferably about 1 to 200 mg/day, more preferably from about 10 to 80 mg/day, and most preferably from about 30 to 40 mg/day. In some preferred embodiments, the gossypol compounds are administered (e.g., orally) in a tolerable daily dose (e.g., 30 to 40 mg/day) shown to have some biologic activity (e.g., alterations in Bcl proteins, angiogenesis proteins, cell cycle alteration, apoptosis markers, or alterations in Rb and Cyclin D1 levels). In a further embodiment, the gossypol compounds are administered at a dosage range of about 40 to about 500 mg/week).

In other embodiments, the effective dose of the gossypol compounds will typically be in the range of about 0.01 to about 50 mg/kg, preferably about 0.1 to about 10 mg/kg of mammalian body weight, administered in single or multiple doses. Generally, the compositions may be administered to subjects in need of such treatment in a daily dose range of about 1 to about 2,000 mg per subject.

Preferred embodiments of the present invention provide pharmaceutical compositions and methods for administering an effective amount of a gossypol compound (and optionally one or more non-gossypol therapeutic agents, such as conventional anticancer drugs) to a subject to inhibit cell (e.g., cancer cell) proliferation. In some other preferred embodiments, the present invention further provides pharmaceutical compositions and methods of coadministering an effective amount of at least one conventional anticancer agent in addition to gossypol to a patient, such that cell (e.g., cancer cell) proliferation is inhibited.

In preferred embodiments, the subject has a disease characterized by the overexpression of a Bcl-2 family protein (e.g., Bcl-2, Bcl-$X_L$, Mcl-1, A1/BFL-1, and BOO-DIVA, etc.). In some embodiments, diseases characterized by overexpression of a Bcl-2 family protein include, but are not limited to, hyperproliferative diseases, cancers, acquired immune deficiency syndrome (AIDS), degenerative conditions, and vascular diseases.

In still further embodiments, neoplastic diseases (e.g. cancers) suitable for treatment (and optionally prevention) by the present compositions and methods include, but are not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. However, the present invention is not intended to be limited to treating (and optionally preventing) any particular type of cancer.

In some embodiments, diseases suspected of being characterized by having elevated levels of Bcl-2 family protein(s) suitable for treatment (and optionally prevention) by the present invention are selected by obtaining a sample of interest (e.g., cells, tissues, fluids, etc.) suspected of having high levels of Bcl-2 family proteins (e.g., Bcl-2, Bcl-$X_L$, Mcl-1, A1/BFL-1, and BOO-DIVA, etc.), measuring the levels of Bcl-2 family proteins in the sample using one or more well established immunohistochemical techniques (e.g., ELISA and Western blots, etc.), and comparing the levels of Bcl-2 family proteins in the sample with levels of Bcl-2 family proteins in relevant reference nonpathological samples. In other embodiments, diseases suspected of being characterized by having elevated levels of one or more Bcl-2 family proteins (e.g., Bcl-2, Bcl-$X_L$, Mcl-1, A1/BFL-1, and BOO-DIVA, etc.) are selected by comparing levels of one or more markers (e.g., polynucleotides, polypeptides, lipids, etc.) in a sample (e.g., cells, tissues, fluids, etc.) that directly or indirectly indicate elevated levels of Bcl-2 family proteins in the sample as compared to levels of these markers in relevant nonpathological samples. In still further embodiments, diseases suspected of being characterized by having elevated levels of Bcl-2 family proteins (e.g., Bcl-2, Bcl-$X_L$, Mcl-1, A1/BFL-1, and BOO-DIVA, etc.) are selected from diseases that do not respond or that stop responding to treatment with one or more conventional anticancer therapies (e.g., chemotherapy, radiation therapy, and/or surgical intervention).

The present invention is not intended to be limited to the administration routes chosen for delivering agents to a subject. Indeed, a number of suitable administration routes are contemplated, the selection of which is within the skill of those in the art.

In still other preferred embodiments taxanes (e.g., docetaxel) are administered to a patient in combination with gossypol compounds. The classic docetaxel dosing schedule is 60-100 mg/m$^2$ every 3 weeks. However, recent studies suggest that taxanes can be given safely, with perhaps higher dose intensity, on a weekly schedule. (See e.g., J. D. Hainsworth et al., J. Clin. Oncology, 16:2164-2168 (1998); J. D. Hainsworth et al., J. Clin. Oncology, 19:3500-3505 (2001); and C. Kouroussis et al., Cancer Chemo. Pharm., 46:488-492 (2000)). The patient toxicities associated with administering taxanes include neutropenia, asthenia, alopecia, hypersensitivity reactions, skin toxicity, and edema. Preferred embodiments of the present invention provide weekly administrations of taxanes to reduce patient toxicities while preserving agent efficacy. In other embodiments, administration of taxanes (e.g. docetaxel) more frequently than once a week during a patient's course of treatment with the disclosed gossypol compounds is expected to produce synergistic effects.

While the present invention is not limited to any particular mechanism, nor to any understanding of the action of the agents being administered, the following example provides a description of an exemplary testing procedure used to determine potential drug interactions between gossypol compounds and one or more anticancer agents that are candidates for co-administration with gossypol.

Docetaxel is extensively metabolized by CYP3A4, a specific cytochrome p450 enzyme. Pharmacokinetic data obtained for docetaxel indicates wide variance in its clearance between patients. Poor docetaxel clearance may result in an increase in the area-under-the-curve (AUC) and thus greater patient toxicity. Several investigations have reported that gossypol decreases cytochrome P-450 and mixed-function oxidases, although these results have been challenged, and no human studies have been performed which specifically address this issue. Thus, it is possible that gossypol could inhibit CYP3A4 activity and lead to toxic docetaxel accumulation in some patients.

In one embodiment, the patient is administered a daily dose of a gossypol compound for 1 week prior to receiving their first dose of docetaxel. The pharmacokinetic profile of docetaxel in the patient's system is evaluated after the patient receives their first dose of docetaxel. (See, R. Bruno et al., J. Clin. Oncol., 16:187-196 (1998)). Docetaxel dosing is started at a reduced dose of about 15 mg/m$^2$/week. The dose of docetaxel is gradually escalated to a maximally tolerated dose of about 35 mg/m$^2$/week. Simultaneously, information will be collected on effects of gossypol administration on the phenotypic expression of CYP3A4. The phenotypic expression of CYP3A4 is measured easily and reproducibly using an erythromycin breath test (ERMBT). (See, e.g., P. Watkins, Pharmacogenetics, 4:171-184 (1994); and J. Hirth et al., Clin. Cancer Res., 6:1255-1258 (2000)). The ERMBT test has been shown to predict steady state trough blood levels of drugs that are CYP3A4 substrates. Consequently, some embodiments of the present invention are directed to the co-administration of gossypol compounds and taxanes (e.g., docetaxel) using an ERMBT to determine potential drug interactions. Those skilled in the art will appreciate that similar testing methodologies can be utilized to determine potential interactions between gossypol compounds and additional candidate compounds for co-administration.

In some embodiments, standard immunohistochemical techniques are used to analyze patient samples before, during, or after treatment with the methods and compositions of the present invention. In some of these embodiments, the immunohistochemical techniques are used to quantify changes in the levels of Bcl-2 family proteins (e.g. Bcl-2, Bcl-$X_L$, and Bax, etc.). For example, in some embodiments, antibodies to Bcl-2 (DAKO, Carpinteria, Calif.), Bcl-$X_L$, and/or Bax (Zymed, South San Francisco, Calif.) are used to determine levels of these Bcl-2 proteins in a patient sample. In preferred embodiments, results from the immunohistochemical studies are interpreted using well-established criteria known to those in the art, wherein any cytoplasmic or nuclear staining are considered positive. The expression levels of Bcl-2, Bcl-$X_L$, and Bax can be determined by counting at least 1,000 neoplastic cells in each case and expressed as a percentage. Expression will be considered high when the percentage of positive cells is >25% for Bcl-2, and Bcl-$X_L$, and >50% for Bax. (See e.g., G. Rassidakis et al., Amer. J. Path., 159:527-535 (2001); and S. Shi et al., J. Histochem. Cytochem., 39:741-748 (1991)). In other embodiments, intermittent sampling of whole blood is conducted. Samples are subsequently prepared for fluorescence activated cell sorting (FACS) analysis of Bcl-2 and Bcl-$X_L$ expression in peripheral blood lymphocytes (PBLs) and for immunomagnetic selection of circulating epithelial cells.

In some embodiments, the primary endpoint of dosing studies occurs when the maximum tolerated dose of a gossypol compound (at a particular daily dose, e.g., 30 mg/day), optionally co-administered with a anticancer drug, is established. In some embodiments, dose-limiting toxicity (DLT) is established when a given sample (e.g., a cell, tissue, or fluid sample) exhibits >500 neutrophils per given unit, or upon observing any Grade 3 or 4 toxicities while the patient is being studied.

In still some other embodiments, to evaluate dose escalation a minimum of 9 weeks of treatment is required for 2 or more patients at each dose level. The maximum tolerated dose (MTD) is defined as the dose at which 33% of patients experience DLT. In preferred embodiments, doses are allocated to patients according to the criteria described in the Continual Reassessment Method (J. O'Quigley et al., Biometrics 46:33-48 (1990)) called Time-to-Event CRM or (TITE-CRM). Briefly, the TITE-CRM method provides a model for the time to occurrence of toxic response as a function of dose, and allows information from all patients enrolled in a trial to be used when allocating new patient dose levels. Because this method is very flexible in terms of the number of patients treated at each dose, subjects may be continuously recruited throughout a trial, without recruitment pauses, as long as patients are treated at a dose consistent with the safety profile.

In preferred embodiments, diseased cells and tissues are subjected to assays for cell viability and signs of induction of apoptosis (e.g., morphological changes, DNA integrity, mitochondria pathways, alterations of expression of Bcl-2 family proteins, and caspase activation as well as upstream and downstream effectors of caspases and caspase inhibitors). Those skilled in the art will be able to readily design and execute assays to test these and other cellular and biochemical parameters in treated cells and tissues.

X. Exemplary Combination Therapies

The present invention provides the following exemplary embodiments comprising the therapeutic administration of a gossypol compound in combination with additional therapeutic agents such as conventional chemotherapy agents (anticancer drugs) and radiation therapy.

A. Exemplary Combination Therapies

Experiments were conducted to further evaluate the in vivo therapeutic efficacy of various gossypol compounds, such as (−)-gossypol, alone and in combination with one or more conventional antineoplastic therapeutic agents. Experiments were conducted in various mouse xenograft tumor models, including breast cancer cell line MDA-231, prostate cancer cell line PC-3, ovarian cancer cell line A2780 and its Bcl-$X_L$ transfected clones, colon cancer cell line HT-29, and non-small cell lung cancer A549 xenograft mouse models. In several models, the administration of (−)-gossypol alone provided good antitumor activity and inhibition of tumor growth. In other models, administration of (−)-gossypol with docetaxel, paclitaxel, or cisplatin achieved superior antitumor activity and cancer cell inhibition as compared to the administration of gossypol alone. Some animals receiving a combination of gossypol and a conventional antineoplastic therapeutic agent showed complete tumor regression.

In certain generalized experiments, 4-6 weeks old male athymic NCr-nu/nu nude mice were used in coadministration studies involving administration of a gossypol compound, e.g. (−)-gossypol, in combination with a conventional anticancer chemotherapeutic agent. In one embodiment, tumor xenografts were established by injecting MDA-MD-231 cells ($1 \times 10^6$) into both side fat pads, or by injecting PC-3, HT-29, or A549 cells ($5 \times 10^6$) into both flanks of each mouse. Tumors were measured with a caliper in two dimensions, length (a), and width (b). The tumor volumes were calculated by (length×width$^2$, a×b$^2$). Treatments were initiated at day 5-10 post inoculation, when the majority of tumor diameters were about 5-7 mm and tumor volume had reached about 50 mm$^3$. For efficacy testing, racemic gossypol and/or isolated (−)-gossypol enantiomer were given orally at 7.5 to 30 mg/kg every day in 0.1 ml of 10% ethanol for four weeks.

In certain other combination treatment experiments, racemic gossypol and/or isolated (−)-gossypol enantiomer were given orally to xenografted mice at daily doses of from 7.5 to 15 mg/kg. 24 hours later after administration of the gossypol compound test animals were given a dose of conventional anticancer chemotherapeutic agent. Conventional anticancer chemotherapeutic agents were administered as follows: docetaxel at 7.5 mg/kg given intravenously once a week; and/or paclitaxel at 10 mg/kg, three times per week intraperitoneally. The combination treatments lasted for 3 consecutive weeks. All mice in the control group were injected with 0.1 ml PBS. Approximate tumor sizes and body weights were measured two to three times a week. Average tumor volumes and standard deviations were calculated for each group and plotted.

Antitumor activity curves for racemic gossypol and the (−)-gossypol enantiomer were plotted with observation time on the X-axis, and corresponding tumor volume (geometric mean) on the Y-axis. The area under the curve (AUC) was calculated by Tai's mathematical model for each curve, and shown as geometric means and 95% confidential intervals. The difference of AUC among treatment groups was compared by ANOVA. T-test was used for other analysis.

Figure 18:
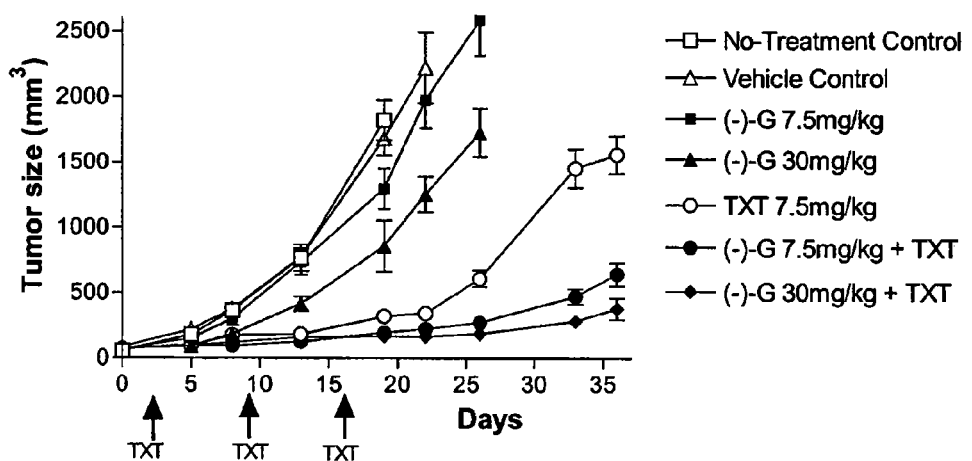
FIG. 18 shows the results of in vivo animal xenograft based assays in various embodiments of the present invention.

Previous studies have shown that overexpression of Bcl-$X_L$ protects cancer cells from docetaxel induced apoptosis. Thus, the present invention contemplates that compositions and methods for coadministering gossypol compounds, e.g., (−)-gossypol with conventional anticancer chemotherapeutics, such as docetaxel, provides a more effective treatment than either agent used alone, especially in disease characterized by high expression levels of Bcl-2 family proteins (e.g., Bcl-2 and/or Bcl-$X_L$). While the present invention is not limited to any particular mechanisms, it is contemplated that administration of gossypol compounds to diseased cells and tissues overexpressing Bcl-2 family proteins (e.g., Bcl-2 and/or Bcl-$X_L$) sensitizes these diseased cells and tissues to the therapeutic effects of conventional chemotherapeutic agents, such as docetaxel and/or radiation therapy. Accordingly, various other experiments were performed to test the effectiveness of coadministering (−)-gossypol with docetaxel as a therapeutic treatment for neoplastic diseases, such as cancer. Representative data from these experiments in a mouse xenograft model of human breast cancer MDA-231 are provided in FIG. 18. Briefly, in FIG. 18 docetaxel treatment was started at day 7 and was given intravenously at a weekly dose of 7.5 mg/kg for 3 weeks. The results show that treatment with docetaxel alone in a sub-optimal dose (7.5 mg/kg weekly) was sufficient to inhibit tumor growth. However, the coadministration of (−)-gossypol, at any one of three doses levels (e.g., 7.5, 15 or 30 mg/kg), with docetaxel achieved greater anticancer activity and inhibition of tumor cell growth. Three out of ten mice treated with the gossypol docetaxel combination had complete tumor regression. Overall, there was more than 90% inhibition of tumor growth in the combination group as compared to the control group. Statistical analyses were performed using a mixed-effects repeated measures model that accurately takes into account the correlation within an animal over time, and between tumors within an animal. The data were modeled using the natural logarithm of tumor volume, which is standard practice for tumor growth models. A comparison of tumor growth in animals receiving (−)-gossypol alone and docetaxel alone was performed. An exemplary comparison of (−)-gossypol at 7.5 mg/kg and docetaxel is provided in Table 7.

TABLE 7

|  | (−)-Gossypol 7.5 mg/kg | Docetaxel 7.5 mg/kg | Combination |
|---|---|---|---|
| (−)-Gossypol 7.5 mg/kg | — | <0.0001 | <0.0001 |
| Docetaxel 7.5 mg/kg | <0.001 | — | <0.0001 |
| Combination | <0.0001 | 0.0028 | — |

Figure 19:
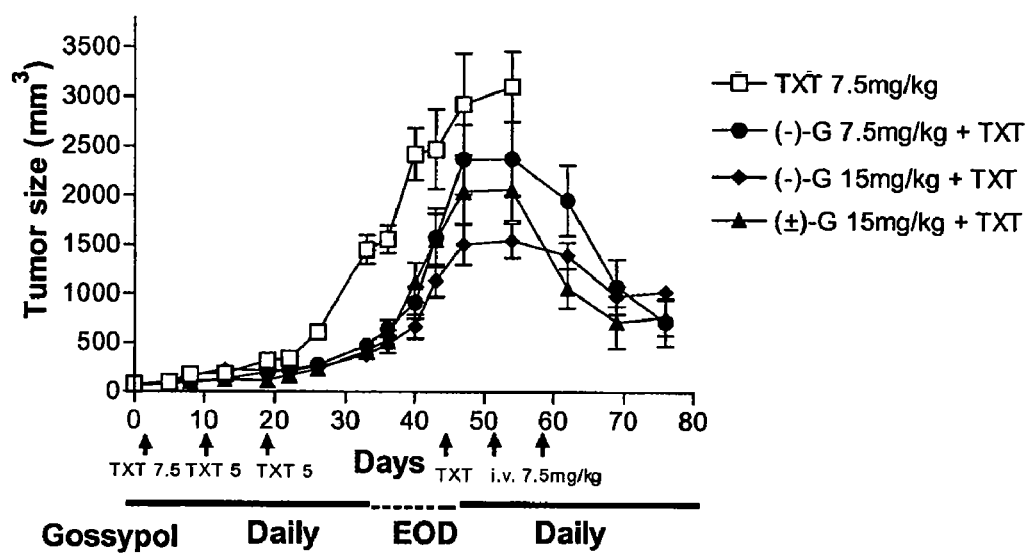
FIG. 19 shows the results of in vivo animal xenograft based assays in various embodiments of the present invention.

In a subset of the mice treated with either docetaxel alone or combination therapy, a second round of treatments with the same regimen was initiated at day 45. The average tumor volume before the second cycle treatments was about 2,000 mm³. Tumors in the docetaxel alone treated group continued to grow, thus all the mice were sacrificed due to the tumor burden. In contrast, in the combination treatment groups, animals displayed tumor regression and a 50% reduction of tumor volume (FIG. 19). The data shows that (−)-gossypol is very effective at potentiating the agent docetaxel when administered in combination treatments even at levels where (−)-gossypol administered alone is not, or only partially, effective.

Figure 20:
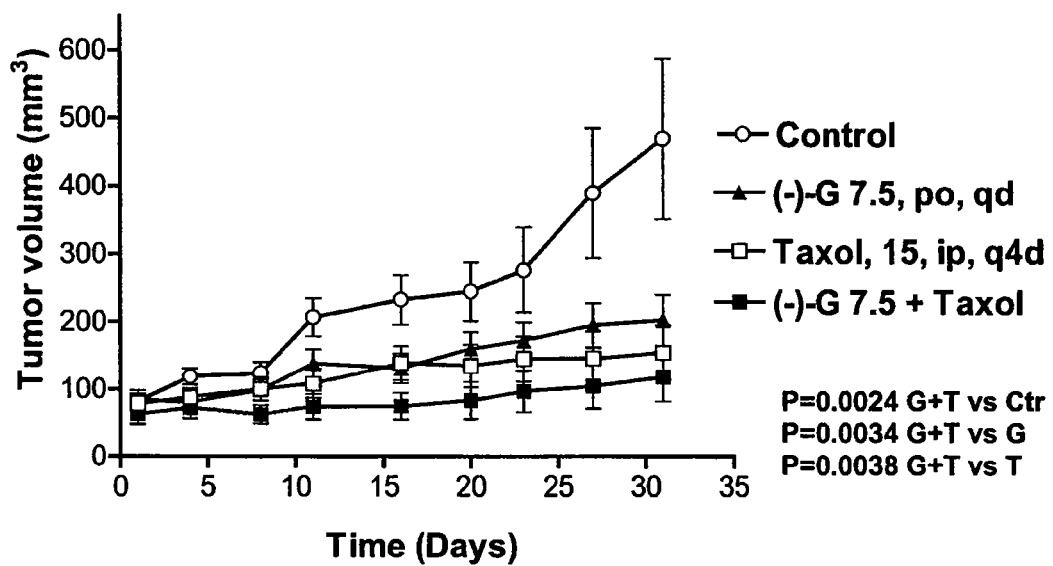
FIG. 20 shows the results of in vivo animal xenograft based assays in one embodiment of the present invention.

The outcome of coadministration of (−)-gossypol and conventional anticancer chemotherapy agents was further tested in additional mouse xenograft cancer models. The results of one experiment conducted in the mouse A549 non-small cell lung carcinoma xenograft are shown in FIG. 20. The A549 cell line expresses high levels of Bcl-$X_L$ protein. The mice were administered a daily oral dose of 7.5 mg/kg (−)-gossypol in combination with a weekly dose of paclitaxel (i.p., 15 mg/kg). Over 90% tumor inhibition was observed. The results of the combination treatment were statistically significant compared to administration of either drug alone (P<0.002 vs. paclitaxel alone; P<0.001 vs. (−)-gossypol alone). No adverse effects were seen with any dose.

Summaries of still other in vivo studies of (−)-gossypol in various cancer xenograft models are provided in Tables 8-15, as shown below.

TABLE 8

| Tumor | Host | Drug/Dose/Route | Regimen | Results |
|---|---|---|---|---|
| MDA-231 human breast cancer, bilateral fat-pad xenografts (~50 mm³ at start of treatment) | Balb/c nude mouse, all female, 4-6 weeks old 8 mice (16 tumors) per group | (−)-Gossypol at 7.5, 15 or 30 mg/kg, p.o. Docetaxel at 7.5 mg/kg, i.v. Controls: Untreated, and vehicle control. | (−)-gossypol q day for 4 weeks beginning ~7 days after tumor cell inoculation Docetaxel q week for 3 weeks beginning ~1 day after gossypol treatment or 8 days after tumor cell inoculation Drugs given alone or in combination | There was no difference between the untreated control and the vehicle control. There was dose-dependent inhibition of tumor growth by (−)-gossypol (G-) alone. At a dose of 30 mg/kg of G-, there was 40% tumor growth inhibition, but lower doses of G- (15 or 7.5 mg/kg) alone did not achieve significant anti-tumor effect in this experiment. Docetaxel on this dose regimen achieved about 70% tumor growth inhibition alone, but tumors grew back 2-3 weeks after treatment stopped. Combinations of G- at any of the three doses with docetaxel at 7.5 mg/kg all achieved significant tumor growth inhibition. At 7.5 mg/kg of G- in combination with docetaxel, there was more than 90% tumor growth inhibition with p < 0.01. There was tumor regression in 3 mice treated with combination regimen. There was no weight loss or death in mice treated with gossypol. |

TABLE 9

| Tumor | Host | Drug/Dose/Route | Regimen | Results |
|---|---|---|---|---|
| PC-3 human prostate cancer, bilateral xenografts in flank region (~100 mm³ at start of treatment) | NCr-nu nude mouse, all male, 5-6 weeks old 5 mice (10 tumors) per group | Both racemic gossypol and (−)-gossypol at 15 mg/kg, p.o. Docetaxel at 7.5 mg/kg, i.v., in combination with (−)-gossypol only And vehicle control | Both racemic gossypol and (−)-gossypol q day for 4 weeks beginning ~7 days after tumor cell inoculation Docetaxel q week for 3 weeks beginning ~11 days after gossypol treatment or 16 days after tumor cell inoculation Drugs given alone or in combination | Racemic gossypol at 15 mg/kg, daily p.o. for 26 days, achieved limited tumor growth inhibition (15.6% on day 42). The (−)-gossypol (G-) alone achieved moderate tumor growth inhibition (52% on day 42, p = 0.08). Docetaxel at this dose regimen achieved about 67% tumor growth inhibition alone (p = 0.005), whereas the combinations of G- with docetaxel at 7.5 mg/kg achieved 84% tumor growth inhibition as compared with vehicle control (p = 0.002). The combination treatment is also more significant than the docetaxel alone (P = 0.059). More importantly, there was complete tumor regression in 3 out of 5 mice treated with combination regimen. |

TABLE 9-continued

| Tumor | Host | Drug/Dose/Route | Regimen | Results |
|---|---|---|---|---|
| | | | | There was no weight loss in mice treated with gossypol. |

TABLE 10

| Tumor | Host | Drug/Dose/Route | Regimen | Results |
|---|---|---|---|---|
| PC-3 human prostate cancer, bilateral xenografts in flank region (~120 mm³ at start of treatment) | NCr-nu nude mouse, all male, 5-6 weeks old 8 mice (16 tumors) per group | Racemic gossypol at 15 mg/kg, p.o. (−)-Gossypol at 7.5 and 15 mg/kg, p.o. Docetaxel at 7.5 mg/kg, i.v. And vehicle control | Both racemic gossypol and (−)-gossypol q day for 4 weeks beginning ~17 days after tumor cell inoculation Docetaxel q week for 3 weeks beginning ~5 days after gossypol treatment or 23 days after tumor cell inoculation Drugs given alone or in combination | Racemic gossypol at 15 mg/kg, daily p.o. for 28 days, achieved limited tumor growth inhibition (39% on day 56, p = 0.145) compared to vehicle controls. The (−)-gossypol (G-) alone achieved moderate antitumor activity (60% on day 56, p = 0.0028). The difference between the racemic and (−)-gossypol is significant (p = 0.0055). Docetaxel at this dose regimen achieved about 70% tumor growth inhibition alone compared to controls (p = 0.0016), whereas the combinations of G- with docetaxel at 7.5 mg/kg achieved 89.9% tumor inhibition as compared with vehicle control (p = 0.004). The combination treatment is more effective as compared with the (−)-gossypol alone or docetaxel alone (p = 0.009). More importantly, there was complete tumor regression in 5 out of 8 mice in the combination treatment regimen, whereas there was no tumor regression with docetaxel alone. There was no weight loss in mice treated with gossypol. |

TABLE 11

| Tumor | Host | Drug/Dose/Route | Regimen | Results |
|---|---|---|---|---|
| PC-3 human prostate cancer, bilateral xenografts in flank region (~74 mm³ at start of treatment) | NCr-nu nude mouse, all male, 5-6 weeks old 8 mice (16 tumors) per group | (−)-Gossypol at 7.5 mg/kg, p.o. Cisplatin at 5 mg/kg, i.v. Controls: Untreated, and vehicle control. | (−)-Gossypol q day for 4 weeks beginning ~11 days after tumor cell inoculation Cisplatin twice q week for 2 weeks beginning ~6 days after gossypol treatment or 17 days after tumor cell inoculation Drugs given alone or in combination | Either (−)-gossypol (G-) or cisplatin (CDDP) alone at this dose regimen achieved only 20-25% tumor growth inhibition. (p = 0.85 for G-, p = 0.79 for CDDP, not significant), whereas the combinations of G- with cisplatin at 5 mg/kg achieved 65% tumor growth inhibition as compared with vehicle control (p = 0.0038) or either drug alone (p = 0.028 for G-, p = 0.013 for CDDP). There was no complete tumor regression in the either drug alone or the combination treatment regimen. There was 10-15% weight loss for CDDP alone, and 20-23% weight loss for the combination regimen during the treatment. Mice started to gain back the weight 1-2 weeks after the CDDP treatment stopped. |

TABLE 12

| Tumor | Host | Drug/Dose/Route | Regimen | Results |
|---|---|---|---|---|
| HT-29 human colon cancer, bilateral xenografts in flank region (~160 mm³ at start of treatment) | NCr-nu nude mouse, all male, 10 weeks old 5 mice (10 tumors) per group | (−)-Gossypol at 7.5 mg/kg, p.o. Cisplatin at 10 mg/kg, i.v. And untreated control | (−)-Gossypol q day for 4 weeks beginning ~6 days after tumor cell inoculation Cisplatin twice q week for 2 weeks beginning ~1 day after gossypol treatment or 7 days after tumor cell inoculation Drugs given alone or in combination | The (−)-gossypol (G-) alone achieved moderate tumor growth inhibition (47% on day 29). The difference between the (−)-gossypol and control is significant (p = 0.02). There was no cisplatin or combination group data as the dose of cisplatin used was too high. Most mice were dead in the cisplatin treated group during the 2$^{nd}$ week of the treatment. |

TABLE 13

| Tumor | Host | Drug/Dose/Route | Regimen | Results |
|---|---|---|---|---|
| A549 human non-small cell lung carcinoma bilateral xenografts in flank region (~75 mm³ at start of treatment) | NCr-nu nude mouse, all female, 5-6 weeks old 5 mice (10 tumors) per group | (−)-Gossypol at 7.5 mg/kg, p.o. Paclitaxel at 15 mg/kg, i.p. And untreated control | (−)-Gossypol q day for 4 weeks beginning ~16 days after tumor cell inoculation Paclitaxel twice q week for 3 weeks beginning ~3 days after gossypol treatment or 19 days after tumor cell inoculation Drugs given alone or in combination | The (−)-gossypol (G-) alone achieved moderate tumor growth inhibition (57% on day 31). The difference between the (−)-gossypol and control group is significant (p = 0.0459). Paclitaxel at this dose regimen achieved about 67% tumor growth inhibition alone (p = 0.0166) whereas the combinations of G- with paclitaxel at 7.5 mg/kg achieved 76% tumor growth inhibition as compared with vehicle control (p = 0.0024). The combination treatment is more effective as compared with the (−)-gossypol alone (p = 0.0034) or paclitaxel alone (p = 0.0038). There were no complete tumor regressions seen in this experiment. There was no weight loss in mice treated with gossypol and/or Paclitaxel. |

TABLE 14

| Tumor | Host | Drug/Dose/Route | Regimen | Results |
|---|---|---|---|---|
| PC-3 human prostate cancer, bilateral xenografts in flank region (~150 mm³ at start of treatment) | NCr-nu nude mouse, all male, 5-6 weeks old 5 mice (10 tumors) per group | (−)-Gossypol at 10 mg/kg, p.o. Radiation at 2 Gy per day, total 30 Gy, locally towards tumor site, this is radiation plus vehicle. Controls: Untreated, and vehicle alone control. | (−)-Gossypol 5 times q week for 4 weeks beginning ~13 days after tumor cell inoculation Radiation 2 Gy 5 times q week for 3 weeks beginning ~5 days after gossypol treatment or 18 days after tumor cell inoculation | The (−)-gossypol (G-) or radiation alone achieved limited tumor growth inhibition in this dose regimen (about 20%, P = 0.3 or 0.7, day 39, not significant). Combinations of G- with radiation achieved 93% tumor growth inhibition as compared with vehicle control (p = 0.0024, day 39). The combination treatment is more effective as compared with the (−)-gossypol alone (p = 0.0013, day 39) or radiation alone (p = 0.0011, day 39). |

TABLE 14-continued

| Tumor | Host | Drug/Dose/ Route | Regimen | Results |
|---|---|---|---|---|
| | | | G- and radiation given alone or in combination | There were no complete tumor regressions seen in this experiment. There was no significant weight loss in mice treated with gossypol and/or radiation. |

TABLE 15

| Tumor | Host | Drug/Dose/ Route | Regimen | Results |
|---|---|---|---|---|
| PC-3 human prostate cancer, bilateral xenografts in flank region (~70 mm$^3$ at start of treatment) | NCr-nu nude mouse, all male, 5-6 weeks old 8 mice (10 tumors) per group | (−)-Gossypol at 10 mg/kg, p.o. Radiation at 2 Gy per day, total 30 Gy, locally towards tumor site, this is radiation plus vehicle. And vehicle alone control. | (−)-Gossypol 5 times q week for 4 weeks beginning ~13 days after tumor cell inoculation Radiation 2 Gy 5 times q week for 3 weeks beginning ~5 days after gossypol treatment or 18 days after tumor cell inoculation G- and radiation given alone or in combination | The (−)-gossypol alone achieved limited tumor growth inhibition in this dose regimen (about 30%, p = 0.549, not significant). The radiation alone achieved moderate tumor growth inhibition in this dose regimen as compared with the control group (55%, p = 0.0459, day 37). Combinations of G- with radiation achieved 91.5% tumor growth inhibition as compared with vehicle control (p = 0.0024, day 37). The combination treatment is more effective as compared with the (−)-gossypol alone (p = 0.0112) or radiation alone (p = 0.0068). There was complete tumor regression in 10 out of 16 tumors in the combination treatment regimen, whereas there was no tumor regression with single agent alone. There was no significant weight loss in mice treated with gossypol and/or radiation. |

B. Gossypol Compounds in the Treatment of Head and Neck Squamous Cell Carcinoma

There are about 40,000 new cases of head and neck squamous cell carcinoma (HNSCC) diagnosed in the United States each year. The 5-year survival rates for patients afflicted with HNSCC are typically not good, in part because the treatment of locally advanced head and neck cancers with conventional chemo- and radiation therapies is hampered by the emergence of resistant cancer cells.

Abnormal programmed cell death plays a critical role in cancer progression and outcome following conventional chemo- and radiation therapies. While the present invention is not limited to any particular mechanisms, it is contemplated that HNSCCs develop resistance to conventional chemo- and radiation therapies by developing the ability to suppress chemotherapy-induced apoptosis. (A. M. Petros et al., Protein Sci., 9:2528-2534 (2000); A. F. Schott et al., Oncogene, 11:1389-1394 (1995); and J. C. Reed et a., Ann. Oncol., 5:61-65 (1994)). Studies have shown that 74% of laryngeal tumors express high levels of Bcl-$X_L$ and 15% overexpress Bcl-2 (D. K. Trask et al., Laryngoscope, 112:638-644 (2002)), and low expression of Bcl-$X_L$ has been associated with excellent response in advanced laryngeal cancers to chemo- and radiation therapies. Bcl-2 and Bcl-$X_L$ are homologous members of the Bcl-2 family of proteins. Bcl-2 and Bcl-$X_L$ function as potent suppressors of mitochondrial-mediated apoptosis.

In in vitro studies, gossypol induced apoptosis in breast, colon, and prostate cancer cells that had high levels of Bcl-2 or Bcl-$X_L$ expression. As the majority of HNSCCs express high levels of Bcl-$X_L$, the present invention provides compositions and methods for administering gossypol compounds, e.g., (−)-gossypol, to treat HNSCCs and other head and neck cancers.

Data obtained during the development of the present invention shows a correlation between response to (−)-gossypol and Bcl-$X_L$/Bcl-$X_S$ expression ratios among the HNSCC cell lines examined. Thus, it is contemplated that anti/pro-apoptotic protein expression ratios represent a predictive measure of cellular apoptotic potential. Additional data suggests that when Bcl-$X_L$ is the dominant anti-apoptotic factor, that Bcl-$X_S$ is the dominant anti-apoptotic factor in HNSCCs. In Example 17, in the panel of 10 HNSCC cell lines, only one, UM-SCC-74B, had no detectable expression of Bcl-$X_L$ but a medium level of Bcl-2 protein expression. All of the tumor HNSCC cell lines tested were much more sensitive to (−)-gossypol than were normal fibroblast cell lines. While not being limited to any particular mechanisms, the present invention contemplates that sensitivity in HNSCC cell lines is related to the absence of a deregulated cell survival pathway in normal cells. Bcl-$X_L$ is expressed in fibroblasts in low levels and (−)-gossypol does not induce either apoptosis or growth inhibition until high concentrations are reached.

Experiments conducted during the development of the present invention found that p53 status plays an important role in (−)-gossypol-induced apoptosis in some cancers (e.g., HNSCCs). In this regard, cell lines with wild type p53 exhibited much more robust induction of apoptosis in response to (−)-gossypol treatment relative to tumor cells with mutant p53. The present invention is not limited however to any particular mechanisms, and indeed a mechanistic understanding of the present invention is not required to make and use the present compositions and methods. Thus, it is contemplated that cell-killing by (−)-gossypol, as determined in the MTT assays conducted in Example 17, is not solely through apoptosis.

In some embodiments, cisplatin resistance in HNSCCs correlates to the presence of wild type p53 and high Bcl-$X_L$ expression in in vitro studies. Animal studies demonstrate that tumors with high expression of p53, correlating to p53 mutation, are more likely to be controlled by chemo- and radiation therapy treatment protocols. In some embodiments, low expression levels of Bcl-$X_L$ correlates to induction chemotherapy using cisplatin and 5-fluorouracil. Thus, the present invention shows that a subset of tumors and cell lines with wild type p53 and high expression of Bcl-$X_L$ are resistant to cisplatin-based therapeutic regimens. However, in some preferred embodiments, the compositions and methods of the present invention show that gossypol compounds, e.g., (−)-gossypol, provides significant antitumor activity against cell lines with wild type p53 and high levels of Bcl-$X_L$ that are unlikely to respond to conventional anticancer chemotherapeutic agents including cisplatin (e.g. UM-SCC-1 and -6; both have high levels of Bcl-$X_L$ expression and wild-type p53). Accordingly, in some embodiments, the present invention provides compositions and methods for the combined administration of conventional anticancer chemotherapeutic agents, such as cisplatin, with gossypol compounds, (e.g., (−)-gossypol), that effectively treat typically chemo- and/or radiation therapy resistant HNSCCs. In some additional embodiments, the present invention contemplates diagnostic methods for detecting expression of a Bcl-2 family protein (e.g. Bcl-2 and/or Bcl-$X_L$) and p53 as an aid in selecting an appropriate therapeutic intervention (e.g., avoidance of cisplatin, or use of cisplatin with the compositions and methods of the present invention).

Figure 21:
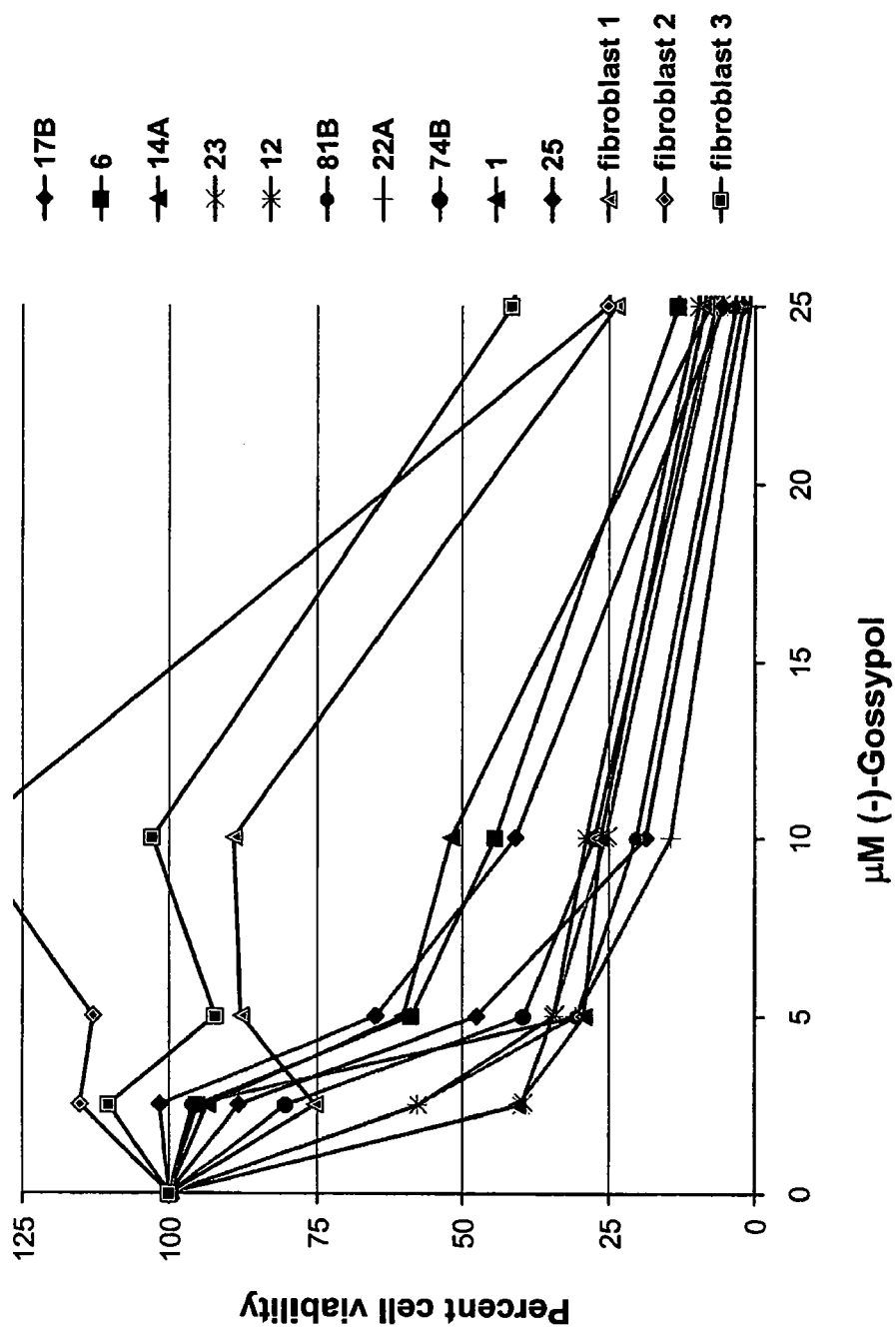
FIG. 21 shows the results of cell based assays (inhibition of cell growth in several head-neck cancer cell lines and three fibroblast cell lines) by (−)-gossypol in one embodiment of the present invention.

(−)-Gossypol selectively inhibits UM-SCC cell growth. Ten UM-SCC cell lines exposed to (−)-gossypol in a 6-day MTT assay (Example 17) showed dose-dependent inhibition of cell growth over a range from 0.5 to 10 µM, while fibroblast cell lines showed little change relative to untreated controls at doses<10 µM (FIG. 21). FIG. 21 shows growth inhibition of HNSCC cells by (−)-gossypol. UM-SCC and human fibroblast cell lines were continuously exposed to varying concentrations of (−)-gossypol in 6-day MTT cell survival assays. Control wells contained media (DMEM) with vehicle alone. For each data point n=5. In this assay, (−)-gossypol had a mean $IC_{50}$ of 5.57±2.57 µM in HNSCC cell lines which is significantly lower than the mean $IC_{50}$ of 20.31±9.20 µM in fibroblasts (p=0.0142). (−)-Gossypol selectively inhibits head and neck squamous cell carcinoma.

Figure 22:
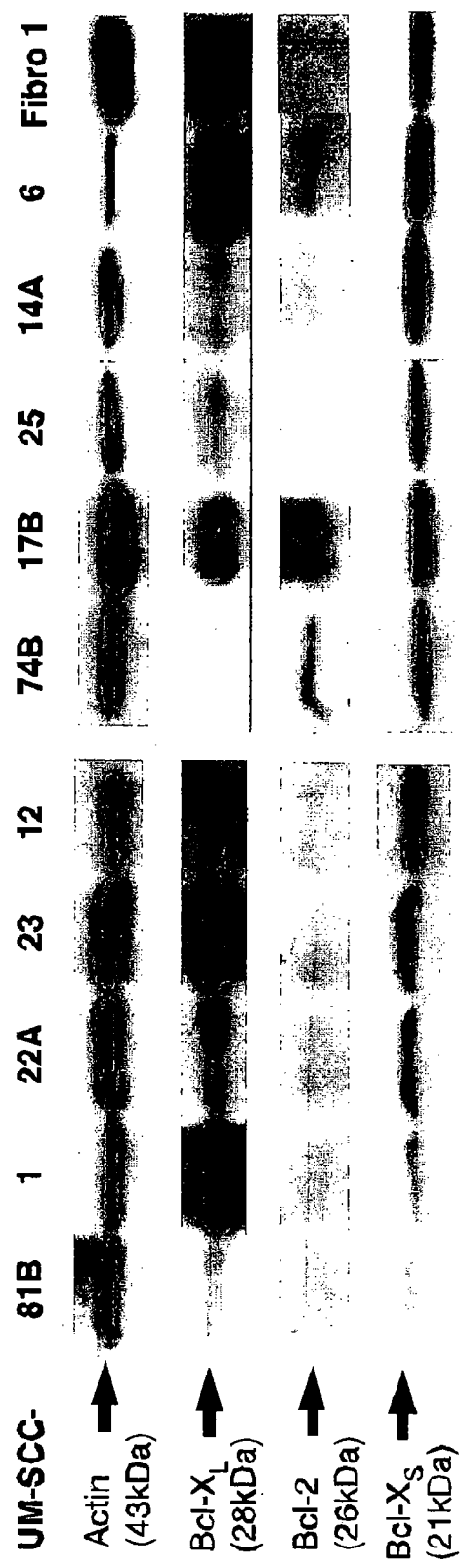
FIG. 22 show the results of Western blotting analysis of the protein levels of Bcl-2, Bcl-$X_L$ and Bcl-$X_S$ in several head-neck cancer cell lines and one fibroblast cell line in various embodiments of the present invention.

Additional experiments described in Example 17 determined the protein expression levels of Bcl-2, -$X_L$, and -$X_S$ in UM-SCC cell lines using Western blot analyses (See, FIG. 22). Bcl-$X_L$ is expressed in the majority of UM-SCC cell lines (9/10) in this panel, with only UM-SCC 74B lacking detectable expression. Bcl-2 is expressed in UM-SCC-74B, -17B and -6. All cell lines expressed Bcl-XS at some level.

Figure 23:
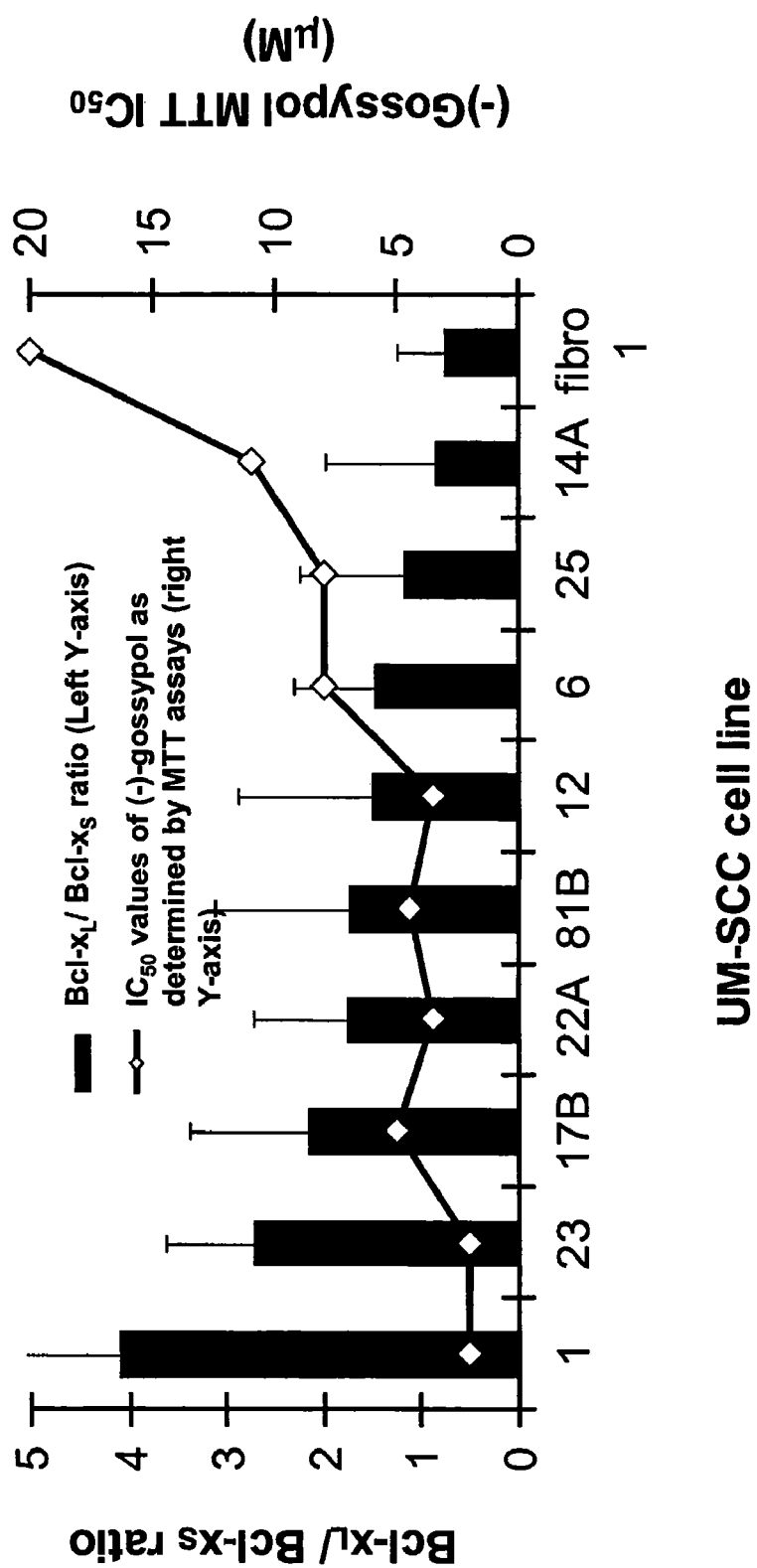
FIG. 23 show the results of cell growth inhibition by (−)-gossypol in a panel of head-neck cancer cell lines and one fibroblast cell line as determined by an MTT assay (right Y-axis) and its relationship with the ratio of Bcl-$X_L$/Bcl-$X_S$ (left Y-axis) in various embodiments of the present invention.

In still other embodiments, levels of Bcl-2 family protein expression were evaluated for correlation with (−)-gossypol's in vitro activity. The relative levels of expression for Bcl-$X_L$ and Bcl-$X_S$ were evaluated by densitometry but no statistically significant correlation with sensitivity to (−)-gossypol was identified (r=−0.14, p=0.70 and r=0.20, p=0.58). As both Bcl-$X_L$ and -$X_S$ expression are common and vary among cell lines, the possibility that the Bcl-$X_L$/Bcl-$X_S$ ratio was associated with (−)-gossypol's in vitro effect was investigated. Interestingly, as shown in FIG. 23, there appeared to be a correlation between the Bcl-$X_L$/Bcl-$X_S$ expression ratios and cell line sensitivity to (−)-gossypol (r=−0.83, p=0.0029) among the cell lines examined. FIG. 23 shows Bcl-$X_L$/Bcl-$X_S$ protein ratios and (−)-gossypol 6-day MTT $IC_{50}$ values. Densitometry measurements for Bcl-$X_L$ and Bcl-$X_S$ were recorded for three independent Western blots performed on cell lines. These ratios were calculated as the Bcl-$X_L$ measurement divided by the Bcl-$X_S$ measurement from the same experiment. Ratios were then averaged and plotted in a linear fashion on the Y1 axis; bars, +SD. $IC_{50}$ values for (−)-gossypol were plotted on the Y2 axis. A clear inverse correlation is shown between Bcl-$X_L$/$X_S$ ratio and sensitivity to (−)-gossypol (r=−0.83, p=0.0029).

In Example 17 four cell lines, UM-SCC-1, -6, -12 and -14A, were shown to exhibit significant cell death following 48 hour exposure to 10 µM (−)-gossypol, with surviving (trypan blue excluding) fractions of 20%, 9%, 14% and 16% respectively relative to untreated controls (p=<0.0001).

Figure 24A:
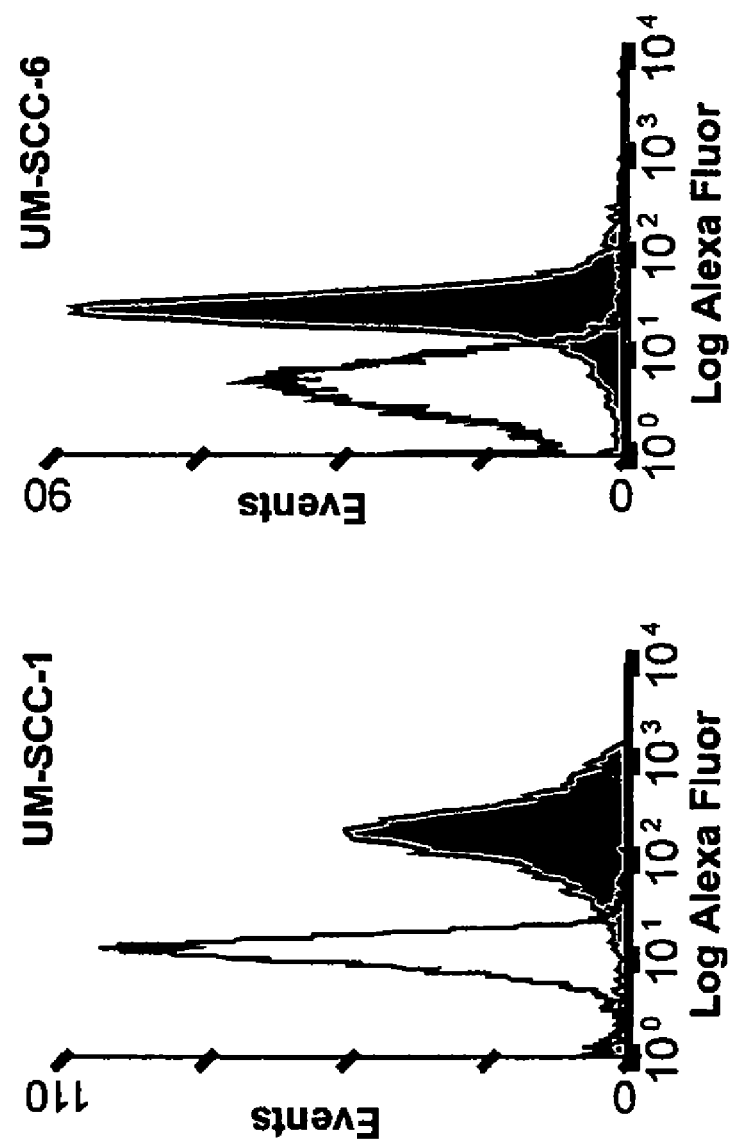
FIGS. 24A-24C show the results of apoptosis induction studies using (−)-gossypol in 6 cell lines as determined by the TUNEL assay (UM-SCC-1, UM-SCC-6, UM-SCC-12, UM-SCC-14A, fibroblast 1 and fibroblast 2) in various embodiments of the present invention.
Figure 24B:
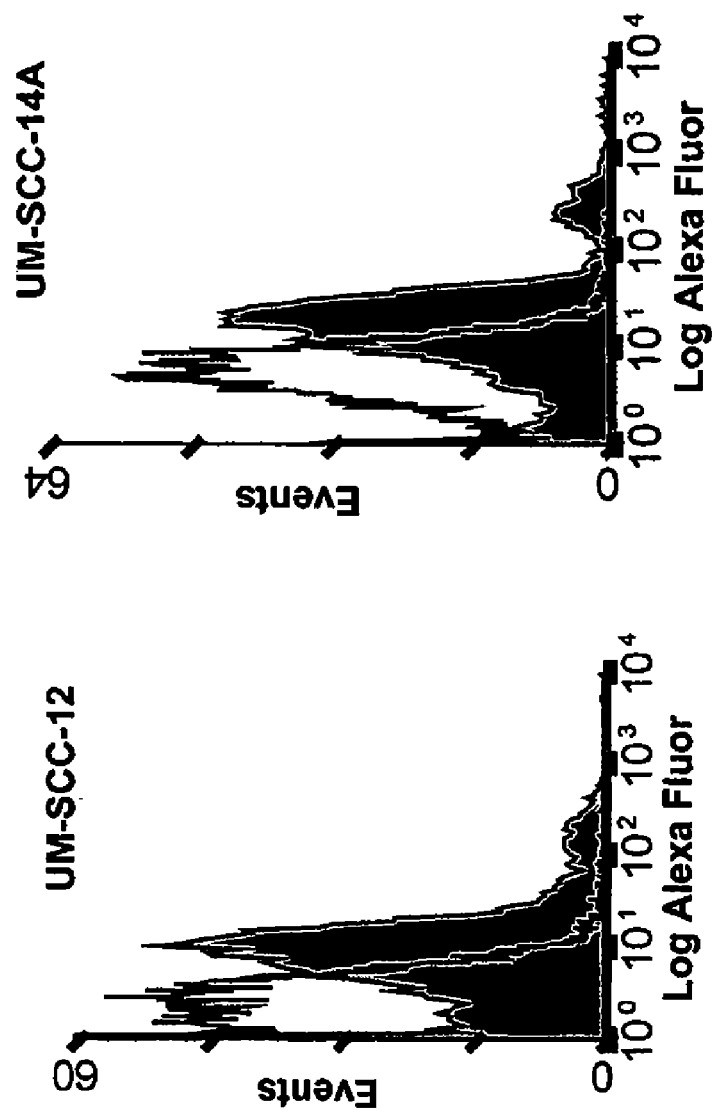
Figure 24C:
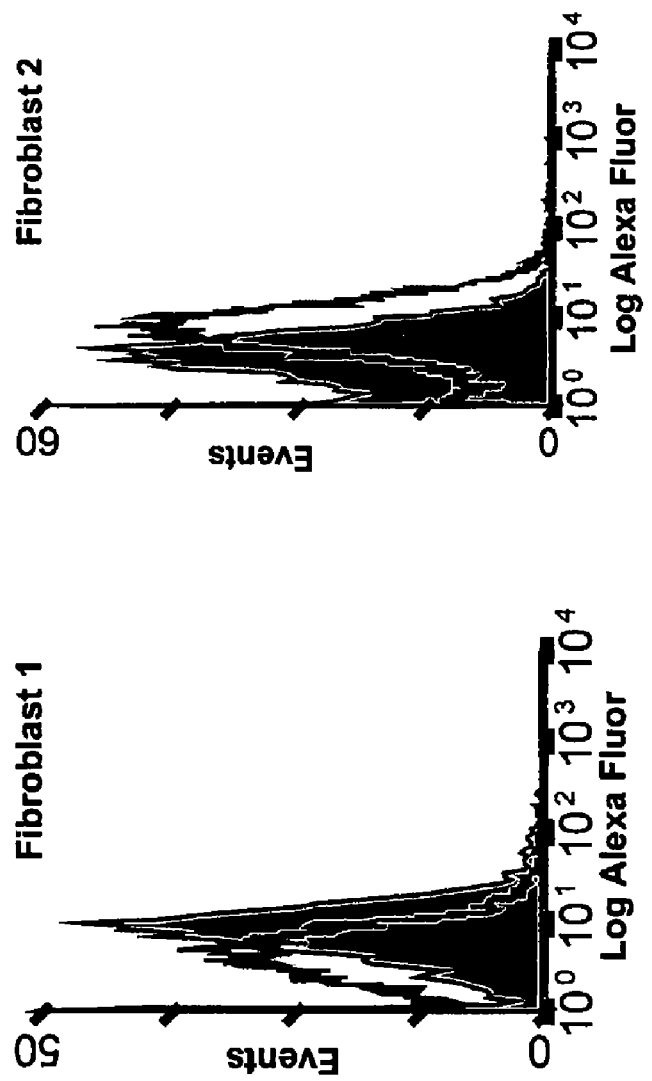

TUNEL assays for apoptosis were performed on fibroblasts and a subset of four UM-SCC cell lines that spanned the spectrum of sensitivity to (−)-gossypol (FIGS. 24A-24C). Briefly, FIGS. 24A-24C show apoptosis after (−)-gossypol as measured by a fluorescent flow cytometric TUNEL assay. Open peaks represent BrdU labeling of untreated cells. Shaded peaks indicate BrdU labeling of cell populations following 48-hour treatment with 10 µM (−)-gossypol; FIG. 24A, UM-SCC-cell lines with wild type p53; FIG. 24B, UM-SCC-cell lines with mutant p53; and FIG. 24C normal fibroblast cells. No clear correlation between proportion of apoptotic cells and cell line sensitivity to (−)-gossypol was found. However, UM-SCC-1, which is very sensitive to (−)-gossypol, displayed the highest apoptotic fraction following (−)-gossypol treatment (AI=90.1%). In contrast, fibroblast cell lines showed no induction of apoptosis. Of the four tumor cell lines, UM-SCC-1 ($IC_{50}$=2 µM) and UM-SCC-6 ($IC_{50}$=8 µM) cell lines have wild type p53, while UM-SCC-12 ($IC_{50}$=4 µM) and UM-SCC-14A ($IC_{50}$=11 µM) contain p53 mutations. The two wild-type p53 tumor cell lines displayed a mean apoptotic index (AI) of 85.2%±6.9 (UM-SCC-1, AI=90.1%, UM-SCC-6, AI=80.3%). In contrast, the two cell lines with mutant p53 have a mean apoptotic index of 20.7%±9.3 (UM-SCC-12, AI=27.2%, UM-SCC-14A, AI=14.1%). This difference is statistically significant with a p-value of 0.0157.

C. Administration of (−)-Gossypol Compounds in Combination with Radiation Therapy The present invention provides methods for administering gossypol compounds with radiation therapy. The methods of the present invention comprising the administration of gossypol compounds (and optionally other chemotherapeutic agents) in conjunction with radiation therapy are not intended to be limited to any particular dosing or administration routes. For example, in some embodiments, the chemotherapeutic agents, including gossypol compounds and any other chemotherapeutic agent(s), are administered prior to the subject receiving at least one session or course of radiation therapy. In other embodiments, the subject receives at least one session of radiation therapy prior to the administration of chemotherapeutics (e.g., gossypol compounds and optionally other anticancer agents). In yet other embodiments, the chemotherapeutic administrations overlap, at least to some extent, with sessions of radiation therapy. Those skilled in the fields of medicine (e.g., oncology, radiology, dosimetry, medical physics, pathology, histology, and the like) and pharmacology will appreciate that, in general, the treatment of diseases, and especially cancers, including the therapeutic administration of compositions and methods of the present invention, is a dynamic process.

In preferred embodiments, when radiation therapy is used with the pharmaceutical compositions and methods of the present invention, the subject's medical team considers a number of factors including, but not limited to, the type, amount, delivery, field size, and duration of the radiation, the subject's health and medical history, the type and stage of cancer being treated, and many other factors.

The present invention is not limited by the types, amounts, or delivery and administration systems used to deliver the therapeutic dose of radiation to a subject. For example, the subject may receive photon radiotherapy, particle beam radiation therapy, other types of radiotherapies, and combinations thereof. In some embodiments, the radiation is delivered to the subject using a linear accelerator. In still other embodiments, the radiation is delivered using a gamma knife.

The source of radiation can be external or internal to the patient. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The subject may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

A typical course of treatment for most types of cancer involves the use of radiation therapy. Radiation therapy uses a beam of high-energy particles or waves, such as X-rays and gamma rays, to eradicate cancer cells by inducing mutations in cellular DNA. In that cancer cells divide more rapidly than normal cells, tumor tissue is more susceptible to radiation than normal tissue. Radiation also has been shown to enhance exogenous DNA expression in exposed cells. In a preferred embodiment, the inventive method further comprises administering a dose or multiple doses of radiation to a patient over the therapeutic period.

In one embodiment, intratumoral delivery of a nucleic acid sequence encoding cytotoxic factors (e.g., TNF-α) and confocal radiation to the tumor site results in localized delivery of two potent anti-cancer treatment modalities. When the nucleic acid sequence encoding the cytotoxic factor is operably linked to a radiation-inducible promoter, radiation potentiates the factor's production and maintains therapeutic levels of factor at the tumor site continuously throughout the period of radiation therapy. The present invention contemplates that the disclosed methods provide additive or synergistic effects of radiation and cytotoxic factor, and gossypol compounds to eradicate tumor cells.

Any type of radiation can be administered to a patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. The dose of radiation is preferably fractionated for maximal target cell exposure and reduced toxicity.

The total dose of radiation administered to a patient preferably is about 0.01 Gray (Gy) to about 100 Gy. More preferably, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments, a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g. about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), preferably 1-2 Gy (e.g., 1.5-2 Gy). The daily dose of radiation should be sufficient to induce destruction of the targeted cells. If stretched over a period, radiation preferably is not administered every day, thereby allowing the subject to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the subject's responsiveness and any potential side effects. Radiation therapy can be initiated at any time in the therapeutic period. Preferably, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended however to limit the present invention.

In modern oncology, radiation therapy is used to treat a wide variety of cancers with varying degrees of effectiveness. X-ray irradiation strongly induces apoptosis. For example, radiation therapy is currently used to treat all stages of localized prostate cancer, however, certain clinical and radiobiological evidence indicates that prostate cancer cells are relatively resistant to radiation therapy. In particular, PC-3, a human prostate cancer cell line, is hormone-refractory and resistant to current chemo- and radiation therapies. The present invention determined that PC-3 cells express very high levels of both Bcl-2 and Bcl-$X_L$ protein. Overexpression of Bcl-2 and Bcl-$X_L$ proteins provides, at least in part, resistance to chemo- or radiation therapy induced apoptosis that is observed in many types of cancer cells (e.g. PC-3 prostate cancer cell line). In some preferred embodiments, chemo- or radiation therapy resistant cancers (e.g., prostate cancer) expressing high levels of Bcl-2 family proteins (e.g., Bcl-2 and/or Bcl-$X_L$, and the like) are targets for treatment using the methods and compositions of the present invention. While any understanding of particular mechanisms is not important to make and use the compositions and methods of the present invention, and the present invention is not so limited, it is contemplated that antagonizing the anti-apoptotic functions of Bcl-2 and/or Bcl-$X_L$ using the gossypol compounds (and optionally administration of other therapeutic agents) of the present invention overcomes the resistance to conventional radiation therapies seen in many types of cancers.

EXAMPLES

The following examples are provided to demonstrate and further illustrate certain preferred embodiments of the present invention. The examples are not to be construed as limiting the scope of the present invention.

Example 1

Homology Modeling

The sequence of human Bcl-2 was obtained from Gene Bank (entry gi4557355) (SEQ ID NO:1). (See, FIG. 1). The NMR structure of Bcl-$X_L$ (pdb code: 1BXL from the protein databank), which has 45% amino acid sequence identity, 56% sequence similarity and 3% gaps with Bcl-2, was used as the template. The structure of Bcl-2 was built using the homology-modeling program MODELLER (version 4.0). (A. Sali et al., Structure, Function, and Genetics, 23:318-326 (1995); and A. Sali, Curr. Opin. Biotech., 6:437-451 (1995)). Further refinement was done using the molecular dynamics program CHARMM (version 27b2). (B. R. Brooks, J. Comput. Chem., 4:187-217 (1983)). Hydrogen atoms were assigned to the modeled structure using the program QUANTA (Molecular Simulations Inc., San Diego, Calif.). The Bak BH3 peptide was placed into the Bcl-2 BH3 domain binding site in the same orientation as in the NMR structure of Bcl-$X_L$ in complex with the Bak BH3 peptide (1BXL in protein databank). (S. Michael et al., Science, 275:983-986 (1997)). The complex structure was solvated by inserting it into a 60 Å diameter TIP3P water sphere and deleting solvent molecules that have heavy atoms at less then 2.5 Å from any protein heavy atom.

MD simulations were done using the all atom parameter set from the MSI CHARMM force field (ref 23) in QUANTA 98, a constant dielectric, $\epsilon=1$ and constant temperature, T=300 K. The leap frog method with 1 fs time step was applied for numerical integration. Long-range electrostatic forces were treated with the force switch method with a switching range of 8-12 Å. (See, B. R. Brooks et al., J. Comput. Chem., 4:187-217 (1983)). Van der Waals forces were calculated with the shift method and a cutoff of 12 Å. The nonbond list was kept to 14 Å and updated heuristically. Solvent waters were kept from evaporating by using a spherical miscellaneous mean field potential as implemented in CHARMM. (B. R. Brooks, supra). The solvated protein was energy minimized using 100 cycles using the Steepest Descent method and additional 1000 cycles using the Adopted-Basis Newton Raphson method. This was followed by 3.0 ns MD simulations. The simulation was performed on an Origin2000 computer at the Advanced Biomedical Computing Center at the National Institutes of Health. The representation of the refined structure of Bcl-2 in complex with Bak BH3 peptide is shown in FIGS. 2A and 2B.

Example 2

Expression and Purification of the Bcl-$X_L$ Protein

Recombinant Bcl-$X_L$ protein with a N-terminal His-tag was overexpressed from the pET15b expression vector (Novagen, Darmstadt, Germany). In this construct, the putative C-terminal membrane-anchoring region (residues 214-237) and a loop between helix 1 and helix 2 (residues 49-88) were removed to facilitate protein purification. This loop was previously shown to be dispensable for the anti-apoptotic activity of the protein. (See, S. W. Muchmore et al., Nature, 381:335-341 (1996)). The current construct of Bcl-$X_L$ produces about 20 mg of the purified Bcl-$X_L$ protein from 1L of cell culture.

The protein samples for NMR studies were uniformly labeled with $^{15}N$ for screening and uniformly double labeled with $^{15}N$ and $^{13}C$ for structure characterization according to the methods described in M. Jansson et al., J. Biomol. NMR, 7:131-141 (1996), and M. L. Cai et al., J. Biomol. NMR, 11:97-102 (1998).

Example 3

Resolution of (−)-Gossypol and (+)-Gossypol from Racemic Gossypol

Racemic gossypol acetic acid purchased from the National Cancer Institute (Bethesda, Md.) or commercial sources (e.g., Sigma-Aldrich Corp., St. Louis, Mo.) was dissolved in diethyl ether, washed twice with water to remove the acid and the ether layer was concentrated by rotary evaporation. To a solution of 1.04 g of gossypol (2 mmol) in 50 ml of $CH_2Cl_2$ was added 1 g of L-phenylalanine methyl ester hydrochloride (4.6 mmol), 0.4 g of $NaHCO_3$ (4.7 mmol), 3 g of 4 Å molecular sieves, and 1 ml of 2-propanol, the resulting mixture was stirred at room temperature overnight under $N_2$ in the dark and filtered. The L-phenylalanine methyl ester reacts with the aldehyde groups of gossypol to form a Schiff's base with two diastereoisomers which were then resolved on a normal silica flash chromatography column. The filtrate was concentrated, and the residue was purified by chromatography on silica gel eluting with hexanes:EtOAc=3:1 to give two fractions. Acid hydrolysis of the two fractions in 5 N H Cl:THF=1:5 (room temperature, overnight) regenerated the individual gossypol enantiomers, respectively. The first fraction with a higher $R_f$ value contained (−)-gossypol, and the second fraction with a lower $R_f$ value contained (+)-gossypol. The crude gossypol fractions were extracted into ether from the residue after removing THF from the reaction mixture. The gossypol fractions were then purified by chromatography on silica gel and eluted with hexanes:EtOAc=3:1 to give optically pure gossypol, with a yield of 30-40% in two steps. The optical rotatory dispersion values for these products were $\alpha_D=-352°$ (c=0.65, $CHCl_3$) for (−)-gossypol, and $\alpha_D=+341°$ (c=0.53, $CHCl_3$), in agreement with literature values. (J. Si and L. Huang, Kexue Tongbao, 28:1574 (1983)) (See, FIG. 25).

Example 4

Fluorescence Polarization Based Binding Assays and Determination of the Binding of Various Gossypol Compounds to Bcl-2 and Bcl-$X_L$ Proteins The present invention used established sensitive and quantitative in vitro fluorescence polarization-based (FP) binding assays to determine the in vitro binding affinity of small molecule inhibitors (e.g., gossypol compounds) to both Bcl-2 and Bcl-$X_L$. (See e.g., J. L. Wang et al., Cancer Res., 60:1498-1502 (2000); J. L. Wang et al., Proc. Natl. Acad. Sci. U.S.A., 97:7124-7129 (2000); A. Degterev et al., Nat. Cell Biolog., 3:173-182 (2001); and I. J. Enyedy et al., J. Med. Chem., 44:4313-4324 (2001)). The FP-based assays were used to monitor the displacement of fluorescently labeled BH3 domain peptides from recombinant Bcl-2 or Bcl-$X_L$ proteins. Once a fluorescently labeled BH3 peptide (e.g., Bad, Bak, Bid BH3 peptides, and the like) binds to Bcl-2 or Bcl-$X_L$ protein, fluorescence polarization is enhanced. When a small molecule inhibitor, such as a gossypol compound, binds to Bcl-2 or Bcl-$X_L$ it displaces the fluorescently labeled BH3 domain peptide, thus decreasing the observed fluorescence polarization. Determination of the binding affinities of the Bcl-2 and Bcl-$X_L$ proteins is important to determining their selectivity. Although the structures of Bcl-2 and Bcl-$X_L$ are very similar, there are some differences between the two proteins. Accordingly, small molecule inhibitors of Bcl-2 and/or Bcl-$X_L$ (e.g., gossypol compounds) may display selectivity between the two proteins. In additional embodiments, the binding of gossypol compounds to Bcl-2 and Bcl-$X_L$ is further determined and confirmed using the NMR methods outlined herein.

Initial screening of Bcl-2 inhibitors (e.g., gossypol, enantiomers, derivatives, and pharmaceutically acceptable salts thereof) was carried out at 200 µM. If significant inhibition was observed for an inhibitor (larger than 50%), its $IC_{50}$ value was determined. Five ml of the test compounds, in reaction buffer, were added to wells containing a tracer and Bcl-2 or Bcl-$X_L$ proteins provided at the same concentration as the test compound. Final FP readings were taken after a 10-min incubation at room temperature. For making $IC_{50}$ determinations of initial test compounds, 9 to 10 test compound concentrations (i.e., between 1 nM and 200 µM) were used. Non-labeled Bak peptide was used as a positive control. Inactive compounds were used as negative controls.

In one embodiment, Bcl-2 fluorescence polarization assays were carried out as follows. Fluorescein-labeled 16-mer peptide tracer Flu-Bak-BH3 (GQVGRQLAIIGDDINR (SEQ ID NO:9) derived from Bak BH3 domain) was synthesized and labeled at the amino terminus. Forty-six-kDa soluble recombinant GST-fused Bcl-2 protein was purchased from Santa Cruz Biotechnology (Santa Cruz, Calif.). Reaction were carried out in a total volume of 20 µl per well (containing 10 µl of 1× phosphate-buffered saline, 5 µl of the GST-Bcl-2 protein, and 5 µl of peptide tracer). The reaction wells were incubated at room temperature for 20 min. FP readings were taken at 485 nm and 535 nm using an ULTRA READER (Tecan U.S. Inc, Research Triangle Park, N.C.). A series of validation experiments were performed by analyzing the maximal and minimal signals obtained from the background, buffer, Bcl-2 protein, tracer, and the mixture of Bcl-2 protein and tracer. The Kd of binding between Bcl-2 protein and the 16-mer fluorescein-labeled peptide was determined by titrating Bcl-2 protein at concentrations ranging from 5.4 nM to 540 nM and fluorescent tracer concentrations ranging from 0.145 nM to 1,450 nM. Optimal binding was obtained at a final concentration of 290 nM fluorescent tracer and 270 nM Bcl-2 protein. To verify the observed specificity, binding of the fluorescently labeled peptide and nonlabeled 16-mer peptide were compared in a binding competition assay. The data indicate that nonlabeled 16-mer peptide was able to abrogate binding of the labeled tracer, with an $IC_{50}$ of approximately 0.3 µM. The binding of racemic gossypol to Bcl-2 protein under these assay conditions is shown in FIG. 3.

In another embodiment, Bcl-$X_L$ fluorescence polarization assays were carried out as follows. Fluorescein-labeled 16-mer peptide tracer Flu-Bak-BH3 (GQVGRQLAIIGDDINR (SEQ ID NO:9) derived from Bak BH3 domain) was synthesized and labeled at the amino terminus. Soluble recombinant His-fused Bcl-$X_L$ protein, as described in Example 2, was used. The competitive binding curve for racemic gossypol is shown in FIG. 3. FIG. 6A shows gossypolone's competitive inhibition of Bak BH3 peptide binding to Bcl-$X_L$ protein under the described assay conditions. FIG. 6B shows that (−)-gossypol ethyl Schiff's base displays time-dependent inhibition of the binding between Bak BH3 peptide and Bcl-$X_L$ protein. The present invention is not limited to any mechanism. Indeed, an understanding of any particular mechanism is unnecessary to practice (make and use) the present invention. Nonetheless, it is contemplated that the above finding results from the hydrolysis of the Schiff's base to form free (−)-gossypol.

Figure 26:
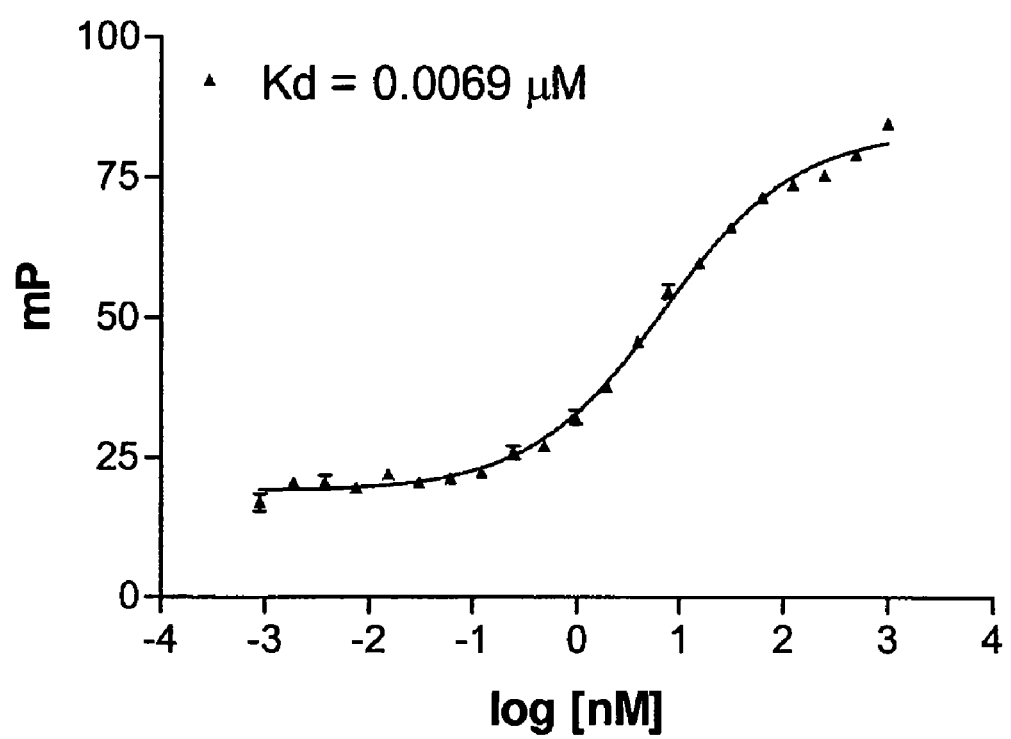
FIG. 26 shows the results of a saturation curve of Bcl-$X_L$ protein to Bad 25-residue BH3 peptide.

In another embodiment, Bcl-2 fluorescence polarization assays were carried out as follows. A 25-residue Bad BH3 peptide (NLWAAQRYGRELRRMSDEFVDSFKK (SEQ. ID. NO.: 10)) labeled at the N-terminus with 6-carboxyfluorescein succinimidyl ester (FAM) as a fluorescence tag (Flu-Bad-25) was synthesized. The Bcl-2 protein used in these assays was a soluble recombinant GST-fusion (Santa Cruz Biotechnology). An aliquote of the test compound and preincubated Bcl-2 protein (0.020 µM) and Flu-Bad-25 peptide (0.005 µM) in the assay buffer (100 mM potassium phosphate, pH 7.5; 100 µg/ml bovine gamma globulin; 0.02% sodium azide (Invitrogen, Corp., Carlsbad, Calif.) were added to black Dynex 96-well round-bottom plates (Fisher Scientific, Inc., Hampton, N.H.). In each experiment, a bound peptide control containing Bcl-2 and Flu-Bad-25 peptide (equivalent to 0% inhibition), and free peptide control containing only free Flu-Bad-25mer (equivalent to 100% inhibition), were included on the assay plate. The polarization values were measured after 4 hrs of incubation when the binding reached equilibrium using an ULTRA READER (Tecan U.S. Inc., Research Triangle Park, N.C.). The $K_d$ value of the binding of Bad 25-mer BH3 peptide to Bcl-2 was determined to be 6.9 nM (FIG. 26). $IC_{50}$ values, the inhibitor concentration at which 50% of bound peptide is displaced, were determined from a plot using nonlinear least-squares analysis. Curve fitting was performed using GRAPHPAD PRISM software (GraphPad Software, Inc., San Diego, Calif.). The non-labeled Bad peptide was used as the positive control. The $K_i$ values were calculated using the following equation:

$$K_i = [I]_{50}/([L]_{50}/K_d + [PL]_0/[L]_0 + 1) = [I]_{50}/([L]_{50}/K_d + [P]_0/K_d + 1) \quad \text{(Equation 1)}$$

The competitive binding curves of racemic gossypol, (−)-gossypol and (+)-gossypol in directly blocking binding between Bad 25-residue BH3 peptide and Bcl-2 are shown in FIG. 4.

Figure 27:
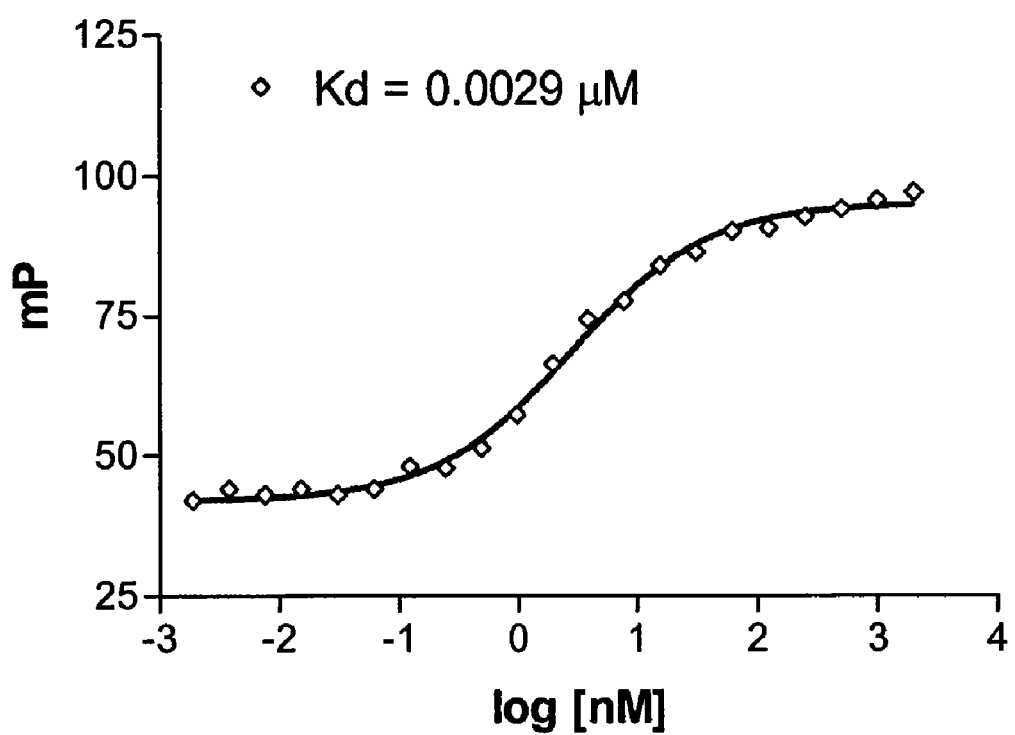
FIG. 27 shows the results of saturation curve of Bcl-2 protein binding to Bid 21-residue BH3 peptide.

In another embodiment, Bcl-$X_L$ fluorescence polarization assays were carried out as follows. Bid 21-residue BH3 peptide labeled with 6-carboxyfluorescein succinimidyl ester (FAM) was synthesized. Recombinant Bcl-$X_L$ proteins, as described in Example 2, were used. Various gossypol compounds (e.g., racemic gossypol, (−)-gossypol, and (+)-gossypol) were analyzed using the following assay conditions: 15 nM Bcl-$X_L$ and 2.5 nM Flu-Bid peptide in assay buffer containing 50 mM Bis-Tris, pH 7.4 with 0.01% bovine gamma globulin. The $K_d$ value of Bid 21-mer BH3 peptide biding to Bcl-$X_L$ was determined to be 2.9 nM (FIG. 27). The competitive binding curves of racemic gossypol, (−)-gossypol, and (+)-gossypol in directly blocking the binding between Bad 21-residue BH3 peptide and Bcl-$X_L$ are shown in FIG. 5.

Figure 45:
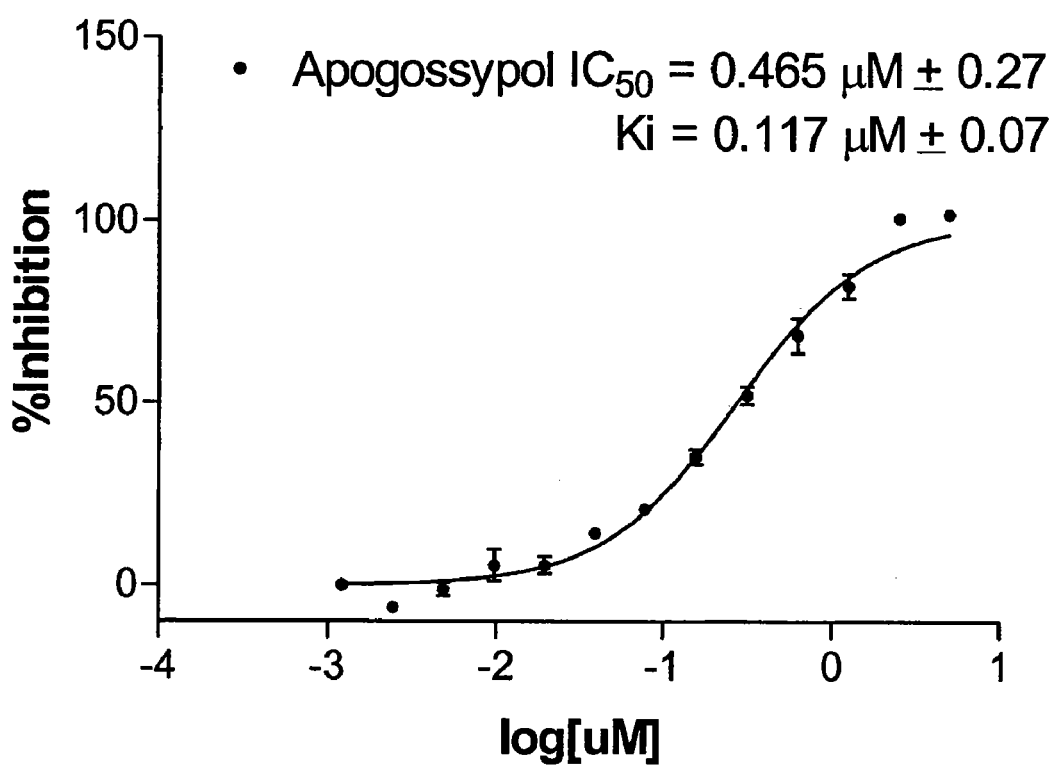
FIG. 45 describes the competitive binding curve of racemic apogossypol in directly blocking binding between Bad 25-residue BH3 peptide and Bcl-2 using an in vitro fluorescence polarization-based assay.

The competitive binding curve of racemic apogossypol in directly blocking binding between Bad 25-residue BH3 peptide and Bcl-2 is shown in FIG. 45.

Figure 46:
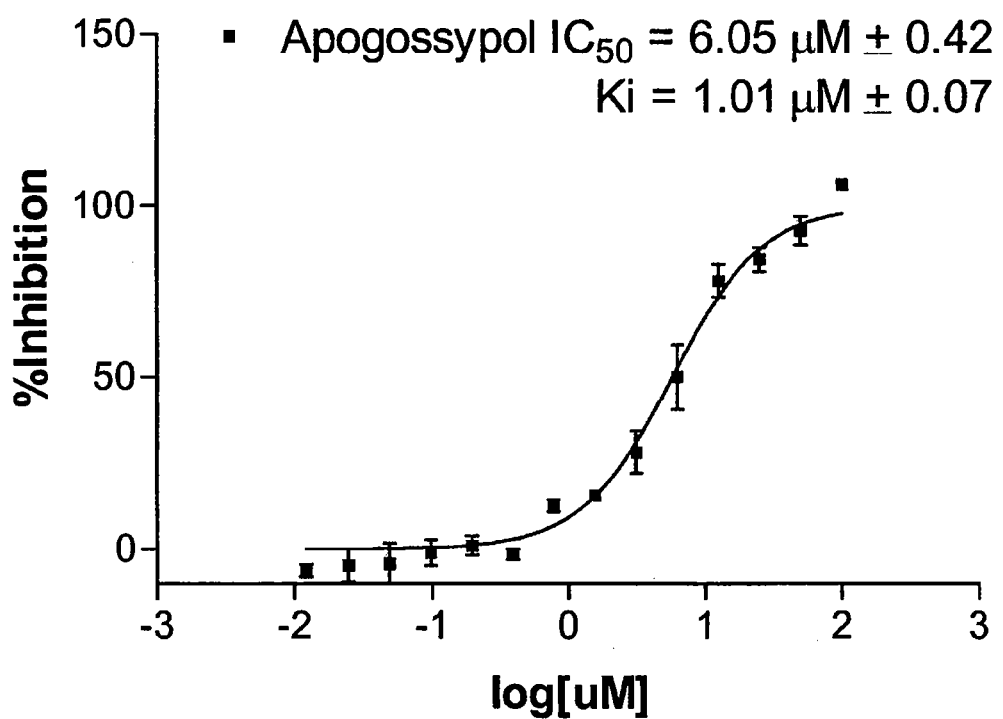
FIG. 46 describes the competitive binding curve of racemic apogossypol in directly blocking the binding between Bad 21-residue BH3 peptide and Bcl-$X_L$ protein using an in vitro fluorescence polarization-based assay.

The competitive binding curve of racemic apogossypol in directly blocking the binding between Bad 21-residue BH3 peptide and Bcl-$X_L$ is shown in FIG. 46.

Example 5

Docking Gossypol into Bcl-2

This example describes docking studies of gossypol performed using the DOCK program (version 4.0.1) (S. Makino et al., J. Comput. Chem., 18:1812-1825 (1997)) and the LigandFit program available in the Cerius2 molecular modeling package. (Molecular Simulations Inc., San Diego, Calif.). The structure of Bcl-2 used for refined docking is the same as that used for database searching. The structure of gossypol used for docking was built and minimized in the QUANTA program (Molecular Simulations Inc., San Diego, Calif.). Atomic charges of gossypol compounds and the Bcl-2 protein were assigned using the Geisteiger method as implemented in the Sybyl program (Tripos, Inc., St. Louis, Mo.). Refined docking was performed with the DOCK program (version 4.0.1) using 500 configurations per ligand building cycle, 5,000 maximum orientations of the anchor, 1,000 maximum minimization cycles and 10,000 maximum iterations per cycle. The default convergence criteria were used for energy refinement of the docked structure. The docking with LigandFit program (Receptor Science, Singapore) was done using a grid that covered the whole BH3 binding site with 0.2 Å grid spacing. Parameters for gossypol and Bcl-2 were assigned using the 1997 release of the CFF force field. The position of the ligand was optimized using the maximum allowed 999,999 Monte Carlo steps. The default parameters were used for convergence criteria during refinement with the LIGAND FIT program (Accelrys, Inc., San Diego, Calif.).

Example 6

Confirmation of Gossypol Binding to Bcl-$X_L$ by NMR

The binding of gossypol compounds (e.g., racemic gossypol, (−)-gossypol, and (+)-gossypol) to Bcl-$X_L$ was determined using $^{15}$N Heteronuclear Single Quantum Coherence Spectroscopy (HSQC) NMR methods.

The protein samples for NMR studies were uniformly labeled with $^{15}$N for screening and uniformly double labeled with $^{15}$N and $^{13}$C for structure characterization according to the methods described in M. Jansson et al., J. Biomol. NMR, 7:131-141 (1996), and M. L. Cai et al., J. Biomol. NMR, 11:97-102 (1998).

Since the NMR experiments were performed at pH 7.2 in a pulse field gradient (PFG), HSQC with water flip back was used to maximize signal intensity (S. Grzesiek and A. Bax, J. Am. Chem. Soc., 115:12593-12594 (1993); and G. S. Sheppard et al., Abstracts of Papers of the Amer. Chem. Soc., 213:81 (1997)) and to minimize destruction from the water signal. HSQC spectra of Bcl-$X_L$ were recorded prior to (free Bcl-$X_L$) and after the addition of the concentrated inhibitor solution. The two spectra were compared to identify the chemical shifts induced by the additions of the inhibitor. Data processing was conducted using nmrPipe, pipp and nmrDraw software (See, D. S. Garrett et al., J. Magn. Reson. Ser., B 95:214-220 (1991); and F. Delaglio et al., J. Biomol. NMR, 6:277-293 (1995)). Shifted peaks were cross-referenced to the assignment table to reveal the residues affected by the presence of gossypol compounds. The residues affected by the binding of (−)-gossypol are shown in FIGS. 11A and 11B, which show that (−)-gossypol binds to the BH3 binding site in Bcl-$X_L$.

Figure 11C:
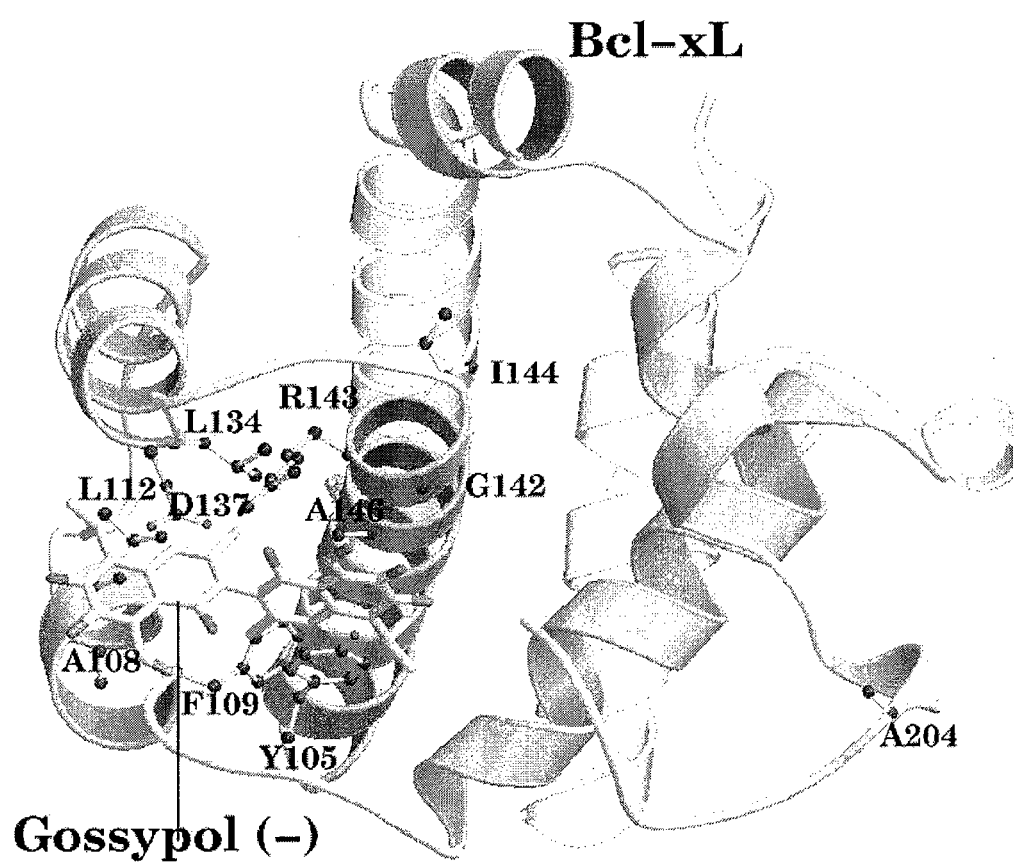
FIG. 11C shows the three-dimensional structural representation of (−)-gossypol in complex with Bcl-$X_L$ protein based upon NMR experimental data and computational modeling in one embodiment of the present invention. The Bcl-$X_L$ protein is represented in a ribbon model and the (−)-gossypol is represented in a stick model.

To provide further insights into the binding of gossypol and its enantiomers, additional embodiments of the present invention used NMR methods to determine the 3D structure of gossypol in complex with Bcl-$X_L$ in solution. To that end, a set of triple resonance NMR experiments were performed, and the backbone and sidechain resonance assignments were assessed. The initial complexed structure, was calculated with the X-PLOR program (Harvard University, Cambridge, Mass.) using a torsion-angle-dynamics protocol. The obtained 3D structure of Bcl-$X_L$ in complex with gossypol was similar to the free form of Bcl-$X_L$ with the hydrophobic BH3 binding pocket formed by the α-helixes of the BH1, BH2, and BH3. To further refine the complexed structure of Bcl-$X_L$ and (−)-gossypol solved by NMR methods, the present invention further performed 4 ns molecular dynamics (MD) simulations. The average complex structure from the computational simulation from the last 50 ps is provided in FIG. 11C.

Figure 28A:
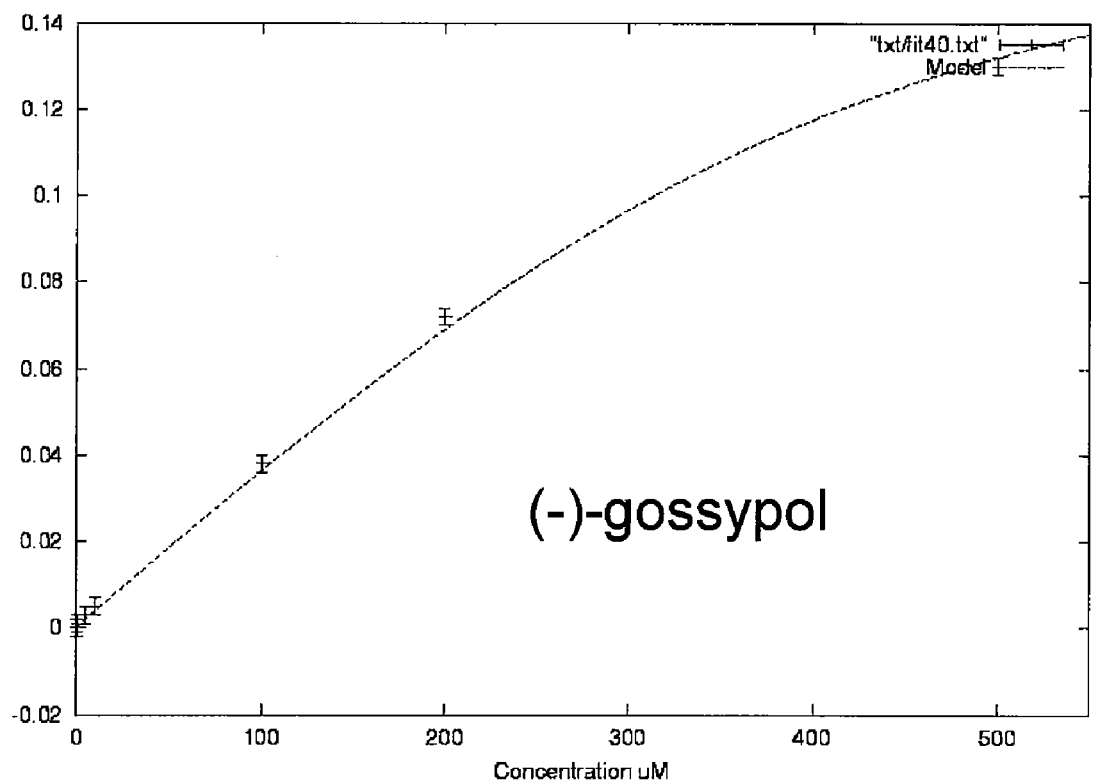
FIGS. 28A and 28B show the results of nuclear magnetic resonance (NMR) based binding assays of (−)-gossypol and (+)-gossypol to Bcl-$X_L$, respectively.
Figure 28B:
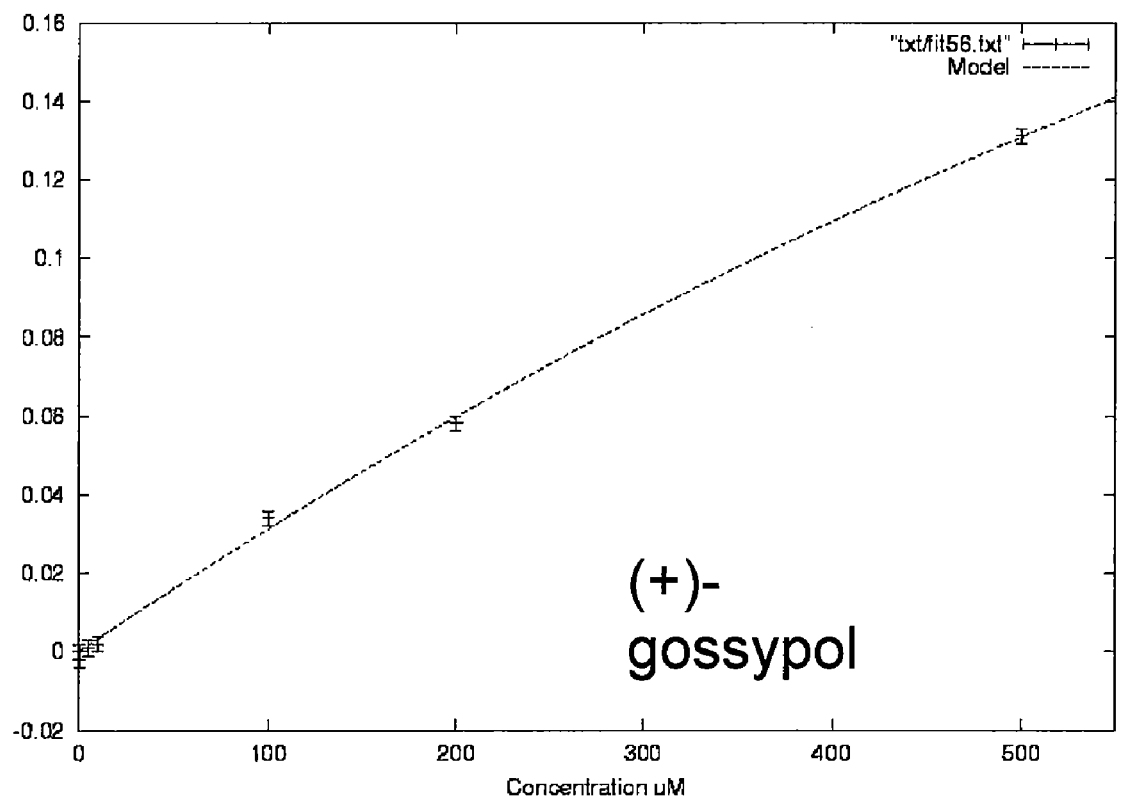
Figure 29:
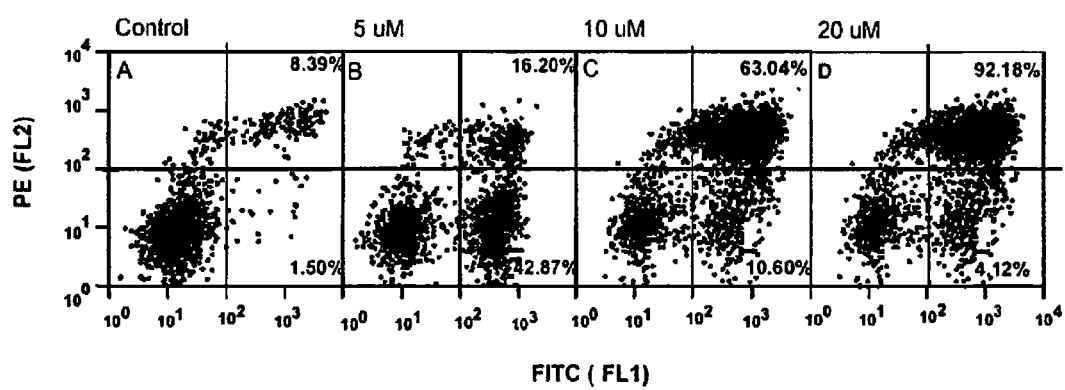
FIG. 29 shows the results of cell based assays in various embodiments of the present invention.
Figure 30:
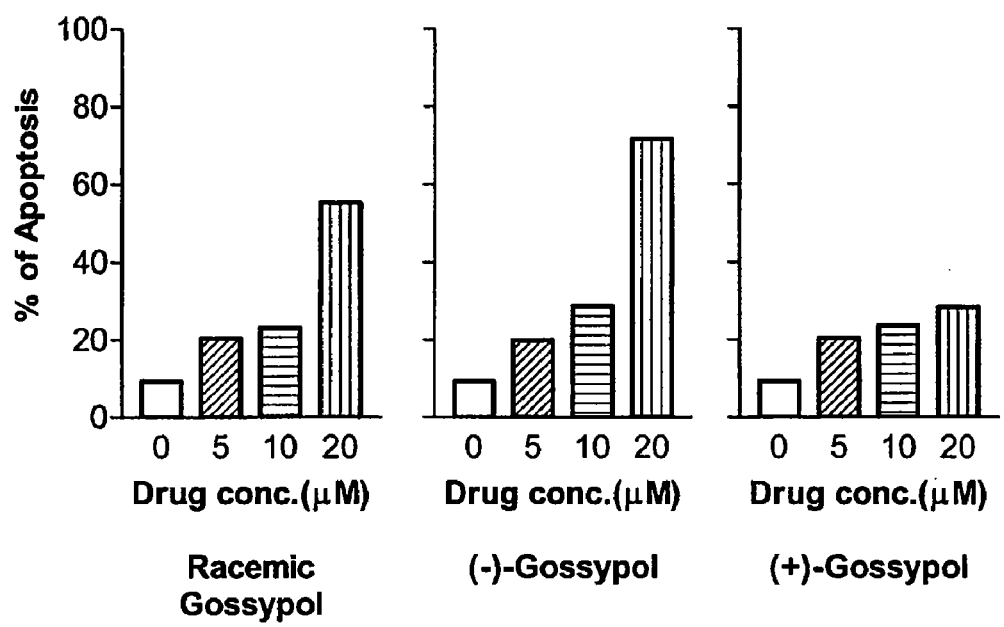
FIG. 30 shows the results of cell based assays of gossypol, (−)-gossypol, and (+)-gossypol in various embodiments of the present invention.

Similar HSQC experiments of Bcl-$X_L$ were performed to obtain the binding affinity of a gossypol compound by titrating a range of inhibitor concentrations from 0.5 μM to 500 μM with a constant concentration (100 μM) of $^{15}$N labeled Bcl-$X_L$ protein. Changes in the chemical shifts of protein residues were monitored by $^{15}$N-HSQC spectra. Using chemical shift data for residue 146, a dose-dependent titration curve by gossypol was developed. FIGS. 28A and 28B show the titration curves of (−)-gossypol and (+)-gossypol with Bcl-$X_L$ protein.

The present invention is not limited to any particular mechanism. Indeed, an understanding of any particular mechanism is unnecessary to practice (make and use) the compositions and methods of the present invention. Nonetheless, it is contemplated that the MD refined complexed structures of the present invention confirm the important interactions between (−)-gossypol and Bcl-$X_L$ observed in the HSQC spectra obtained from previous NMR experiments. Furthermore, MD refined structures identified by the present invention indicate that (−)-gossypol interacts with hydrophobic residues Y105 and L134 as well as with charged residues G142 and R143. The present invention is not limited to any particular mechanism or mechanisms. Indeed, an understanding of any particular mechanisms is unnecessary to practice (make and use) the compositions and methods of the present invention. Nonetheless, certain embodiments of the present invention show that gossypol targets the hydrophobic cleft on the surface of Bcl-$X_L$, which is a docking site for the BH3 domain of pro-apoptotic proteins (e.g. Bid, Bad, Bax and Bak). Binding of (−)-gossypol to this region alters the accessibility or binding properties of Bcl-$X_L$ and Bcl-2 proteins to pro-apoptotic proteins leads to the inhibition of the function of these proteins. Thus, in some embodiments, the present invention provides compounds that bind to the hydrophobic cleft on the surface of Bcl-2 and/or Bcl-$X_L$ by, for example, interacting with residues Y105, L134, G142, and/or R143.

The function of such compounds (whether natural or synthesized) can be assessed by testing the ability of the compound to disrupt or displace gossypol compound/Bcl-2/Bcl-$X_L$ interactions.

Example 7

Expression of Bcl-2 Family Proteins in Human Cancer Cells

Several cancer cell lines (Table 16 and FIG. 7) that express various levels of Bcl-2 and/or Bcl-$X_L$ proteins were selected in order to test the activity of gossypol to inhibit proliferation of human cancer cells.

TABLE 16

|  | Cancer Cell Line | Bcl-2 expression | Bcl-$X_L$ expression |
| --- | --- | --- | --- |
| Group I | T47 breast cancer | ± | +++ |
|  | MDA-453 breast cancer | − | +++ |
| Group II | MDA-435 breast cancer | +++ | ± |
| Group III | MDA-231 breast cancer | +++ | +++ |
| Group IV | WI-38 normal | − | − |
|  | SK-MEL-28 melanoma | ± | − |

Experiments using the cancer cell lines shown in Table 16 allowed for the testing of several important features of gossypol as an anticancer agent. The activity and selectivity of gossypol in binding assays with a number of cancer cell types that express various levels of Bcl-2 family proteins indicates the range of cancer types that are suitable candidates for treatment with gossypol. Testing gossypol in cancer cells with high Bcl-2 and high Bcl-$X_L$ expression levels indicates whether inhibition of either protein alone was sufficient for induction of apoptosis or whether simultaneous inhibition of both proteins achieves greater anticancer potency. Assays using a number of cancer cell types expressing various levels of Bcl-2 family proteins indicate whether gossypol displays selectivity in cancer cells with both low Bcl-2 and low Bcl-$X_L$ expression.

Example 8

Investigations into the Mechanisms of Apoptosis Induced by Gossypol

A series of biochemical assays were carried out to determine the mechanisms of action of the gossypol compounds as small molecule inhibitors of Bcl-2 family proteins (e.g., Bcl-2 and/or Bcl-$X_L$). Although an understanding of the mechanism is not necessary to practice the present invention and the present invention is not so limited, it is contemplated that an understanding of the mechanisms by which gossypol compounds act on cells and tissues that overexpress Bcl-2 family proteins is advantageous to the present invention.

Following the treatment of cells with inhibitors, qualitative assessments of cell morphology were made to determine features related to apoptosis such as cellular swelling, nuclear swelling, membrane blebbing, vacuolization, and apoptotic body formation.

In some embodiments, DNA level detection of apoptosis was made by detecting DNA fragmentation using TUNEL assays. When cells are undergoing apoptosis, apoptotic endonucleases not only affect cellular DNA by producing the classical DNA ladder but also generate free 3'-OH groups at the ends of these DNA fragments. These groups were end-labeled by the TdT-FragFLTM DNA Fragmentation Kit (Oncogene, Boston, Mass.) thus allowing detection of apoptotic cells using molecular biology-based, end-labeling, histochemical, or cytochemical techniques. The rationale of this assay is that terminal deoxynucleotidyl transferase (TdT) binds to exposed 3'-OH ends of DNA fragments generated in response to apoptotic signals and catalyses the addition of biotin-labeled and unlabeled deoxynucleotides. Biotinylated nucleotides were detected using a streptavidin-horseradish peroxidase (HRP) conjugate. Diaminobenzidine reacts with the labeled sample to generate an insoluble colored substrate at the site of DNA fragmentation (See e.g., L. Lagneaux et al., Br. J. Haematol., 112:344-352 (2001); and K. Kitamura, Leukemia, 14:1743-1750 (2000)).

In other embodiments, nuclei level detection methods (e.g., fluorescent dye Hoechst 33258 and propidium iodide staining) were used to quantify signs of apoptosis in treated cells. Morphological changes in the nuclear chromatin of cells undergoing apoptosis were detected by staining with 2.5 μg/ml of bisbenzimide Hoechst 33258 fluorochrome (Calbiochem, La Jolla, Calif.) followed by examination on a fluorescence microscope. A representative example of chromatin changes in cancer cells with high expression levels of Bcl-2 and Bcl-$X_L$ versus normal human fibroblast cells is provided in FIGS. 8A and 8B. In some experiments, cells were double-stained with propidium iodide (PI, 2.5 μg/ml) and Hoechst 33258 (2.5 μg/ml) to distinguish apoptotic cells from necrotic cells. Intact blue nuclei, condensed/fragmented blue nuclei, condensed/fragmented pink nuclei, and intact pink nuclei were considered viable, early apoptotic, late apoptotic, and necrotic cells, respectively (See e.g., B. R. Gastman et al. Cancer Res., 60:6811-6817 (2000); and N. Hail Jr., and R. Lotan, Cancer Epidemiol. Biomarkers Prev., 9:1293-1301 (2000)).

In still further embodiments, the present invention used cell level detection of apoptotic events by flow cytometry. Cells that had undergone apoptotic events were detected by flow cytometry using a FACSCAN instrument (Becton Dickinson, Franklin Lakes, N.J.) with 488-nm laser line and analyzed using CELL QUEST software (Becton Dickinson, Franklin Lakes, N.J.). Phosphatidylserine exposed on the outside of the cells (one of the major characteristics of apoptosis) was determined by TACSTM Annexin V-FITC Kit (Trevigen, Gaithersburg, Md.). Annexin V-FITC fluorescence is detected in FL-1, and propidium iodide was detected in FL-2. (Hail Jr., and R. Lotan, R. Cancer Epidemiol. Biomarkers Prev., 9:1293-1301 (2000)).

Apoptosis was further detected and quantified using Annexin-V-fluorescence assays. Cells were treated with different concentrations of (−)-gossypol or its enantiomers alone, docetaxel alone, or (−)-gossypol and docetaxel for 48 hrs. Cells were collected and washed with PBS and stained with Annexin-V-Fluorescein and propidium iodide (PI) following standard protocols. Stained cells were analyzed with a flow cytometer (Becton Dickinson) using 488 nm excitation and a 515 nm bandpass filter for fluorenscein detection, and a >600 nm filter for PI detection. Representations of induction of apoptosis by gossypol (at various doses) in MDAMB-231 or T47D cells are shown in FIGS. 9, 10, 29, and 30.

The expression and phosphorylation status of Bcl-2 proteins in cells treated with gossypol compounds at various doses and times was determined. In particular, the expression levels of Bcl-2, Bcl-$X_L$, Bcl-$X_S$, Bak, Bad, Bax, and Bid was determined by specific antibodies using Western blot analysis. Phosphorylation status for proteins such as Bcl-2, Bcl-$X_L$, and Bad was determined by Western blotting using specific antibodies that recognize the phosphorylated proteins.

The effects of gossypol on cellular mitochondria were examined by several methods (e.g., cytochrome c release and pore formation assays). Cells were treated with inhibitors for 24-48 hrs and cell fractionation was performed as described in R. M. Kluck et al., Science, 275:1132-1136 (1997) with some modifications as follows. Briefly, cells were harvested and washed once with ice-cold PBS and resuspended in 1 ml ice-cold buffer C (10 mM Hepes-KOH at pH 7.4, 0.42 M NaCl, 2.5% (v/v) glycerol, 1.5 mM $MgCl_2$, 0.5 mM sodium EDTA, 0.5 mM EGTA, 1 mM dithiothreitol) and a protease inhibitor mix (PIM). The cell suspension was homogenized on ice by passage 15 times through a 22 gauge needle. The homogenates were centrifuged twice at 750 g for 10 min at 4° C. to remove nuclei. The post-nuclear supernatant fractions were centrifuged at 10,000 g for 15 min at 4° C., and the resulting mitochondria-enriched pellets were resuspended in 100 ml buffer C+PIM (cold). The post-mitochondrial supernatant was centrifuged at 10,000 g for 1 hr at 4° C. to remove membrane contaminants and the resulting supernatant (soluble portion) was used for cytosolic cytochrome-c release detection (the pellet is the mitochondrial membrane (heavy membrane proteins) portion). Soluble fraction proteins and an equivalent amount of heavy membrane proteins were subjected to SDS-PAGE and analyzed by Western blotting with antibodies against cytochrome c (Becton Dickinson, Franklin Lakes, N.J.), voltage-dependent anion channel (VDAC) (Calbiochem, La Jolla, Calif.), Smac, and AIF (apoptosis inducing factor) (Santa Cruz Biotechnology, Santa Cruz, Calif.) analyses. These methods determined apoptosis signaling following treatment of the test cells (e.g., cancer cells) with gossypol compounds through three mitochondrial pathways: cyto-c release, Smac release, and AIF release.

Figure 31:
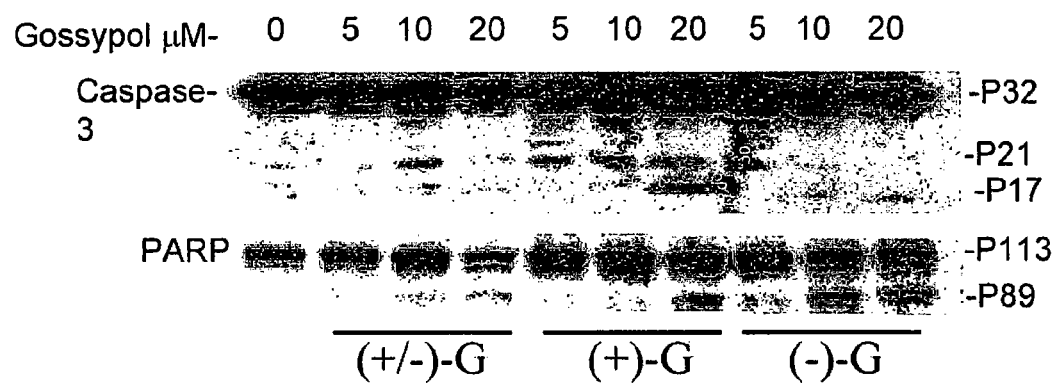
FIG. 31 shows the results of cell based assays in one embodiment of the present invention.

Breast cancer cell lines MDA-231 and T47D were treated with either 5 or 20 μM of gossypol for 24 hrs. FIG. 13 shows that cytochrome c was released from the mitochondria into the cytosol after treatment with 5-20 μM of gossypol in MDA-231 cells or T47D cells which provides further evidence of gossypol compound mediated apoptosis in these cells. Additional assays measured the activation of caspase-3, or the cleavage of PARP protein, a down-stream protein target of caspases. Treatment with (−)-gossypol also resulted in more cleavage of PARP protein under identical doses (FIGS. 14 and 31).

Treatment of cells with 10 or 20 μM of gossypol for 8 hrs also provided a decrease in the mitochondrial transmembrane potential of the test MDA-231 cells as assessed by the cationic lipophilic cell-permeable fluorescent dye 3,3'-dihexy (−)-oxacarbocyanine iodide ($DiOC_6$) assays. The present invention is not limited to any particular mechanisms. Indeed, an understanding of any particular mechanism is unnecessary to practice (make and use) the present invention. Nonetheless, the data indicate that gossypol compounds inhibit the anti-apoptotic functions of Bcl-2 proteins by suppressing the mitochondrial functions regulated by these proteins.

In additional embodiments, the activation of caspases was determined by collecting and washing treated cells with PBS and suspending the cells in 25 mM HEPES (pH 7.5), 5 mM $MgCl_2$, 5 mM EDTA, 5 mM dithiothione, 2 mM phenylmethylsulfonyl fluoride, 10 g/mL pepstatin A, and 10 g/mL leupeptin after treatment. The treated cells were then lysed. The cell lysates were clarified by centrifugation at 12000×g for 20 min at 4° C. Caspase-1, -2, -3, -6, -8, and -9 activity in the supernatant was determined using the fluorogenic CaspACE Assay System (Promega Corp., Madison, Wis.). Briefly, 50 mg aliquots of total protein, determined by the bicinchoninic acid assay (Promega Corp.), were incubated with 50 mM substrate Ac-YVAD-AMC, Ac-VDVAD-AMC, Ac-DEVD-AMC, Ac-VEID-AMC, Ac-IETD-AMC, or Ac-LEHD-AMC at 30° C. for 1 hr. The release of methylcoumaryl-7-amine (AMC) was measured by excitation at 360 nm and emission at 460 nm using a fluorescence spectrophotometer (Hitachi F-4500) according to G. Denecker et al., Cell Mol. Life Sci., 58:356-370 (2001); and V. M. Kolenko et al., Apoptosis, 5:17-20 (2000)).

Figure 32A:
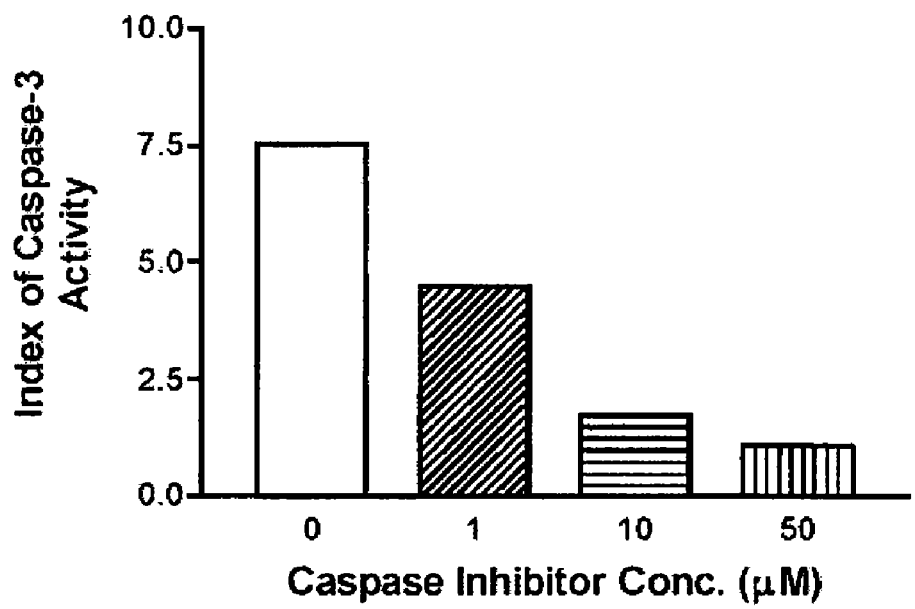
FIGS. 32A and 32B shows the results of cell based assays in one embodiment of the present invention.
Figure 32B:
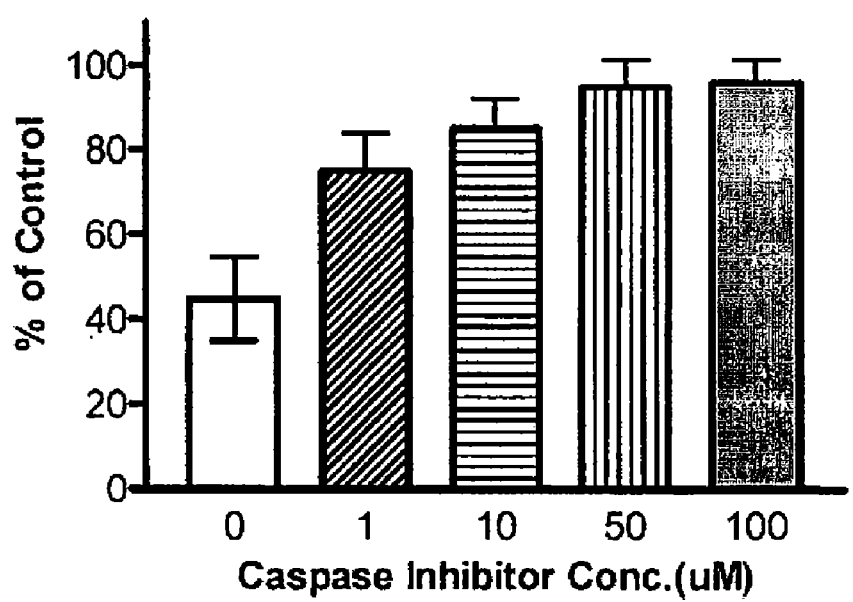

The effects of caspase inhibitors (e.g., Z-VAD-FMK, nonspecific, Z-DEVD-FMK, caspases-3, -6, -7, -8, and -10, and Z-LEHID-FMK, caspase-9) on the activity of the gossypol compounds was determined using standard caspase inhibitor assays. All of the caspase inhibitors used are commercially available (Enzyme System Products, Livermore, Calif.). FIGS. 32A and 32B show caspase inhibitors in gossypol-mediated caspase activation and growth inhibition.

Example 9

Cell Survival Assay

Cells were seeded in 24 or 96-well-plates and gossypol compounds were prepared at 2-10 fold dilutions in suitable medium. Inhibition of cell viability was determined by treating the cells with the gossypol compounds for 24 hrs. Cell viability was then determined by the trypan-blue assays. Inhibition of cell growth was determined by treating cells with gossypol compounds for 3-6 days. Cell inhibition was determined using XTT. In some embodiments, MTT assays are used to determine cell inhibition.

In one embodiment, to evaluate cell proliferation, soluble XTT (Sodium, 3'-(1-((phenylamino)-carbonyl)-3,4-tetrazolium)-bis(4-methoxy-6-nitro) benzenesulfonic acid hydrate (Polysciences, Inc., Warrington, Pa.) assays were performed on cells growing in 96-well plates. After 5 days of incubation, when the control untreated cells reached confluence, 50 μl of XTT (1 ng/ml) was added to each well and incubation continued for 4 hrs at 37° C. Absorbance at 450 nm was measured using a Dynatech Model MR700 device (Dynatech Laboratories Ltd. Billinghurst, United Kingdom). The percentage of surviving cells was defined as mean absorbance of treated wells/mean absorbance of untreated wells×100.

MTT assays provide a fast, accurate, and reliable method for obtaining cell viability measurements. MTT assays are simple and colorimetric. Numerous laboratories have utilized MTT assays for toxicity studies (See e.g., Kuhlmann et al., Arch. Toxicol., 72:536 (1998)). Briefly, mitochondria produce ATP to provide sufficient energy for the cell. In order to do this, the mitochondria metabolize pyruvate to produce acetyl CoA. Within the mitochondria, acetyl CoA reacts with various enzymes in the tricarboxylic acid cycle resulting in subsequent production of ATP. Succinate dehydrogenase is one of the enzymes measured by MTT assays. The MTT compound (3-(4,5-dimethylthiazol-2-yl)-2 diphenyl tetrazolium bromide) is a yellow substrate that is cleaved by succinate dehydrogenase to form a purple formazan product. The colorimetric response of MTT (yellow to purple) thus identifies changes in mitochondria function. Nonviable cells are unable to produce the MTT formazan product; therefore, the amount of purple MTT formazan product produced directly correlates to the quantity of viable cells. Absorbance at 540 nm is used to measure the amount of formazan product.

The present invention is not limited to any particular mechanisms. Indeed, an understanding of any particular mechanism is unnecessary to practice (make and use) the present invention. Nonetheless, it is contemplated that FIG. 12 shows that, in certain embodiments, (−)-gossypol is 2 times more potent than (+)-gossypol and is 5-10 times more potent than (+)-gossypol in inhibition of cell growth in breast cancer cell lines with high levels of Bcl-$X_L$. The data suggest that (−)-gossypol is more potent than (+)-gossypol, and is more selective between cancer cells with high levels of Bcl-$X_L$ expression and cancer or normal cells with low levels of Bcl-$X_L$ such as DU-145 or WI-38.

Example 10

Colony-Formation in Soft-Agarose

The soft-agar colony formation assays were used to directly measure the transforming ability of cancer cells. These assays are known to correlate well with in vivo tumorigenicity.

Experiments were conducted using combination treatments to assess the apoptotic effects or inhibition of cell proliferation obtained by administration of Bcl-2 inhibitors in combination with known chemotherapeutic agents. In preferred embodiments, these results were used to select synergistic agent combinations.

Figure 33:
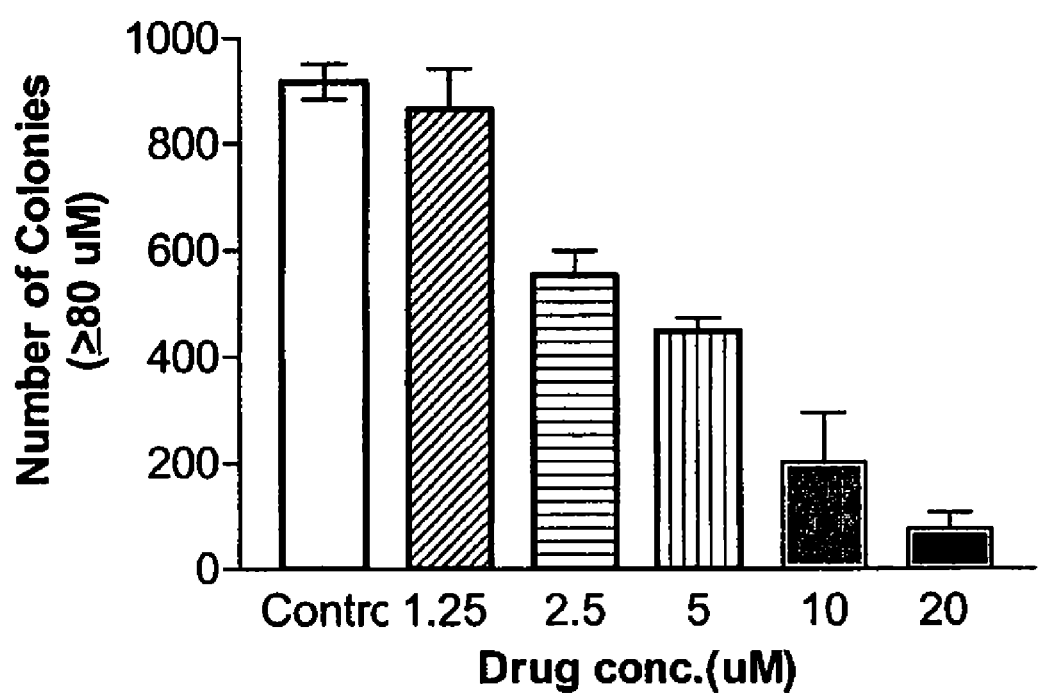
FIG. 33 shows the results of cell based colony formation assays in one embodiment of the present invention.

Cells were trypsinized and resuspended in 1 ml 0.33% top agarose (10,000 cells/ml) on 1% bottom agarose. The next day, 1 ml aliquots of regular medium containing (−)-gossypol were gently layered to the top of the agarose and incubation continued for 2 weeks. The number of colonies greater than 80 μm in diameter were counted using a Bausch and Lomb Image Analysis System (Omega 3800). FIG. 33 shows a representative example of inhibition of soft agar colony formation in these experiments.

Example 11

In Vivo Antitumor Activity Studies

Preliminary in vivo studies showed that gossypol is a potent Bcl-$X_L$ inhibitor, and that it exhibits significant antitumor activity alone and in combination with additional conventional anticancer agents (e.g., docetaxel). Preferred embodiments of the present invention provide in vivo antitumor efficacy and selectivity studies using human cancer xenograft models.

The results of in vitro experiments can be compared to in vivo toxicity tests to extrapolate live animal conditions. Typically, toxicity from a single dose of a substance is assessed. In some embodiments, animals were monitored over 14 days for any signs of toxicity (increased temperature, breathing difficulty, death, etc.). Typically, the standard of toxicity is the measurement of the maximal tolerated dose (MTD). The MTD is the highest dose that results in no lethality/tissue abnormality or causes them to gain 10% less weight than control animals.

The determination of the MTD occurred by exposing test animals to a geometric series of doses under controlled conditions. Other tests included subacute toxicity testing, which measures the animal's response to repeated doses of gossypol compounds (or one or more conventional anticancer agents) for no longer than 14 days. Subchronic toxicity testing involved testing of a repeated dose for 90 days. Chronic toxicity testing is similar to subchronic testing but lasts for more than 90 days. In vivo testing was conducted to determine toxicity with respect to certain tissues. For example, in some embodiments of the present invention, tumor toxicity (e.g., effect of the compositions of the present invention on the survival of tumor tissue) was determined (e.g., by detecting changes in the size and/or growth of tumor tissues).

In order to design optimal dose schedules for gossypol therapies, studies first utilized human breast cancer cell lines MDA-231 (clone 2LMP), and then additional tumor xenograft models such as MDA-435 (LCC6), and T47D. MDA-231 expresses high levels of both Bcl-2 and Bcl-$X_L$; MDA-435 expresses high levels of Bcl-2 but low levels of Bcl-$X_L$; T47D expresses low levels of Bcl-2 but high levels of Bcl-$X_L$. Among all of the 7 human breast cancer cell lines examined, no cell line had both low Bcl-2 and low Bcl-$X_L$. The human prostate DU-145 mice xenograft model, however, expresses low levels of both Bcl-2 and Bcl-$X_L$ and was thus used as a negative control in some embodiments to test the specificity of gossypol compounds and gossypol derivatives.

In one embodiment using the MDA-231 model, a series of comprehensive dose and schedule investigations was performed to determine: 1) the minimal active dose, defined as inhibition of tumor growth by 50% as compared to control with a statistical confidence level of 95%; 2) the optimal schedule of administration in inhibition of tumor growth while not causing toxicity defined as weight loss of more than 25%; 3) the effect of gossypol compounds on large tumors (more than 2,000 mm$^3$); 4) how long could gossypol can be administered to mice in the control group without causing morbidity or mortality (e.g., weight loss).

After identifying optimal doses and dosing schedules, testing of combination therapies with at least one additional conventional chemotherapeutic agent was conducted, including, but not limited to, 1) doxorubicin (4 mg/kg); 2) 5-FU (10 mg/kg); 3) VP-16/etoposide (40 mg/kg); and 4) cyclophosphamide (100 mg/kg); and 5) cisplatin (10 mg/kg). As a positive control, TAXOTERE was used at a dose of 7.5 mg/kg. Control group mice received either no treatment or vehicle alone. To achieve statistic significance, a minimum of 10 mice per group was used in the combination regimes.

For all tests, mice were randomized and then injected in the fat pad with 1-5×10$^6$ cells prepared in serum-free medium. The animals were measured and weighed twice each week during the treatment period, followed by twice a week measurements for an additional 4-6 weeks. A gross visual necropsy of each animal was performed at death or terminal sacrifice. A representative example of in vivo animal testing data of gossypol either alone or in combination with TAXOTERE is provided in FIG. 15.

The rate of apoptosis in tissues was determined using the TUNEL method (terminal deoxyribonucleotidyl transferase (TdT)-mediated dUTP-digoxigenin nick end labeling). The TUNEL, method is extremely sensitive (See. Y. Gavrieli et al., J. Cell Biol., 119:493-501 (1992); and M. Dowsett et al., Cytometry, 32:291-300 (1998)). Paraffin-embedded tissues were sectioned, and slides were incubated in labeling buffer for 5 min. then placed in a humid chamber with TdT, dNTP mix, and Mg$^{++}$ in labeling buffer. Strepavidin-Horseradish Peroxidase was applied onto each sample for 10 min., the samples were washed and counter stained with methyl green or hematoxylin. The rate of apoptosis was calculated by counting and dividing the number of apoptotic cells by the total number of cells seen per light microscopy field at 40× magnification, and is expressed by percent.

Example 12

Drug Interactions between Gossypol and Docetaxel

Figure 34:
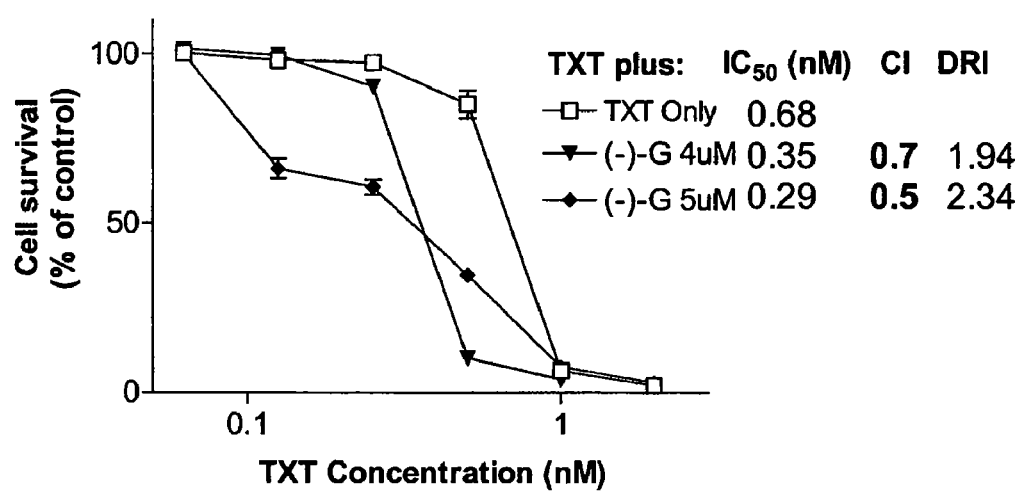
FIG. 34 shows the results of cell based assays in various embodiments of the present invention.

The present invention is not limited to any particular mechanisms. Indeed, an understanding of any particular mechanism is unnecessary to practice (make and use) the present invention. Nonetheless, it is contemplated that, in certain embodiments, gossypol compounds are likely to be used in combination with standard chemotherapeutic agents. Although gossypol alone inhibited cell proliferation, combination treatments resulted in enhanced effects (e.g., greater induction of apoptosis in target cells). Experiments show that (−)-gossypol acts in synergy with docetaxel (TAXOTERE, or TXT), or paclitaxel (TAXOL) to inhibit the growth of breast cancer cells such as MDA-MB-231 (FIG. 34), or MCF-7 (FIG. 16).

Isobologram analyses (See, T. C. Chou and P. Talalay, Adv. Enzyme Regulation, 22:27 55 (1984)), are widely used to determine synergism of two or more drugs when used in combination. In some embodiments, isobologram analyses show that the combination of TAXOTERE with (−)-gossypol resulted in significant synergy, with a Combination Index (CI) of 0.7 and 0.5, and a Dose Reduction Index (DRI) of 1.94 and 2.34 for administration of TAXOTERE with either 4 µM or 5 µM of (−)-gossypol, respectively. Briefly, FIGS. 17A and 17B show the in vitro effects of (−)-gossypol in combination with various doses of TAXOL in MDA-MB-231 based growth assays, wherein: CI value<1 indicates synergistic effects; CI=1 indicates additive effects; CI value>1 indicates antagonistic effects; DRI>1.0 indicates synergistic effects. Treatment of MDA-MB-231 cells with (−)-gossypol significantly potentiated the cells' response to TAXOL mediated cytotoxicity and resulted in further reductions in cell survival from controls. Thus, in some embodiments, gossypol compounds provide a synergistic effect when used in combination with cytotoxic agents such as taxanes (e.g., TAXOTERE). The present invention is not limited to any particular mechanisms. Indeed, an understanding of any particular mechanism is unnecessary to practice (make and use) the present invention. Nonetheless, the data indicate, in some embodiments, that gossypol compound mediated inhibition of cell proliferation is enhanced when combined with chemotherapeutic agents and that the combined effect are specific for gossypol. Other chemotherapeutic drugs were also tested in combination with gossypol.

The effect of gossypol alone on the erythromycin breath test (ERMBT), a phenotypic test for CYP3A4 metabolism, was evaluated by comparing baseline ERMBT levels at baseline and after 1-week pretreatment with gossypol (See, e.g., P. Watkins, Pharmacogenetics, 4:171-184 (1994); and J. Hirth et al., Clin. Cancer Res., 6:1255-1258 (2000)). ERMBT assays produce a measurement of the percentage of $^{14}C$ exhaled per hour, that is usually approximated using the Normal distribution (See, D. Wagner, Clin. Pharm. Therap., 64:129-130 (1998)). The mean levels of $^{14}C$ exhaled/hr were compared using a standard (alpha=0.05), two-sided, paired t test. Using estimates from previous work (J. Hirth et al., Clin. Cancer Res., 6:1255-1258 (2000) for the baseline mean $^{14}C$ exhaled/h (n=21, mean=2.41), its standard deviation (SD=1.08), correlation of ERMBT measurements over time (r=0.81), and assuming constant variance at each measurement, the current example with data from 30 subjects has 96% power to detect a 20% decrease (2.41 to 1.93), and 81% power to detect a 15% decrease (2.41 to 2.05) in mean ERMBT levels. The mean, standard deviation, and range of ERMBT values was tabulated and reported, along with the significance of the paired t test.

Example 13

Pharmacokinetic Description of Docetaxel in Patient Samples

Blood is drawn for a pharmacokinetic description of docetaxel when administered in combination with gossypol using an optimal sampling strategy (See, P. Baille et al., Clin. Cancer Res., 3:1535-1538 (1997)). Blood is drawn directly before the end of infusion (EOI) of docetaxel, at 0.25, 0.75, 3.00, 6.50, and at 24 hrs following EOI. All samples are assayed at the same time. A Bayesian criterion is used to calculate the docetaxel plasma concentration area under the curve (AUC) based upon measured drug levels and population pharmacokinetic parameters previously estimated (See, R. Bruno et al., J. Clin. Oncol., 16:187-196 (1998)) for docetaxel alone, using NONMEM software (S. L. Beal and L. B. Shener, Nonlinear Mixed Effects Model Users Guides (San Francisco, Calif., NONMEM Project Group, University of California at San Francisco) (1999)). Clearance (CL) is directly estimated by fitting the nonlinear mixed effects model (R. Bruno et al., J. Clin. Oncol., 16:187-196 (1998)). The AUC is calculated as a function of dose and clearance, defined as AUC=dose/CL. ERMBT values from baseline and 1-week following gossypol pretreatment are plotted separately against Clearance. Ordinary least squares regression is used to defined the relationship between docetaxel CL and the ERMBT or the natural logarithm of ERMBT. The estimated slopes are displayed along with previously published values for single treatment docetaxel CL (J. Hirth et al., Clin. Cancer Res., 6:1255-1258 (2000)) in order to describe any differences in docetaxel CL when administered in combination with gossypol versus single agent administration.

Example 14

Expression of Bcl-2 Family Protein in Patient Samples

The expression of Bcl-2 and Bcl-$X_L$ in tissue samples collected in paraffin blocks was assayed using standard immunohistochemical (IHC) assay methods. IHC results were dichotomized and tabulated to show the percentage of patients expressing these markers. Results were tabulated against anti-tumor response. Chi-square statistic and Fisher's exact tests were performed to assess the relationship between expression and anti-tumor response, depending on the size of the cell counts in the resulting table.

In some embodiments, tissues were fixed in 4% buffered formalin, processed, and embedded in paraffin according to the normal schedule used in the laboratory. From each block, 5 µm-thick sections were cut on coated slides and dried overnight at 37° C. The sections were deparaffinized in xylene and rehydrated through graded concentrations of ethanol to distilled water. Sections to be stained with antibodies against Bcl-2, Bax, Bcl-$X_L$, and Bag-1 were pretreated by boiling them for 20 min in citrate buffer (pH 6.0) or pretreated by digestion in 0.5% trypsin (pH 7.2) at 37° C. for 30 min. Immunohistochemical stainings were performed using commercial Elite ABC kits (VECTASTAIN, Vector Laboratories, Burlingame, Calif.). Blocking serum was applied for 15 min followed by overnight incubation with the diluted primary antibody: Bcl-2, 1:200 (clone 124, DakoCytomation, Inc., Carpinteria, Calif.); Bax, 1:100 (clone 2D2; Zymed Laboratories, Inc., South San Francisco, Calif.); Bcl-$X_L$, 1:50 (clone 2H12; Zymed); Bag-1, 1:200 (monoclonal mouse (12), (Santa Cruz Biotechnology, Inc., Santa Cruz, Calif.); the sections were then incubated with the biotinylated secondary antibody and the peroxidase-labeled ABC solution (VECTASTAIN) for 30 min each. All of the dilutions were made in PBS (pH 7.2), and all of the incubations were performed in humid chambers at room temperature. Between each step in the staining procedures (except before incubation with the primary antibody), the slides were rinsed three times in PBS. Bound peroxidase was visualized in all of the slides with a 3-amino-9-ethyl-carbazole solution (0.2 mg/ml in 0.05 M acetate buffer containing 0.03% perhydrol (pH 5.0); AEC; Sigma Chemical Co., Saint Louis, Mo.) at room temperature for 15 min. The sections were lightly counterstained in Mayer's hematoxylin and mounted in Aquamount Mountant (BDH Ltd., Poole, United Kingdom). For each antibody, a known positive case of cancer was included in every staining batch as a positive control. Cells were considered positive when a distinct cellular micropunctate pattern of staining was seen, except for Bag-1, for which nuclear staining was also accepted. The percentage of immunoreactive cells was evaluated as the amount of positive tumor cells per all of the tumor cells on the section. All of the stained sections were scored by two investigators, who were blinded to the clinical data. Median values were then used as the cut-points for low and high expression. Spearman correlation coefficients were calculated for the investigated tumor biological factors.

In some embodiments, 5 μm-thick sections of the formalin-fixed, paraffin-embedded tumors were immunostained using monoclonal Bcl-2 (1:160) (DakoCytomation), polyclonal Bax (1:1500) (PharMingen, San Diego, Calif.), and polyclonal Bcl-X (1:1500) (PharMingen). An avidin-biotin enzyme complex kit (Signet Laboratories Inc., Dedham, Mass.) with steam antigen retrieval was used in combination with the automated TechMate 1000 immunostaining system (Biotek Solutions Inc., Santa Barbara, Calif.). Hematoxylin and eosin were used as counterstains. Sections of tonsil were used as positive controls for Bcl-2, while normal breast ducts and lobules were used as positive controls for Bax and Bcl-$X_L$. In some embodiments, negative controls had primary antibody replaced by buffer. The immunostaining was recorded as 0 to 3+ according to stain intensity, distribution in cytoplasm and/or nucleus, and percentage of cancerous cells that stained positive. Tumors with less than 5% of carcinoma cells staining with 1+ positivity were considered negative.

In some embodiments, the percentage of nuclear and cytoplasmic immunostain for the antigens (Bcl-2, Bax, Bcl-$X_L$) were quantitated using the CAS 200 image cytometer (Becton Dickinson Cellular Imaging Systems, San Jose, Calif.). The immunoperoxidase/diaminobenzidine procedure stained positive nuclei and cytoplasm brown and negative areas blue and pink, respectively. At 620 nm, brown, blue, and pink absorb, providing a measure of total nuclear and cytoplasmic area. At 500 nm, thresholds were set so that only the brown stained areas absorbed, allowing the immunopositive nuclear and cytoplasmic areas to be measured independently. Comparison with the 620 nm mask gave the percent positive area immunostained (PPA). Fifteen fields were analyzed in each slide so as to minimize the standard deviation. Areas were isolated from adjacent stroma by using the scene segmentation function, which allows the operator to precisely define portions of the image to be analyzed. This prevents positive staining of non-cancerous tissue elements such as lymphocytes, from being included in the PPA. Computer generated histograms showed PPA on the vertical axis and nuclear/cytoplasmic optical density (OD) on the horizontal axis. The OD of the chromogen was proportional to the amount of immunostain. The computer calculated the number of fields, total nuclear/cytoplasmic area analyzed, and PPA as averages of intensity of immunostaining. A ratio was then obtained of the PPA Bcl-2 divided by the PPA of Bax and Bcl-$X_L$. Basic descriptive statistics, including means, standard deviations, and ranges were used to characterize the study sample. Pearson's correlation coefficients were used to explore the association between continuous measures. P-values less than 0.05 were considered statistically significant.

In some embodiments, the level of target antigen expression was quantified as follows: samples with more than 50% positive cells were classified as strongly positive (++), while samples with 5-50% positive cells were classified as moderately positive (+), and samples with fewer than 5% positive cells were classified as negative (−) (See, Alderson et al., Cancer Res., 999-1001 (1995)). Areas free of necrosis and capillary endothelial proliferation were chosen for analysis. The infiltrative edge of the tumor where normal neurons and glia are surrounded by neoplastic cells was also excluded. An eyepiece grid was used for counting at a magnification of 400×. Three high-power fields were counted for each sample and antigen. The correlation between the expression of different proteins was analyzed with the Chi-square test of independence with Yates' correction for continuity (P, 0.05).

Example 15

Peripheral Blood Lymphocytes Studies

Blood samples collected from study participants before study treatment, on day 8 (following 1 week gossypol pretreatment), and at week 9 (after completion of one cycle of gossypol plus docetaxel) are used for exploratory studies involving peripheral blood lymphocytes (PBL) and circulating epithelial cells (CEC). Using fluorescent activated cell sorting techniques (FACS), PBLs are characterized for their expression of Bcl-2 and Bcl-$X_L$ before and after gossypol administration. The mean number of PBLs with expression and its standard deviation will be reported at each time point. Using an immunomagnetic separation method previously described (See, T. Walker et al., Proc. Amer. Soc. Clin. Oncology, 19:54b (2001)) the feasibility of finding CECs is determined for each patient. The mean number of CECs per 10 ml of blood collected and its standard deviation across patients at each time point will be reported.

Example 16

Administration of (−)-Gossypol in Combination with Conventional Chemotherapeutic Agents in a Mouse Xenograft Model This example describes experiments conducted to evaluate the in vivo antitumor efficacy of (−)-gossypol in human xenograft models either alone or in combination with chemotherapy. Docetaxel (TAXOTERE or TXT) was administered as described herein.

In this experiment, male 5 to 6 week old NCI athymic NCr-nu/nu nude mice were inoculated subcutaneously in the mammary fat pad on each side with an injection of about 1×10$^6$ MDA-MB-231 (2LMP) in 0.3 ml serum free medium (SFM). The best xenograft recipients were used. Treatments began when tumors averaged about 50 mm$^3$ (5-7 mm in diameter, usually at day 7). Treatments ran for 4 weeks with a 2 month follow up period. Resolution of gossypol enantiomers was carried out as described previously. (−)-Gossypol compounds were dissolved in ethanol and diluted with final 10% ethanol in PBS before injection. All oral administrations of (−)-gossypol and 10% alcohol were given by gavage.

Test animals were divided into cohort groups of 8 animals into the following treatment groups: Control (Group 1); Vehicle control (Group 2), daily oral administration of 10% alcohol only; (−)-gossypol (Group 3), 7.5 mg/kg administered orally per day for 4 weeks; (−)-gossypol (Group 4), 15 mg/kg administered orally per day for 4 weeks; (−)-gossypol (Group 5), 30 mg/kg administered orally per day for 4 weeks;

docetaxel (or TAXOTERE, TXT) (Group 6), 7.5 mg/kg administered intravenously once per week for 4 weeks; (−)-gossypol plus TXT (Group 7), 7.5 mg/kg (−)-gossypol administered orally per day for 4 weeks, plus 7.5 mg/kg TXT administered intravenously once per week for 4 weeks; (−)-gossypol plus TXT (Group 8), 15 mg/kg (−)-gossypol administered orally per day for 4 weeks, plus 7.5 mg/kg TXT administered intravenously once per week for 4 weeks; and (−)-gossypol plus TXT (Group 9), 30 mg/kg (−)-gossypol administered orally per day for 4 weeks, plus 7.5 mg/kg TXT administered intravenously once per week for 4 weeks.

During the treatment course, tumor sizes and animal weights were measured 3 times per/week for each animal. Following treatment, tumor sizes were measured 2 times per/week, and animal weights once per/week. Tumor and weight observation were made without knowledge of the animal's treatment group. A representative example of in vivo xenograft based experiments used to investigate the anti-tumor activity of (−)-gossypol in combination with docetaxel is provided in FIG. 18. Docetaxel treatment started at day 7 and was given i.v. at a weekly dose of 7.5 mg/kg for 3 weeks. The results show that treatment by docetaxel alone in sub-optimal dose (7.5 mg/kg weekly) inhibited tumor growth. But, the combination of gossypol at three doses level (7.5, 15, and 30 mg/kg, respectively) with docetaxel achieved a much greater activity in inhibition of tumor growth. In the group of 10 mice treated with a combination therapy, 3 out of 10 mice (6 tumors) had complete tumor regression. Overall, there was more than 90% of inhibition in tumor growth in the combination group as compared to the group control. Statistical analyses were performed using a mixed-effects repeated measures model which accurately takes into account the correlation within an animal over time, and between tumors within an animal. The data was modeled using the natural logarithm of tumor volume. Comparisons of the growth rates of animals administered (−)-gossypol alone and docetaxel alone were performed. Table 17 provides an example of one such comparison with (−)-gossypol at 7.5 mg/kg and docetaxel.

TABLE 17

| Treatment | Tumor Growth Inhibition (T/C %) | Tumor Growth Delay (T − C Days) |
|---|---|---|
| Radiation | 77.7 | 8.5 |
| (−)-gossypol | 98.6 | 0 |
| Radiation + (−)-gossypol | 12.6 | 54.5 |

Table 17 shows a comparison of the tumor growth rate between (−)-gossypol 7.5 mg/kg, docetaxel 7.5 mg/kg, and the combination; P-values for the linear contrast are reported. Findings were statistically significant findings when $p<0.05$.

In a subset of the mice treated with either Docetaxel alone or a combination therapy, a second round of treatments with the same regimen was initiated at day 45. The average tumor volume before the second cycle treatment was about 2000 mm$^3$. Tumors in the Docetaxel alone treated group continued to grow and all the mice were sacrificed due to the tumor burden. The combination treatment groups displayed tumor regression and total 50% reduction of tumor volume (FIG. 19). The data clearly shows that (−)-gossypol was very effective in potentiating docetaxel in combination treatments even at a doses where it is less effective when administered as a single agent.

In yet another embodiment, the in vivo anti-tumor activity of (−)-gossypol was investigated in non-small cell lung carcinoma line A549 cells. A549 cells express high levels of Bcl-X$_L$. FIG. 20 shows the results from these experiments. Briefly, in FIG. 20, gossypol was administered in combination with paclitaxel (TAXOL), wherein paclitaxel was administered at a weekly dose of 15 mg/kg with daily p.o. administration of (−)-gossypol at 7.5 mg/kg.

Example 17

Treatment of Squamous Head and Neck Cancer with Gossypol Compounds

The following experiments were conducted to determine the suitability and efficacy of gossypol compounds, e.g., (−)-gossypol, to therapeutically treat squamous head and neck cancers. The results are summarized in FIGS. 21, 22, 23, and 24A-24C.

Ten squamous cell carcinoma cell lines established at the University of Michigan (UM-SCC) and three human fibroblast lines were grown in Dulbecco's modified Eagle's medium (DMEM) supplemented with 10% fetal bovine serum. UM-SCC cell lines originated from the larynx (n=2; UM-SCC-12, -23), oral cavity/oropharynx (n=5; UM-SCC-1, -6, -14A, -74B, -81B), hypopharynx (n=1; UM-SCC-22A) and metastases from laryngeal cancers (n=2; UM-SCC-17B, -25). Human fibroblast cell lines originated from surgical specimens (fibroblast cell lines 2 and 3) and neonatal foreskin samples (fibroblast cell line 1).

Cell-Growth Inhibition Assays (MTT Assays)

Logarithmically growing cell lines were cultured, washed, counted, and plated at 5,000-15,000 cells per well in duplicate wells of 96-well plates and incubated in DMEM overnight. The following day, serial dilutions were made from stock solutions of racemic, (+)-, or (−)-gossypol to achieve the desired concentrations. All experimental conditions were performed with 5 replicates. The sample plates were incubated for 6 days in 300 µL of DMEM containing gossypol or solvent controls. MTT assays were then performed according to the manufacturer's protocol (Roche Diagnostics, Mannheim, Germany). The MTT assay measures cell survival based on mitochondrial conversion of MTT from a soluble tetrazolium salt into an insoluble colored formazan precipitate, which is dissolved in dimethyl sulfoxide and quantitated by spectrophotometry. (M. C. Alley et al., Cancer Res., 48:589-601 (1988)). Percent absorbance relative to control was plotted as a linear function of drug concentration. The 50% inhibitory concentrations (IC$_{50}$s) were identified as the concentration of drug required to achieve 50% growth inhibition relative to untreated control populations. The cell growth inhibition curves by (−)-gossypol in a panel of squamous cell carcinoma cell lines (UM-SCC) and three fibroblast cell lines are provided in FIG. 21.

Western Blot Analysis

Proteins were harvested during log phase growth by lysing cells in the flask using a solution of phosphate buffered saline (PBS) (BioWhittaker, Walkersville, Md.) containing 1% NP-40 (Sigma; St. Louis, Mo.), 1 mM PMSF (Sigma) and 1 tablet of a cocktail of protease inhibitors (Boehringer Mannheim, Germany) per 100 ml of PBS. The protein extracts were quantified using a calorimetric assay (Bradford Reagent) (BioRad, Hercules, Calif.). Thirty micrograms of protein were resolved on 12% Tris-glycine sodium dodecyl sulfate polyacrylamide gels (115V) under denaturing conditions and transferred to Hybond-P PVDF membranes (Amersham Pharmacia Biotech, Buckinghamshire, England) at 30V overnight. Membranes were blocked in Tris-buffered saline containing 5% nonfat dry milk at room temperature for 1 hour and then incubated with primary antibody. Primary antibodies included murine anti-human Bcl-2 oncoprotein (124) monoclonal antibody (Dako, Glostrup, Denmark), murine anti-Bcl-xL (YTH-2H12) monoclonal antibody (Trevigen Inc., Gaithersburg, Md.) and rabbit anti-Bcl-XS (Ab-1) polyclonal antibody (Oncogene Research Products; Boston, Mass.). Equivalency of protein loading was evaluated using either murine anti-actin monoclonal antibody (Chemicon International, Temecula, Calif.) or murine anti-GAPDH monoclonal antibody (Chemicon). Membranes were then incubated with a secondary horseradish peroxidase-conjugated anti-mouse (or rabbit) antibody (Amersham Pharmacia Biotech) and analyzed using Enhanced Chemiluminescence Plus reagent (Amersham Pharmacia Biotech). Densitometry readings for three independent blots were taken using AlphaEase software version 5.5 (Alpha Innotech Corp., San Leandro, Calif.) for statistical analysis.

Expression levels of Bcl-2, Bcl-$X_L$ and Bcl-$X_S$ proteins in a panel of squamous cell carcinoma cell lines (UM-SCC) and one fibroblast cell line are provided in FIG. 22. FIG. 23 plots the relationship between the ratio of Bcl-$X_L$ and Bcl-$X_S$ and the $IC_{50}$ values (concentration required to inhibit 50% of cell growth related to untreated control cells) of (−)-gossypol in a panel of squamous cell carcinoma cell lines (UM-SCC) and one fibroblast cell line.

Apoptosis Assays

Apoptosis of UM-SCC cell lines following (−)-gossypol treatment was quantitatively detected by enzymatic labeling of DNA strand breaks using terminal deoxynucleotidyltransferase (TdT) and Alexa Fluor-BrdUTP, known as the TdT-UTP nick end-labeling (TUNEL) assay by flow cytometry. Cells were exposed to (−)-gossypol for 48 hours, harvested, fixed and TUNEL stained according to the manufacturer's protocol (Molecular Probes Inc., Eugene, Oreg.). Ten thousand cells were analyzed per sample using excitation of Alexa Fluor at 488 nm. Apoptotic index (AI) was defined as percent of apoptotic cells in the treatment population minus that in the vehicle control population.

The results on 4 representative squamous cell carcinoma cell lines (UM-SCC-1, UM-SCC-6, UM-SCC-12, UM-SCC-14A) and two fibroblast cell lines (fibroblast 1 and 2) are provided in FIGS. 24A, 24B, and 24C, respectively.

Example 18

Clonogenic Assay of Administration of (−)-Gossypol and Radiation Therapy

PC-3 cells obtained from the American Type Culture Collection and the National Cancer Institute were cultured in improved minimal essential medium (IMEM) (Biofluids, Rockville, Md.) with 10% fetal bovine serum (PBS) and 2 mM L-glutamine. Cultures were maintained in a humidified incubator at 37° C. and 5% $CO_2$. Resolution of gossypol enantiomers was carried out as described in Example 3. Gossypol compounds were first dissolved in ethanol and diluted with sterile water within 5 min to a final ethanol concentration of 10% prior to each administration.

The PC-3 cells were used in a standard clonogenic assay to investigate the effects of gossypol compounds, e.g., (−)-gossypol, on the cell's response to subsequent radiation therapy. Briefly, at day 1, 200 to 10,000 PC-3 cells per well were plated into 6 well plates using standard techniques. The cells were then treated with 1-5 μM (−)-gossypol and then exposed to 2 to 8 Gy, 300 keV, X-ray irradiation within 1 h. One ml of complete medium was added per well on Day 5. After 10 to 12 days in culture, the plates were stained with crystal violet and colonies with over 50 cells were counted using a ColCount (Oxford Optronix Ltd., Oxford, U.K.) colony counter. For each combination treatment, parallel analyses with each agent alone were also performed.

Figure 35A:
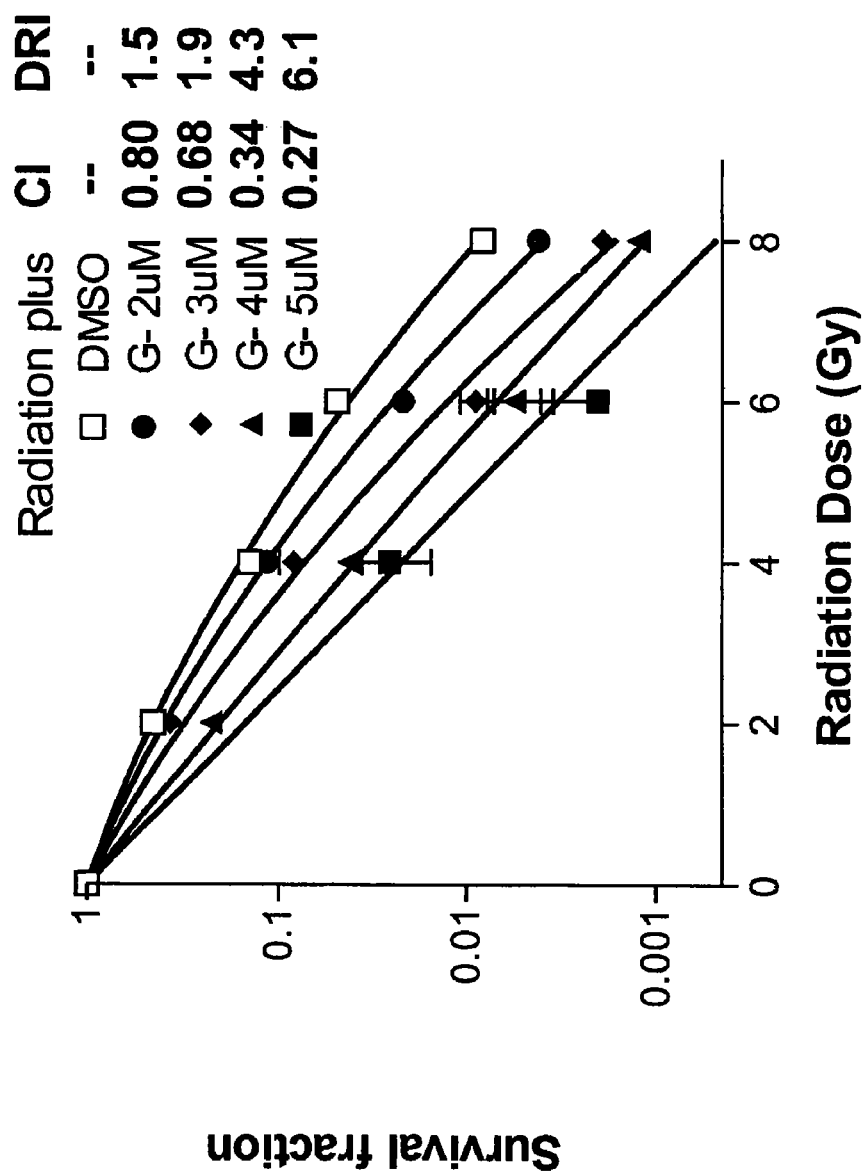

The data generated during the course of development of the present invention show that (−)-gossypol sensitizes PC-3 cells to radiation therapy in the clonogenic assay tested. The cell survival curves were plotted with linear-quadratic model as shown in (FIGS. 35A and 35B). Briefly, FIG. 35A shows the in vitro effects of (−)-gossypol in combination with various doses of radiation on PC-3 clonogenic assays, wherein: CI=Combination index; CI value<1 indicating synergistic effects; CI=1 indicating additive effects; CI value>1 indicating antagonistic effects; DRI=Dose Reduction Index; DRI>1.0 indicating synergistic effect. Treatment of PC-3 cells with (−)-gossypol significantly reduced PC-3 cells' resistance to accompanying radiation therapy, resulting in 10- and 20-fold reductions in colony formation from controls at doses of 6 Gy and 8 Gy, respectively. The isobologram analyses (See, T. C. Chou and P. Talalay, Adv. Enzyme Regulation, 22:27-55 (1984)), widely used analyses used to determine synergism, show that the combination of radiation with (−)-gossypol resulted in significant synergy, with the Combination Index (CI) of 0.27 and 0.34, and the Dose Reduction Index (DRI) of 6.1 and 4.3 for administration of 8 Gy radiation with either 5 μM or 4 μM gossypol, respectively. The results demonstrate that (−)-gossypol sensitizes PC-3 cells to X-ray irradiation in a dose-dependent manner.

Example 19

Administration of Gossypol Compounds and Radiation Therapy in an In Vivo Mouse PC-3 Xenograft Model In this experiment, 34 male 5 to 6 week old NCI athymic NCr-nu/nu nude mice were inoculated in each flank with an injection of about $5 \times 10^6$ PC-3 cells. The best 25 xenograft recipients were used. Tumors averaged about 50 $mm^3$. (−)-Gossypol was first dissolved in ethanol and diluted with sterile water within 5 min to a final ethanol concentration of 10% prior to each administration. Irradiated test animals were restrained, placed under the X-ray head, and covered with lead shields to ensure that the tumor area was exposed to radiation. All oral administrations of (−)-gossypol and 10% alcohol were given by gavage (Table 18).

The 25 best xenograft mice were divided into 5 experimental groups (5 mice per group) as follows: Vehicle control (Group 1), daily oral administration of 10% alcohol; radiation only (Group 2), 2 Gy administered 5 times/week for 2 weeks, and daily oral administration of 10% alcohol; radiation plus gossypol (Group 3), 2 Gy administered 5 times/week for 3 weeks, and 10 mg/kg of (−)-gossypol administered orally every day for 4 weeks; gossypol only (Group 4), 10 mg/kg (−)-gossypol administered orally every day for 4 weeks; control (Group 5), no treatment. During the treatment course, tumor sizes and animal weights were measured 3 times per/week for each animal. Following treatment, tumor sizes were measured 2 times per/week, and animal weights once per/week. Tumor and weight observations were made without knowledge of the animal's treatment group.

Treatment with (−)-gossypol alone had minimal antitumor effect (Table 18). However, the data generated during the course of the development of the present invention shows that (−)-gossypol sensitizes PC-3 cells to radiation therapy in the xenograft animal model. (−)-Gossypol treatment was started at day 13 where the average tumor volume was at 150 $mm^3$ and was given orally at five times weekly in doses of 10 mg/kg for 4 weeks. X-ray irradiation was given at day 5 after treatment with (−)-gossypol. Radiation therapy alone achieved limited antitumor effect (23%). Radiation therapy in combination with administration of gossypol (at the same dose level (10 mg/kg)) provided potent tumor growth inhibition (88% growth inhibition).

TABLE 18

| Treatment | Tumor Growth Inhibition (T/C %) | Tumor Growth Delay (T − C Days) |
| --- | --- | --- |
| Radiation | 77.7 | 8.5 |
| (−)-gossypol | 98.6 | 0 |
| Radiation + (−)-gossypol | 12.6 | 54.5 |

Figure 36:
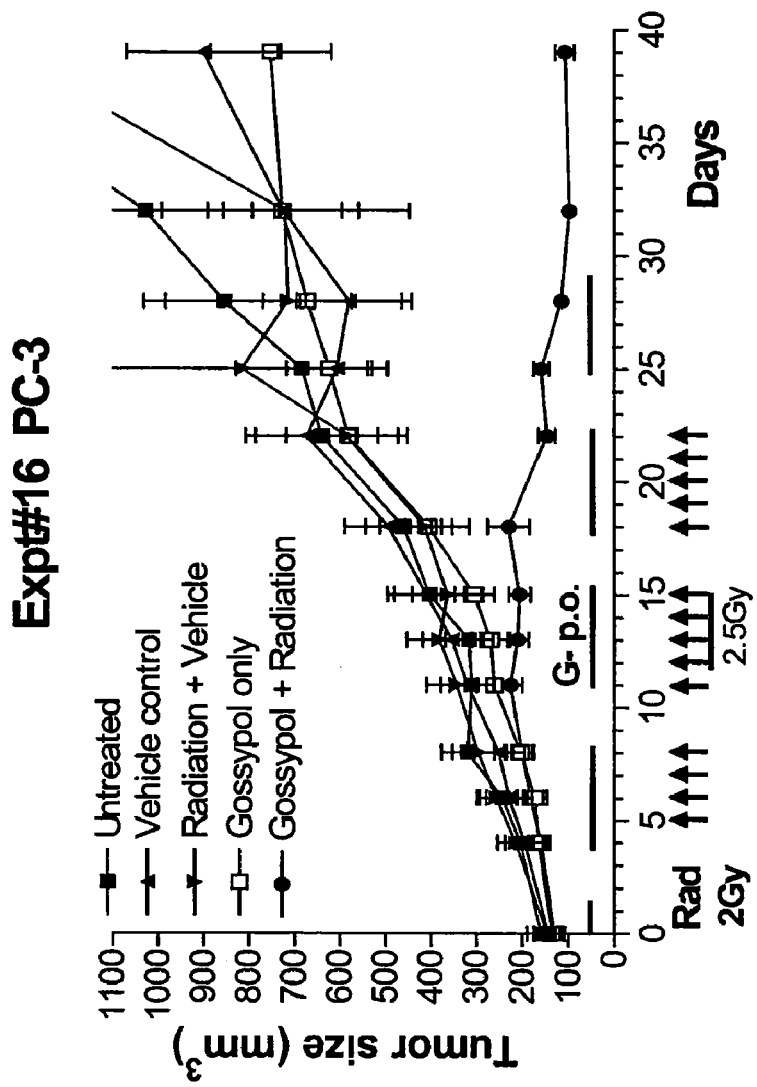
FIG. 36 shows the results of in vivo animal xenograft based assays in one embodiment of the present invention.
Figure 37:
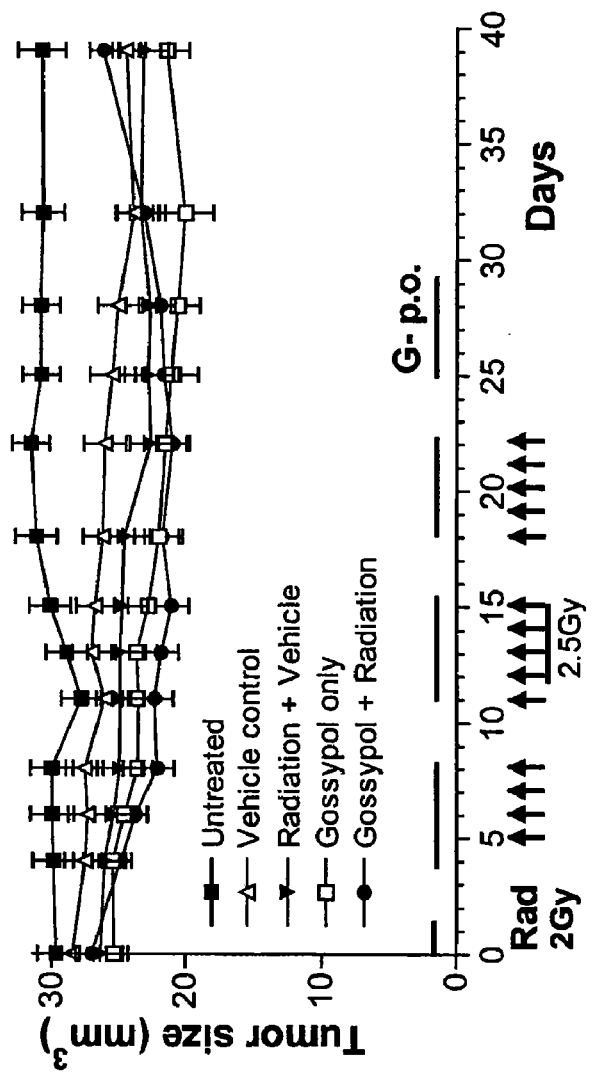
FIG. 37 shows the results of in vivo animal xenograft based assays in one embodiment of the present invention.

Overall, there was more than 90% inhibition in tumor cell growth in animals receiving radiation therapy in combination with gossypol as compared to the group controls (FIG. 36). Briefly, in FIG. 36 day 0 is the starting day of (−)-gossypol treatment; starting tumor size was 150 mm³; (−)-gossypol was administered at 10 mg/kg, orally 5 times per week for 4 weeks; radiation: X-ray, 2 Gy, 5 times per week for 3 weeks (at the second week the radiation was adjusted to 2.5 Gy) for a total dose of 30 Gy. Significantly, there was no significant toxicity in either group as shown by bodyweight measurements (FIG. 37). At the end of treatment (day 25), one mouse from each single agent and combination therapy group was sacrificed and tumor tissues were stained for both apoptosis and angiogenesis analysis. The results showed that (−)-gossypol was very effective in potentiating radiation in combination treatment regimens to induce apoptosis and to inhibit angiogenesis even at dose levels where it was not very effective as a single agent.

Example 20

Administration of Gossypol Compounds and Radiation Therapy in an In Vivo Mouse PC-3 Xenograft Model In this experiment, 60 male 5 to 6 week old NCI athymic NCr-nu/nu nude mice were inoculated in each flank with an injection of about 5×10⁶ PC-3 cells. The best 40 xenograft recipients were used. Tumors averaged about 70 mm³. (−)-Gossypol compounds were first dissolved in ethanol and diluted with sterile water within 5 min to a final ethanol concentration of 10% prior to each administration. Irradiated test animals were restrained, placed under the X-ray head, and covered with lead shields to ensure that the tumor area was exposed to radiation. All oral administrations of (−)-gossypol and 10% alcohol were given by gavage.

The 40 best xenograft mice were divided into experimental groups as follows: radiation only (Groups 1 and 2), 2 Gy administered 5 times/week for 3 weeks, and daily oral administration of 10% alcohol (as vehicle control); radiation plus gossypol (Groups 3 and 4), 2 Gy administered 5 times a week for 3 weeks, and 10 mg/kg of (−)-gossypol administered orally 5 times/week for 4 weeks (8 mice each Group); gossypol only (Groups 5 and 6), 10 mg/kg (−)-gossypol administered orally every day for 4 weeks (8 mice each Group); vehicle control (Groups 7 and 8), daily oral administration of 10% alcohol (8 mice each Group as vehicle control); large tumor animals (combination of Groups 9-12), tumors allowed to reach 500 mm³.

Figure 38:
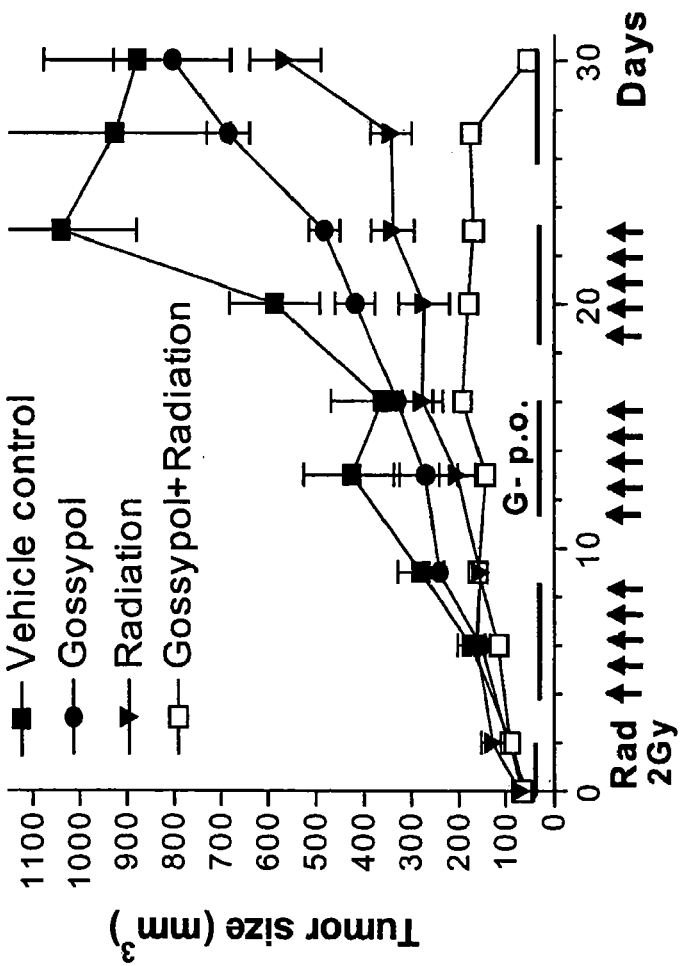
FIG. 38 shows the results of in vivo animal xenograft based assays in one embodiment of the present invention.

FIG. 38 shows yet another embodiment wherein (−)-gossypol in combination with radiation achieves tumor regression in an androgen-independent prostate PC-3 xenograft model, wherein: day 0 is the starting day of gossypol treatment; starting tumor size: 70 mm³; (−)-gossypol 10 mg/kg, p.o., q.d.×5, for 4 weeks; radiation, X-ray, 2 Gy, q.d.×5 for 3 weeks, total dose=30 Gy; large tumors in the vehicle control group were sacrificed when they reached over 2-3,000 mm³.

At least 10 out of 16 tumors in the combination group exhibited complete regression with only tiny scars left (from peak tumor sizes of 200 mm³). Other remaining tumors in this group appear pale yellowish and soft as compared with that in control group with hard solid and reddish appearance, indicating tumor blood supply was inhibited.

Example 21

Figure 39:
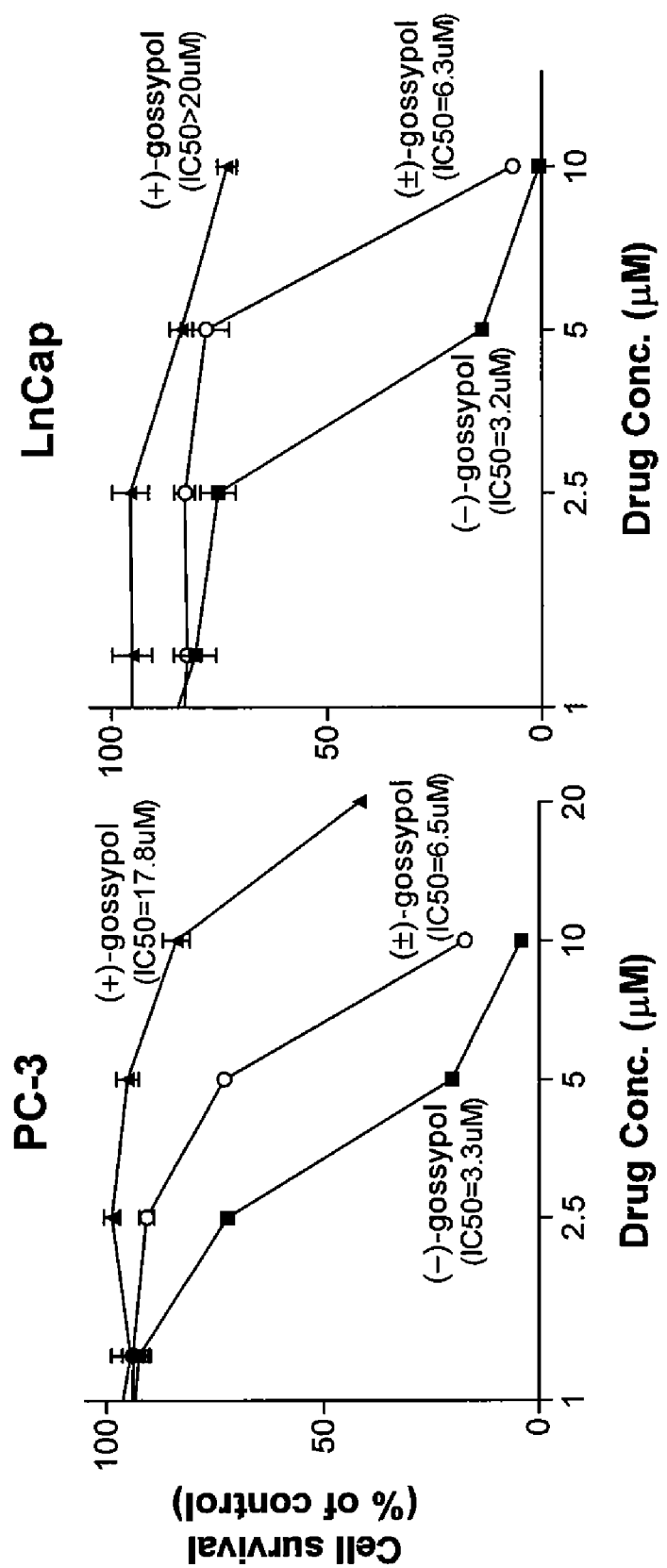
FIG. 39 shows the results of cell based assays of the inhibition of cell growth in 2 prostate cancer cell lines PC-3 and LnCaP by racemic gossypol, (−)-gossypol, and (+)-gossypol in various embodiments of the present invention.
Figure 40:
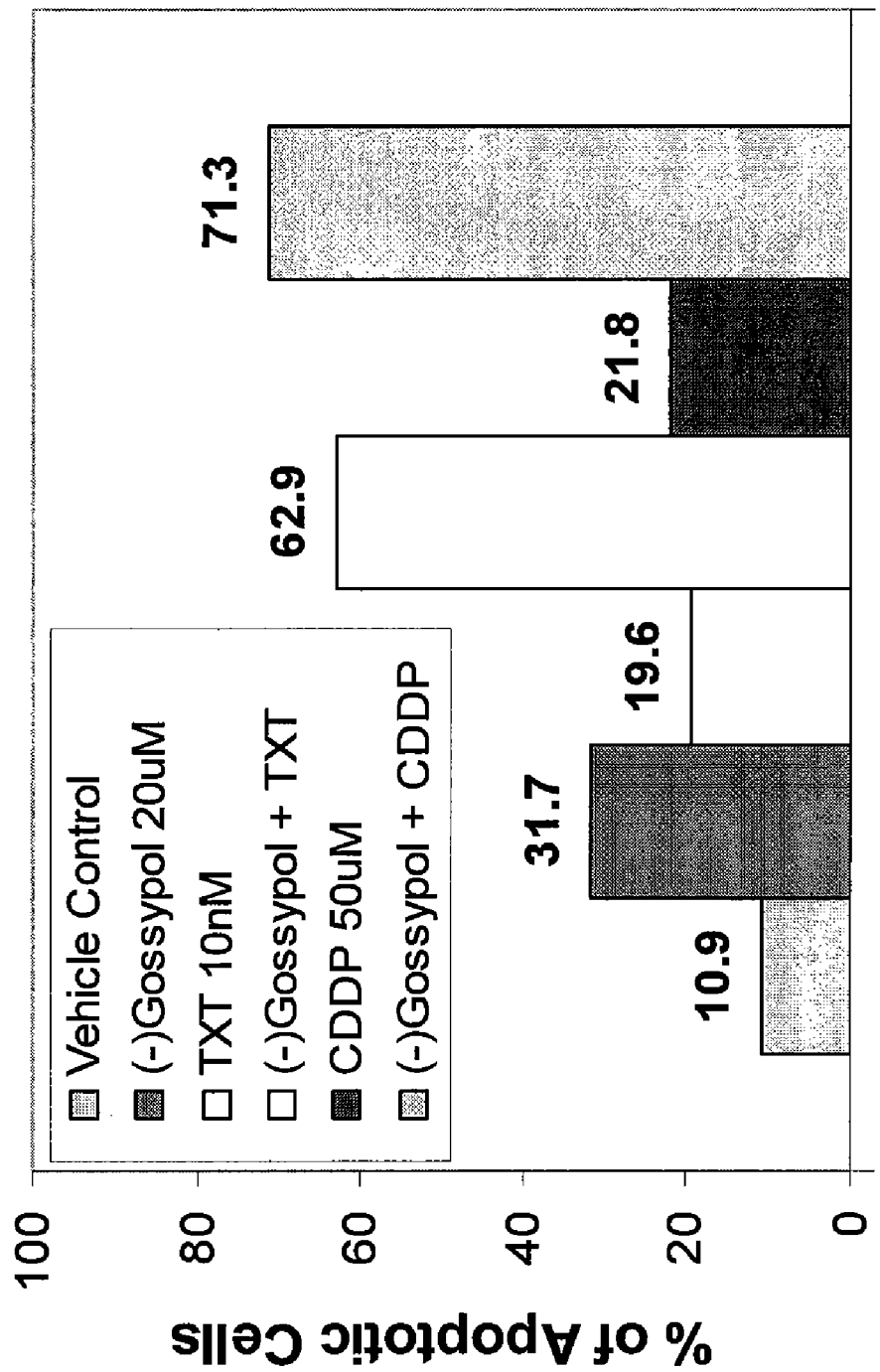
FIG. 40 shows the results of cell based assays in one embodiment of the present invention.
Figure 41:
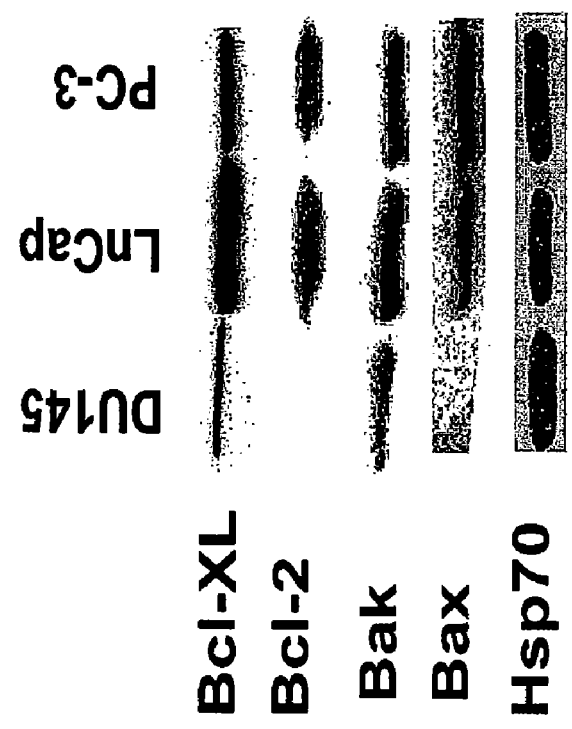
FIG. 41 shows the results of Western blotting analysis of several Bcl-2 family proteins in one embodiment of the present invention.
Figure 42:
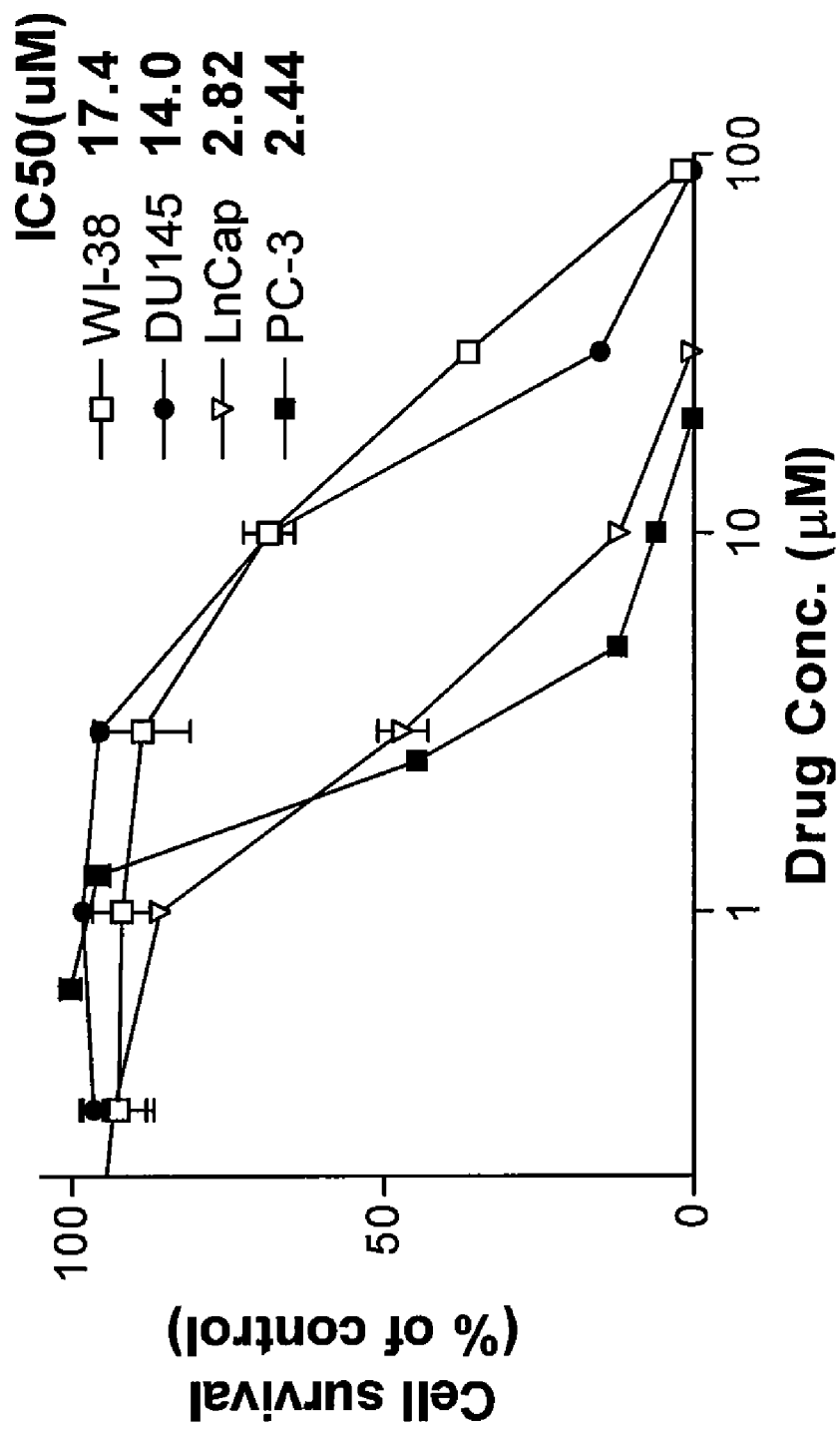
FIG. 42 shows the results of cell based assays in one embodiment of the present invention.

(−)-Gossypol Inhibits Prostate Cancer Cell Growth (−)-Gossypol is 5-10 times more potent than (+)-gossypol and 2 times more potent than racemic gossypol (50% (−)-gossypol) in inhibiting cancer cell growth in human prostate cancer cells PC-3 and LnCap (FIG. 39) both of which express high levels of Bcl-$X_L$. FIG. 39 shows prostate cancer cell growth inhibition by gossypol; PC-3 and LnCap cells in 96 well plates were treated in triplicate with gossypol and its enantiomers; MTT-based 5-day cell proliferation assays were performed and $IC_{50}$ values determined. The present invention is not limited to any mechanism. Indeed, a mechanistic understanding of the invention is unnecessary to practice (make and use) the present compositions and methods. Nonetheless, data generated during the course of the development of the present invention using 10 head-neck cancer cell lines shows that the ability of (−)-gossypol to inhibit cell growth is inversely related to the level of Bcl-xL protein, i.e., the higher the level of Bcl-$X_L$ protein, the more sensitive the cells (e.g., cancer cells) are to (−)-gossypol. The activity profile of (−)-gossypol is different from that of chemotherapeutic agents, which often show resistance in cancer cell lines with high levels of Bcl-$X_L$ and Bcl-2 proteins. Further in vitro studies demonstrated that (−)-gossypol induces apoptosis in variety of cancer cell lines with high expression levels of Bcl-xL and achieves synergistic effects with docetaxel (TAXOTERE, TXT). In the human prostate cancer cell line PC-3, which has high levels of Bcl-$X_L$ and Bcl-2 proteins, (−)-gossypol enhanced the activities of docetaxel and cisplatin (CDDP) in inhibiting cell growth and inducing apoptosis (FIG. 40). Briefly, in FIG. 40, cells were treated with (−)-gossypol alone or in combination with TXT or CDDP for 48 hrs, then stained with Annexin V-FITC and PI for flow cytometry; values are percent of apoptotic cells. FIG. 41 shows the Bcl-2 family proteins expression in three prostate cancer cell lines; HSP70 heat shock protein 70 kDa fro gel loading. FIG. 42 shows cytotoxicity of (−)-gossypol on prostate cancer cell lines; MTT based 5-day cell proliferation assays were performed and $IC_{50}$ values determined. (−)-Gossypol while showing cytotoxicity in prostate cancer PC-3 and LnCap cells, has very limited effect on DU145 and normal human fibroblast WI-38 cells (FIG. 42).

Example 22

Anti-Tumor Activity of (−)-Gossypol Alone and in Combination with Docetaxel in Androgen Independent Prostate Cancer PC-3 Xenograft Model Further embodiments of the present invention provide studies of (−)-gossypol using a PC-3 xenograft model in nude mice to evaluate (−)-gossypol's anti-tumor activity in vivo alone and in combination with docetaxel. In some experiments, the antitumor efficacy of (−)-gossypol was compared with that of racemic gossypol. Data generated during the development of the present invention shows that (−)-gossypol is significantly more potent in tumor growth inhibition than racemic gossypol (50% (−)-gossypol) (FIGS. 43A and 43B). Briefly, in FIG. 43A, 15 mg/kg (±)- or (−)-gossypol p.o. was administered to a PC-3 nude mouse xenograft model for 26 days; (−)-gossypol is more potent than (±)-gossypol (P<0.001). FIG. 43B shows tumor inhibition by (−)-gossypol was significantly enhanced when used in combination with docetaxel (TXT); (−)-gossypol (7.5 mg/kg, p.o. daily for 4 weeks) or docetaxel (7.5 mg/kg once a week for 3 weeks); ** student's t-test. While docetaxel alone did not achieve complete tumor regression, (−)-gossypol alone achieved complete tumor regression in 2 out of 12 tumors after the 4-week-treatment (Table 19).

TABLE 19

| Treatment | Complete tumor regression/Total | Percent regression |
|---|---|---|
| Vehicle Control | 0/16 | 0% |
| (−)-gossypol | 2/12 | 17% |
| (−)-gossypol + TXT | 9/14 | 64%* |
| TXT | 0/16 | 0% |

*(−)-gossypol + TXT versus (−)-gossypol, p = 0.0143; (−)-gossypol + TXT versus TXT, p = 0.0001; two sided Chi-square test When used in combination with docetaxel, over 90% of tumor growth inhibition was observed, significantly more effective than either drug alone (FIG. 43B). Nine out of 14 tumors (64%) treated with the combination of (−)-gossypol+TXT showed complete tumor regression with only scar tissue left. Six out of these 9 regressed tumors did not grow back 8 weeks after the combination therapy ended. Data generated during the course of development of the present invention indicates (−)-gossypol has a potent anti-tumor activity in the androgen-independent human prostate cancer PC-3 xenograft model, and achieves much greater anticancer efficacy in vivo when used in combination with docetaxel (64% complete tumor regression).

Example 23

Blocking of Heterodimerization by (−)-Gossypol in HT-29 Colon Cancer Cells

Figure 44:
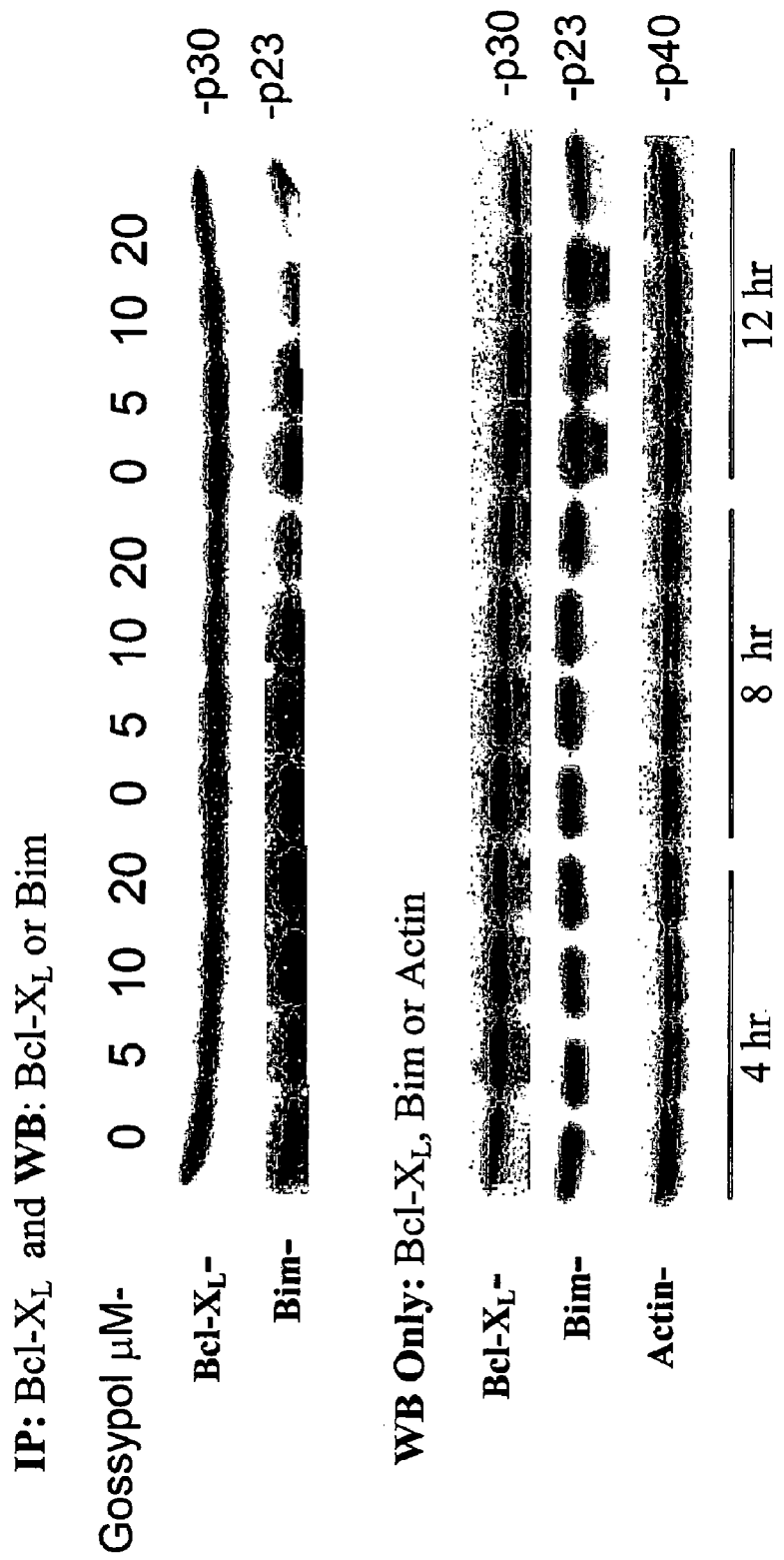
FIG. 44 shows the results of cell based assays in one embodiment of the present invention.

In one embodiment HT-29 colon cancer cells, which express only the Bcl-xL protein, were treated with (−)-gossypol at various doses for 4 hrs, 8 hrs, and 12 hrs. To avoid the detergent effects on the dimerization of Bcl-xL proteins in immunoprecipitation experiments, following the treatment of cells with gossypol, immunoprecipitation of cell lysates was carried out in the Chaps buffer with the anti-Bcl-$X_L$ antibody. The Bcl-$X_L$ bound proteins were then immunoblotted with anti-Bim antibody. Treatment with (−)-gossypol resulted in a dose-dependent decrease in the binding of Bcl-$X_L$ and pro-apoptotic protein Bim, starting at 8 hrs following the gossypol treatment (FIG. 44). There is no change in the total Bcl-$X_L$ or Bim protein in the same lysates following the (−)-gossypol treatment. These results are consistent with in vitro binding data (FP-based displacement assay and NMR binding assay) and cellular activity of gossypol at similar doses and support the notion that (−)-gossypol can enter the cells and has the ability to inhibit the interaction of Bcl-$X_L$ with pro-apoptotic proteins such as Bim in intact cells.

Example 24

Synthesis of Other Gossypol Compounds

Many simple gossypol compounds have been described in literature (See e.g., L. D. David et al., Current Medicinal Chemistry, 7:479-498 (2000)). The synthesis of apogossypol, gossypolone, and several other gossypol compounds has been carried out by the inventors and is provided below.
Synthesis of Apogossypol
Synthetic methods of preparing apogossypol have been reported (See e.g., P. C. Meltzer et al., J. Org. Chem., 50(17): 3121-3124 (1985)). Briefly, apogossypol was prepared by heating racemic gossypol (1.6 g) in aqueous NaOH (40%, 10 mL) at 85° C. for 2 hrs under the protection of nitrogen. The reaction mixture was then cooled down, poured into a mixture of ice and sulfuric acid (from 15 g of concentrated $H_2SO_4$), the resultant was extracted with ether twice, and the combined organic phase was washed with water, dried over anhydrous $Na_2SO_4$, and concentrated in vacuum to yield apogossypol.
Synthesis of Gossypolone
Synthetic methods of preparing gossypolone have been reported (See e.g., R. H. Hass et al., J. Org. Chem., 30:4111-4113 (1965)). Briefly, a solution of 2.0 g (3.5 mmol) of gossypol acetic acid purchased from a commercial supplier (e.g., Sigma-Aldrich) in 100 ml of acetone and 200 ml of acetic acid was stirred at room temperature during the addition of 150 ml of a 10% aqueous solution of ferric chloride hexahydrate (56 mmol) and stirring was maintained for 12 hrs. The solution was cooled and 250 ml of water was added to precipitate a dark iron-containing compound which was removed and treated with a mixture of ether and aqueous 20% sulfuric acid. The liberated phenol was taken into the ether layer. The ether layer was separated and dried, and the ether was evaporated. The residue was recrystallized from aqueous acetic acid to yield 1.2 g of orange product.

All publications, patent applications, and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method of treating or ameliorating glioblastoma in a subject comprising administering to said subject a therapeutically effective dose of (−)-gossypol and.

2. A method of treating or ameliorating esophageal carcinoma in a subject comprising administering to said subject a therapeutically effective dose of (−)-gossypol and docetaxel.

3. A method of treating or ameliorating head-neck cancer in a subject comprising administering to said subject a therapeutically effective dose of (−)-gossypol and docetaxel.

4. A method of treating or ameliorating lymphocytic leukemia in a subject comprising administering to said subject a therapeutically effective dose of (−)-gossypol and docetaxel.

5. The method of claim 1, wherein said (−)-gossypol and said docetaxel are administered simultaneously to said subject.

6. The method of claim 1, wherein said (−)-gossypol and said docetaxel are administered sequentially to said subject.

7. The method of claim 6, wherein said (−)-gossypol is administered to said subject prior to said docetaxel.

8. The method of claim 6, wherein said (−)-gossypol is administered to said subject after said docetaxel.

9. The method of claim 2, wherein said (−)-gossypol and said docetaxel are administered simultaneously to said subject.

10. The method of claim 2, wherein said (−)-gossypol and said docetaxel are administered sequentially to said subject.

11. The method of claim 10, wherein said (−)-gossypol is administered to said subject prior to said docetaxel.

12. The method of claim 10, wherein said (−)-gossypol is administered to said subject after said docetaxel.

13. The method of claim 3, wherein said (−)-gossypol and said docetaxel are administered simultaneously to said subject.

14. The method of claim 3, wherein said (−)-gossypol and said docetaxel are administered sequentially to said subject.

15. The method of claim 14, wherein said (−)-gossypol is administered to said subject prior to said docetaxel.

16. The method of claim 14, wherein said (−)-gossypol is administered to said subject after said docetaxel.

17. The method of claim 4, wherein said (−)-gossypol and said docetaxel are administered simultaneously to said subject.

18. The method of claim 4, wherein said (−)-gossypol and said docetaxel are administered sequentially to said subject.

19. The method of claim 18, wherein said (−)-gossypol is administered to said subject prior to said docetaxel.

20. The method of claim 18, wherein said (−)-gossypol is administered to said subject after said docetaxel.

* * * * *

UNITED STATES PATENT AND TRADEMARK OFFICE
CERTIFICATE OF CORRECTION

PATENT NO. : 8,163,805 B2
APPLICATION NO. : 12/242380
DATED : April 24, 2012
INVENTOR(S) : Shaomeng Wang, Dajun Yang and Liang Xu It is certified that error appears in the above-identified patent and that said Letters Patent is hereby corrected as shown below:

Claim 1 in Column 157, lines 26-28 should read: --A method of treating or ameliorating glioblastoma in a subject comprising administering to said subject a therapeutically effective dose of (-) gossypol and docetaxel.--

Signed and Sealed this
Third Day of July, 2012

David J. Kappos
*Director of the United States Patent and Trademark Office*

SEQUENCE LISTING

<160> NUMBER OF SEQ ID NOS: 10

<210> SEQ ID NO 1
<211> LENGTH: 155

```
<212> TYPE: PRT
<213> ORGANISM: Artificial Sequence
<220> FEATURE:
<223> OTHER INFORMATION: Synthetic

<400> SEQUENCE: 1

Asn Arg Glu Ile Val Met Lys Tyr Ile His Tyr Lys Leu Ser Gln Arg
1               5                   10                  15

Gly Tyr Glu Trp Asp Ala Gly Asp Val Gly Ala Pro Pro Gly Ala
            20                  25                  30

Ala Pro Ala Pro Gly Ile Phe Ser Ser Gln Pro Val His Leu Thr
        35                  40                  45

Leu Arg Gln Ala Gly Asp Asp Phe Ser Arg Arg Tyr Arg Arg Asp Phe
    50                  55                  60

Ala Glu Met Ser Arg Gln Leu His Leu Thr Pro Phe Thr Ala Arg Gly
65                  70                  75                  80

Arg Phe Ala Thr Val Val Glu Glu Leu Phe Arg Asp Gly Val Asn Trp
                85                  90                  95

Gly Arg Ile Val Ala Phe Phe Glu Phe Gly Gly Val Met Cys Val Glu
            100                 105                 110

Ser Val Asn Arg Glu Met Ser Pro Leu Val Asp Asn Ile Ala Leu Trp
        115                 120                 125

Met Thr Glu Tyr Leu Asn Arg His Leu His Thr Trp Ile Gln Asp Asn
130                 135                 140

Gly Gly Trp Asp Ala Phe Val Glu Leu Tyr Gly
145                 150                 155

<210> SEQ ID NO 2
<211> LENGTH: 152
<212> TYPE: PRT
<213> ORGANISM: Artificial Sequence
<220> FEATURE:
<223> OTHER INFORMATION: Synthetic

<400> SEQUENCE: 2

Asn Arg Glu Leu Val Val Asp Phe Leu Ser Tyr Lys Leu Ser Gln Lys
1               5                   10                  15

Gly Tyr Ser Trp Ser Gln Phe Ser Asp Val Glu Glu Asn Arg Thr Glu
            20                  25                  30

Ala Pro Glu Gly Thr Glu Ser Glu Ala Val Lys Gln Ala Leu Arg Glu
        35                  40                  45

Ala Gly Asp Glu Phe Glu Leu Arg Tyr Arg Arg Ala Phe Ser Asp Leu
    50                  55                  60

Thr Ser Gln Leu His Ile Thr Pro Gly Thr Ala Tyr Gln Ser Phe Glu
65                  70                  75                  80

Gln Val Val Asn Glu Leu Phe Arg Asp Gly Val Asn Trp Gly Arg Ile
                85                  90                  95

Val Ala Phe Phe Ser Phe Gly Gly Ala Leu Cys Val Glu Ser Val Asp
            100                 105                 110

Lys Glu Met Gln Val Leu Val Ser Arg Ile Ala Ala Trp Met Ala Thr
        115                 120                 125

Tyr Leu Asn Asp His Leu Glu Pro Trp Ile Gln Glu Asn Gly Gly Trp
130                 135                 140

Asp Thr Phe Val Glu Leu Tyr Gly
145                 150

<210> SEQ ID NO 3
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 3

Gly Phe Leu Gly
1

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Cys Asp Cys Arg Gly Asp Cys Phe Cys
1               5

<210> SEQ ID NO 5
<211> LENGTH: 13
<212> TYPE: PRT
<213> ORGANISM: Artificial Sequence
<220> FEATURE:
<223> OTHER INFORMATION: Synthetic

<400> SEQUENCE: 5

Cys Asn Gly Arg Cys Val Ser Gly Cys Ala Gly Arg Cys
1               5                   10

<210> SEQ ID NO 6
<211> LENGTH: 3
<212> TYPE: PRT
<213> ORGANISM: Artificial Sequence
<220> FEATURE:
<223> OTHER INFORMATION: Synthetic

<400> SEQUENCE: 6

Gly Ser Leu
1

<210> SEQ ID NO 7
<211> LENGTH: 18
<212> TYPE: PRT
<213> ORGANISM: Artificial Sequence
<220> FEATURE:
<223> OTHER INFORMATION: Synthetic

<400> SEQUENCE: 7

Met Leu Ser Leu Arg Gln Ser Ile Arg Phe Phe Lys Pro Ala Thr Arg
1               5                   10                  15

Thr Leu

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Pro Pro Lys Lys Lys Arg Lys Val
1               5

<210> SEQ ID NO 9
<211> LENGTH: 16
```

```
<212> TYPE: PRT
<213> ORGANISM: Artificial Sequence
<220> FEATURE:
<223> OTHER INFORMATION: Synthetic

<400> SEQUENCE: 9

Gly Gln Val Gly Arg Gln Leu Ala Ile Ile Gly Asp Asp Ile Asn Arg
1               5                   10                  15

<210> SEQ ID NO 10
<211> LENGTH: 25
<212> TYPE: PRT
<213> ORGANISM: Artificial Sequence
<220> FEATURE:
<223> OTHER INFORMATION: Synthetic

<400> SEQUENCE: 10

Asn Leu Trp Ala Ala Gln Arg Tyr Gly Arg Glu Leu Arg Arg Met Ser
1               5                   10                  15

Asp Glu Phe Val Asp Ser Phe Lys Lys
                20                  25
```